United States Patent
Maier et al.

(10) Patent No.: US 7,666,868 B2
(45) Date of Patent: Feb. 23, 2010

(54) N-SULPHONYLPYRROLES AND THEIR USE AS HISTONE DEACETYLASE INHIBITORS

(75) Inventors: Thomas Maier, Stockach (DE); Thomas Bär, Reichenau (DE); Thomas Beckers, Constance (DE); Astrid Zimmermann, Constance (DE); Siegfried Schneider, Radolfzell (DE); Volker Gekeler, Constance (DE)

(73) Assignee: 4SC AG, Planegg Martinsrid (DE)

( * ) Notice: Subject to any disclaimer, the term of this patent is extended or adjusted under 35 U.S.C. 154(b) by 0 days.

(21) Appl. No.: 11/885,832

(22) PCT Filed: Mar. 14, 2006

(86) PCT No.: PCT/EP2006/060712

§ 371 (c)(1),
(2), (4) Date: Sep. 7, 2007

(87) PCT Pub. No.: WO2006/097474

PCT Pub. Date: Sep. 21, 2006

(65) Prior Publication Data

US 2008/0176848 A1 Jul. 24, 2008

(30) Foreign Application Priority Data

Mar. 15, 2005 (EP) .................................. 05102019
Sep. 21, 2005 (EP) .................................. 05108735

(51) Int. Cl.
| | |
|---|---|
| A61K 31/5377 | (2006.01) |
| A61K 31/496 | (2006.01) |
| A61K 31/4439 | (2006.01) |
| A61K 31/4155 | (2006.01) |
| C07D 413/02 | (2006.01) |
| C07D 403/00 | (2006.01) |
| C07D 401/00 | (2006.01) |
| C07D 231/10 | (2006.01) |

(52) U.S. Cl. .............................. 514/235.5; 514/254.01; 514/343; 514/406; 544/141; 544/372; 546/278.4; 548/364.1

(58) Field of Classification Search .............. 514/235.5, 514/254.01, 343, 406; 544/141, 372; 546/278.4; 548/364.1
See application file for complete search history.

(56) References Cited

U.S. PATENT DOCUMENTS

| 4,960,787 | A | 10/1990 | Wasley |
| 5,534,654 | A | 7/1996 | Ohtani et al. |
| 6,432,999 | B2 | 8/2002 | Talley et al. |
| 2002/0026052 | A1 | 2/2002 | Boschelli et al. |
| 2005/0234033 | A1 | 10/2005 | Anandan et al. |
| 2005/0288282 | A1 | 12/2005 | Delorme et al. |
| 2006/0258728 | A1 | 11/2006 | Tani et al. |
| 2007/0184979 | A1 | 8/2007 | Maier et al. |

FOREIGN PATENT DOCUMENTS

| EP | 0 570 594 A1 | 11/1993 |
| EP | 1 431 267 A1 | 6/2004 |
| WO | 9312075 A1 | 6/1993 |
| WO | 01/38322 A1 | 5/2001 |
| WO | 0138323 A1 | 5/2001 |
| WO | 03016254 A1 | 2/2003 |
| WO | 03/024448 A2 | 3/2003 |
| WO | 2004/037751 A2 | 5/2004 |
| WO | 2004/046094 A1 | 6/2004 |
| WO | 2005/020921 A2 | 3/2005 |
| WO | 2005/070900 A1 | 8/2005 |
| WO | 2005/086898 A2 | 9/2005 |
| WO | 2005/087724 A2 | 9/2005 |
| WO | PCTEP2005051086 R | 10/2005 |
| WO | 2006066189 A3 | 6/2006 |
| WO | PCTEP2006003171 R | 8/2006 |
| WO | 2006097474 A1 | 9/2006 |
| WO | 2006/105979 A1 | 10/2006 |
| WO | PCTEP2006066197 R | 12/2006 |
| WO | 2007039404 A1 | 4/2007 |

OTHER PUBLICATIONS

Almenara, J., et al., "Synergistic induction of mitochondrial damage and apoptosis in human leukemia cells by flavopiridol and the histone deacetylase inhibitor suberoylanilide hydroxamic acid (SAHA)", Leukemia, vol. 16, pp. 1331-1343, (2002).

Angle, S. R., et al., "A Simple Method for the Synthesis of Substituted Benzylic Ketones: Homologation of Aldehydes via the in Situ Generation of Aryldiazomethanes from Aromatic Aldehydes", J. Org. Chem., vol. 65, pp. 6458-6461, (2000).

(Continued)

*Primary Examiner*—Kamal A Saeed
*Assistant Examiner*—Samantha L Shterengarts
(74) *Attorney, Agent, or Firm*—Millen, White, Zelano & Branigan, P.C.

(57) ABSTRACT

Compounds of a certain formula (I)

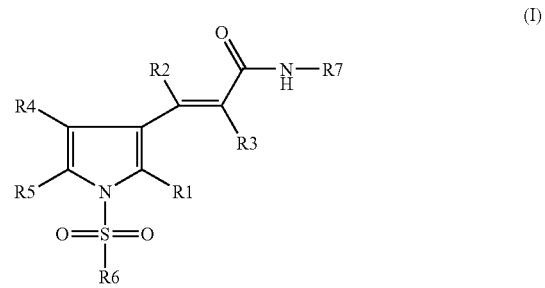

in which R1, R2, R3, R4, R5, R6 and R7 have the meanings indicated in the description, are novel effective HDAC inhibitors.

18 Claims, No Drawings

OTHER PUBLICATIONS

Bouchain, G., et al., "Development of Potential Antitumor Agents. Synthesis and Biological Evaluation of a New Set of Sulfonamide Derivatives as Histone Deacetylase Inhibitors", J. Med. Chem., vol. 46, pp. 820-830, (2003).

Chung, Y-L., et al., "A Therapeutic Strategy Uses Histone Deacetylase Inhibitors to Modulate the Expression of Genes Involved in the Pathogenesis of Rheumatoid Arthritis", Molecular Therapy, vol. 8, pp. 707-717, (2003).

Dhordain, P., et al., "The LAZ3(BCL-6) oncoprotein recruits a SMRT/mSIN3A/histone deacetylase containing complex to mediate transcriptional repression", Nucleic Acids Research, vol. 26, pp. 4645-4651, (1998).

Engman, L., et al., "Tetrahydrofuran Derivatives from Epoxides via Group Transfer Cyclization or Reductive Radical Cyclization of Organotellurium and Organoselenium Intermediates", J. Org. Chem., vol. 62, pp. 157-173, (1997).

Fischle, W., et al., "Enzymatic Activity Associated with Class II HDACs is Dependent on a Multiprotein Complex Containing HDAC3 and SMRT/N-CoR", Molecular Cell., vol. 9, pp. 45-47, (2002).

Gao, L., et al., "Cloning and Functional Characterization of HDAC11, a Novel Member of the Human Histone Deacetylase Family",Journal Biol. Chem., vol. 277, pp. 25748-25755, (2002).

George, P., et al., "Combination of the histone deacetylase inhibitor LBH589 and the hsp90 inhibitor 17-AAG is highly active against human CML-BC cells and AML cells with activating mutation of FLT-3", Blood, vol. 105, pp. 1768-1777, (2005).

Glaser, K. B., et al., "Role of Class I and Class II histone deacetylase in carcinoma cells using siRNA", Biochemical an Biophysical Research Communications, vol. 31, pp. 529-536, (2003).

Haggarty, S., et al., "Domain-selective small-molecule inhibitor of histone deacetylase 6 (HDAC6)-mediated tubulin deacetylation", J. Proc. Natl. Acad. Sci. USA, vol. 100, pp. 4389-4394, (2003).

He, L. Z., et al., "Distinct Interactions of PML-RARα and PLZF-RARα with co-repressors determine differential responses to RA in APL", Nature Genetics, vol. 18, pp. 126-135, (1998).

Hockly, E., et al., "Suberoylanilide hydroxamic acid, a histone deacetylase inhibitor, ameliorates motor deficits in a mouse model of Huntington's disease", Proc. Natl. Acad. Sci. USA, vol. 100, pp. 2041-2046, (2003).

Johnstone, W. R., et al., "Histone deacetylase inhibitors in cancer therapy: Is transcription the primary target?", Cancer Cell., vol. 4, pp. 13-18, (2003).

Kelly, W. K., et al., "Phase I Study of an Oral Histone Deacetylase Inhibitor, Suberoylanilide Hydroxamic Acid, in Patients with Advanced Cancer", J. Clin. Oncol., vol. 23, pp. 3923-3931, (2005).

Khochbin., S., et al., "Functional significance of histone deacetylase diversity", Current Opinion Gen. Dev., vol. 11, pp. 162-166, (2001).

Kim, M. S., et al., "Inhibition of Histone Deacetylase Increases Cytotoxicity to Anticancer Drugs Targeting DNA", Cancer Research, vol. 63, pp. 7291-7300, (2003).

Kraemer, O. H., et al., "Histone deacetylase as a therapeutic target", Trends Endocrin. Metabol., vol. 12, pp. 294-300, (2001).

Lagger, G., et al., "Essential Function of histone deacetylase 1 in proliferation control and CDK inhibitor repression", EMBO, vol. 21, pp. 2672-2681, (2002).

Leoni, F., et al., "The antitumor histone deacetylase inhibitor suberoylanilide hydroxamic acid exhibits antiinflammatory properties via suppression of cytokines", Proc. Natl., Acad. Sci. USA, vol. 99, pp. 2995-3000, (2002).

Mai, A., et al., "3-(4-Aroyl-1-methyl-1H-2-pyrrolyl)-N-hydroxy-2-alkylamides as a New Class of Synthetic Histone Deacetylase Inhibitors. 1. Design, Synthesis, Biological Evaluation, and Binding Mode Studies Performed through Three Different Docking Procedures", J. Med. Chem., vol. 46, pp. 512-524, (2003).

Mai, A., et al., "3-(4-Aroyl-1-methy1-1H-2-pyrrolyl)-N-hydroxy-2-alkylamides as a New Class of Synthetic Histone Deacetylase Inhibitors. 2. Effect of Pyrrole-C2 and/or -C4 Substitutions on Biological Activity", Journal Medicinal Chem., vol. 47, pp. 1098-1109, (2004).

Marks, P. A., et al., "Histone Deacetylases and Cancer: Causes and Therapies", Nature Reviews Cancer, vol. 1, pp. 194-202, (2001).

Miller, T., et al., "Patent status of histone deacetylase inhibitors", Expert Opin. Ther. Patents, vol. 14, pp. 791-804, (2004).

Miller, T. A., et al., "Histone Deacetylase Inhibitors", Journal Med. Chem., vol. 46, pp. 5097-5116, (2003).

Mishra, N., et al., "Histone deacetylase inhibitors modulate renal disease in the MRL-1pr mouse", Journal Clinical Invest., vol. 111, pp. 539-552, (2003).

Mitsiades, C. S., et al., "Transcriptional signature of histone deacetylase inhibition in multiple myeloma: Biological and clinical implications", PNAS, vol. 101, pp. 540-546, (2004).

Munster, R. N., et al., "The Histone Deacetylase Inhibitor Suberoylanilide Hydroxamic Acid Induces Differentiation of Human Breast Cancer Cells", Cancer Research, vol. 61, pp. 8492-8497, (2001).

Murata, T., et al., "Defect of histone acetyltransferase activity of the nuclear transcriptional coactivator CBP in Rubinstein-Taybi syndrome", Human Molecular Genetics, vol. 10, pp. 1071-1076, (2001).

Nakayama, T., et al., "Epigenetic Regulation of Androgen Receptor Gene Expression in Human Prostate Cancers", Laboratory Inv., vol. 80, pp. 1789-1796, (2000).

Nimmanapalli, R., et al., "Histone Deacetylase Inhibitor LAQ824 Both Lowers Expression and Promotes Proteasomal Degradation of Ber-Abl and Induces Apoptosis of Imatinib Mesylate-sensitive or -refractory Chronic Myelogenous Leukemia-Blast Crisis Cells," Cancer Research, vol. 63, pp. 5126-5315, (2003).

Nishida, K., et al., "Histone Deacetylase Inhibitor Suppression of Autoantibody-Mediated Arthritis in Mice via Regulation of p16INK4a and p21WAF/Cip1 Expression", Arthritis Rheumatism, vol. 50, pp. 3365-3376, (2004).

Piekarz, R. L., et al., "Inhibitor of histone deacetylation, depsipeptide (FR901228), in the treatment of pereipheral and cutaneous T-cell lymphoma: a case report", Blood, vol. 98, pp. 2865-2868, (2001).

Ragno, R., et al., "3-(4-Aroyl-1-methyl-1H-2-pyrrolyl)-N-hydroxy-2-alkylamides as a New Class of Synthetic Histone Deacetylase Inhibitors. 3. Discovery of Novel Lead Compounds through Structure-Based Drug Design and Docking Studies", J. Med. Chem., vol. 47, pp. 1351-1359, (2004).

Reilly, C. M., et al., "Modulation of Renal Disease in MRL/lpr Mice by Suberoylanilide Hydroxamic Acid", J. Immunol, vol. 173, pp. 4171-4178, (2004).

Remiszewski, S. W., "Recent advances in the discovery of small molecule histone deacetylase inhibitors", Current Opinion Drug Disc. Devel., vol. 5, pp. 487-499, (2002).

Ruijter, A. J. M., et al., "Histone deacetylases (HDACs): characterization of the classical HDAC family", Biochem. Journal, vol. 370, pp. 737-749, (2003).

Sandor, V., et al., "P21-dependent G1 Arrest with downregulation of cyclin D1 and upregulation of cyclin E by the histone deacetylase inhibitor FR901228", British Journal Cancer, vol. 83, pp. 817-825, (2000).

Steffan, J. S., et al., "Histone deacetylase inhibitors arrest polyglutamine-dependent neurodegeneration in Drosophila", Nature, vol. 413, pp. 739-743, (2001).

Strahl, B. D., et al., "The language of covalent histone modifications", Nature, vol. 403, pp. 41-45, (2000).

Tatamiya, T., et al., "Isozyme-selective activity of the HDAC inhibitor MS-275", AACR Annual Meeting, Abstract 2451, (2004).

Tyrell, E., et al., "The Synthesis and Applications of Heterocyclic Boronic Acids", Synthesis, vol. 4, pp. 469-483, (2004).

Van Lint, C., et al., "The Expression of a Small Fraction of Cellular Genes is Changed in Response to Histone Hyperacetylation", Gene Expression, vol. 5, pp. 245-253, (1996).

Verdin, E., et al., "Class II histone deacetylases: versatile regulators", Trends Genetics, vol. 19, pp. 286-293, (2003).

Wang, J., et al., "ETO, fusion partner in t(8;21) acute myeloid leukemia, represses transcription by interaction with the human N-CoR/mSin3/HDAC1 complex", Proc. Natl. Acad. Sci. USA, vol. 95, pp. 10860-10865, (1998).

Yang, X., et al., "Transcriptional Activation of Estrogen Receptor α in Human Breast Cancer Cells by Histone Deacetylase Inhibition", Cancer Research, vol. 60, pp. 6890-6894, (2000).

Zhu, P., et al., "Induction of HDAC2 expression upon loss of APC in colorectal tumorigenesis", Cancer Cells, vol. 5, pp. 455-463, (2004).

N-SULPHONYLPYRROLES AND THEIR USE AS HISTONE DEACETYLASE INHIBITORS

This application was filed under 35 U.S.C. 371 as a national stage of PCT/EP2006/060712, filed Mar. 14, 2006.

FIELD OF APPLICATION OF THE INVENTION

The invention relates to novel sulphonylpyrrole derivatives, which are used in the pharmaceutical industry for the production of pharmaceutical compositions.

KNOWN TECHNICAL BACKGROUND

Transcriptional regulation in cells is a complex biological process. One basic principle is regulation by posttranslational modification of histone proteins, namely histone proteins H2A/B, H3 and H4 forming the octameric histone core complex. These complex N-terminal modifications at lysine residues by acetylation or methylation and at serine residues by phosphorylation constitute part of the so called "histone code" (Strahl & Ellis, Nature 403, 41-45, 2000). In a simple model, acetylation of positively charged lysine residues decreases affinity to negatively charged DNA, which now becomes accessible for the entry of transcription factors.

Histone acetylation and deacetylation is catalysed by histone acetyltransferases (HATs) and histone deacetylases (HDACs). HDACs are associated with transcriptional repressor complexes, switching chromatin to a transcriptionally inactive, silent structure (Marks et al. Nature Cancer Rev 1, 194-202, 2001). The opposite holds true for HATs which are associated with transcriptional activator complexes. Three different classes of HDACs have been described so far, namely class I (HDAC1-3, 8) with Mr=42-55 kDa primarily located in the nucleus and sensitive towards inhibition by Trichostatin A (TSA), class II (HDAC 4-7, 9, 10) with Mr=120-130 kDa and TSA sensitivity and class III (Sir2 homologues) which are quite distinct by their $NAD^+$ dependency and TSA insensitivity (Ruijter et al. Biochem.J. 370, 737-749, 2003; Khochbin et al. Curr Opin Gen Dev 11, 162-166, 2001; Verdin et al. Trends Gen 19, 286-293, 2003). HDAC II with Mr=39 kDa was cloned recently and displayed homology to class I and II family members (Gao et al. J Biol Chem 277,25748-25755, 2002). HATs and HDACs exist in large complexes together with transcription factor and platform proteins in cells (Fischle et al. Mol Cell 9, 45-47, 2002). Surprisingly, only about 2% of all genes are regulated by histone acetylation as estimated based on differential display analysis of 340 genes and TSA as the reference HDI (von Lint et al. Gene Expression 5, 245-253, 1996). New studies with SAHA in multiple myeloma cells showed that these transcriptional changes can be grouped into distinct functional gene classes important for eg regulation of apoptosis or proliferation (Mitsiades et al. Proc Natl Acad Sci 101, pp 540, 2004). Substrates different to histone proteins exist. For HDACs these include transcription factors like p53 and TFII E/or chaperones like Hsp90 (Johnstone & Licht, Cancer Cell 4, 13-18, 2003). Therefore the correct name for HDACs would be lysine-specific protein deacetylases. As a consequence of these findings, inhibitors of HDACs effect not only chromatin structure and gene transcription but also protein function and stability by regulating protein acetylation in general. This function of HDACs in protein acetylation might also be important for understanding of immediate gene repression by treatment with HDIs (von Lint et al. Gene Expression 5, 245-253, 1996). In this regard, proteins involved in oncogenic transformation, apoptosis regulation and malignant cell growth are of particular importance.

Different publications highlight the importance of histone acetylation for cancer development (reviewed by Kramer et al. Trends Endocrin Metabol 12, 294-300, 2001; Marks et al. Nature Cancer Rev 1, 194-202, 2001). These diseases include
(i) mutations of the HAT CAMP response element binding protein (CBP) associated with Rubinstein-Taybi syndrome, a cancer predisposition (Murata et al. Hum Mol Genet. 10, 1071-1076, 2001),
(ii) aberrant recruitment of HDAC1 activity by transcription factors in acute promyelocytic leukemia (APL) by the PML-retinoic acid receptor a fusion gene (He et al. Nat genet 18, 126-135, 1998)
(iii) aberrant recruitment of HDAC activity by the overexpressed BCL6 protein in non-Hodgkins lymphoma (Dhordain et al. Nucleic Acid Res 26, 4645-4651, 1998) and finally
(iv) aberrant recruitment of HDAC activity by the AML-ETO fusion protein in acute myelogenous leukemia (AML M2 subtype; Wang et al. Proc Natl Acad Sci USA 95, 10860-10865, 1998). In this AML subtype, the recruitment of HDAC1 activity causally leads to gene silencing, a differentiation block and oncogenic transformation.
(v) HDAC1 gene knock-out in mice showed that HDAC1 has a profound function in embryonal stem cell proliferation by repressing cyclin-dependent kinase inhibitors $p21^{waf1}$ and $p27^{kip1}$ (Lagger et al. Embo J. 21, 2672-2681, 2002). Since $p21^{waf1}$ is induced by HDIs in many cancer cell lines, HDAC1 might be a crucial component in cancer cell proliferation as well. Initial siRNA based gene-knock down experiments in HeLa cells support this hypothesis (Glaser et al. 310, 529-536, 2003).
(vi) HDAC2 is overexpressed in colon carcinoma upon constitutive activation of the wnt/β-catenin/TCF signalling pathay by loss of functional adenomatosis polyposis coli (APC) protein as reported by Zhu et al. recently (Cancer cell 5, 455-463, 2004).

On the molecular level, a plethora of published data with various HDAC inhibitors like Trichostatin A (TSA) showed that many cancer relevant genes are up- or down regulated. These include $p21^{waf1}$, Cyclin E, transforming growth factor β (TGFβ), p53 or the von Hippel-Lindau (VHL) tumor suppressor genes, which are upregulated, whereas Bcl-XL, bcl2, hypoxia inducible factor (HIF)1α, vascular endothelial growth factor (VEGF) and cyclin A/D are down-regulated by HDAC inhibition (reviewed by Kramer et al. Trends Endocrin Metabol 12, 294-300, 2001). HDAC inhibitors arrest cells at G1 and G2/M within the cell cycle and deplete S-phase cells, as shown for Depsipeptide as an example (Sandor et al., British J Cancer 83, 817-825, 2000). HDAC inhibitory compounds induce p53 and caspase3/8 independent apoptosis and have broad anti-tumor activity. Anti-angiogenic activity was described also, which might be related to down-regulation of VEGF and HIF1α. In summary, HDAC inhibition effects tumor cells at different molecular levels and multiple cellular proteins are targeted.

Interestingly, HDAC inhibitors were found to induce cellular differentiation and this pharmacological activity might contribute to their anti-cancer activity as well. For example it was shown recently that suberoylanilide hydroxamic acid (SAHA) induces differentiation of breast cancer cell lines, exemplified by resynthesis of milk fat membrane globule protein (MFMG), milk fat globule protein and lipid (Munster et al. Cancer Res. 61, 8492, 2001).

There is growing rational for synergism of HDAC inhibitors with chemotherapeutic as well as target specific cancer drugs. For example, synergism was shown for SAHA with the kinase/cdk inhibitor flavopiridol (Alemenara et al. Leukemia 16, 1331-1343, 2002), for LAQ-824 with the bcr-abl kinase inhibitor Glivec in CML cells (Nimmanapalli et al. Cancer Res. 63, 5126-5135, 2003), for SAHA and Trichostatin A (TSA) with etoposide (VP16), cisplatin and doxorubicin (Kim et al. Cancer Res. 63, 7291-7300, 2003) and LBH589 with the hsp90 inhibitor 17-allyl-amino-demethoxy-geldanamycin (17-AAG; George et al. Blood online, Oct. 28, 2004). Also it was shown that HDAC inhibition causes reexpression of estrogen or androgen receptors in breast and prostate cancer cells with the potential to resensitize these tumors to anti-hormone therapy (Yang et al. Cancer Res. 60, 6890-6894, 2000; Nakayama et al. Lab Invest 80, 1789-1796, 2000).

HDAC inhibitors from various chemical classes were described in the literature with four most important classes, namely (i) hydroxamic acid analogs, (ii) benzamide analogs, (iii) cyclic peptides/peptides and (iv) fatty acid analogs. A comprehensive summary of known HDAC inhibitors was published recently by Miller et al. (J Med Chem 46, 5097-5116, 2003). There is only limited data published regarding specificity of these histone deacetylase inhibitors. In general most hydroxamate based HDI are not specific regarding class I and II HDAC enzymes. For example, TSA inhibits HDACs 1, 3, 4, 6 and 10 with $IC_{50}$ values around 20 nM, whereas HDAC8 was inhibited with $IC_{50}$=0.49 µM (Tatamiya et al, MCR Annual Meeting 2004, Abstract #2451). But there are exceptions like the experimental HDI Tubacin, selective for the class II enzyme HDAC 6 (Haggarty et al. Proc natl Acad Sci USA 100, 4389-4394, 2003). In addition, data on class I selectivity of benzamide HDIs are emerging. MS-275 inhibited class I HDAC1 and 3 with $IC_{50}$=0.51 µM and 1.7 µM, respectively. In contrast class II HDACs 4, 6, 8 and 10 were inhibited with $IC_{50}$ values of >100 µM, >100 µM, 82.5 µM and 94.7 µM, respectively (Tatamiya et al, MCR Annual Meeting 2004, Abstract #2451). So far it is not clear if specificity towards HDAC class I or II enzymes or a defined single isoenzyme should be superior regarding therapeutic efficacy and index.

Clinical studies in cancer with HDAC inhibitors are ongoing, namely with SAHA (Merck Inc.), Valproic acid, FK228/Depsipeptide (Gloucester Pharmaceuticals/NCI), MS275 (Berlex-Schering), NVP LBH-589 (Novartis), PXD-101 (Topotarget/Curagen), MGCD0103 (Methylgene Inc) and Pivaloyloxymethylbutyrate/Pivanex (Titan Pharmaceuticals). These studies showed first evidence of clinical efficacy, highlighted recently by partial and complete responses with FK228/Depsipeptide in patients with peripheral T-cell lymphoma (Plekarz et al. Blood, 98, 2865-2868, 2001) and diffuse large B-cell lymphoma by SAHA (Kelly et al. J. Clin. Oncol. 23, 3923-3931, 2005).

Recent publications also showed possible medical use of HDAC inhibitors in disease different to cancer. These diseases include systemic lupus erythematosus (Mishra et al. J Clin Invest 111, 539-552, 2003, Reilly et al. J. Immunol. 173, 4171-4178, 2004), rheumatoid arthritis (Chung et al. Mol Therapy 8, 707-717, 2003; Nishida et al. Arthritis & Rheumatology 50, 3365-3376, 2004), inflammatory diseases (Leoni et al. Proc Natl Aced Sci USA 99, 2995-3000, 2002) and neurodegenerative diseases like Huntington's disease (Steffan et al. Nature 413, 739-743, 2001, Hockly et al. Proc Natl Aced Sci USA 100(4):2041-6, 2003).

Cancer chemotherapy was established based on the concept that cancer cells with uncontrolled proliferation and a high proportion of cells in mitosis are killed preferentially. Standard cancer chemotherapeutic drugs finally kill cancer cells upon induction of programmed cell death ("apoptosis") by targeting basic cellular processes and molecules, namely RNA/DNA (alkylating and carbamoylating agents, platin analogs and topoisomerase inhibitors), metabolism (drugs of this class are named anti-metabolites) as well as the mitotic spindle apparatus (stabilizing and destabilizing tubulin inhibitors). Inhibitors of histone deacetylases (HDIs) constitute a new class of anti cancer drugs with differentiation and apoptosis inducing activity. By targeting histone deacetylases, HDIs effect histone (protein) acetylation and chromatin structure, inducing a complex transcriptional reprogramming, exemplified by reactivation of tumor suppressor genes and repression of oncogenes. Beside effecting acetylation of N-terminal lysine residues in core histone proteins, non-histone targets important for cancer cell biology like heat-shock-protein 90 (Hsp90) or the p53 tumor suppressor protein exist. The medical use of HDIs might not be restricted to cancer therapy, since efficacy in models for inflammatory diseases, rheumatoid arthritis and neurodegeneration was shown.

Benzoyl or acetyl substituted pyrrolyl propenamides are described in the public literature as HDAC-inhibitors, whereas the connectivity of the acyl-group is at position 2 or 3 of the pyrrole scaffold. (Mai et. al., Journal Med. Chem. 2004, Vol. 47, No. 5, 1098-1109; or Ragno et al., Journal Med. Chem. 2004, Vol. 47, No. 5, 1351-1359). Further pyrrolyl substituted hydroxamic acid derivatives are described in U.S. Pat. No. 4,960,787 as lipoxygenase inhibitors or in U.S. Pat. No. 6,432,999 as cyclooxygenase inhibitors. Various compounds, which are said to be HDAC inhibitors, are reported in WO 01/38322; Journal Med. Chem. 2003, Vol. 46, No. 24, 5097-5116; Journal Med. Chem. 2003, Vol. 46, No. 4, 512-524; Journal Med. Chem. 2003, Vol. 46, No. 5, 820-830; and in Current Opinion Drug Discovery 2002, Vol. 5, 487-499.

There remains a need in the art for new, well-tolerated and more efficacious inhibitors of HDACs.

DESCRIPTION OF THE INVENTION

It has now been found that the N-sulphonylpyrrole derivatives, which are described in greater details below, differ profoundly from prior art compounds and are effective inhibitors of histone deacetylases and have surprising and particularly advantageous properties.

The invention thus relates in a first aspect (aspect A) to compounds of formula I

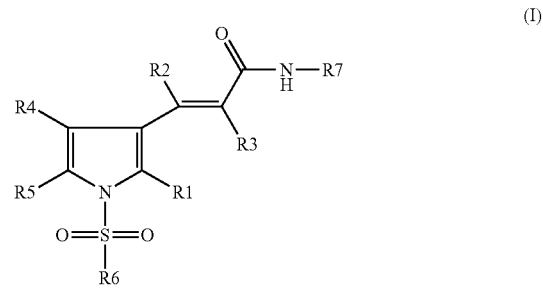

in which
R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond or 1-4C-alkylene, either Q1 is substituted by R61 and/or R62, and is Aa1, Hh1, Ha1, Ha2, Ha3, Ha4 or Ah1, or Q1 is unsubstituted, and is Ha2, Ha3 or Ha4, in which R61 is 1-4C-alkyl, phenyl-1-4C-alkyl, 1-4C-alkoxy, hydroxyl, trifluoromethyl, cyano, halogen, completely or predominantly fluorine-substituted 1-4C-alkoxy, hydroxy-1-4C-alkyl, 1-4C-alkoxy-1-4C-alkyl, 1-4C-alkylsulphonylamino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)R612, —U-T3-N(R613)R614, -T4-Het3, or —V-T5-Het4, in which T2 is a bond or 1-4C-alkylene, R611 is hydrogen, 1-4C-alkyl, 3-7C-cycloalkyl, 3-7C-cycloalkylmethyl, hydroxy-2-4C-alkyl, 1-4C-alkoxy-2-4C-alkyl, 1-4C-alkylcarbonyl, or 1-4C-alkylsulphonyl, R612 is hydrogen or 1-4C-alkyl, or R611 and R612 together and with inclusion of the nitrogen atom, to which they are bonded, form a heterocyclic ring Het1, in which Het1 is morpholino, thiomorpholino, S-oxo-thiomorpholino, S,S-dioxo-thiomorpholino, piperidino, pyrrolidino, piperazino, or 4N-(1-4C-alkyl)-piperazino, U is —O— (oxygen) or —C(O)NH—, T3 is 2-4C-alkylene, R613 is hydrogen, 1-4C-alkyl, 3-7C-cycloalkyl, 3-7C-cycloalkylmethyl, hydroxy-2-4C-alkyl or 1-4C-alkoxy-2-4C-alkyl, 1-4C-alkylcarbonyl, or 1-4C-alkylsulphonyl R614 is hydrogen or 1-4C-alkyl, or R613 and R614 together and with inclusion of the nitrogen atom, to which they are bonded, form a heterocyclic ring Het2, in which Het2 is morpholino, thiomorpholino, S-oxo-thiomorpholino, S,S-dioxo-thiomorpholino, piperidino, pyrrolidino, piperazino, or 4N-(1-4C-alkyl)-piperazino, T4 is a bond or 1-4C-alkylene, Het3 is 1N-(1-4C-alkyl)-piperidinyl or 1N-(1-4C-alkyl)-pyrrolidinyl, V is —O— (oxygen) or —C(O)NH—, T5 is a bond or 1-4C-alkylene, Het4 is 1N-(1-4C-alkyl)-piperidinyl or 1N-(1-4C-alkyl)-pyrrolidinyl, R62 is 1-4C-alkyl, 1-4C-alkoxy or halogen, Aa1 is a bisaryl radical made up of two aryl groups, which are selected independently from a group consisting of phenyl and naphthyl, and which are linked together via a single bond, Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group, Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group, Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the parent molecular group, Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, Ha4 is a heteroarylaryl radical made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha4 is bonded via said aryl moiety to the to the parent molecular group, R7 is hydroxyl, or Cyc1, in which Cyc1 is a ring system of formula Ia

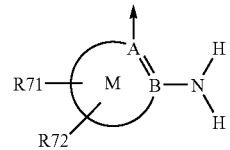

(Ia)

in which

A is C (carbon),

B is C (carbon),

R71 is hydrogen, halogen, 1-4C-alkyl, or 1-4C-alkoxy,

R72 is hydrogen, halogen, 1-4C-alkyl, or 1-4C-alkoxy,

M with inclusion of A and B is either a ring Ar2 or a ring Har2, in which

Ar2 is a benzene ring,

Har2 is a monocyclic 5- or 6-membered unsaturated heteroaromatic ring comprising one to three heteroatoms, each of which is selected from the group consisting of nitrogen, oxygen and sulfur, and the salts of these compounds.

The invention relates in a second aspect (aspect B), which is an embodiment of aspect A, to compounds of formula I, in which R1 is hydrogen, 1-4C-alkyl, halogen, or 1-4C-alkoxy, R2 is hydrogen or 1-4C-alkyl, R3 is hydrogen or 1-4C-alkyl, R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond or 1-4C-alkylene, either Q1 is substituted by R61 and/or R62, and is Aa1, Hh1, Ha1, Ha2, Ha3 or Ah1, or Q1 is unsubstituted, and is Ha2 or Ha3, in which R61 is 1-4C-alkyl, phenyl-1-4C-alkyl, 1-4C-alkoxy, hydroxyl, trifluoromethyl, cyano, halogen, completely or predominantly fluorine-substituted 1-4C-alkoxy, hydroxy-1-4C-alkyl, 1-4C-alkoxy-1-4C-alkyl, 1-4C-alkylsulphonylamino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)R612, or —U-T3-N(R613)R614, in which T2 is a bond or 1-4C-alkylene,
R611 is hydrogen, 1-4C-alkyl, 3-7C-cycloalkyl, 3-7C-cycloalkylmethyl, hydroxy-2-4C-alkyl or 1-4C-alkoxy-2-4C-alkyl,
R612 is hydrogen or 1-4C-alkyl, or R611 and R612 together and with inclusion of the nitrogen atom, to which they are bonded, form a heterocyclic ring Het1, in which Het1 is morpholino, thiomorpholino, S-oxo-thiomorpholino, S,S-dioxo-thiomorpholino, piperidino, pyrrolidino, piperazino, or 4N-(1-4C-alkyl)-piperazino, U is —O— (oxygen) or —C(O)NH—,
T3 is 2-4C-alkylene,
R613 is hydrogen, 1-4C-alkyl, 3-7C-cycloalkyl, 3-7C-cycloalkylmethyl, hydroxy-2-4C-alkyl or 1-4C-alkoxy-2-4C-alkyl,
R614 is hydrogen or 1-4C-alkyl, or R613 and R614 together and with inclusion of the nitrogen atom, to which they are bonded, form a heterocyclic ring Het2, in which Het2 is morpholino, thiomorpholino, S-oxo-thiomorpholino, S,S-dioxo-thiomorpholino, piperidino, pyrrolidino, piperazino, or 4N-(1-4C-alkyl)-piperazino, R62 is 1-4C-alkyl, 1-4C-alkoxy or halogen, Aa1 is a bisaryl radical made up of two aryl groups, which are selected independently from a group consisting of phenyl and naphthyl, and which are linked together via a single bond, Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group, Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group, Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the parent molecular group, Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, R7 is hydroxyl, or Cyc1, in which Cyc1 is a ring system of formula Ia

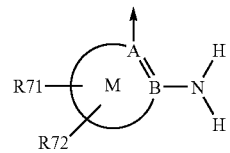

(Ia)

in which

A is C (carbon),
B is C (carbon),
R71 is hydrogen, halogen, 1-4C-alkyl, or 1-4C-alkoxy,
R72 is hydrogen, halogen, 1-4C-alkyl, or 1-4C-alkoxy,
M with inclusion of A and B is either a ring Ar2 or a ring Har2, in which
Ar2 is a benzene ring,
Har2 is a monocyclic 5- or 6-membered unsaturated heteroaromatic ring comprising one to three heteroatoms, each of which is selected from the group consisting of nitrogen, oxygen and sulfur, and the salts of these compounds.

The invention relates in a third aspect (aspect C), which is also an embodiment of aspect A, to compounds of formula I, in which R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond, or 1-4C-alkylene, either Q1 is substituted by R61 and/or R62, and is Aa1, Hh1, Ha1, Ha2, Ha3 or Ah1, or Q1 is unsubstituted, and is Ha2 or Ha3, in which R61 is 1-4C-alkyl, 1-4C-alkoxy, hydroxyl, trifluoromethyl, cyano, halogen, completely or predominantly fluorine-substituted 1-4C-alkoxy, or -T2-N(R611)R612, in which T2 is a bond or 1-4C-alkylene,
R611 is hydrogen or 1-4C-alkyl,
R612 is hydrogen or 1-4C-alkyl,
or R611 and R612 together and with inclusion of the nitrogen atom, to which they are bonded, form a heterocyclic ring Het1, in which
Het1 is morpholino, thiomorpholino, S-oxo-thiomorpholino, S,S-dioxo-thiomorpholino, piperidino, pyrrolidino, piperazino, or 4N-(1-4C-alkyl)-piperazino,
R62 is 1-4C-alkyl, 1-4C-alkoxy or halogen,
Aa1 is a bisaryl radical made up of two aryl groups, which are selected independently from a group consisting of phenyl and naphthyl, and which are linked together via a single bond,
Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond,
Ah1 is an aryl-heteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group,
Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group,
Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the parent molecular group,
Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group,
R7 is hydroxyl, or Cyc1, in which
Cyc1 is a ring system of formula Ia

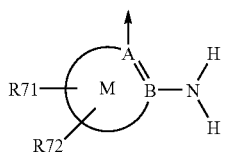

(Ia)

in which
A is C (carbon),
B is C (carbon),
R71 is hydrogen, halogen, 1-4C-alkyl, or 1-4C-alkoxy,
R72 is hydrogen, halogen, 1-4C-alkyl, or 1-4C-alkoxy,
M with inclusion of A and B is either a ring Ar2 or a ring Har2, in which
Ar2 is a benzene ring,
Har2 is a monocyclic 5- or 6-membered unsaturated heteroaromatic ring comprising one to three heteroatoms, each of which is selected from the group consisting of nitrogen, oxygen and sulfur, and the salts of these compounds.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

2-4C-Alkyl represents a straight-chain or branched alkyl radical having 2 to 4 carbon atoms. Examples which may be mentioned are the butyl, isobutyl, sec-butyl, tert-butyl, propyl, isopropyl and preferably the ethyl radicals.

3-7C-Cycloalkyl stands for cyclopropyl, cyclobutyl, cyclopentyl, cyclohexyl and cycloheptyl, of which cyclopropyl, cyclobutyl and cyclopentyl are preferred.

3-7C-Cycloalkylmethyl stands for a methyl radical, which is substituted by one of the abovementioned 3-7C-cycloalkyl radicals. Preferred examples which may be mentioned are the cyclopropylmethyl, the cyclobutylmethyl and the cyclopentylmethyl radicals.

1-4C-Alkylene is a branched or, particularly, straight chain alkylene radical having 1 to 4 carbon atoms. Examples which may be mentioned are the methylene ($-CH_2-$), ethylene (dimethylene) ($-CH_2-CH_2-$), trimethylene ($-CH_2-CH_2-CH_2-$) and the tetramethylene ($-CH_2-CH_2-CH_2CH_2-$) radical.

2-4C-Alkylene is a branched or, particularly, straight chain alkylene radical having 2 to 4 carbon atoms. Examples which may be mentioned are the ethylene (dimethylene) ($-CH_2-CH_2-$), trimethylene ($-CH_2-CH_2-CH_2-$) and the tetramethylene ($-CH_2-CH_2-CH_2-CH_2-$) radical.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy groups are replaced by fluorine atoms.

1-4C-Alkoxy-1-4C-alkyl stands for one of the abovementioned 1-4C-alkyl radicals, which is substituted by one of the abovementioned 1-4C-alkoxy radicals. Examples which may be mentioned are the methoxymethyl, 2-methoxyethyl, 3-methoxypropyl and the 2-ethoxyethyl radical.

1-4C-Alkoxy-2-4C-alkyl stands for one of the abovementioned 2-4C-alkyl radicals, which is substituted by one of the abovementioned 1-4C-alkoxy radicals. Examples which may be mentioned are the 2-methoxyethyl, 3-methoxypropyl and the 2-ethoxyethyl radical.

Hydroxy-1-4C-alkyl stands for one of the abovementioned 1-4C-alkyl radicals which is substituted by hydroxyl. Examples which may be mentioned are the hydroxymethyl radical, the 2-hydroxyethyl radical or the 3-hydroxypropyl radical.

Hydroxy-2-4C-alkyl stands for one of the abovementioned 2-4C-alkyl radicals which is substituted by hydroxyl. Examples which may be mentioned are the 2-hydroxyethyl radical or the 3-hydroxypropyl radical.

Phenyl-1-4C-alkyl represents one of the abovementioned 1-4C-alkyl radicals, which is substituted by a phenyl radical. Examples which may be mentioned are the benzyl and phenethyl radicals.

Mono- or Di-1-4C-alkylamino radicals contain in addition to the nitrogen atom, one or two of the abovementioned 1-4C-alkyl radicals. Preferred are the di-1-4C-alkylamino radicals, especially the dimethylamino, the diethylamino and the diisopropylamino radical.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical, of which the N,N-dimethylaminocarbonyl radical is preferred.

Mono- or Di-1-4C-alkylaminosulphonyl stands for a sulphonyl group to which one of the abovementioned mono- or di-1-4C-alkylamino radicals is bonded. Examples which may be mentioned are the methylaminosulphonyl, the dimethylaminosulphonyl and the ethylaminosulphonyl radical, of which the N,N-dimethylaminosulphonyl (dimethylsulphamoyl) radical [$(CH_3)_2NS(O)_2$—] is preferred.

An 1-4C-Alkylcarbonylamino radical is, for example, the propionylamino ($C_2H_5C(O)NH$—) and the acetylamino (acetamido) radical ($CH_3C(O)NH$—).

An 1-4C-Alkylsulphonylamino radical is, for example, the ethanesulphonylamino (ethylsulphonylamino) ($C_2H_5S(O)_2NH$—) and the methanesulphonylamino (methylsulphonylamino) radical ($CH_3S(O)_2NH$—).

1-4C-Alkylsulfonyl is a sulfonyl group to which one of the abovementioned 1-4C-alkyl radicals is bonded. An example is the methanesulphonyl (methylsulphonyl) radical ($CH_3SO_2$—).

1-4C-Alkylcarbonyl is a carbonyl group to which one of the abovementioned 1-4C-alkyl radicals is bonded. An example is the acetyl radical ($CH_3CO$—).

Tolyl alone or as part of another group includes o-tolyl, m-tolyl and p-tolyl.

Halogen within the meaning of the invention is bromine or, in particular, chlorine or fluorine.

Aa1 is a bisaryl radical made up of two aryl groups, which are selected independently from a group consisting of phenyl and naphthyl, and which are linked together via a single bond.

Aa1 may include, without being restricted thereto, the biphenyl radical, e.g. the 1,1'-biphenyl-4-yl or 1,1'-biphenyl-3-yl radical.

As non-limiting examples of R61-substituted derivatives of Aa1 may be mentioned the following radicals:

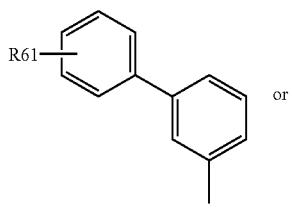

or

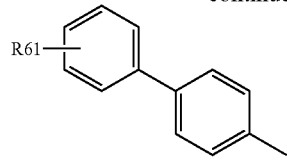

in which the substituent R61 can be attached in the ortho, or, in particular, meta or para position with respect to the binding position in which the benzene ring is bonded to the phenyl radical, such as e.g. 2'-(R61)-1,1'-biphenyl-3-yl, 2'-(R61)-1,1'-biphenyl-4-yl, or, in particular, 3'-(R61)-1,1'-biphenyl-3-yl or 3'-(R61)-1,1'-biphenyl-4-yl, or, yet in particular, 4'-(R61)-1,1'-biphenyl-3-yl or 4'-(R61)-1,1'-biphenyl-4-yl.

As exemplary R61-substituted Aa1 radicals may be more detailed mentioned, for example, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which R61 is -T2-N(R611)R612, in which T2 is methylene, dimethylene or trimethylene, and R611 and R612 together and with inclusion of the nitrogen atom, to which they are bonded, form a morpholino or 4N-methyl-piperazino, or a piperidino or pyrrolidino radical;

such as, for example, any selected from

3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 3'-(morpholin-4-yl-methyl)-biphenyl-4-yl, 4'-(morpholin-4-yl-methyl)-biphenyl-4-yl, 4'-(3-morpholin-4-yl-propyl)-biphenyl-3-yl and 4'-(4-methyl-piperazin-1-ylmethyl)-biphenyl-3-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which R61 is -T2-N(R611)R612, in which T2 is methylene, dimethylene or trimethylene, and R611 and R612 are both methyl;

such as, for example, any selected from

2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl and 3'-dimethylaminomethyl-biphenyl-3-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which R61 is -T2-N(R611)R612, in which T2 is methylene, dimethylene or trimethylene, and R611 is hydrogen, cyclopropyl, cyclopentyl, 2-methoxyethyl, acetyl or methylsulfonyl, R612 is hydrogen;

for example, either

R611 is cyclopropyl or 2-methoxyethyl, and

R612 is hydrogen, such as, for example, any selected from
4'-(2-methoxy-ethylamino)methyl-biphenyl-3-yl and 4'-cyclopropylaminomethyl-biphenyl-3-yl, or R611 is hydrogen, cyclopentyl, acetyl or methylsulfonyl, and R612 is hydrogen, such as, for example, any selected from
4'-aminomethyl-biphenyl-3-yl, 4'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl and 4'-cyclopentylaminomethyl-biphenyl-4-yl.

Yet as exemplary R61-substituted Aa1 radicals may be more detailed mentioned, for example, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is —O-T3-N(R613)R614, in which
T3 is dimethylene or trimethylene, and
R613 and R614 together and with inclusion of the nitrogen atom, to which they are bonded, form a morpholino, pyrrolidino or 4N-methyl-piperazino, or a piperidino radical;

such as, for example, any selected from
4'-(2-morpholin-4-yl-ethoxy)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, 4'-(2-pyrrolidin-1-yl-ethoxy]-biphenyl-3-yl, 3'-(3-pyrrolidin-1-yl-propoxy]-biphenyl-4-yl, 4'-(3-pyrrolidin-1-yl-propoxy]-biphenyl-4-yl, 3'-(2-pyrrolidin-1-yl-ethoxy]-biphenyl-4-yl, 4'-(3-morpholin-4-yl-propoxy)-biphenyl-4-yl, 3'-(3-morpholin-4-yl-propoxy)-biphenyl-4-yl, 3'-(2-morpholin-4-yl-ethoxy)-biphenyl-4-yl, 4'-(2-morpholin-4-yl-ethoxy)-biphenyl-4-yl, 4'-[2-(4-methyl-piperazin-1-yl)-ethoxy]-biphenyl-4-yl, 4'-[3-(4-methyl-piperazin-1-yl)-propoxy]-biphenyl-4-yl and 3'-[3-(4-methyl-piperazin-1-yl)-propoxy]-biphenyl-4-yl.

Yet as exemplary R61-substituted Aa1 radicals may be more detailed mentioned, for example, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is —O-T5-Het4, in which
T5 is a bond, methylene, dimethylene or trimethylene, and
Het4 is 1-methyl-piperidin-4-yl;

such as e.g. 4'-(2-(1-methyl-piperidin-4-yl)-ethoxy)-biphenyl-4-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is methylsulphonylamino, N,N-dimethylaminosulphonyl, acetamido, hydroxymethyl, amino, dimethylamino, morpholino, hydroxyl, trifluoromethyl or methoxy;

for example, either

R61 is methylsulphonylamino, N,N-dimethylaminosulphonyl, acetamido or hydroxymethyl, such as, for example, any selected from
2'-methylsulphonylamino-biphenyl-4-yl, 3'-methylsulphonylamino-biphenyl-4-yl, 4'-methylsulphonylamino-biphenyl-4-yl, 4'-methylsulphonylamino-biphenyl-3-yl, 4'-dimethylsulphamoyl-biphenyl-4-yl, 3'-acetamido-biphenyl-4-yl, 4'-acetamido-biphenyl-4-yl and 3'-hydroxymethyl-biphenyl-4-yl, or R61 is amino, dimethylamino, morpholino, hydroxyl, trifluoromethyl or methoxy, such as, for example, any selected from
3'-amino-biphenyl-4-yl, 4'-morpholin-4-yl-biphenyl-4-yl, 4'-hydroxy-biphenyl-4-yl, 3'-trifluoromethyl-biphenyl-4-yl, 3'-dimethylamino-biphenyl-4-yl and 4'-methoxy-biphenyl-4-yl.

Yet as exemplary R61-substituted Aa1 radicals may be more detailed mentioned, for example, 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is —C(O)—N(H)-T3-N(R613)R614, in which
T3 is dimethylene or trimethylene, and
R613 and R614 are both methyl;

such as, for example, any selected from
3'-[(2-dimethylamino-ethylamino)-carbonyl]-biphenyl-4-yl, 4'-[(2-dimethylamino-ethylamino)-carbonyl]-biphenyl-4-yl and 4'-[(2-dimethylamino-ethylamino)-carbonyl]-biphenyl-3-yl.

An example of R61-substituted Aa1 radicals may be 3'-(R61)-1,1'-biphenyl-3-yl, in which R61 is any one selected from the group $G_{As1}$ consisting of 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl.

Another example of R61-substituted Aa1 radicals may be 3'-(R61)-1,1'-biphenyl-4-yl, in which R61 is any one selected from the group $G_{As1}$ given above.

Another example of R61-substituted Aa1 radicals may be 4'-(R61)-1,1'-biphenyl-3-yl, in which R61 is any one selected from the group $G_{As1}$ given above.

Another example of R61-substituted Aa1 radicals may be 4'-(R61)-1,1'-biphenyl-4-yl, in which R61 is any one selected from the group $G_{Aa1}$ given above.

Specifically, as an exemplary R61-substituted Aa1 radical may be explicitely mentioned, for example, any one selected from
3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 3'-(morpholin-4-yl-methyl)-biphenyl-4-yl, 4'-(morpholin-4-yl-methyl)-biphenyl-4-yl, 4'-(3-morpholin-4-yl-propyl)-biphenyl-3-yl, 4'-(4-methylpiperazin-1-ylmethyl)-biphenyl-3-yl, 4'-(2-morpholin-4-yl-ethoxy)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, 4'-(2-pyrrolidin-1-yl-ethoxy]-biphenyl-3-yl, 3'-(3-pyrrolidin-1-yl-propoxy]-biphenyl-4-yl, 4'-(3-pyrrolidin-1-yl-propoxy]-biphenyl-4-yl, 3'-(2-pyrrolidin-1-yl-ethoxy]-biphenyl-4-yl, 4'-(3-morpholin-4-yl-propoxy)-biphenyl-4-yl, 3'-(3-morpholin-4-yl-propoxy)-biphenyl-4-yl, 3'-(2-morpholin-4-yl-ethoxy)-biphenyl-4-yl, 4'-(2-morpholin-4-yl-ethoxy)-biphenyl-4-yl, 4'-[2-(4-methyl-piperazin-1-yl)-ethoxy]-biphenyl-4-yl, 4'-[3-(4-methyl-piperazin-1-yl)-propoxy]-biphenyl-4-yl, 3'-[3-(4-methyl-piperazin-1-yl)-propoxy]-biphenyl-4-yl, 4'-(2-(1-methyl-piperidin-4-yl)-ethoxy)-biphenyl-4-yl 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl, 3'-dimethylaminomethyl-biphenyl-3-yl, 3'-[(2-dimethylamino-ethylamino)-carbonyl]-biphenyl-4-yl, 4'-[(2-dimethylamino-ethylamino)-carbonyl]-biphenyl-4-yl, 4'-[(2-dimethylamino-ethylamino)-carbonyl]-biphenyl-3-yl, 2'-methylsulphonylamino-biphenyl-4-yl, 3'-methylsulphonylamino-biphenyl-4-yl, 4'-methylsulphonylamino-biphenyl-4-yl, 4'-methylsulphonylamino-biphenyl-3-yl, 4'-dimethylsulphamoyl-biphenyl-4-yl, 3'-acetamido-biphenyl-4-yl, 4'-acetamido-biphenyl-4-yl, 3'-amino-biphenyl-4-yl, 4'-morpholin-4-yl-biphenyl-4-yl, 4'-hydroxy-biphenyl-4-yl, 3'-trifluoromethyl-biphenyl-4-yl and 4'-methoxy-biphenyl-4-yl, 4'-(2-methoxy-ethylamino) methyl-biphenyl-3-yl, 4'-aminomethyl-biphenyl-3-yl, 4'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl, 4'-cyclopentylaminomethyl-biphenyl-4-yl, 4'-cyclopropylaminomethyl-biphenyl-3-yl, and 3'-hydroxymethyl-biphenyl-4-yl.

More specifically, as an exemplary R61-substituted Aa1 radical may be more explicitly mentioned, for example, any one selected from
4'-(2-morpholin-4-yl-ethyl)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, and 4'-dimethylaminomethyl-biphenyl-4-yl.

Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond.

Hh1 may include, without being restricted thereto, the bithiophenyl e.g. thiophen-3-yl-thiophenyl or thiophen-2-yl-thiophenyl, bipyridyl, pyrazolyl-pyridinyl e.g. pyrazol-1-yl-pyridinyl or pyrazol-4-yl-pyridinyl like 6-(pyrazol-4-yl)-pyridin-3-yl, imidazolyl-pyridinyl e.g. imidazol-1-yl-pyridinyl, pyrazolyl-thiophenyl e.g. pyrazol-4-yl-thiophenyl like 5-(pyrazol-4-yl)-thiophen-2-yl, or pyridinyl-thiophenyl radical e.g. pyridin-2-yl-thiophenyl, pyridin-3-yl-thiophenyl or pyridin-4-yl-thiophenyl like 5-(pyridin-2-yl)-thiophen-2-yl or 5-(pyridin-4-yl)-thiophen-2-yl, or the thiazolyl-thiophenyl e.g. thiazol-4-yl-thiophenyl like 5-(thiazol-4-yl)-thiophen-2-yl, or thiazolyl-pyridinyl radical like 6-(thiazol-4-yl)-pyridin-3-yl.

In a special detail, exemplary Hh1 radicals may include pyridinyl-thiophenyl, e.g. 5-(pyridin-4-yl)-thiophen-2-yl.

In another special detail, exemplary Hh1 radicals may include pyrazolyl-thiophenyl, e.g. 5-(pyrazol-4-yl)-thiophen-2-yl.

In another special detail, exemplary Hh1 radicals may include bipyridyl, e.g. 2,4'-bipyridyl-5-yl.

In another special detail, exemplary Hh1 radicals may include thiazolyl-thiophenyl, e.g. 5-(thiazol-4-yl)-thiophen-2-yl.

In another special detail, exemplary Hh1 radicals may include pyrazolyl-pyridinyl, e.g. 6-(pyrazol-4-yl)-pyridin-3-yl.

In another special detail, exemplary Hh1 radicals may include thiazolyl-pyridinyl, e.g. 6-(thiazol-4-yl)-pyridin-3-yl.

As non-limiting example of R61-substituted derivatives of Hh1 may be mentioned [1N-(1-4C-alkyl)-pyrazolyl]-thiophenyl, such as e.g. [1N-(1-4C-alkyl)-pyrazol-4-yl]-thiophenyl, like 5-[1N-(1-2C-alkyl)-pyrazol-4-yl]-thiophen-2-yl, e.g. 5-(1N-methyl-pyrazol-4-yl)-thiophen-2-yl.

Yet as non-limiting example of R61-substituted derivatives of Hh1 may be mentioned [1N-(1-4C-alkyl)-pyrazolyl]-pyridinyl, such as e.g. [1N-(1-4C-alkyl)-pyrazol-4-yl]-pyridinyl or 6-[1N-(1-4C-alkyl)-pyrazolyl]-pyridin-3-yl, like 6-[1N-(1-2C-alkyl)-pyrazol-4-yl]-pyridin-3-yl, e.g. 6-(1N-methyl-pyrazol-4-yl)-pyridin-3-yl.

Yet as non-limiting example of R61-substituted derivatives of Hh1 may be mentioned [(R61)-pyridinyl]-thiophenyl, such as e.g. the following radicals:

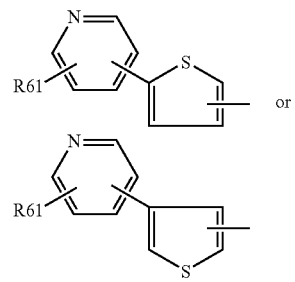

in which the substituent R61 can be attached in the ortho, or, in particular, meta or para position with respect to the binding position in which the pyridinyl ring is bonded to the thiophenyl radical, such as e.g. [2-(R61)-pyridin-4-yl]-thiophenyl or [6-(R61)-pyridin-3-yl]-thiophenyl, like 5-[2-(R61)-pyridin-4-yl]-thiophen-2-yl or 5-[6-(R61)-pyridin-3-yl]-thiophen-2-yl.

Yet as non-limiting example of R61-substituted derivatives of Hh1 may be mentioned [(R61)-thiazolyl]-thiophenyl, such as e.g. the following radicals:

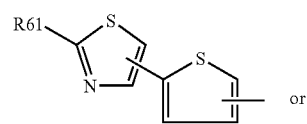

-continued

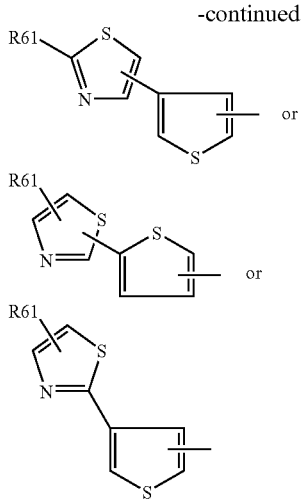

such as e.g. [2-(R61)-thiazol-4-yl]-thiophenyl, like 5-[2-(R61)-thiazol-4-yl]-thiophen-2-yl.

Yet as non-limiting example of R61-substituted derivatives of Hh1 may be mentioned [(R61)-pyridinyl]-pyridinyl, such as e.g. the following radicals:

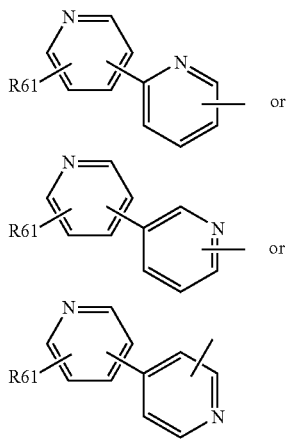

in which the substituent R61 can be attached in the ortho, or, in particular, meta or para position with respect to the binding position in which the terminal pyridinyl ring is bonded to the other pyridinyl radical, such as e.g. [2-(R61)-pyridin-4-yl]-pyridinyl or [6-(R61)-pyridin-3-yl]-pyridinyl or 6-[(R61)-pyridinyl]-pyridin-3-yl, like 6-[2-(R61)-pyridin-4-yl]-pyridin-3-yl [i.e. 2'-(R61)-2,4'-bipyridyl-5-yl] or 6-[6-(R61)-pyridin-3-yl]-pyridin-3-yl [i.e. 6'-(R61)-2,3'-bipyridyl-5-yl].

As exemplary R61-substituted Hh1 radicals may be more detailed mentioned, for example, 5-[2-(R61) -pyridin-4-yl]-thiophen-2-yl or 5-[6-(R61)-pyridin-3-yl]-thiophen-2-yl, in which
R61 is -T2-N(R611)R612, in which
T2 is a bond, and
R611 and R612 are both hydrogen, or
R611 and R612 together and with inclusion of the nitrogen atom, to which they are bonded, form a morpholino or 4N-methyl-piperazino, or a piperidino or pyrrolidino radical;

such as e.g. 5-[2-(4-methyl-piperazin-1-yl)-pyridin-4-yl]-thiophen-2-yl.

Yet as exemplary R61-substituted Hh1 radicals may be more detailed mentioned, for example, 2'-(R61)-2,4'-bipyridyl-5-yl or 6'-(R61)-2,3'-bipyridyl-5-yl, in which
R61 is -T2-N(R611)R612, in which
T2 is a bond, and
R611 and R612 are both hydrogen, or
R611 and R612 together and with inclusion of the nitrogen atom, to which they are bonded, form a morpholino, 4N-methyl-piperazino, piperidino or pyrrolidino radical;

such as e.g. 2'-(4-methyl-piperazin-1-yl)-2,4'-bipyridyl-5-yl.

Specifically, as an exemplary R61-substituted Hh1 radical may be explicitly mentioned, for example, any one selected from
5-[2-(4-methyl-piperazin-1-yl)-pyridin-4-yl]-thiophen-2-yl, 5-(1N-methyl-pyrazol-4-yl)-thiophen-2-yl, 2'-(4-methyl-piperazin-1-yl)-2,4'-bipyridyl-5-yl, 5-(2-methyl-thiazol-4-yl)-thiophen-2-yl, and 6-(1N-methyl-pyrazol-4-yl)-pyridin-3-yl.

More specifically, as an exemplary R61-substituted Hh1 radical may be more explicitly mentioned, for example, 5-[2-(4-methyl-piperazin-1-yl)-pyridin-4-yl]-thiophen-2-yl.

Ah1 is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group.

Ah1 may include, without being restricted thereto, the phenyl-thiophenyl e.g. 5-phenyl-thiophen-2-yl, or the phenyl-pyridyl e.g. 6-phenyl-pyridin-3-yl, radical.

In a special detail, exemplary Ah1 radicals may include phenyl-thiophenyl, e.g. 5-(phenyl)-thiophen-2-yl.

Yet in a special detail, exemplary Ah1 radicals may include phenyl-pyridinyl, e.g. 6-(phenyl)-pyridin-3-yl.

As non-limiting example of R61-substituted derivatives of Ah1 may be mentioned [(R61)-phenyl]-thiophenyl, such as e.g. the following radicals:

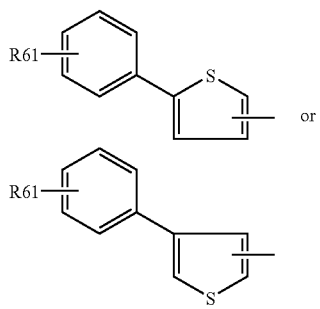

in which the substituent R61 can be attached in the ortho, or, in particular, meta or para position with respect to the binding position in which the phenyl ring is bonded to the thiophenyl radical, such as e.g. [3-(R61)-phenyl]-thiophenyl or [4-(R61)-phenyl]-thiophenyl, like 5-[3-(R61)-phenyl]-thiophen-2-yl or 5-[4-(R61)-phenyl]-thiophen-2-yl.

Yet as non-limiting example of R61-substituted derivatives of Ah1 may be mentioned [(R61)-phenyl]-pyridinyl, such as e.g. the following radicals:

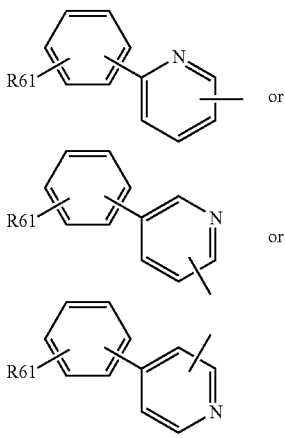

in which the substituent R61 can be attached in the ortho, or, in particular, meta or para position with respect to the binding position in which the phenyl ring is bonded to the pyridinyl radical, such as e.g. [3-(R61)-phenyl]-pyridinyl or [4-(R61)-phenyl]-pyridinyl or 6-[(R61)-phenyl]-pyridin-3-yl, like 6-[3-(R61)-phenyl]-pyridin-3-yl or 6-[4-(R61)-phenyl]-pyridin-3-yl.

As exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is -T2-N(R611)R612, in which
T2 is methylene, dimethylene or trimethylene, and
R611 and R612 together and with inclusion of the nitrogen atom, to which they are bonded, form a morpholino or 4N-methyl-piperazino, or a piperidino or pyrrolidino radical;

such as, for example, any selected from
5-[4-(2-morpholin-4-yl-ethyl)-phenyl]-thiophen-2-yl, 5-[4-(morpholin-4-yl-methyl)-phenyl]-thiophen-2-yl and 5-[3-(morpholin-4-yl-methyl)-phenyl]-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is -T2-N(R611)R612, in which
T2 is methylene, dimethylene or trimethylene, and
R611 and R612 are both methyl;

such as, for example, any selected from
5-(4-dimethylaminomethyl-phenyl)-thiophen-2-yl and 5-(3-dimethylaminomethyl-phenyl)-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is -T2-N(R611)R612, in which
T2 is methylene, dimethylene or trimethylene, and
R611 is hydrogen, cyclopropyl, cyclopentyl, 2-methoxyethyl, acetyl or methylsulfonyl,
R612 is hydrogen;

such as, for example, any selected from
5-(3-aminomethyl-phenyl)-thiophen-2-yl, 5-[3-(acetylamino)-methyl-phenyl]-thiophen-2-yl and 5-[3-(methylsulphonylamino)-methyl-phenyl]-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is methylsulphonylamino, N,N-dimethylaminosulphonyl, acetamido, hydroxymethyl, amino, dimethylamino, morpholino, hydroxyl, trifluoromethyl or methoxy;

such as e.g. 5-(4-dimethylsulphamoyl-phenyl)-thiophen-2-yl.

Yet as exemplary R61-substituted Ah1 radicals may be more detailed mentioned, for example, 5-[3-(R61)-phenyl]-thiophen-2-yl or 5-[4-(R61)-phenyl]-thiophen-2-yl, in which
R61 is —O-T3-N(R613)R614, in which
T3 is dimethylene or trimethylene, and
R613 and R614 together and with inclusion of the nitrogen atom, to which they are bonded, form a morpholino, pyrrolidino or 4N-methyl-piperazino, or a piperidino radical;

such as, for example, any selected from
5-[4-(2-morpholin-4-yl-ethoxy)-phenyl]-thiophen-2-yl,
  5-[4-(3-morpholin-4-yl-propoxy)-phenyl]-thiophen-2-yl,
  5-{4-[2-(4-methyl-piperazin-1-yl)-ethoxy]-phenyl}-thiophen-2-yl and 5-[4-(2-pyrrolidin-1-yl-ethoxy)-phenyl]-thiophen-2-yl.

Yet as exemplary R61-substituted Ah1 radicals may be more detailed mentioned, for example, 6-[3-(R61)-phenyl]-pyridin-3-yl or 6-[4-(R61)-phenyl]-pyridin-3-yl, in which
R61 is -T2-N(R611)R612, in which
T2 is methylene, dimethylene or trimethylene, and
R611 and R612 are both methyl;

such as, for example, any selected from
6-(4-dimethylaminomethyl-phenyl)-pyridin-3-yl and 6-(3-dimethylaminomethyl-phenyl)-pyridin-3-yl.

Yet as exemplary R61-substituted Ah1 radicals may be more detailed mentioned, for example, 6-[3-(R61)-phenyl]-pyridin-3-yl or 6-[4-(R61)-phenyl]-pyridin-3-yl, in which
R61 is —O-T3-N(R613)R614, in which
T3 is dimethylene or trimethylene, and
R613 and R614 together and with inclusion of the nitrogen atom, to which they are bonded, form a morpholino, piperidino, pyrrolidino or 4N-methyl-piperazino radical;

such as e.g. 6-[4-(2-pyrrolidin-1-yl-ethoxy)-phenyl]-pyridin-3-yl.

An example of R61-substituted Ah1 radicals may be [4-(R61)-phenyl]-pyridinyl, e.g. 6-[4-(R61)-phenyl]-pyridin-3-yl, in which R61 is any one selected from the group $G_{Ah1}$ consisting of 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl.

Another example of R61-substituted Ah1 radicals may be [3-(R61)-phenyl]-pyridinyl, e.g. 6-[3-(R61) -phenyl]-pyridin-3-yl, in which R61 is any one selected from the group $G_{Ah1}$ given above.

A further example of R61-substituted Ah1 radicals may be [4-(R61)-phenyl]-thiophenyl, e.g. 5-[4-(R61)-phenyl]-thiophen-2-yl, in which R61 is any one selected from the group $G_{Ah1}$ given above.

Another example of R61-substituted Ah1 radicals may be [3-(R61) phenyl]-thiophenyl, e.g. 5-[3-(R61)-phenyl]-thiophen-2-yl, in which R61 is any one selected from the group $G_{Ah1}$ given above.

Specifically, as an exemplary R61-substituted Ah1 radical may be explicitly mentioned, for example, any one selected from
5-[4-(2-morpholin-4-yl-ethyl)-phenyl]-thiophen-2-yl,
5-[4-(morpholin-4-yl-methyl)-phenyl]-thiophen-2-yl, 5-[3-(morpholin-4-yl-methyl)-phenyl]-thiophen-2-yl,
5-[4-(2-morpholin-4-yl-ethoxy)-phenyl]-thiophen-2-yl,
5-[4-(3-morpholin-4-yl-propoxy)-phenyl]-thiophen-2-yl,
5-{4-[2-(4-methyl-piperazin-1-yl)-ethoxy]-phenyl}-thiophen-2-yl, 5-[4-(2-pyrrolidin-1-yl-ethoxy)-phenyl]-thiophen-2-yl,
5-(4-dimethylaminomethyl-phenyl)-thiophen-2-yl, 5-(3-dimethylaminomethyl-phenyl)-thiophen-2-yl,
6-(4-dimethylaminomethyl-phenyl)-pyridin-3-yl, 6-(3-dimethylaminomethyl-phenyl)-pyridin-3-yl, and
6-[4-(2-pyrrolidin-1-yl-ethoxy)-phenyl]-pyridin-3-yl,
5-(3-aminomethyl-phenyl)-thiophen-2-yl, 5-[3-(acetylamino)-methyl-phenyl]-thiophen-2-yl, 5-[3-(methylsulphonylamino)-methyl-phenyl]-thiophen-2-yl, and
5-(4-dimethylsulphamoyl-phenyl)-thiophen-2-yl.

More specifically, as an exemplary R61-substituted Ah1 radical may be more explicitly mentioned, for example, 5-(4-dimethylaminomethyl-phenyl)-thiophen-2-yl.

It is to be stated, that each of the radicals Hh1 and Ah1 is bonded via a ring carbon atom to the moiety T1.

Ha1 is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group.

A particular embodiment of said Ha1 radicals refers to heteroaryl-phenyl radicals, particularly 3-(heteroaryl)-phenyl or 4-(heteroaryl)-phenyl radicals.

Ha1 may include, without being restricted thereto, the furanyl-phenyl, thiophenyl-phenyl, pyrazolyl-phenyl e.g. pyrazol-1-yl-phenyl or pyrazol-4-yl-phenyl, imidazolyl-phenyl e.g. imidazol-1-yl-phenyl, isoxazolyl-phenyl, or pyridinyl-phenyl radicals, or the thiazolyl-phenyl e.g. thiazol-4-yl-phenyl radical.

In a special detail, exemplary Ha1 radicals may include pyrazolyl-phenyl, e.g. 3-(pyrazolyl)-phenyl or 4-(pyrazolyl)-phenyl.

Yet in a special detail, exemplary Ha1 radicals may include pyridinyl-phenyl, e.g. 4-(pyridinyl)-phenyl or 3-(pyridinyl)-phenyl.

Yet in a special detail, exemplary Ha1 radicals may include isoxazolyl-phenyl, e.g. 4-(isoxazolyl)-phenyl or 3-(isoxazolyl)-phenyl.

Yet in a special detail, exemplary Ha1 radicals may include thiazolyl-phenyl, e.g. 4-(thiazolyl)-phenyl or 3-(thiazolyl)-phenyl.

In a further special detail, exemplary Ha1 radicals may include 3-(pyrazol-1-yl)-phenyl, 4-(pyrazol-1-yl)-phenyl, 4-(pyridin-4-yl)-phenyl, 3-(pyridin-4-yl)-phenyl, 4-(pyridin-3-yl)-phenyl, 3-(pyridin-3-yl)-phenyl, 4-(isoxazol-4-yl)-phenyl, 3-(isoxazol-4-yl)-phenyl, 3-(pyrazol-4-yl)-phenyl or 4-(pyrazol-4-yl)-phenyl.

As non-limiting example of R61-substituted derivatives of Ha1 may be mentioned [1N-(1-4C-alkyl)-pyrazolyl]-phenyl, such as e.g. [1N-(1-4C-alkyl)-pyrazolyl]-phenyl, like 3-[1N-(1-2C-alkyl)-pyrazol-4-yl]-phenyl or 4-[1N-(1-2C-alkyl)-pyrazol-4-yl]-phenyl, e.g. 3-(1N-methyl-pyrazol-4-yl)-phenyl or 4-(1N-methyl-pyrazol-4-yl)-phenyl.

As non-limiting example of R61- and/or R62-substituted derivatives of Ha1 may be mentioned (methyl-isoxazolyl)-phenyl or (dimethyl-isoxazolyl)-phenyl, such as e.g. 3-(3,5-dimethyl-isoxazol-4-yl)-phenyl or 4-(3,5-dimethyl-isoxazol-4-yl)-phenyl.

Yet as non-limiting example of R61-substituted derivatives of Ha1 may be mentioned [(R61)-pyridinyl]-phenyl, such as e.g. the following radicals:

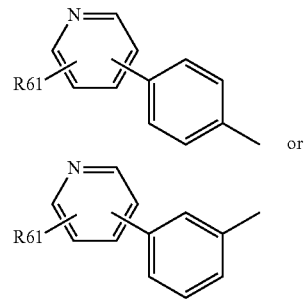

in which the substituent R61 can be attached in the ortho, or, in particular, meta or para position with respect to the binding position in which the pyridinyl ring is bonded to the phenyl radical, such as e.g. 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl.

As exemplary R61-substituted Ha1 radicals may be more detailed mentioned, for example, 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which
R61 is -T2-N(R611)R612, in which
T2 is a bond, and
R611 and R612 together and with inclusion of the nitrogen atom, to which they are bonded, form a morpholino or 4N-methyl-piperazino, or a piperidino or pyrrolidino radical;

such as, for example, any selected from
4-[2-(4-methyl-piperazin-1-yl)-pyridin-4-yl]-phenyl and 3-[2-(4-methyl-piperazin-1-yl)-pyridin-4-yl]-phenyl.

Yet as exemplary R61-substituted Ha1 radicals may be more detailed mentioned, for example, 3-[2-(R61)-pyridin-4-yl]-phenyl, 4-[2-(R61)-pyridinyl]-phenyl, 3-[6-(R61)-pyridin-3-yl]-phenyl or 4-[6-(R61)-pyridin-3-yl]-phenyl, in which
R61 is -T2-N(R611)R612, in which
T2 is a bond, and
R611 and R612 are both hydrogen;

such as, for example, any selected from
4-[6-amino-pyridin-3-yl]-phenyl and 3-[6-amino-pyridin-3-yl]-phenyl.

Yet as exemplary R61-substituted Ha1 radicals may be more detailed mentioned, for example, 3-[2-(R61)-pyridin- 4-yl]-phenyl, 4-[2-(R61)-pyridinyl]-phenyl, 3-[6-(R61)-pyridin-3-yl]-phenyl or 4-[6-(R61)-pyridin-3-yl]-phenyl, in which R61 is methoxy;

such as, for example, any selected from

4-[6-methoxy-pyridin-3-yl]-phenyl and 3-[6-methoxy-pyridin-3-yl]-phenyl.

Specifically, as an exemplary R61-substituted Ha1 radical may be explicitly mentioned, for example, any one selected from 4-[2-(4-methyl-piperazin-1-yl)-pyridin-4-yl]-phenyl, 3-[2-(4-methyl-piperazin-1-yl)pyridin-4-yl]-phenyl, 4-[6-amino-pyridin-3-yl]-phenyl, 3-[6-amino-pyridin-3-yl]-phenyl, 4-[6-methoxy-pyridin-3-yl]-phenyl, 3-[6-methoxy-pyridin-3-yl]-phenyl, 3-(1N-methyl-pyrazol-4-yl)-phenyl, 4-(1N-methyl-pyrazol-4-yl)-phenyl, and 4-(3,5-dimethyl-isoxazol-4-yl)-phenyl.

More specifically, as an exemplary R61-substituted Ha1 radical may be more explicitly mentioned, for example, any one selected from 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, and 4-(1N-methyl-pyrazol-4-yl)-phenyl.

As part of the radicals Hh1, Ah1 and Ha1, the mentioned heteroaryl group selected from a group consisting of monocyclic 5- or 6-membered heteroaryl radicals comprising one or two heteroatoms, each of which is selected from the group consisting of nitrogen, oxygen and sulphur, may be chosen, for example, from the group consisting of, the 5-membered heteroaryl radicals, pyrrolyl, furanyl, thiophenyl, oxazolyl, isoxazolyl, thiazolyl, isothiazolyl, imidazolyl and pyrazolyl, and, the 6-membered heteroaryl radicals, pyridinyl, pyrimidinyl, pyrazinyl and pyridazinyl.

Ha2 is a heteroarylaryl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha2 is bonded via said aryl moiety to the to the parent molecular group.

A particular embodiment of said Ha2 radicals refers to heteroaryl-phenyl radicals, particularly 3-(heteroaryl)-phenyl or 4-(heteroaryl)-phenyl radicals.

Another particular embodiment of said Ha2 radicals refers to heteroaryl-phenyl radicals, particularly 3-(heteroaryl)-phenyl or 4-(heteroaryl)-phenyl radicals, in which the heteroaryl moiety contains a benzene ring.

Another particular embodiment of said Ha2 radicals refers to heteroaryl-phenyl radicals, particularly 3-(heteroaryl)-phenyl or 4-(heteroaryl)-phenyl radicals, in which the heteroaryl moiety contains a benzene ring, and whereby the heteroaryl moiety is attached via said benzene ring to the phenyl moiety.

Ha2 may include, without being restricted thereto, the indolyl-phenyl, benzothiophenyl-phenyl, benzofuranyl-phenyl, benzoxazolyl-phenyl, benzothiazolyl-phenyl, indazolyl-phenyl, benzimidazolyl-phenyl, benzisoxazolyl-phenyl, benzisothiazolyl-phenyl, benzofurazanyl-phenyl, benzotriazolyl-phenyl, benzothiadiazolyl-phenyl, quinolinyl-phenyl, isoquinolinyl-phenyl, quinazolinyl-phenyl, quinoxalinyl-phenyl, cinnolinyl-phenyl, indolizinyl-phenyl or naphthyridinyl-phenyl.

In a special detail, exemplary Ha2 radicals may include 3-(indolyl)-phenyl or 4-(indolyl)-phenyl.

In a further special detail, exemplary Ha2 radicals may include 3-(indol-5-yl)-phenyl or 4-(indol-5-yl)-phenyl.

Ha3 is a heteroarylaryl radical made up of a heteroaryl group selected from a group consisting of monocyclic 5-membered heteroaryl radicals comprising three or four heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha3 is bonded via said aryl moiety to the to the parent molecular group, A particular embodiment of said Ha3 radicals refers to heteroaryl-phenyl radicals, particularly 3-(heteroaryl)-phenyl or 4-(heteroaryl)-phenyl radicals.

Ha3 may include, without being restricted thereto, the thiadiazolyl-phenyl (e.g. [1,3,4]thiadiazol-2-yl-phenyl or [1,2,5] thiadiazol-3-yl-phenyl), oxadiazolyl-phenyl (e.g. [1,3,4]oxadiazol-2-yl-phenyl or [1,2,4]oxadiazol-5-yl-phenyl), triazolyl-phenyl (e.g. triazol-1-yl-phenyl or [1,2,3]triazolyl) or tetrazolyl-phenyl (e.g. tetrazol-1-yl-phenyl or tetrazol-5-yl-phenyl) radicals.

In a special detail, exemplary Ha3 radicals may include triazolyl-phenyl, e.g. 3-(triazolyl)-phenyl or 4-(triazolyl)-phenyl.

In a further special detail, exemplary Ha3 radicals may include 3-[1,2,3]triazol-4-yl-phenyl or 4-[1,2,3]triazol-4-yl-phenyl.

As non-limiting example of R61-substituted derivatives of Ha3 may be mentioned {1N—(R61)-[1,2,3]triazolyl}-phenyl, such as e.g. {1N—(R61)-[1,2,3]triazolyl}-phenyl, like 3-{1N—(R61)-[1,2,3]triazol-4-yl}phenyl or 4-{1N—(R61)-[1,2,3]triazol-4-yl}-phenyl.

As exemplary R61-substituted Ha3 radicals may be more detailed mentioned, for example, 3-[1N—(R61)-1,2,3-triazol-4-yl]-phenyl or 4-{1N—(R61)-[1,2,3]triazol-4-yl}-phenyl, in which R61 is -T2-N(R611)R612, in which T2 is dimethylene or trimethylene, and R611 and R612 together and with inclusion of the nitrogen atom, to which they are bonded, form a piperidino, pyrrolidino, morpholino or 4N-methyl-piperazino radical;

such as e.g. 4-{1-(2-morpholin-4-yl-ethyl)-[1,2,3]triazol-4-yl}-phenyl or 4-{1-(2-piperidin-1-yl-ethyl)-[1,2,3]triazol-4-yl}phenyl.

Ha4 is a heteroarylaryl radical made up of a heteroaryl group selected from a group consisting of partially saturated fused bicyclic 9 or 10-membered heteroaryl radicals comprising a heteroatom-free benzene ring and one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha4 is bonded via said aryl moiety to the to the parent molecular group, A particular embodiment of said Ha4 radicals refers to heteroaryl-phenyl radicals, particularly 3-(heteroaryl)-phenyl or 4-(heteroaryl)-phenyl radicals.

Another particular embodiment of said Ha4 radicals refers to heteroaryl-phenyl radicals, particularly 3-(heteroaryl)- phenyl or 4-(heteroaryl)-phenyl radicals, whereby the heteroaryl moiety is attached via its benzene ring to the phenyl moiety.

Ha4 may include, without being restricted thereto, the indolinyl-phenyl, isoindolinyl-phenyl, (1,2,3,4-tetrahydroquinolinyl)-phenyl or (1,2,3,4-tetrahydroisoquinolinyl)-phenyl, (2,3-dihydrobenzofuranyl)-phenyl, (2,3-dihydrobenzothiophenyl)-phenyl, (benzo[1,3]dioxolyl)-phenyl, (2,3-dihydrobenzo[1,4]dioxinyl)-phenyl, chromanyl-phenyl, chromenyl-phenyl or (2,3-dihydrobenzo[1,4]oxazinyl)-phenyl.

In a special detail, exemplary Ha4 radicals may include (benzo[1,3]dioxolyl)-phenyl, e.g. 3-(benzo[1,3]dioxolyl)-phenyl or 4-(benzo[1,3]dioxolyl)-phenyl, such as, for example, (benzo[1,3]dioxol-5-yl)-phenyl, e.g. 3-(benzo[1,3]dioxol-5-yl)-phenyl or 4-(benzo[1,3]dioxol-5-yl)-phenyl.

Yet in a special detail, exemplary Ha4 radicals may include (2,3-dihydrobenzofuranyl)-phenyl, e.g. 3-(2,3-dihydrobenzofuranyl)-phenyl or 4-(2,3-dihydrobenzofuranyl)-phenyl, such as, for example, (2,3-dihydrobenzofuran-5-yl)-phenyl or (2,3-dihydrobenzofuran-6-yl)-phenyl, e.g. 3-(2,3-dihydrobenzofuran-5-yl)-phenyl or 4-(2,3-dihydrobenzofuran-5-yl)-phenyl.

In a further special detail, exemplary Ha4 radicals may include 4-(2,3-dihydrobenzofuran-5-yl)-phenyl.

Har2 stands for a monocyclic 5- or 6-membered unsaturated heteroaromatic ring comprising one to three heteroatoms, each of which is selected from the group consisting of nitrogen, oxygen and sulfur. Har2 may include, without being restricted thereto, thiophene, oxazole, isoxazole, thiazole, isothiazole, imidazole, pyrazole, triazole, thiadiazole, oxadiazole, pyridine, pyrimidine, pyrazine or pyridazine.

In a special detail, an exemplary Har2 radical may be pyridine.

Cyc1 stands for a ring system of formula Ia, which is bonded to the nitrogen atom of the carboxamide group via the moiety A. Cyc1 may include, without being restricted thereto, 2-aminophenyl substituted by R71 and/or R72.

In a special detail, an exemplary Cyc1 radical may be 2-aminophenyl.

Naphthyl, alone or as part of another group, includes naphthalen-1-yl and naphthalen-2-yl.

In the meaning of the present invention, it is to be understood, that, when two structural portions of the compounds according to this invention are linked via a constituent which has the meaning "bond", then said two portions are directly attached to another via a single bond.

When R61 has the meaning of —U-T3-N(R613)R614, in which U stands for —C(O)NH—, then R61 is the radical —C(O)NH-T3-N(R613)R614.

As it is known for the skilled person, the expressions morpholino, 4N-(1-4C-alkyl)-piperazino, pyrrolidino and the like stand for morpholin-4-yl, 4N-(1-4C-alkyl)-piperazin-1-yl, pyrrolidin-1-yl and the like, respectively.

In general, unless otherwise mentioned the heterocyclic groups mentioned herein refer to all of the possible isomeric forms thereof.

The heterocyclic groups mentioned herein refer, unless otherwise noted, in particular to all of the possible positional isomers thereof.

Thus, for example, the term pyridyl or pyridinyl, alone or as part of another group, includes pyridin-2-yl, pyridin-3-yl and pyridinyl.

Constituents which are optionally substituted as stated herein, may be substituted, unless otherwise noted, at any possible position.

The carbocyclic groups, alone or as part of other groups, mentioned herein may be substituted by their given substituents or parent molecular groups, unless otherwise noted, at any substitutable ring carbon atom.

The heterocyclic groups, alone or as part of other groups, mentioned herein may be substituted by their given substituents or parent molecular groups, unless otherwise noted, at any possible position, such as e.g. at any substitutable ring carbon or ring nitrogen atom.

Rings containing quaternizable imino-type ring nitrogen atoms (—N═) may be preferably not quaternized on these imino-type ring nitrogen atoms by the mentioned substituents or parent molecular groups.

Any heteroatom of a heterocyclic ring with unsatisfied valences mentioned herein is assumed to have the hydrogen atom(s) to satisfy the valences.

When any variable occurs more than one time in any constituent, each definition is independent.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid such as (−)-L-malic acid or (+)-D-malic acid, fumaric acid, succinic acid, oxalic acid, tartaric acid such as (+)-L-tartaric acid or (−)-D-tartaric acid or meso-tartaric acid, embonic acid, stearic acid, toluenesulphonic acid, methanesulphonic acid or 3-hydroxy-2-naphthoic acid, the acids being employed in salt preparation—depending on whether a mono- or polybasic add is concerned and depending on which salt is desired—in an equimolar quantitative ratio or one differing therefrom.

In the context of the foregoing, as further acids, which may be used in the preparation of possible salts of compounds of formula I, can be mentioned any selected from adipic acid, L-ascorbic acid, L-aspartic acid, benzenesulfonic acid, 4-acetamido-benzoic acid, (+)-camphoric acid, (+)-camphor-10-sulfonic acid, caprylic acid (octanoic acid), dodecylsulfonic acid, ethane-1,2-disulfonic acid, ethanesulfonic acid, 2-hydroxy-ethanesulfonic acid, formic acid, galactaric acid, gentisic acid, D-glucoheptonic acid, D-glucuronic acid, glutamic acid, 2-oxo-glutaric acid, hippuric acid, lactic acid such as D-lactic acid or L-lactic acid, malonic acid, mandelic acid such as (+)-mandelic acid or (−)-mandelic acid, naphthalene-1,5-disulfonic acid, naphthalene-2-sulfonic acid, nicotinic acid, palmitic acid, pyroglutamic acid such as L-pyroglutamic acid, hydroiodic acid, cyclamic acid, thiocyanic acid, 2,2-dichloroacetic acid, glycerophosphoric acid, 1-hydroxy-2-naphthoic acid, salicyclic acid, 4 aminosalicyclic acid, glycolic acid, oleic acid, glutaric acid, cinnamic acid, capronic acid, isobutyric acid, propionic acid, capric acid, undecylenic acid and orotic acid.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of formula I of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

In one embodiment of this invention, salts of the compounds of formula I include salts of compounds of formula I with hydrochloric acid.

The substituents R61 and R62 of compounds of formula I can be attached in any possible position of the Aa1, Hh1, Ha1, Ha2, Ha3, Ha4 or Ah1 radical, whereby emphasis is given to the attachement at the terminal ring;

in another embodiment, Q1 is monosubstituted by R61, and is Aa1, Hh1, Ha1 or Ah1, whereby emphasis is given to the attachement of R61 at the terminal ring;

in yet another embodiment, R6 is Aa1, Ha1 or Ha2, each of which is monosubstituted by R61, whereby emphasis is given to the attachement of R61 at the terminal ring;

in yet another embodiment, R6 is Aa1, Hh1, Ha1, Ha2 or Ah1, each of which is monosubstituted by R61, whereby emphasis is given to the attachement of R61 at the terminal ring;

in yet another embodiment, R6 is Aa1, Hh1, Ha1, Ha2, Ha3 or Ah1, each of which is monosubstituted by R61, whereby emphasis is given to the attachement of R61 at the terminal ring;

in yet another embodiment, R6 is Ha2, Ha3 or Ha4, each of which is unsubstituted.

Within the meaning of this invention, the terminal ring of Aa1, Hh1, Ha1, Ha2, Ha3, Ha4 or Ah1 refers to those ring portion of these radicals which is not directly attached to the T1 moiety.

The person skilled in the art is aware on account of his/her expert knowledge that certain combinations of the variable characteristics mentioned in the description of this invention may lead to chemically less stable compounds. This can apply, for example, to certain compounds, in which—in a manner being disadvantageous for chemical stability—two heteroatoms (S, N or O) would directly meet or would only be separated by one carbon atom. Those compounds according to this invention, in which the combination of the abovementioned variable substituents does not lead to chemically less stable compounds, are therefore preferred.

Compounds according to aspect A of the present invention more worthy to be mentioned are those compounds of formula I in which
R1 is hydrogen or 1-4C-alkyl,
R2 is hydrogen or 1-4C-alkyl,
R3 is hydrogen or 1-4C-alkyl,
R4 is hydrogen or 1-4C-alkyl,
R5 is hydrogen or 1-4C-alkyl,
R6 is -T1-Q1, in which
T1 is a bond, either Q1 is substituted by R61 and/or R62, and is Aa1, Hh1, Ha1, Ha2, Ha3, Ha4 or Ah1, or Q1 is unsubstituted, and is Ha2, Ha3 or Ha4, in which
R61 is 1-4C-alkyl, 1-4C-alkoxy, hydroxyl, trifluoromethyl, halogen, hydroxy-1-4C-alkyl, 1-4C-alkylsulphonylamino, tolylsulphonylamino, phenylsulphonylamino, 1-4C-alkylcarbonylamino, di-1-4C-alkylaminosulphonyl, -T2-N(R611)R612, —U-T3N(R613)R614, -T4-Het3, or —V-T5-Het4, in which
T2 is a bond or 1-4C-alkylene,
R611 is hydrogen, 1-4C-alkyl, 3-7C-cycloalkyl, 1-4C-alkoxy-2-4C-alkyl, 1-4C-alkylcarbonyl, or 1-4C-alkylsulphonyl,
R612 is hydrogen or 1-4C-alkyl, or R611 and R612 together and with inclusion of the nitrogen atom, to which they are bonded, form a heterocyclic ring Het1, in which
Het1 is morpholino, piperidino, pyrrolidino, piperazino or 4N-(1-4C-alkyl)-piperazino,
U is —O— (oxygen) or —C(O)NH—,
T3 is 2-4C-alkylene,
R613 is hydrogen, 1-4C-alkyl, 3-7C-cycloalkyl, 1-4C-alkoxy-2-4C-alkyl, 1-4C-alkylcarbonyl, or 1-4C-alkylsulphonyl,
R614 is hydrogen or 1-4C-alkyl, or R613 and R614 together and with inclusion of the nitrogen atom, to which they are bonded, form a heterocyclic ring Het2, in which
Het2 is morpholino, piperidino, pyrrolidino, piperazino or 4N-(1-4C-alkyl)-piperazino,
T4 is a bond or 1-4C-alkylene,
Het3 is 1N-(1-4C-alkyl)-piperidinyl or 1N-(1-4C-alkyl)-pyrrolidinyl,
V is —O— (oxygen) or —C(O)NH—,
T5 is a bond, or 1-4C-alkylene,
Het4 is 1N-(1-4C-alkyl)-piperidinyl or 1N-(1-4C-alkyl)-pyrrolidinyl,
R62 is 1-4C-alkyl,
Aa1 is biphenyl,
Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group, Ha1 is a heteroaryl-phenyl radical made up of a heteroaryl group selected from a group consisting of monocyclic 5 or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group, Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group, Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group, Ha4 is a heteroaryl-phenyl radical made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and a phenyl group, whereby said heteroaryl and phenyl groups are linked together via a single bond, and whereby Ha4 is bonded via said phenyl moiety to the to the parent molecular group, R7 is hydroxyl, or 2-aminophenyl, and the salts of these compounds.

Compounds according to aspect A of the present invention in particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond, either
Q1 is substituted by R61 and/or R62 on the terminal ring, and is Aa1, Hh1, Ha1, Ha2, Ha3, Ha4 or Ah1, or
Q1 is unsubstituted, and is Ha2, Ha3 or Ha4, in which
R61 is 1-2C-alkyl, 1-2C-alkoxy, hydroxyl, trifluoromethyl, halogen, hydroxy-1-2C-alkyl, 1-2C alkylsulphonylamino, 1-2C-alkylcarbonylamino, di-1-2C-alkylaminosulphonyl, -T2-N(R611)R612, —U-T3-N(R613)R614, -T4-Het3, or —V-T5-Het4, in which
T2 is a bond or straight chain 1-4C-alkylene,
R611 is hydrogen, 1-2C-alkyl, 3-5C-cycloalkyl, 1-2C-alkoxy-2-3C-alkyl, 1-2C-alkylcarbonyl, or 1-2C-alkylsulphonyl,
R612 is hydrogen or 1-2C-alkyl,
or R611 and R612 together and with inclusion of the nitrogen atom, to which they are bonded, form a heterocyclic ring Het1, in which
Het1 is morpholino, piperidino, pyrrolidino, piperazino or 4N-(1-2C-alkyl)-piperazino,
U is —O— (oxygen) or —C(O)NH—,
T3 is straight chain 2-4C-alkylene,
R613 is hydrogen, 1-2C-alkyl, 3-5C-cycloalkyl, 1-2C-alkoxy-2-3C-alkyl, 1-2C-alkylcarbonyl, or 1-2C-alkylsulphonyl, R614 is hydrogen or 1-2C-alkyl,
or R613 and R614 together and with inclusion of the nitrogen atom, to which they are bonded, form a heterocyclic ring Het2, in which
Het2 is morpholino, piperidino, pyrrolidino, piperazino or 4N-(1-2C-alkyl)-piperazino,
T4 is a bond or straight chain 1-4C-alkylene,
Het3 is 1N-(1-2C-alkyl)-piperidinyl or 1N-(1-2C-alkyl)-pyrrolidinyl,
V is —O— (oxygen) or —C(O)NH—,
T5 is a bond or straight chain 1-4C-alkylene,
Het4 is 1N-(1-2C-alkyl)-piperidinyl or 1N-(1-2C-alkyl)-pyrrolidinyl,
R62 is 1-2C-alkyl,
Aa1 is 1,1'-biphenyl-3-yl or 1,1'-biphenyl-4-yl,
Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond,
Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group,
Ha1 is a 3-(heteroaryl)-phenyl or 4-(heteroaryl)-phenyl radical each made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group,
Ha2 is a 3-(heteroaryl)-phenyl or 4-(heteroaryl)-phenyl radical each made up of a heteroaryl group selected from a group consisting of fused bicyclic 9- or 10-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group,
Ha3 is a 3-(heteroaryl)-phenyl or 4-(heteroaryl)-phenyl radical each made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group,
Ha4 is a 3-(heteroaryl)-phenyl or 4-(heteroaryl)-phenyl radical each made up of a heteroaryl group selected from a group consisting of partially saturated fused bicyclic 9- or 10-membered heteroaryl radicals comprising a heteroatom-free benzene ring and one or two heteroatoms, each of which is selected from the group consisting of nitrogen, oxygen and sulfur, and a phenyl group, whereby said heteroaryl and phenyl groups are linked together via a single bond, and whereby Ha4 is bonded via said phenyl moiety to the to the parent molecular group, R7 is hydroxyl, or 2-aminophenyl, and the salts of these compounds.

Compounds according to aspect A of the present invention in more particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond, either Q1 is substituted by R61 and/or R62 on the terminal ring, and is Aa1, Hh1, Ha1, Ha2, Ha3, Ha4 or Ah1, or Q1 is unsubstituted, and is Ha2, Ha3 or Ha4, in which
R61 is methyl, methoxy, hydroxyl, trifluoromethyl, hydroxymethyl, methylsulphonylamino, methylcarbonylamino, dimethylaminosulphonyl, -T2-N(R611)R612, —U-T3-N(R613)R614, -T4-Het3, or —V-T5-Het4, in which
T2 is a bond, methylene, dimethylene or trimethylene,
R611 is hydrogen, methyl, cyclopropyl, cyclopentyl, 2-methoxyethyl, acetyl or methylsulphonyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino, piperazino or 4-methyl-piperazino,
U is —O— (oxygen) or —C(O)NH—,
T3 is dimethylene or trimethylene,
R613 is hydrogen, methyl, cyclopropyl, cyclopentyl, 2-methoxyethyl, acetyl or methylsulphonyl,
R614 is hydrogen or methyl, or R613 and R614 together and with inclusion of the nitrogen atom, to which they are bonded, form a heterocyclic ring Het2, in which
Het2 is morpholino, piperidino, pyrrolidino, piperazino or 4-methyl-piperazino,
T4 is a bond, methylene, dimethylene or trimethylene,
Het3 is 1-methyl-piperidinyl or 1-methyl-pyrrolidinyl,
V is —O— (oxygen) or —C(O)NH—,
T5 is a bond, methylene, dimethylene or trimethylene,
Het4 is 1-methyl-piperidinyl or 1-methyl-pyrrolidinyl,
R62 is methyl,
Aa1 is 1,1'-biphenyl-3-yl, or 1,1'-biphenyl-4-yl,
Hh1 is a bisheteroaryl radical made up of two heteroaryl groups, which are selected independently from a group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, and which are linked together via a single bond, such as, for example,
Hh1 is pyridinyl-thiophenyl, thiazolyl-thiophenyl, pyrazolyl-thiophenyl, bipyridyl, pyrazolyl-pyridinyl, or thiazolyl-pyridinyl, Ah1 is a phenyl-heteroaryl radical made up of an phenyl group and a heteroaryl group selected from a group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, whereby said phenyl and heteroaryl groups are linked together via a single bond, and whereby Ah1 is bonded via said heteroaryl moiety to the parent molecular group, such as, for example,
Ah1 is phenyl-thiophenyl, or phenyl-pyridinyl, Ha1 is a 3-(heteroaryl)-phenyl or 4-(heteroaryl)-phenyl radical each made up of a heteroaryl group selected from a group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, and a phenyl group, whereby said heteroaryl and phenyl groups are linked together via a single bond, and whereby Ha1 is bonded via said phenyl moiety to the to the parent molecular group, such as, for example,
Ha1 is 3-(pyridinyl)-phenyl, 3-(thiazolyl)-phenyl, 3-(pyrazolyl)-phenyl, 3-(isoxazolyl)-phenyl, 4-(pyridinyl)-phenyl, 4-(thiazolyl)-phenyl, 4-(pyrazolyl)-phenyl, or 4-(isoxazolyl)-phenyl, Ha2 is a 3-(heteroaryl)-phenyl or 4-(heteroaryl)-phenyl radical each made up of a heteroaryl group selected from a group consisting of indolyl, benzothiophenyl, benzofuranyl, benzoxazolyl, benzothiazolyl, indazolyl, benzimidazolyl, benzisoxazolyl, benzisothiazolyl, benzofurazanyl, benzotriazolyl, benzothiadiazolyl, quinolinyl, isoquinolinyl, quinazolinyl, quinoxalinyl, cinnolinyl, indolizinyl and naphthyridinyl, and a phenyl group, whereby said heteroaryl and phenyl groups are linked together via a single bond, and whereby Ha2 is bonded via said phenyl moiety to the to the parent molecular group, such as, for example,
Ha2 is 3-(indolyl)-phenyl, or 4-(indolyl)-phenyl, Ha3 is a 3-(heteroaryl)-phenyl or 4-(heteroaryl)-phenyl radical each made up of a heteroaryl group selected from a group consisting of thiadiazolyl, oxadiazolyl, triazolyl and tetrazolyl, and a phenyl group, whereby said heteroaryl and phenyl groups are linked together via a single bond, and whereby Ha3 is bonded via said phenyl moiety to the to the parent molecular group, such as, for example,
Ha3 is 3-(triazolyl)-phenyl, or 4-(triazolyl)-phenyl, Ha4 is a 3-(heteroaryl)-phenyl or 4-(heteroaryl)-phenyl radical each made up of a heteroaryl group selected from a group consisting of indolinyl, isoindolinyl, 1,2,3,4-tetrahydroquinolinyl, 1,2,3,4-tetrahydroisoquinolinyl, 2,3-dihydrobenzofuranyl, 2,3-dihydrobenzothiophenyl, benzo[1,3]dioxolyl, 2,3-dihydrobenzo[1,4]dioxinyl, chromanyl, chromenyl and 2,3-dihydrobenzo[1,4]oxazinyl, and a phenyl group, whereby said heteroaryl and phenyl groups are linked together via a single bond, and whereby Ha3 is bonded via said phenyl moiety to the to the parent molecular group, such as, for example,
Ha4 is 3-(benzo[1,3]dioxolyl)-phenyl, 4-(benzo[1,3]dioxolyl)-phenyl, 3-(2,3-dihydrobenzofuranyl)-phenyl, or 4-(2,3-dihydrobenzofuranyl)-phenyl, R7 is hydroxyl, or 2-aminophenyl, and the salts of these compounds.

Compounds according to aspect A of the present invention to be emphasized are those compounds of formula I
in which
R1 is hydrogen,
R2 is hydrogen,
R3 is hydrogen,
R4 is hydrogen,
R5 is hydrogen,
R6 is -T1-Q1, in which
T1 is a bond;

either
Q1 is substituted by R61 on the terminal ring, and is Aa1 or Ah1, in which
Aa1 is 1,1'-biphenyl-3-yl, or 1,1'-biphenyl-4-yl, such as, for example,
3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl,
Ah1 is phenyl-thiophenyl, or phenyl-pyridinyl, such as, for example,
[3-(R61)-phenyl]-thiophenyl, [4-(R61)-phenyl]-thiophenyl, [3-(R61)-phenyl]-pyridinyl or [4-(R61)-phenyl]-pyridinyl,
e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl, in which
R61 is methoxy, hydroxyl, trifluoromethyl, hydroxymethyl, methylsulphonylamino, methylcarbonylamino, dimethylaminosulphonyl, -T2-N(R611)R612, —U-T3-N(R613)R614, -T4-Het3, or —V-T5-Het4, in which
T2 is a bond, methylene, dimethylene or trimethylene,
R611 is hydrogen, methyl, cyclopropyl, cyclopentyl, 2-methoxyethyl, acetyl or methylsulphonyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4-methyl-piperazino,
U is —O— (oxygen) or —C(O)NH—,
T3 is dimethylene or trimethylene,
R613 is methyl,
R614 is methyl, or R613 and R614 together and with inclusion of the nitrogen atom, to which they are bonded, form a heterocyclic ring Het2, in which
Het2 is morpholino, piperidino, pyrrolidino or 4-methyl-piperazino,
T4 is a bond, methylene, dimethylene or trimethylene,
Het3 is 1-methyl-piperidinyl or 1-methyl-pyrrolidinyl,
V is —O— (oxygen) or —C(O)NH—,
T5 is a bond, methylene, dimethylene or trimethylene,
Het4 is 1-methyl-piperidinyl or 1-methyl-pyrrolidinyl;

or
Q1 is substituted by R61 on the terminal ring, and is Hh1 or Ha1, in which
Hh1 is pyridinyl-thiophenyl, or bipyridyl, such as, for example,
[2-(R61)-pyridinyl]-thiophenyl or [6-(R61)-pyridin-3-yl]-thiophenyl, e.g. 5-[2-(R61)-pyridin-4-yl]-thiophen-2-yl or 5-[6-(R61)-pyridin-3-yl]-thiophen-2-yl, or [2-(R61)-pyridin-4-yl]-pyridinyl or [6-(R61)-pyridin-3-yl]-pyridinyl,
e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl,
Ha1 is 3-(pyridinyl)-phenyl, or 4-(pyridinyl)-phenyl, such as, for example,
3-[2-(R61)-pyridin-4-yl]-phenyl, 3-[6-(R61)-pyridin-3-yl]-phenyl, 4-[2-(R61)-pyridin-4-yl]-phenyl or 4-[6-(R61)-pyridin-3-yl]-phenyl, in which
R61 is methoxy, or -T2-N(R611)R612, in which
T2 is a bond,
R611 is hydrogen or methyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4N-methyl-piperazino;

or
Q1 is 3-(1-methyl-pyrazolyl)-phenyl, 4-(1-methyl-pyrazolyl)-phenyl, 3-(methyl-thiazolyl)-phenyl, 4-(methyl-thiazolyl)-phenyl, 3-(dimethyl-isoxazolyl)-phenyl, 4-(dimethyl-isoxazolyl)-phenyl, (1-methyl-pyrazolyl)-thiophenyl, (1-methyl-pyrazolyl)-pyridinyl, (methyl-thiazolyl)-thiophenyl, (methyl-thiazolyl)-pyridinyl, 3-(benzo[1,3]dioxolyl)-phenyl, 4-(benzo[1,3]dioxolyl)-phenyl, 3-(2,3-dihydrobenzofuranyl)-phenyl, 4-(2,3-dihydrobenzofuranyl)-phenyl, 3-(1-methyl-indolyl)-phenyl, or 4-(1-methyl-indolyl)-phenyl, such as, for example,
3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-thiazol-4-yl)-pyridin-3-yl or 2-(2-methyl-thiazol-4-yl)-pyridin-4-yl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl or 4-(1-methyl-indol-5-yl)-phenyl;

or
Q1 is 3-[1N—(R61)-pyrazolyl]-phenyl, 4-[1N—(R61)-pyrazolyl]-phenyl, [1N—(R61)-pyrazolyl]-thiophenyl, [1N—(R61)-pyrazolyl]-pyridinyl, 3-[1N—(R61)-triazolyl]-phenyl, or 4-[1N—(R61)-triazolyl]-phenyl, such as, for example,
3-[1N—(R61)-pyrazol-4-yl]-phenyl, 4-[1N—(R61)-pyrazol-4-yl]-phenyl, [1N—(R61)-pyrazol-4-yl)-thiophenyl e.g. 5-[1N—(R61)-pyrazol-4-yl]-thiophen-2-yl, [1N—(R61)-pyrazol-4-yl)-pyridinyl e.g. 2-[1N—(R61)-pyrazol-4-yl)-pyridin-4-yl or 6-[1N—(R61)-pyrazol-4-yl)-pyridin-3-yl, 3-[1N—(R61)-triazol-4-yl]-phenyl or 4-[1N—(R61)-triazol-4-yl]-phenyl, in which
R61 is -T2-N(R611)R612, or -T4-Het3, in which
T2 is dimethylene or trimethylene,
R611 is hydrogen, methyl, cyclopropyl, cyclopentyl, 2-methoxyethyl, acetyl or methylsulphonyl, R612 is hydrogen or methyl, or R611 and R612 together and with inclusion of the nitrogen atom, to which they are bonded, form a heterocyclic ring Het1, in which Het1 is morpholino, piperidino, pyrrolidino or 4-methyl-piperazino, T4 is a bond, methylene, dimethylene or trimethylene, Het3 is 1-methyl-piperidinyl or 1-methyl-pyrrolidinyl;

R7 is hydroxyl;

and the salts of these compounds.

Other compounds according to aspect A of the present invention to be emphasized are those compounds of formula I in which
R1 is hydrogen,
R2 is hydrogen,
R3 is hydrogen,
R4 is hydrogen,
R5 is hydrogen,
R6 is -T1-Q1, in which
T1 is a bond;

either
Q1 is substituted by R61 on the terminal ring, and is Aa1 or Ah1, in which
Aa1 is 1,1'-biphenyl-3-yl, or 1,1'-biphenyl-4-yl, such as, for example,
  3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl, Ah1 is phenyl-thiophenyl, or phenyl-pyridinyl, such as, for example,
  [3-(R61)-phenyl]-thiophenyl, [4-(R61-phenyl]-thiophenyl, [3-(R61)-phenyl]-pyridinyl or [4-(R61)-phenyl]-pyridinyl, e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl, in which
R61 is methoxy, hydroxyl, trifluoromethyl, hydroxymethyl, methylsulphonylamino, methylcarbonylamino, dimethylaminosulphonyl, -T2-N(R611)R612, —U-T3-N(R613)R614, -T4-Het3, or —V-T5-Het4, in which
T2 is a bond, methylene, dimethylene or trimethylene,
R611 is hydrogen, methyl, cyclopropyl, cyclopentyl, 2-methoxyethyl, acetyl or methylsulphonyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4-methyl-piperazino,
U is —O— (oxygen) or —C(O)NH—,
T3 is dimethylene or trimethylene,
R613 is methyl,
R614 is methyl, or R613 and R614 together and with inclusion of the nitrogen atom, to which they are bonded, form a heterocyclic ring Het2, in which
Het2 is morpholino, piperidino, pyrrolidino or 4-methyl-piperazino,
T4 is a bond, methylene, dimethylene or trimethylene, Het3 is 1-methyl-piperidinyl or 1-methyl-pyrrolidinyl,
V is —O— (oxygen) or —C(O)NH—,
T5 is a bond, methylene, dimethylene or trimethylene,
Het4 is 1-methyl-piperidinyl or 1-methyl-pyrrolidinyl;

or
Q1 is substituted by R61 on the terminal ring, and is Hh1 or Ha1, in which
Hh1 is pyridinyl-thiophenyl, or bipyridyl, such as, for example,
  [2-(R61)-pyridin-4-yl]-thiophenyl or [6-(R61)-pyridin-3-yl]-thiophenyl, e.g. 5-[2-(R61)-pyridin-4-yl]-thiophen-2-yl or 5-[6-(R61)-pyridin-3-yl]-thiophen-2-yl, or
  [2-(R61)-pyridin-4-yl]-pyridinyl or [6-(R61)-pyridin-3-yl]-pyridinyl, e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl, Ha1 is 3-(pyridinyl)-phenyl, or 4-(pyridinyl)-phenyl, such as, for example,
  3-[2-(R61)-pyridin-4-yl]-phenyl, 3-[6-(R61)-pyridin-3-yl]-phenyl, 4-[2-(R61)-pyridin-4-yl]-phenyl or 4-[6-(R61)-pyridin-3-yl]-phenyl, in which
R61 is methoxy, or -T2-N(R611)R612, in which
T2 is a bond,
R611 is hydrogen or methyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4N-methyl-piperazino;

or
Q1 is 3-(1-methyl-pyrazolyl)-phenyl, 4-(1-methyl-pyrazolyl)-phenyl, 3-(methyl-thiazolyl)-phenyl, 4-(methyl-thiazolyl)-phenyl, 3-(dimethyl-isoxazolyl)-phenyl, 4-(dimethyl-isoxazolyl)-phenyl, (1-methyl-pyrazolyl)-thiophenyl, (1-methyl-pyrazolyl)-pyridinyl, (methyl-thiazolyl)-thiophenyl, (methyl-thiazolyl)-pyridinyl, 3-(benzo[1,3]dioxolyl)-phenyl, 4-(benzo[1,3]dioxolyl)-phenyl, 3-(2,3-dihydrobenzofuranyl)-phenyl, 4-(2,3-dihydrobenzofuranyl)-phenyl, 3-(1-methyl-indolyl)-phenyl, or 4-(1-methyl-indolyl)-phenyl, such as, for example,
  3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-thiazol-4-yl)-pyridin-3-yl or 2-(2-methyl-thiazolyl)-pyridin-4-yl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl or 4-(1-methyl-indol-5-yl)-phenyl;

or
Q1 is 3-[1N—(R61)-pyrazolyl]-phenyl, 4-[1N—(R61)-pyrazolyl]-phenyl, [1N—(R61)-pyrazolyl]-thiophenyl, [1N—(R61)-pyrazolyl]-pyridinyl, 3-[1N—(R61)-triazolyl]-phenyl, or 4-[1N—(R61)-triazolyl]-phenyl, such as, for example,
3-[1N—(R61)-pyrazol-4-yl]-phenyl, 4-[1N—(R61)-pyrazol-4-yl]-phenyl, [1N—(R61)-pyrazol-4-yl]-thiophenyl e.g. 5-[1N—(R61)-pyrazol-4-yl]-thiophen-2-yl, [1N—(R61)-pyrazol-4-yl]-pyridinyl e.g. 2-[1N—(R61)-pyrazol-4-yl]-pyridin-4-yl or 6-[1N—(R61)-pyrazol-4-yl]-pyridin-3-yl, 3-[1N—(R61)-triazol-4-yl]-phenyl or 4-[1N—(R61)-triazol-4-yl]-phenyl, in which
R61 is -T2-N(R611)R612, or -T4-Het3, in which
T2 is dimethylene or trimethylene,
R611 is hydrogen, methyl, cyclopropyl, cyclopentyl, 2-methoxyethyl, acetyl or methylsulphonyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4-methyl-piperazino,
T4 is a bond, methylene, dimethylene or trimethylene,
Het3 is 1-methyl-piperidinyl or 1-methyl-pyrrolidinyl;
R7 is 2-aminophenyl;

and the salts of these compounds.

Compounds according to aspect A of the present invention to be more emphasized are those compounds of formula I
in which
R1 is hydrogen,
R2 is hydrogen,
R3 is hydrogen,
R4 is hydrogen,
R5 is hydrogen,
R6 is -T1-Q1, in which
T1 is a bond;

either
Q1 is substituted by R61 on the terminal ring, and is Aa1 or Ah1, in which
Aa1 is 1,1'-biphenyl-3-yl, or 1,1'-biphenyl-4-yl, such as, for example,
3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl,
Ah1 is phenyl-thiophenyl, or phenyl-pyridinyl, such as, for example,
[3-(R61)-phenyl]-thiophenyl, [4-(R61)-phenyl]-thiophenyl, [3-(R61)-phenyl]-pyridinyl or [4-(R61)-phenyl]-pyridinyl, e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl, in which
R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidinyl)-propoxy, 2-(1-methyl-piperidinyl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl;

or
Q1 is substituted by R61 on the terminal ring, and is Hh1 or Ha1, in which
Hh1 is pyridinyl-thiophenyl, or bipyridyl, such as, for example,
[2-(R61)-pyridin-4-yl]-thiophenyl or [6-(R61)-pyridin-3-yl]-thiophenyl, e.g. 5-[2-(R61)-pyridin-4-yl]-thiophen-2-yl or 5-[6-(R61)-pyridin-3-yl]-thiophen-2-yl, or [2-(R61)-pyridin-4-yl]-pyridinyl or [6-(R61)-pyridin-3-yl]-pyridinyl, e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl,
Ha1 is 3-(pyridinyl)-phenyl, or 4-(pyridinyl)-phenyl, such as, for example,
3-[2-(R61)-pyridin-4-yl]-phenyl, 3-[6-(R61)-pyridin-3-yl]-phenyl, 4-[2-(R61)-pyridinyl]-phenyl or 4-[6-(R61)-pyridin-3-yl]-phenyl, in which
R61 is any one selected from methylsulphonylamino, acetamido, amino, dimethylamino, morpholino, piperidino, pyrrolidino, 4-methyl-piperazino, hydroxy, trifluoromethyl and methoxy;

or
Q1 is 3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-4-thiazol-4-yl)-pyridin-3-yl or 2-(2-methyl-4-thiazol-4-yl)-pyridin-4-yl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl, or 4-(1-methyl-indol-5-yl)-phenyl;

or
Q1 is 3-[1N—(R61)-pyrazol-4-yl]-phenyl, 4-[1N—(R61)-pyrazol-4-yl]-phenyl, [1N—(R61)-pyrazol-4-yl]-thiophenyl e.g. 5-[1N—(R61)-pyrazol-4-yl]-thiophen-2-yl, [1N—(R61)-pyrazol-4-yl]-pyridinyl e.g. 2-[1N—(R61)-pyrazol-4-yl)pyridin-4-yl or 6-[1N—(R61)-pyrazol-4-yl)-pyridin-3-yl, 3-[1N—(R61)-triazol-4-yl]-phenyl or 4-[1N—(R61)-triazol-4-yl]-phenyl, in which R61 is any one selected from 3-morpholin-4-yl-propyl, 2-morpholin-4-yl-ethyl, 3-(4-methyl-piperazin-1-yl)-propyl, 2-(4-methyl-piperazin-1-yl)-ethyl, 3-pyrrolidin-1-yl-propyl, 2-pyrrolidin-1-yl-ethyl, 3-piperidin-1-yl-propyl, 2-piperidin-1-yl-ethyl, 2-dimethylamino-ethyl and 3-dimethylamino-propyl;

R7 is hydroxyl;

and the salts of these compounds.

Other compounds according to aspect A of the present invention to be more emphasized are those compounds of formula I in which R1 is hydrogen,
R2 is hydrogen,
R3 is hydrogen,
R4 is hydrogen,
R5 is hydrogen,
R6 is -T1-Q1, in which
T1 is a bond;

either

Q1 is substituted by R61 on the terminal ring, and is Aa1 or Ah1, in which

Aa1 is 1,1'-biphenyl-3-yl, or 1,1'-biphenyl-4-yl, such as, for example,
3'-(R61)-1,1'-biphenyl-3-yl, 4'-(R61)-1,1'-biphenyl-3-yl, 3'-(R61)-1,1'-biphenyl-4-yl or 4'-(R61)-1,1'-biphenyl-4-yl, Ah1 is phenyl-thiophenyl, or phenyl-pyridinyl, such as, for example,
[3-(R61)-phenyl]-thiophenyl, [4-(R61)-phenyl]-thiophenyl, [3-(R61)-phenyl]-pyridinyl or [4-(R61)-phenyl]-pyridinyl, e.g. 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl, in which R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidinyl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsulphonylamino-methyl, cyclopentylaminomethyl, cyclopropylaminomethyl and hydroxymethyl;

or

Q1 is substituted by R61 on the terminal ring, and is Hh1 or Ha1, in which

Hh1 is pyridinyl-thiophenyl, or bipyridyl, such as, for example,
[2-(R61)-pyridin-4-yl]-thiophenyl or [6-(R61)-pyridin-3-yl]-thiophenyl, e.g. 5-[2-(R61)-pyridin-4-yl]-thiophen-2-yl or 5-[6-(R61)-pyridin-3-yl]-thiophen-2-yl, or
[2-(R61)-pyridin-4-yl]-pyridinyl or [6-(R61)-pyridin-3-yl]-pyridinyl, e.g. 2-[2-(R61)-pyridin-4-yl]-pyridin-4-yl, 2-[6-(R61)-pyridin-3-yl]-pyridin-4-yl, 6-[2-(R61)-pyridin-4-yl]-pyridin-3-yl or 6-[6-(R61)-pyridin-3-yl]-pyridin-3-yl, Ha1 is 3-(pyridinyl)-phenyl, or 4-(pyridinyl)-phenyl, such as, for example,
3-[2-(R61)-pyridin-4-yl]-phenyl, 3-[6-(R61)-pyridin-3-yl]-phenyl, 4-[2-(R61)-pyridin-4-yl]-phenyl or 4-[6-(R61)-pyridin-3-yl]-phenyl, in which R61 is any one selected from methylsulphonylamino, acetamido, amino, dimethylamino, morpholino, piperidino, pyrrolidino, 4-methyl-piperazino, hydroxy, trifluoromethyl and methoxy;

or

Q1 is 3-(1-methyl-pyrazol-4-yl)-phenyl, 4-(1-methyl-pyrazol-4-yl)-phenyl, 3-(2-methyl-thiazol-4-yl)-phenyl, 4-(2-methyl-4-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)-thiophenyl e.g. 5-(1-methyl-pyrazol-4-yl)-thiophen-2-yl, (1-methyl-pyrazol-4-yl)-pyridinyl e.g. 6-(1-methyl-pyrazol-4-yl)-pyridin-3-yl or 2-(1-methyl-pyrazol-4-yl)-pyridin-4-yl, (2-methyl-thiazol-4-yl)-thiophenyl e.g. 5-(2-methyl-thiazol-4-yl)-thiophen-2-yl, (2-methyl-thiazol-4-yl)-pyridinyl e.g. 6-(2-methyl-thiazol-4-yl)-pyridin-3-yl or 2-(2-methyl-thiazol-4-yl)-pyridin-4-yl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl, or 4-(1-methyl-indol-5-yl)-phenyl;

or Q1 is 3-[1N—(R61)-pyrazol-4-yl]-phenyl, 4-[1N—(R61)-pyrazol-4-yl]-phenyl,
[1N—(R61)-pyrazol-4-yl)-thiophenyl e.g. 5-[1N—(R61)-pyrazol-4-yl)-thiophen-2-yl,
[1N—(R61)-pyrazol-4-yl)-pyridinyl e.g. 2-[1N—(R61)-pyrazol-4-yl)-pyridin-4-yl or 6-[1N—(R61)-pyrazol-4-yl)-pyridin-3-yl, 3-[1N—(R61)-triazol-4-yl]-phenyl, or 4-[1N—(R61)-triazol-4-yl]-phenyl, in which R61 is any one selected from 3-morpholin-4-yl-propyl, 2-morpholin-4-yl-ethyl, 3-(4-methyl-piperazin-1-yl)-propyl, 2-(4-methyl-piperazin-1-yl)-ethyl, 3-pyrrolidin-1-yl-propyl, 2-pyrrolidin-1-yl-ethyl, 3-piperidin-1-yl-propyl, 2-piperidin-1-yl-ethyl, 2-dimethylamino-ethyl and 3-dimethylamino-propyl;

R7 is 2-aminophenyl;

and the salts of these compounds.

Compounds according to aspect A of the present invention to be in particular emphasized are those compounds of formula I in which R1 is hydrogen,
R2 is hydrogen,
R3 is hydrogen,
R4 is hydrogen,
R5 is hydrogen,
R6 is -T1-Q1, in which T1 is a bond, Q1 is any one selected from the group consisting of 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 3'-(morpholin-4-yl-methyl)-biphenyl-4-yl, 4'-(morpholin-4-yl-methyl)-biphenyl-4-yl, 4'-(3-morpholin-4-yl-propyl)biphenyl-3-yl, 4'-(3-morpholin-4-yl-propyl)-biphenyl-4-yl, 3'-(3-morpholin-4-yl-propyl)-biphenyl-3-yl, 3'-(3-morpholin-4-yl-propyl)-biphenyl-4-yl, 4'-(4-methyl-piperazin-1-ylmethyl)-biphenyl-3-yl, 4'-(4-methyl-piperazin-1-ylmethyl)-biphenyl-4-yl, 3'-(4-methyl-piperazin-1-ylmethyl)-biphenyl-3-yl, 3'-(4-methyl-piperazin-1-ylmethyl)-biphenyl-4-yl, 4'-(2-morpholin-4-yl-ethoxy)-biphenyl-3-yl, 4'-(2-morpholin-4-yl-ethoxy)-biphenyl-4-yl, 3'-(2-morpholin-4-yl-ethoxy)-biphenyl-3-yl, 3'-(2-morpholin-4-yl-ethoxy)-biphenyl-4-yl, 4'-(3-morpholin-4-yl-propoxy)-biphenyl-3-yl, 4'-(3-morpholin-4-yl-propoxy)-biphenyl-4-yl, 3'-(3-morpholin-4-yl-propoxy)-biphenyl-3-yl, 3'-(3-morpholin-4-yl-propoxy)-biphenyl-4-yl, 4'-[2-(4-methyl-piperazin-1-yl)-ethoxy]-biphenyl-3-yl, 4'-[2-(4-methyl-piperazin-1-yl)-ethoxy]-biphenyl-4-yl, 3'-[2-(4-methyl-piperazin-1-yl)-ethoxy]-biphenyl-3-yl, 3'-[2-(4-methyl-piperazin-1-yl)ethoxy]-biphenyl-4-yl, 4'-(2-pyrrolidin-1-yl-ethoxy]-biphenyl-3-yl, 4'-(2-pyrrolidin-1-yl-ethoxy]-biphenyl-4-yl, 3'-(2-pyrrolidin-1-yl-ethoxy]-biphenyl-3-yl, 3'-(2-pyrrolidin-1-yl-ethoxy]-biphenyl-4-yl, 3'-(3-pyrrolidin-1-yl-propoxy]-biphenyl-4-yl, 4'-(3-pyrrolidin-1-yl-propoxy]-biphenyl-4-yl, 3'-(3-pyrrolidin-1-yl-propoxy]-biphenyl-3-yl, 4'-(3-pyrrolidin-1-yl-propoxy]-biphenyl-3-yl, 4'-[3-(4-methyl-piperazin-1-yl)-propoxy]-biphenyl-4-yl, 3'-[3-(4-methyl-piperazin-1-yl)-propoxy]-biphenyl-4-yl, 4'-[3-(4-methyl-piperazin-1-yl)-propoxy]-biphenyl-3-yl, 3'-[3-(4-methyl-piperazin-1-yl)-propoxy]-biphenyl-3-yl, 4'-(2-(1-methyl-piperidin-4-yl)-ethoxy)-biphenyl-4-yl, 4'-(2-(1-methyl-piperidin-4-yl)ethoxy)-biphenyl-3-yl, 3'-(2-(1-methyl-piperidin-4-yl)-ethoxy)-biphenyl-4-yl, 3'-(2-(1-methyl-piperidin-4-yl)-ethoxy)-biphenyl-3-yl 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl, 3'-dimethylaminomethyl-biphenyl-3-yl, 3'-[(2-dimethylamino-ethylamino)-carbonyl]-biphenyl-4-yl, 4'-[(2-dimethylamino-ethylamino)-carbonyl]-biphenyl-4-yl, 4'-[(2-dimethylamino-ethylamino)-carbonyl]-biphenyl-3-yl, 3'-[(2-dimethylamino-ethylamino)-carbonyl]-biphenyl-3-yl, 2'-methylsulphonylamino-biphenyl-4-yl, 3'-methylsulphonylamino-biphenyl-4-yl, 4'-methylsulphonylamino-biphenyl-4-yl, 2'-methylsulphonylamino-biphenyl-3-yl, 3'-methylsulphonylamino-biphenyl-3-yl, 4'-methylsulphonylamino-biphenyl-3-yl, 4'-methylsulphonylamino-biphenyl-3-yl, 4'-dimethylsulphamoyl-biphenyl-4-yl, 4'-dimethylsulphamoyl-biphenyl-3-yl, 3'-dimethylsulphamoyl-biphenyl-4-yl, 3'-dimethylsulphamoyl-biphenyl-3-yl, 3'-acetamido-biphenyl-4-yl, 4'-acetamido-biphenyl-4-yl, 3'-acetamido-biphenyl-3-yl, 4'-acetamido-biphenyl-3-yl, 3'-amino-biphenyl-4-yl, 3'-dimethylamino-biphenyl-4-yl, 4'-morpholin-4-yl-biphenyl-4-yl, 4'-hydroxy-biphenyl-4-yl, 3'-trifluoromethyl-biphenyl-4-yl, 4'-methoxy-biphenyl-4-yl, 3'-amino-biphenyl-3-yl, 3'-dimethylamino-biphenyl-3-yl, 4'-morpholin-4-yl-biphenyl-3-yl, 4'-hydroxy-biphenyl-3-yl, 3'-trifluoromethyl-biphenyl-3-yl, 4'-methoxy-biphenyl-3-yl, 4'-amino-biphenyl-4-yl, 4'-dimethylamino-biphenyl-4-yl, 3'-morpholin-4-yl-biphenyl-4-yl, 3'-hydroxy-biphenyl-4-yl, 4'-trifluoromethyl-biphenyl-4-yl, 3'-methoxy-biphenyl-4-yl, 4'-amino-biphenyl-3-yl, 4'-dimethylamino-biphenyl-3-yl, 3'-morpholin-4-yl-biphenyl-3-yl, 3'-hydroxy-biphenyl-3-yl, 4'-trifluoromethyl-biphenyl-3-yl and 3'-methoxy-biphenyl-3-yl, 4'-(2-methoxy-ethylamino)methyl-biphenyl-3-yl, 4'-(2-methoxy-ethylamino)methyl-biphenyl-4-yl, 3'-(2-methoxy-ethylamino)methyl-biphenyl-3-yl, 3'-(2-methoxy-ethylamino)methyl-biphenyl-4-yl, 4'-aminomethyl-biphenyl-3-yl, 4'-aminomethyl-biphenyl-4-yl, 3'-aminomethyl-biphenyl-3-yl, 3'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl, 4'-(acetylamino)-methyl-biphenyl-3-yl, 4'-(methylsulphonylamino)-methyl-biphenyl-3-yl, 3'-(acetylamino)-methyl-biphenyl-4-yl, 3'-(methylsulphonylamino)-methyl-biphenyl-4-yl, 4'-cyclopentylaminomethyl-biphenyl-4-yl, 4'-cyclopentylaminomethyl-biphenyl-3-yl, 3'-cyclopentylaminomethyl-biphenyl-3-yl, 3'-cyclopentylaminomethyl-biphenyl-3-yl, 4'-cyclopropylaminomethyl-biphenyl-3-yl, 4'-cyclopropylaminomethyl-biphenyl-4-yl, 3'-cyclopropylaminomethyl-biphenyl-3-yl, 3'-cyclopropylaminomethyl-biphenyl-3-yl, 3'-hydroxymethyl-biphenyl-4-yl, 3'-hydroxymethyl-biphenyl-3-yl, 4'-hydroxymethyl-biphenyl-4-yl, 4'-hydroxymethyl-biphenyl-3-yl, 5-[2-(4-methyl-piperazin-1-yl)-pyridin-4-yl]-thiophen-2-yl, 5-(1-methyl-pyrazol-4-yl)-thiophen-2-yl, 6-(1-methyl-pyrazol-4-yl)-pyridin-3-yl, 2'-(4-methyl-piperazin-1-yl)-2,4'-bipyridyl-5-yl 5-(2-methyl-thiazol-4-yl)-thiophen-2-yl, 5-[4-(2-morpholin-4-yl-ethyl)-phenyl]-thiophen-2-yl, 5-[3-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 5-[4-(2-morpholin-4-yl-ethoxy)-phenyl]-thiophen-2-yl, 5-[3-(2-morpholin-4-yl-ethoxy)-phenyl]-thiophen-2-yl, 5-[4-(3-morpholin-4-yl-propoxy)-phenyl]-thiophen-2-yl, 5-[3-(3-morpholin-4-yl-propoxy)-phenyl]-thiophen-2-yl, 5-{4-[2-(4-methyl-piperazin-1-yl)-ethoxy]-phenyl}-thiophen-2-yl, 5-{3-[2-(4-methyl-piperazin-1-yl)-ethoxy]-phenyl}-thiophen-2-yl, 5-[4-(2-pyrrolidin-1-yl-ethoxy)-phenyl]-thiophen-2-yl, 5-[3-(2-pyrrolidin-1-yl-ethoxy)phenyl]-thiophen-2-yl, 5-(4-dimethylaminomethyl-phenyl)-thiophen-2-yl, 5-(3-dimethylaminomethyl-phenyl)-thiophen-2-yl, 6-(4-dimethylaminomethyl-phenyl)-pyridin-3-yl, 6-(3-dimethylaminomethyl-phenyl)-pyridin-3-yl, 6-[4-(2-pyrrolidin-1-yl-ethoxy)-phenyl]-pyridin-3-yl, 6-[3-(2-pyrrolidin-1-yl-ethoxy)-phenyl]-pyridin-3-yl, 5-(3-aminomethyl-phenyl)-thiophen-2-yl, 5-[3-(acetylamino)-methyl-phenyl]-thiophen-2-yl, 5-[3-(methylsulphonylamino)-methyl-phenyl]-thiophen-2-yl, 5-(4-dimethylsulphamoyl-phenyl)-thiophen-2-yl, 5-(4-aminomethyl-phenyl)-thiophen-2-yl, 5-[4-(acetylamino)-methyl-phenyl]-thiophen-2-yl, 5-[4-(methylsulphonylamino)-methyl-phenyl]-thiophen-2-yl, 5-(3-dimethylsulphamoyl-phenyl)-thiophen-2-yl, 4-[2-(4-methyl-piperazin-1-yl)-pyridin-4-yl]-phenyl, 3-[2-(4-methyl-piperazin-1-yl pyridin-4-yl]-phenyl, 4-(6-amino-pyridin-3-yl)-phenyl, 3-(6-amino-pyridin-3-yl)-phenyl, 4-(6-methoxy-pyridin-3-yl)-phenyl, 3-(6-methoxy-pyridin-3-yl)-phenyl, 3-(1-methyl-pyrazol-4-yl)-phenyl, 4-(1-methyl-pyrazol-4-yl)-phenyl, 4-(3,5-dimethyl-isoxazol-4-yl)-phenyl, 3-(3,5-dimethyl-isoxazol-4-yl)-phenyl, 4-(1-methyl-indol-5-yl)-phenyl, 3-(1-methyl-indol-5-yl)- phenyl, 4-(1-(2-morpholin-4-yl-ethyl)-[1,2,3]triazol-4-yl)-phenyl, 4-{1-(2-piperidin-1-yl-ethyl)-[1,2,3]triazol-4-yl}-phenyl, 3-{1-(2-morpholin-4-yl-ethyl)-[1,2,3]triazol-4-yl}-phenyl, 3-{1-(2-piperidin-1-yl-ethyl)-[1,2,3]triazol-4-yl}-phenyl, 4-(2,3-dihydrobenzofuran-5-yl)-phenyl, and 4-(benzo[1,3]dioxol-5-yl)-phenyl, 3-(2,3-dihydrobenzofuran-5-yl)-phenyl, and 3-(benzo[1,3]dioxol-5-yl)-phenyl, R7 is hydroxyl, and the salts of these compounds.

Other compounds according to aspect A of the present invention to be in particular emphasized are those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is any one selected from the group consisting of 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 3'-(morpholin-4-yl-methyl)-biphenyl-4-yl, 4'-(morpholin-4-yl-methyl)-biphenyl-4-yl, 4'-(3-morpholin-4-yl-propyl)-biphenyl-3-yl, 4'-(3-morpholin-4-yl-propyl)-biphenyl-4-yl, 3'-(3-morpholin-4-yl-propyl)-biphenyl-3-yl, 3'-(3-morpholin-4-yl-propyl)-biphenyl-4-yl, 4'-(4-methyl-piperazin-1-ylmethyl)-biphenyl-3-yl, 4'-(4-methyl-piperazin-1-ylmethyl)biphenyl-4-yl, 3'-(4-methyl-piperazin-1-ylmethyl)-biphenyl-3-yl, 3'-(4-methyl-piperazin-1-ylmethyl)-biphenyl-4-yl, 4'-(2-morpholin-4-yl-ethoxy)-biphenyl-3-yl, 4'-(2-morpholin-4-yl-ethoxy)-biphenyl-4-yl, 3'-(2-morpholin-4-yl-ethoxy)-biphenyl-3-yl, 3'-(2-morpholin-4-yl-ethoxy)-biphenyl-4-yl, 4'-(3-morpholin-4-yl-propoxy)-biphenyl-3-yl, 4'-(3-morpholin-4-yl-propoxy)-biphenyl-4-yl, 3'-(3-morpholin-4-yl-propoxy)-biphenyl-3-yl, 3'-(3-morpholin-4-yl-propoxy)-biphenyl-4-yl, 4'-[2-(4-methyl-piperazin-1-yl)-ethoxy]-biphenyl-3-yl, 4'-[2-(4-methyl-piperazin-1-yl)-ethoxy]-biphenyl-4-yl, 3'-[2-(4-methyl-piperazin-1-yl)-ethoxy]-biphenyl-3-yl, 3'-[2-(4-methyl-piperazin-1-yl)-ethoxy]-biphenyl)-4-yl, 4'-(2-pyrrolidin-1-yl-ethoxy]-biphenyl-3-yl, 4'-(2-pyrrolidin-1-yl-ethoxy]-biphenyl-4-yl, 3'-(2-pyrrolidin-1-yl-ethoxy]-biphenyl-3-yl, 3'-(2-pyrrolidin-1-yl-ethoxy]-biphenyl-4-yl, 3'-(3-pyrrolidin-1-yl-propoxy]-biphenyl-4-yl, 4'-(3-pyrrolidin-1-yl-propoxy]-biphenyl-4-yl, 3'-(3-pyrrolidin-1-yl-propoxy]-biphenyl-3-yl, 4'-(3-pyrrolidin-1-yl-propoxy]-biphenyl-3-yl, 4'-[3-(4-methyl-piperazin-1-yl)-propoxy]-biphenyl)-4-yl, 3'-[3-(4-methyl-piperazin-1-yl)-propoxy]-biphenyl)-4-yl, 4'-[3-(4-methyl-piperazin-1-yl)-propoxy]-biphenyl-3-yl, 3'-[3-(4-methyl-piperazin-1-yl)-propoxy]-biphenyl-3-yl, 4'-(2-(1-methyl-piperidin-4-yl)-ethoxy)-biphenyl-4-yl, 4'-(2-(1-methyl-piperidin-4-yl)ethoxy)-biphenyl-3-yl, 3'-(2-(1-methyl-piperidin-4-yl)-ethoxy)-biphenyl-4-yl, 3'-(2-(1-methyl-piperidin-4-yl)-ethoxy)-biphenyl-3-yl, 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-dimethylaminomethyl-biphenyl-4-yl, 3'-dimethylaminomethyl-biphenyl-3-yl, 3'-[(2-dimethylamino-ethylamino)-carbonyl]-biphenyl-4-yl, 4'-[(2-dimethylamino-ethylamino)-carbonyl]-biphenyl-4-yl, 4'-[(2-dimethylamino-ethylamino)-carbonyl]-biphenyl-3-yl, 3'-[(2-dimethylamino-ethylamino)-carbonyl]-biphenyl-3-yl, 2'-methylsulphonylamino-biphenyl-4-yl, 3'-methylsulphonylamino-biphenyl-4-yl, 4'-methylsulphonylamino-biphenyl-4-yl, 2'-methylsulphonylamino-biphenyl-3-yl, 3'-methylsulphonylamino-biphenyl-3-yl, 4'-methylsulphonylamino-biphenyl-3-yl, 4'-methylsulphonylamino-biphenyl-3-yl, 4'-dimethylsulphamoyl-biphenyl-4-yl, 4'-dimethylsulphamoyl-biphenyl-3-yl, 3'-dimethylsulphamoyl-biphenyl-4-yl, 3'-dimethylsulphamoyl-biphenyl-3-yl, 3'-acetamido-biphenyl-4-yl, 4'-acetamido-biphenyl-4-yl, 3'-acetamido-biphenyl-3-yl, 4'-acetamido-biphenyl-3-yl, 3'-amino-biphenyl-4-yl, 3'-dimethylamino-biphenyl-4-yl, 4'-morpholin-4-yl-biphenyl-4-yl, 4'-hydroxy-biphenyl-4-yl, 3'-trifluoromethyl-biphenyl-4-yl, 4'-methoxy-biphenyl-4-yl, 3'-amino-biphenyl-3-yl, 3'-dimethylamino-biphenyl-3-yl, 4'-morpholin-4-yl-biphenyl-3-yl, 4'-hydroxy-biphenyl-3-yl, 3'-trifluoromethyl-biphenyl-3-yl, 4'-methoxy-biphenyl-3-yl, 4'-amino-biphenyl-4-yl, 4'-dimethylamino-biphenyl-4-yl, 3'-morpholin-4-yl-biphenyl-4-yl, 3'-hydroxy-biphenyl-4-yl, 4'-trifluoromethyl-biphenyl-4-yl, 3'-methoxy-biphenyl-4-yl, 4'-amino-biphenyl-3-yl, 4'-dimethylamino-biphenyl-3-yl, 3'-morpholin-4-yl-biphenyl-3-yl, 3'-hydroxy-biphenyl-3-yl, 4'-trifluoromethyl-biphenyl-3-yl and 3'-methoxy-biphenyl-3-yl, 4'-(2-methoxy-ethylamino)methyl-biphenyl-3-yl, 4'-(2-methoxy-ethylamino)methyl-biphenyl-4-yl, 3'-(2-methoxy-ethylamino)methyl-biphenyl-3-yl, 3'-(2-methoxy-ethylamino)methyl-biphenyl-4-yl, 4'-aminomethyl-biphenyl-3-yl, 4'-aminomethyl-biphenyl-4-yl, 3'-aminomethyl-biphenyl-3-yl, 3'-aminomethyl-biphenyl-4-yl, 4'-(acetylamino)-methyl-biphenyl-4-yl, 4'-(methylsulphonylamino)-methyl-biphenyl-4-yl, 3'-(acetylamino)-methyl-biphenyl-3-yl, 3'-(methylsulphonylamino)-methyl-biphenyl-3-yl, 4'-(acetylamino)-methyl-biphenyl-3-yl, 4'-(methylsulphonylamino)-methyl-biphenyl-3-yl, 3'-(acetylamino)-methyl-biphenyl-4-yl, 3'-(methylsulphonylamino)-methyl-biphenyl-4-yl, 4'-cyclopentylaminomethyl-biphenyl-4-yl, 4'-cyclopentylaminomethyl-biphenyl-3-yl, 3'-cyclopentylaminomethyl-biphenyl-4-yl, 3'-cyclopentylaminomethyl-biphenyl-3-yl, 4'-cyclopropylaminomethyl-biphenyl-4-yl, 4'-cyclopropylaminomethyl-biphenyl-3-yl, 3'-cyclopropylaminomethyl-biphenyl-4-yl, 3'-cyclopropylaminomethyl-biphenyl-3-yl, 3'-hydroxymethyl-biphenyl-4-yl, 3'-hydroxymethyl-biphenyl-3-yl, 4'-hydroxymethyl-biphenyl-4-yl, 4'-hydroxymethyl-biphenyl-3-yl, 5-[2-(4-methyl-piperazin-1-yl)-pyridin-4-yl]-thiophen-2-yl, 5-(1-methyl-pyrazolyl)-thiophen-2-yl, 6-(1-methyl-pyrazol-4-yl)-pyridin-3-yl, 2'-(4-methyl-piperazin-1-yl)-2,4'-bipyridyl-5-yl 5-(2-methyl-thiazol-4-yl)-thiophen-2-yl, 5-[4-(2-morpholin-4-yl-ethyl)-phenyl]-thiophen-2-yl, 5-[3-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 5-[4-(2-morpholin-4-yl-ethoxy)-phenyl]-thiophen-2-yl, 5-[3-(2-morpholin-4-yl-ethoxy)-phenyl]-thiophen-2-yl, 5-[4-(3-morpholin-4-yl-propoxy)-phenyl]-thiophen-2-yl, 5-[3-(3-morpholin-4-yl-propoxy)-phenyl]-thiophen-2-yl, 5-{4-[2-(4-methyl-piperazin-1-yl)-ethoxy]-phenyl}-thiophen-2-yl, 5-{3-[2-(4-methyl-piperazin-1-yl)-ethoxy]-phenyl}-thiophen-2-yl, 5-[4-(2-pyrrolidin-1-yl-ethoxy)-phenyl]-thiophen-2-yl, 5-[3-(2-pyrrolidin-1-yl-ethoxy)-phenyl]-thiophen-2-yl, 5-(4-dimethylaminomethyl-phenyl)-thiophen-2-yl, 5-(3- dimethylaminomethyl-phenyl)-thiophen-2-yl, 6-(4-dimethylaminomethyl-phenyl)-pyridin-3-yl, 6-(3-dimethylaminomethyl-phenyl)-pyridin-3-yl, 6-[4-(2-pyrrolidin-1-yl-ethoxy)-phenyl]-pyridin-3-yl, 6-[3-(2-pyrrolidin-1-yl-ethoxy)-phenyl]-pyridin-3-yl, 5-(3-aminomethyl-phenyl)-thiophen-2-yl, 5-[3-(acetylamino)-methyl-phenyl]-thiophen-2-yl, 5-[3-(methylsulphonylamino)-methyl-phenyl]-thiophen-2-yl, 5-(4-dimethylsulphamoyl-phenyl)-thiophen-2-yl, 5-(4-aminomethyl-phenyl)-thiophen-2-yl, 5-[4-(acetylamino)-methyl-phenyl]-thiophen-2-yl, 5-[4-(methylsulphonylamino)-methyl-phenyl]-thiophen-2-yl, 5-(3-dimethylsulphamoyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-(6-amino-pyridin-3-yl)-phenyl, 3-(6-amino-pyridin-3-yl)-phenyl, 4-(6-methoxy-pyridin-3-yl)-phenyl, 3-(6-methoxy-pyridin-3-yl)-phenyl, 3-(1-methyl-pyrazol-4-yl)-phenyl, 4-(1-methyl-pyrazol-4-yl)-phenyl, 4-(3,5-dimethyl-isoxazol-4-yl)-phenyl, 3-(3,5-dimethyl-isoxazol-4-yl)-phenyl, 4-(1-methyl-indol-5-yl)-phenyl, 3-(1-methyl-indol-5-yl)-phenyl, 4-{1-(2-morpholin-4-yl-ethyl)-[1,2,3]triazol-4-yl}-phenyl, 4-{1-(2-piperidin-1-yl-ethyl)-[1,2,3]triazol-4-yl}-phenyl, 3-{1-(2-morpholin-4-yl-ethyl)-[1,2,3]triazol-4-yl}-phenyl, 3-{1-(2-piperidin-1-yl-ethyl)-[1,2,3]triazol-4-yl}-phenyl, 4-(2,3-dihydrobenzofuran-5-yl)-phenyl, and 4-(benzo[1,3]dioxol-5-yl)-phenyl, 3-(2,3-dihydrobenzofuran-5-yl)-phenyl, and 3-(benzo[1,3]dioxol-5-yl)-phenyl, R7 is 2-aminophenyl, and the salts of these compounds.

Compounds according to aspect B of the present invention more worthy to be mentioned are those compounds of formula I in which
R1 is hydrogen or 1-4C-alkyl,
R2 is hydrogen or 1-4C-alkyl,
R3 is hydrogen or 1-4C-alkyl,
R4 is hydrogen or 1-4C-alkyl,
R5 is hydrogen or 1-4C-alkyl,
R6 is -T1-Q1, in which
T1 is a bond, either
Q1 is substituted by R61 and/or R62, and is Aa1, Hh1, Ha1, Ha2, Ha3 or Ah1, or
Q1 is unsubstituted, and is Ha2 or Ha3, in which
R61 is 1-4C-alkyl, 1-4C-alkoxy, halogen, hydroxy-1-4C-alkyl, 1-4C-alkylsulphonylamino, tolylsulphonylamino, phenylsulphonylamino, 1-4C-alkylcarbonylamino, di-1-4C-alkylaminosulphonyl, -T2-N(R611)R612, or —U-T3-N(R613)R614, in which
T2 is a bond or 1-4C-alkylene,
R611 is hydrogen, 1-4C-alkyl, 3-7C-cycloalkyl or 1-4C-alkoxy-2-4C-alkyl,
R612 is hydrogen or 1-4C-alkyl, or R611 and R612 together and with inclusion of the nitrogen atom, to which they are bonded, form a heterocyclic ring Het1, in which
Het1 is morpholino, piperidino, pyrrolidino, piperazino or 4N-(1-4C-alkyl)-piperazino,
U is —O— (oxygen) or —C(O)NH—,
T3 is 2-4C-alkylene,
R613 is hydrogen, 1-4C-alkyl, 3-7C-cycloalkyl or 1-4C-alkoxy-2-4C-alkyl,
R614 is hydrogen or 1-4C-alkyl, or R613 and R614 together and with inclusion of the nitrogen atom, to which they are bonded, form a heterocyclic ring Het2, in which
Het2 is morpholino, piperidino, pyrrolidino, piperazino or 4N-(1-4C-alkyl)-piperazino,
R62 is 1-4C-alkyl,
Aa1 is biphenyl,
Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond,
Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group,
Ha1 is a heteroaryl-phenyl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group,
Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group,
Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group,
R7 is hydroxyl, or 2-aminophenyl, and the salts of these compounds.

Compounds according to aspect B of the present invention in particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond, Q1 is substituted by R61 and/or R62 on the terminal ring, and is Aa1, Hh1, Ha1, Ha2 or Ah1, in which R61 is 1-2C-alkyl, 1-2C-alkoxy, halogen, hydroxy-1-2C-alkyl, 1-2C-alkylsulphonylamino, 1-2C-alkylcarbonylamino, di-1-2C-alkylaminosulphonyl, —T2-N(R611)R612, or —U-T3-N(R613)R614, in which T2 is a bond or straight chain 1-4C-alkylene, R611 is hydrogen, 1-2C-alkyl, 3-5C-cycloalkyl or 1-2C-alkoxy-2-3C-alkyl, R612 is hydrogen or 1-2C-alkyl, or R611 and R612 together and with inclusion of the nitrogen atom, to which they are bonded, form a heterocyclic ring Het1, in which Het1 is morpholino, piperidino, pyrrolidino, piperazino or 4N-(1-2C-alkyl)-piperazino, U is —O— (oxygen) or —C(O)NH—, T3 is straight chain 2-4C-alkylene, R613 is hydrogen, 1-2C-alkyl, 3-5C-cycloalkyl or 1-2C-alkoxy-2-3C-alkyl, R614 is hydrogen or 1-2C-alkyl, or R613 and R614 together and with inclusion of the nitrogen atom, to which they are bonded, form a heterocyclic ring Het2, in which Het2 is morpholino, piperidino, pyrrolidino, piperazino or 4N-(1-4C-alkyl)-piperazino, R62 is 1-2C-alkyl, Aa1 is 1,1'-biphenyl-3-yl or 1,1'-biphenyl-4-yl, Hh1 is a bisheteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a thiophenyl group, whereby said heteroaryl and thiophenyl groups are linked together via a single bond, and whereby Hh1 is bonded via said thiophenyl moiety to the to the parent molecular group, Ah1 is phenyl-thiophenyl, Ha1 is a 3-(heteroaryl)-phenyl or 4-(heteroaryl)-phenyl radical each made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group, Ha2 is a 3-(heteroaryl)-phenyl or 4-(heteroaryl)-phenyl radical each made up of a heteroaryl group selected from a group consisting of fused bicyclic 9 or 10-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group, R7 is hydroxyl, or 2-aminophenyl, and the salts of these compounds.

In another embodiment, yet compounds according to aspect B of the present invention in particular worthy to be mentioned are those compounds of formula I in which R1 is hydrogen, R2 is hydrogen, R3 is hydrogen, R4 is hydrogen, R5 is hydrogen, R6 is -T1-Q1, in which T1 is a bond, Q1 is substituted by R61 and/or R62 on the terminal ring, and is Aa1, Hh1, Ha1, Ha2 or Ah1, in which R61 is 1-2C-alkyl, 1-2C-alkoxy, hydroxyl, trifluoromethyl, halogen, hydroxy-1-2C-alkyl, 1-2C-alkylsulphonylamino, 1-2C-alkylcarbonylamino, di-1-2C-alkylaminosulphonyl, —T2-N(R611)R612, or —U-T3-N(R613)R614, in which T2 is a bond or straight chain 1-4C-alkylene, R611 is hydrogen, 1-2C-alkyl, 3-5C-cycloalkyl or 1-2C-alkoxy-2-3C-alkyl, R612 is hydrogen or 1-2C-alkyl, or R611 and R612 together and with inclusion of the nitrogen atom, to which they are bonded, form a heterocyclic ring Het1, in which Het1 is morpholino, piperidino, pyrrolidino, piperazino or 4N-(1-2C-alkyl)-piperazino, U is —O— (oxygen) or —C(O)NH—, T3 is straight chain 2-4C-alkylene, R613 is hydrogen, 1-2C-alkyl, 3-5C-cycloalkyl or 1-2C-alkoxy-2-3C-alkyl, R614 is hydrogen or 1-2C-alkyl, or R613 and R614 together and with inclusion of the nitrogen atom, to which they are bonded, form a heterocyclic ring Het2, in which Het2 is morpholino, piperidino, pyrrolidino, piperazino or 4N-(1-4C-alkyl)-piperazino, R62 is 1-2C-alkyl, Aa1 is 1,1'-biphenyl-3-yl or 1,1'-biphenyl-4-yl, Hh1 is a bisheteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a thiophenyl group, whereby said heteroaryl and thiophenyl groups are linked together via a single bond, and whereby Hh1 is bonded via said thiophenyl moiety to the to the parent molecular group, Ah1 is phenyl-thiophenyl or phenyl-pyridinyl, Ha1 is a 3-(heteroaryl)-phenyl or 4-(heteroaryl)-phenyl radical each made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group, Ha2 is a 3-(heteroaryl)-phenyl or 4-(heteroaryl)-phenyl radical each made up of a heteroaryl group selected from a group consisting of fused bicyclic 9 or 10-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group, R7 is hydroxyl, or 2-aminophenyl, and the salts of these compounds.

Compounds according to aspect B of the present invention in more particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is substituted by R61 on the terminal ring, and is Aa1 or Ah1, in which
Aa1 is 1,1'-biphenyl-3-yl or 1,1'-biphenyl-4-yl,
Ah1 is phenyl-thiophenyl,
R61 is methoxy, hydroxymethyl, methylsulphonylamino, methylcarbonylamino, dimethylaminosulphonyl, -T2-N(R611)R612, or —U-T3-N(R613)R614, in which
T2 is a bond, methylene, dimethylene or trimethylene,
R611 is hydrogen, methyl, cyclopropyl or 2-methoxyethyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino, piperazino or 4N-methyl-piperazino,
U is —O— (oxygen) or —C(O)NH—,
T3 is dimethylene or trimethylene,
R613 is hydrogen, methyl, cyclopropyl or 2-methoxyethyl,
R614 is hydrogen or methyl, or R613 and R614 together and with inclusion of the nitrogen atom, to which they are bonded, form a heterocyclic ring Het2, in which
Het2 is morpholino, piperidino, pyrrolidino, piperazino or 4N-methyl-piperazino, or
Q1 is substituted by R61 on the terminal ring, and is Hh1 or Ha1, in which
Hh1 is pyridinyl-thiophenyl,
Ha1 is 3-(pyridinyl)-phenyl or 4-(pyridinyl)-phenyl,
R61 is methoxy, or -T2-N(R611)R612, in which
T2 is a bond, methylene, dimethylene or trimethylene,
R611 is hydrogen, methyl, cyclopropyl or 2-methoxyethyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino, piperazino or 4N-methyl-piperazino, or
Q1 is 3-(1N-methyl-pyrazolyl)-phenyl, 4-(1N-methyl-pyrazolyl)-phenyl, 3-(1N-methyl-indolyl)-phenyl or 4-(1N-methyl-indolyl)-phenyl,
R7 is hydroxyl, or 2-aminophenyl, and the salts of these compounds.

Yet compounds according to aspect B of the present invention in more particular worthy to be mentioned are those compounds of formula I in which
R1, R2, R3, R4 and R5 are all hydrogen,
R6 is -T1-Q1, in which
T1 is a bond,
Q is (1N-methyl-pyrazolyl)-thiophenyl,
3-(dimethyl-isoxazolyl)-phenyl or 4-(dimethyl-isoxazolyl)-phenyl, and the salts of these compounds.

In another embodiment, still yet compounds according to aspect B of the present invention in more particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is substituted by R61 on the terminal ring, and is Aa1 or Ah1, in which
Aa1 is 1,1'-biphenyl-3-yl or 1,1'-biphenyl-4-yl,
Ah1 is phenyl-thiophenyl or phenyl-pyridinyl,
R61 is methoxy, hydroxyl, trifluoromethyl, hydroxymethyl, methylsulphonylamino, methylcarbonylamino, dimethylaminosulphonyl, -T2-N(R611)R612, or —U-T3-N(R613)R614, in which
T2 is a bond, methylene, dimethylene or trimethylene,
R611 is hydrogen, methyl, cyclopropyl, cyclopentyl or 2-methoxyethyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino, piperazino or 4N-methyl-piperazino,
U is —O— (oxygen) or —C(O)NH—,
T3 is dimethylene or trimethylene,
R613 is hydrogen, methyl, cyclopropyl, cyclopentyl or 2-methoxyethyl,
R614 is hydrogen or methyl, or R613 and R614 together and with inclusion of the nitrogen atom, to which they are bonded, form a heterocyclic ring Het2, in which
Het2 is morpholino, piperidino, pyrrolidino, piperazino or 4N-methyl -piperazino, or
Q1 is substituted by R61 on the terminal ring, and is Hh1 or Ha1, in which
Hh1 is pyridinyl-thiophenyl or bipyridyl,
Ha1 is 3-(pyridinyl)-phenyl or 4-(pyridinyl)-phenyl,
R61 is methoxy, or -T2-N(R611)R612, in which
T2 is a bond, methylene, dimethylene or trimethylene,
R611 is hydrogen, methyl, cyclopropyl, cyclopentyl or 2-methoxyethyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino, piperazino or 4N-methyl-piperazino, or
Q1 is 3-(1N-methyl-pyrazolyl)-phenyl, 4-(1N-methyl-pyrazolyl)-phenyl, (1N-methyl-pyrazolyl)-thiophenyl, (1N-methyl-pyrazolyl)-pyridinyl, 3-(methyl-thiazolyl)-phenyl, 4-(methyl-thiazolyl)-phenyl, (methyl-thiazolyl)-thiophenyl, (methyl-thiazolyl)-pyridinyl, 3-(dimethyl-isoxazolyl)-phenyl, 4-(dimethyl-isoxazolyl)-phenyl, 3-(1N-methyl-indolyl)-phenyl or 4-(1N-methyl-indolyl)-phenyl,
R7 is hydroxyl, or 2-aminophenyl, and the salts of these compounds.

Compounds according to aspect B of the present invention to be emphasized are those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is substituted by R61 on the terminal ring, and is Aa1 or Ah1, in which
Aa1 is 1,1'-biphenyl-3-yl or 1,1'-biphenyl-4-yl,
Ah1 is phenyl-thiophenyl,
R61 is hydroxymethyl, methylsulphonylamino, methylcarbonylamino, dimethylaminosulphonyl, -T2-N(R611)R612, or —U-T3-N(R613)R614, in which
T2 is methylene, dimethylene or trimethylene,
R611 is methyl, cyclopropyl or 2-methoxyethyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4N-methyl-piperazino,
U is —O— (oxygen) or —C(O)NH—,
T3 is dimethylene or trimethylene,
R613 is methyl,
R614 is methyl, or R613 and R614 together and with inclusion of the nitrogen atom, to which they are bonded, form a heterocyclic ring Het2, in which
Het2 is morpholino, piperidino, pyrrolidino or 4N-methyl-piperazino,
or
Q1 is substituted by R61 on the terminal ring, and is Hh1 or Ha1, in which
Hh1 is pyridinyl-thiophenyl,
Ha1 is 3-(pyridinyl)-phenyl or 4-(pyridinyl)-phenyl,
R61 is methoxy, or -T2-N(R611)R612, in which
T2 is a bond,
R611 is hydrogen or methyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4N-methyl-piperazino,
or
Q1 is 3-(1N-methyl-pyrazolyl)-phenyl, 4-(1N-methyl-pyrazolyl)-phenyl, 3-(1N-methyl-indolyl)-phenyl or 4-(1N-methyl-indolyl)-phenyl,
R7 is hydroxyl, or 2-aminophenyl, and the salts of these compounds.

Yet compounds according to aspect B of the present invention to be emphasized are those compounds of formula I in which
R1, R2, R3, R4 and R5 are all hydrogen,
R6 is -T1-Q1, in which
T1 is a bond,
Q is (1N-methyl-pyrazol-4-yl)-thiophenyl, 3-(dimethyl-isoxazolyl)-phenyl or 4-(dimethyl-isoxazolyl)-phenyl, and the salts of these compounds.

In another embodiment, still yet compounds according to aspect B of the present invention to be emphasized are those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is methoxy, hydroxyl, trifluoromethyl, hydroxymethyl, methylsulphonylamino, methylcarbonylamino, dimethylaminosulphonyl, -T2-N(R611)R612, or —U-T3-N(R613)R614, in which
T2 is a bond, methylene, dimethylene or trimethylene,
R611 is hydrogen, methyl, cyclopropyl, cyclopentyl or 2-methoxyethyl,
R612 is hydrogen or methyl, or R611 and R612 together and with inclusion of the nitrogen atom, to which they are bonded, form a heterocyclic ring Het1, in which
Het1 is morpholino, piperidino, pyrrolidino or 4N-methyl-piperazino,
either
U is —O— (oxygen),
T3 is dimethylene or trimethylene,
R613 and R614 together and with inclusion of the nitrogen atom, to which they are bonded, form a heterocyclic ring Het2, in which
Het2 is morpholino, piperidino, pyrrolidino or 4N-methyl-piperazino,
or
U is —C(O)NH—,
T3 is dimethylene or trimethylene,
R613 is methyl,
R614 is methyl,
or
Q1 is 5-[3-(R61)-phenyl]-thiophen-2-yl, 5-[4-(R61)-phenyl]-thiophen-2-yl, 2-[3-(R61)-phenyl]-pyridin-4-yl, 2-[4-(R61)-phenyl]-pyridin-4-yl, 6-[3-(R61)-phenyl]-pyridin-3-yl or 6-[4-(R61)-phenyl]-pyridin-3-yl, in which
R61 is methoxy, hydroxyl, trifluoromethyl, hydroxymethyl, methylsulphonylamino, methylcarbonylamino, dimethylaminosulphonyl, -T2-N(R611)R612, or —U-T3-N(R613)R614, in which
T2 is a bond, methylene, dimethylene or trimethylene,
either
R611 is methyl, cyclopropyl, cyclopentyl or 2-methoxyethyl,
R612 is hydrogen,
or
R611 is hydrogen,
R612 is hydrogen, or
R611 is methyl,
R612 is methyl, or R611 and R612 together and with inclusion of the nitrogen atom, to which they are bonded, form a heterocyclic ring Het1, in which
Het1 is morpholino, piperidino, pyrrolidino or 4N-methyl-piperazino, either
U is —O— (oxygen),
T3 is dimethylene or trimethylene,
R613 and R614 together and with inclusion of the nitrogen atom, to which they are bonded, form a heterocyclic ring Het2, in which
Het2 is morpholino, piperidino, pyrrolidino or 4N-methyl-piperazino, or
Q1 is 5-[2-(R61)-pyridin-4-yl]-thiophen-2-yl or 5-[6-(R61)-pyridin-3-yl]-thiophen-2-yl, in which
R61 is amino, methoxy, dimethylamino, or -T2-N(R611)R612, in which
T2 is a bond,
R611 and R612 together and with inclusion of the nitrogen atom, to which they are bonded, form a heterocyclic ring Het1, in which
Het1 is morpholino, piperidino, pyrrolidino or 4N-methyl-piperazino, or
Q1 is 2-[2-(R61)-pyridin-4-yl]-pyridin-4-yl, 2-[6-(R61)-pyridin-3-yl]-pyridin-4-yl, 3-[2-(R61)-pyridin-4-yl]-pyridin-6-yl or 3-[6-(R61)-pyridin-3-yl]-pyridin-6-yl, in which
R61 is amino, methoxy, dimethylamino, or -T2-N(R611)R612, in which
T2 is a bond,
R611 and R612 together and with inclusion of the nitrogen atom, to which they are bonded, form a heterocyclic ring Het1, in which
Het1 is morpholino, piperidino, pyrrolidino or 4N-methyl-piperazino, or
Q1 is 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which
R61 is amino, methoxy, dimethylamino, or -T2-N(R611)R612, in which
T2 is a bond,
R611 and R612 together and with inclusion of the nitrogen atom, to which they are bonded, form a heterocyclic ring Het1, in which
Het1 is morpholino, piperidino, pyrrolidino or 4N-methyl-piperazino, or
Q1 is 3-(1N-methyl-pyrazolyl)-phenyl, 4-(1N-methyl-pyrazol-4-yl)-phenyl, 5-(1N-methyl-pyrazol-4-yl)-thiophen-2-yl, 6-(1N-methyl-pyrazol-4-yl)-pyridin-3-yl, 5-(2-methyl-thiazol-4-yl)-thiophen-2-yl, 3-(3,5-dimethyl-isoxazol-4-yl)-phenyl, 4-(3,5-dimethyl-isoxazol-4-yl)-phenyl, 3-(1N-methyl-indol-5-yl)-phenyl or 4-(1N-methyl-indol-5-yl)-phenyl,
R7 is hydroxyl, or 2-aminophenyl, and the salts of these compounds.

Compounds according to aspect B of the present invention to be more emphasized are those compounds of formula I
in which
R1 is hydrogen,
R2 is hydrogen,
R3 is hydrogen,
R4 is hydrogen,
R5 is hydrogen,
R6 is -T1-Q1, in which
T1 is a bond,
Q1 is 2'-(R61)-1,1'-biphenyl-3-yl, 2'-(R61)-1,1'-biphenyl-4-yl, 3'-(R61)-1,1'-biphenyl-3-yl, 3'-(R61)-1,1'-biphenyl-4-yl, 4'-(R61)-1,1'-biphenyl-3-yl or 4'-(R61)-1,1'-biphenyl-4-yl, in which
R61 is hydroxymethyl, methylsulphonylamino, methylcarbonylamino, dimethylaminosulphonyl, -T2-N(R611)R612, or —U-T3-N(R613)R614, in which
T2 is methylene, dimethylene or trimethylene,
R611 is methyl, cyclopropyl or 2-methoxyethyl,
R612 is hydrogen or methyl, or R611 and R612 together and with inclusion of the nitrogen atom, to which they are bonded, form a heterocyclic ring Het1, in which
Het1 is morpholino, pyrrolidino or 4N-methyl-piperazino, either
U is —O— (oxygen),
T3 is dimethylene or trimethylene,
R613 and R614 together and with inclusion of the nitrogen atom, to which they are bonded, form a heterocyclic ring Het2, in which
Het2 is morpholino, pyrrolidino or 4N-methyl-piperazino, or
U is —C(O)NH—,
T3 is dimethylene or trimethylene,
R613 is methyl,
R614 is methyl, or
Q1 is 5-[3-(R61)-phenyl]-thiophen-2-yl or 5-[4-(R61)-phenyl]-thiophen-2-yl, in which
R61 is -T2-N(R611)R612, or —U-T3-N(R613)R614, in which
T2 is methylene, dimethylene or trimethylene,
R611 is methyl,
R612 is methyl, or R611 and R612 together and with inclusion of the nitrogen atom, to which they are bonded, form a heterocyclic ring Het1, in which
Het1 is morpholino, pyrrolidino or 4N-methyl-piperazino,
U is —O— (oxygen),
T3 is dimethylene or trimethylene,
R613 and R614 together and with inclusion of the nitrogen atom, to which they are bonded, form a heterocyclic ring Het2, in which
Het2 is morpholino, pyrrolidino or 4N-methyl-piperazino, or
Q1 is 5-[2-(R61)-pyridin-4-yl]-thiophen-2-yl or 5-[6-(R61)-pyridin-3-yl]-thiophen-2-yl, in which
R61 is amino, or -T2-N(R611)R612, in which
T2 is a bond,
R611 and R612 together and with inclusion of the nitrogen atom, to which they are bonded, form a heterocyclic ring Het1, in which
Het1 is morpholino, pyrrolidino or 4N-methyl-piperazino, or Q1 is 3-[2-(R61)-pyridin-4-yl]-phenyl, 4-[2-(R61)-pyridin-4-yl]-phenyl, 3-[6-(R61)-pyridin-3-yl]-phenyl or 4-[6-(R61)-pyridin-3-yl]-phenyl, in which R61 is amino, methoxy, or -T2-N(R611)R612, in which T2 is a bond, R611 and R612 together and with inclusion of the nitrogen atom, to which they are bonded, form a heterocyclic ring Het1, in which Het1 is morpholino, pyrrolidino or 4N-methyl-piperazino, or Q1 is 3-(1N-methyl-pyrazol-4-yl)-phenyl, 4-(1N-methyl-pyrazol-4-yl)-phenyl, 3-(1N-methyl-indol-5-yl)-phenyl or 4-(1N-methyl-indol-5-yl)-phenyl, R7 is hydroxyl, or 2-aminophenyl, and the salts of these compounds.

Yet compounds according to aspect B of the present invention to be more emphasized are those compounds of formula I in which R1, R2, R3, R4 and R5 are all hydrogen, R6 is -T1-Q1, in which T1 is a bond, Q is 5-(1N-methyl-pyrazol-4-yl)-thiophen-2-yl, 3-(3,5-dimethyl-isoxazol-4-yl)-phenyl or 4-(3,5-dimethyl-isoxazol-4-yl)-phenyl, and the salts of these compounds.

Compounds according to aspect B of the present invention to be in particular emphasized are those compounds of formula I in which R1 is hydrogen, R2 is hydrogen, R3 is hydrogen, R4 is hydrogen, R5 is hydrogen, R6 is -T1-Q1, in which T1 is a bond, Q1 is any one selected from the group consisting of 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 4'-(3-morpholin-4-yl-propyl)-biphenyl-3-yl, 4'-(4-methyl-piperazin-1-ylmethyl)-biphenyl-3-yl, 4'-(2-morpholin-4-yl-ethoxy)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, 4'-(2-pyrrolidin-1-yl-ethoxy]-biphenyl-3-yl, 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 3'-[(2-dimethylamino-ethylamino)-carbonyl]-biphenyl-4-yl, 4'-[(2-dimethylamino-ethylamino)-carbonyl]-biphenyl-4-yl, 4'-[(2-dimethylamino-ethylamino)-carbonyl]-biphenyl-3-yl, 2'-methylsulphonylamino-biphenyl-4-yl, 3'-methylsulphonylamino-biphenyl-4-yl, 4'-methylsulphonylamino-biphenyl-4-yl, 4'-dimethylsulphamoyl-biphenyl-4-yl, 3'-acetamido-biphenyl-4-yl, 4'-acetamido-biphenyl-4-yl, 4'-(2-methoxy-ethylamino)methyl-biphenyl-3-yl, 4'-cyclopropylaminomethyl-biphenyl-3-yl, 3'-hydroxymethyl-biphenyl-4-yl, 5-[2-(4-methyl-piperazin-1-yl)-pyridin-4-yl]-thiophen-2-yl, 5-(1N-methyl-pyrazol-4-yl)-thiophen-2-yl, 5-[4-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 5-[4-(2-morpholin-4-yl-ethoxy)-phenyl]-thiophen-2-yl, 5-[4-(3-morpholin-4-yl-propoxy)-phenyl]-thiophen-2-yl, 5-{4-[2-(4-methyl-piperazin-1-yl)-ethoxy]-phenyl}-thiophen-2-yl, 5-(4-dimethylaminomethyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, 3-[6-amino-pyridin-3-yl]-phenyl, 4-[6-methoxy-pyridin-3-yl]-phenyl, 3-[6-methoxy-pyridin-3-yl]-phenyl, 3-(1N-methyl-pyrazol-4-yl)-phenyl, 4-(1N-methyl-pyrazol-4-yl)-phenyl, 4-(3,5-dimethyl-isoxazol-4-yl)-phenyl, and 4-(1N-methyl-indol-5-yl)-phenyl, R7 is hydroxyl, or 2-aminophenyl, and the salts of these compounds.

In one embodiment, compounds according to aspect B of the present invention to be in more particular emphasized are those compounds of formula I in which R1 is hydrogen, R2 is hydrogen, R3 is hydrogen, R4 is hydrogen, R5 is hydrogen, R6 is -T1-Q1, in which T1 is a bond, Q1 is any one selected from the group consisting of 4'-(2-morpholin-4-yl-ethyl)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, 4'-dimethylaminomethyl-biphenyl-4-yl, 5-[2-(4-methyl-piperazin-1-yl)-pyridin-4-yl]-thiophen-2-yl, 5-(4-dimethylaminomethyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, and 4-(1N-methyl-pyrazol-4-yl)-phenyl.

R7 is hydroxyl, and the salts of these compounds.

In another embodiment, compounds according to aspect B of the present invention to be in more particular emphasized are those compounds of formula I in which R1 is hydrogen, R2 is hydrogen, R3 is hydrogen, R4 is hydrogen, R5 is hydrogen, R6 is -T1-Q1, in which T1 is a bond, Q1 is any one selected from the group consisting of 4'-(2-morpholin-4-yl-ethyl)-biphenyl-3-yl, 4'-(3-morpholin-4-yl-propoxy)-biphenyl-3-yl, 4'-[2-(4-methyl-piperazin-1-yl)-ethoxy]-biphenyl-3-yl, 4'-dimethylaminomethyl-biphenyl-4-yl, 5-[2-(4-methyl-piperazin-1-yl)-pyridin-4-yl]-thiophen-2-yl, 5-(4-dimethylaminomethyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, and 4-(1N-methyl-pyrazol-4-yl)-phenyl, R7 is 2-aminophenyl, and the salts of these compounds.

In a first embodiment of aspect C (embodiment C1) of the present invention, compounds according to aspect C of the present invention more worthy to be mentioned are those compounds of formula I in which
R1 is hydrogen, or 1-4C-alkyl,
R2 is hydrogen, or 1-4C-alkyl,
R3 is hydrogen, or 1-4C-alkyl,
R4 is hydrogen, or 1-4C-alkyl,
R5 is hydrogen, or 1-4C-alkyl,
R6 is -T1-Q1, in which
T1 is a bond, either Q1 is substituted by R61 and/or R62, and is Aa1, Hh1, Ha1, Ha2, Ha3 or Ah1, or Q1 is unsubstituted, and is Ha2 or Ha3, in which
R61 is 1-4C-alkyl, 1-4C-alkoxy, halogen, or -T2-N(R611)R612, in which
T2 is a bond or 1-4C-alkylene,
R611 is hydrogen or 1-4C-alkyl,
R612 is hydrogen or 1-4C-alkyl, or R611 and R612 together and with inclusion of the nitrogen atom, to which they are bonded, form a heterocyclic ring Het1, in which
Het1 is morpholino, piperidino, pyrrolidino, piperazino, or 4N-methyl-piperazino,
R62 is 1-4C-alkyl,
Aa1 is biphenyl,
Hh1 is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond,
Ah1 is an phenyl-heteroaryl radical made up of an phenyl group and a heteroaryl group selected from a group consisting of monocyclic 5- or 6-membered heteroaryl radicals comprising one or two heteroatoms, each of which is selected from the group consisting of nitrogen, oxygen and sulfur, whereby said phenyl and heteroaryl groups are linked together via a single bond, and whereby Ah1 is bonded via said heteroaryl moiety to the parent molecular group,
Ha1 is a heteroaryl-phenyl radical made up of a heteroaryl group selected from a group consisting of monocyclic 5- or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group,
Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group,
Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group,
R7 is hydroxyl, or 2-aminophenyl, and the salts of these compounds.

In a second embodiment of aspect C (embodiment C2), compounds according to aspect C of the present invention more worthy to be mentioned are those compounds of formula I in which
R1 is hydrogen, or 1-4C-alkyl,
R2 is hydrogen, or 1-4C-alkyl,
R3 is hydrogen, or 1-4C-alkyl,
R4 is hydrogen, or 1-4C-alkyl,
R5 is hydrogen, or 1-4C-alkyl,
R6 is -T1-Q1, in which
T1 is a bond, either Q1 is substituted by R61, and is Aa1, Ha1, Ha2 or Ha3, or Q1 is unsubstituted, and is Ha2 or Ha3, in which
R61 is 1-4C-alkyl, 1-4C-alkoxy, halogen, or -T2-N(R611)R612, in which
T2 is a bond or 1-4C-alkylene,
R611 is hydrogen or 1-4C-alkyl,
R612 is hydrogen or 1-4C-alkyl, or R611 and R612 together and with inclusion of the nitrogen atom, to which they are bonded, form a heterocyclic ring Het1, in which
Het1 is morpholino, piperidino, pyrrolidino, piperazino, or 4N-methyl-piperazino,
Aa1 is biphenyl,
Ha1 is a heteroaryl-phenyl radical made up of a heteroaryl group selected from a group consisting of monocyclic 5 or 6-membered heteroaryl radicals comprising one or two heteroatoms, each of which is selected from the group consisting of nitrogen, oxygen and sulfur, and a phenyl group, whereby said heteroaryl and phenyl groups are linked together via a single bond, and whereby Ha1 is bonded via said phenyl moiety to the to the parent molecular group,
Ha2 is a heteroaryl-phenyl radical made up of a heteroaryl group selected from a group consisting of fused bicyclic 9- or 10-membered heteroaryl radicals comprising one, two or three heteroatoms, each of which is selected from the group consisting of nitrogen, oxygen and sulfur, and a phenyl group, whereby said heteroaryl and phenyl groups are linked together via a single bond, and whereby Ha2 is bonded via said phenyl moiety to the to the parent molecular group,
Ha3 is a heteroaryl-phenyl radical made up of a heteroaryl group selected from a group consisting of monocyclic 5-membered heteroaryl radicals comprising three or four heteroatoms, each of which is selected from the group consisting of nitrogen, oxygen and sulfur, and a phenyl group, whereby said heteroaryl and phenyl groups are linked together via a single bond, and whereby Ha3 is bonded via said phenyl moiety to the to the parent molecular group, R7 is hydroxyl, or 2-aminophenyl, and the salts of these compounds.

Compounds according to embodiment C1 of aspect C of the present invention in particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond, either Q1 is substituted by R61 on the terminal ring, and is Aa1, Hh1, Ha1 or Ah1, or Q1 is [1N-(1-4C-alkyl)-indolyl]-phenyl, [1N-(1-4C-alkyl)-pyrazolyl]-phenyl, [1N-(1-4C-alkyl)-imidazolyl]-phenyl, [1N-(1-4C-alkyl)-triazolyl]-phenyl, [1N-(1-4C-alkyl)-tetrazolyl]-phenyl, [1N-(1-4C-alkyl)-benzimidazolyl]-phenyl, [1N-(1-4C-alkyl)-benztriazolyl]-phenyl, or [1N-(1-4C-alkyl)-indazol]-phenyl, or Q1 is [1N-(1-4C-alkyl)-indolyl]-thiophenyl, [1N-(1-4C-alkyl)-pyrazolyl]-thiophenyl, [1N-(1-4C-alkyl)-imidazolyl]-thiophenyl, [1N-(1-4C-alkyl)-triazolyl]-thiophenyl, [1N-(1-4C-alkyl)-tetrazolyl]-thiophenyl, [1N-(1-4C-alkyl)-benzimidazolyl]-thiophenyl, [1N-(1-4C-alkyl) benztriazolyl]-thiophenyl, or [1N-(1-4C-alkyl)-indazol]-thiophenyl, or Q1 is [mono- or di-(1-4C-alkyl)-isoxazolyl]-phenyl, or [mono- or di-(1-4C-alkyl)-isoxazolyl]-thiophenyl, in which
R61 is 1-4C-alkyl, 1-4C-alkoxy, halogen, or -T2-N(R611)R612, in which
T2 is a bond or 1-4C-alkylene,
R611 is hydrogen or 1-4C-alkyl,
R612 is hydrogen or 1-4C-alkyl, or R611 and R612 together and with inclusion of the nitrogen atom, to which they are bonded, form a heterocyclic ring Het1, in which
Het1 is morpholino, piperidino, pyrrolidino, piperazino, or 4N-methyl-piperazino,
Aa1 is 1,1'-biphenyl-4-yl or 1,1'-biphenyl-3-yl,
Hh1 is pyridinyl-thiophenyl,
Ha1 is 3-(pyridinyl)-phenyl or 4-(pyridinyl)-phenyl,
Ah1 is phenyl-thiophenyl,
R7 is hydroxyl, or 2-aminophenyl, and the salts of these compounds.

Compounds according to embodiment C2 of aspect C of the present invention in particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond, either Q1 is substituted by R61 on the terminal ring, and is Aa1 or Ha1, or Q1 is [1N-(1-4C-alkyl)-indolyl]-phenyl, [1N—(–4C-alkyl)-pyrazolyl]-phenyl, [1N-(1-4C-alkyl)-imidazolyl]-phenyl, [1N-(1-4C-alkyl)-triazolyl]-phenyl, [1N-(1-4C-alkyl)-tetrazolyl]-phenyl, [1N-(1-4C-alkyl)-benzimidazolyl]-phenyl, [1N-(1-4C-alkyl)-benztriazolyl]-phenyl, or [1N-(1-4C-alkyl)-indazol]-phenyl, in which
R61 is 1-4C-alkyl, 1-4C-alkoxy, halogen, or -T2-N(R611)R612, in which
T2 is a bond or 1-4C-alkylene,
R611 is hydrogen or 1-4C-alkyl,
R612 is hydrogen or 1-4C-alkyl, or R611 and R612 together and with inclusion of the nitrogen atom, to which they are bonded, form a heterocyclic ring Het1, in which
Het1 is morpholino, piperidino, pyrrolidino, piperazino, or 4N-methyl-piperazino,
Aa1 is 1,1'-biphenyl-4-yl or 1,1'-biphenyl-3-yl,
Ha1 is 3-(pyridinyl)-phenyl or 4-(pyridinyl)-phenyl,
R7 is hydroxyl, or 2-aminophenyl, and the salts of these compounds.

Compounds according to embodiment C1 of aspect C of the present invention in more particular worthy to be mentioned are those compounds of formula I in which
R1 is hydrogen,
R2 is hydrogen,
R3 is hydrogen,
R4 is hydrogen,
R5 is hydrogen,
R6 is -T1-Q1, in which
T1 is a bond, either Q1 is substituted by R61 on the pyridine ring, and is 3-(pyridinyl)-phenyl or 4-(pyridinyl)-phenyl, or Q1 is 2'-(R61)-1,1'-biphenyl-4-yl, 3'-(R61)-1,1'-biphenyl-4-yl, 4'-(R61)-1,1'-biphenyl-4-yl, 2'-(R61)-1,1'-biphenyl-3-yl, 3'-(R61-1,1'-biphenyl-3-yl or 4'-(R61)-1,1'-biphenyl-3-yl, or Q1 is substituted by R61 on the pyridine ring, and is pyridinyl-thiophenyl, or Q1 is substituted by R61 on the phenyl ring, and is phenyl-thiophenyl, or Q1 is 3-[1N-methyl-indolyl]-phenyl, 4-[1N-methyl-indolyl]-phenyl, 3-[1N-methyl-pyrazolyl]-phenyl or 4-[1N-methyl-pyrazolyl]-phenyl, or Q1 is [1N-methyl-pyrazolyl]-thiophenyl, or
Q1 is 3-[dimethyl-isoxazolyl]-phenyl or 4-[dimethyl-isoxazolyl]-phenyl, in which
R61 is 1-2C-alkoxy, amino, or -T2-N(R611)R612, in which
T2 is a bond, methylene, dimethylene or trimethylene,
R611 is 1-2C-alkyl,
R612 is 1-2C-alkyl, or R611 and R612 together and with inclusion of the nitrogen atom, to which they are bonded, form a heterocyclic ring Het1, in which
Het1 is morpholino, pyrrolidino or 4N-methyl-piperazino,
R7 is hydroxyl, or 2-aminophenyl, and the salts of these compounds.

Compounds according to embodiment C2 of aspect C of the present invention in more particular worthy to be mentioned are those compounds of formula I
in which
R1 is hydrogen,
R2 is hydrogen,
R3 is hydrogen,
R4 is hydrogen,
R5 is hydrogen,
R6 is -T1-Q1, in which
T1 is a bond, either
Q1 is substituted by R61 on the pyridine ring, and is 3-(pyridinyl)-phenyl or 4-(pyridinyl)-phenyl, or
Q1 is 3'-(R61)-1,1'-biphenyl-4-yl or 4'-(R61)-1,1'-biphenyl-4-yl, or
Q1 is 3-[1N-methyl-indolyl]-phenyl, 4-[1N-methyl-indolyl]-phenyl, 3-[1N-methyl-pyrazolyl]-phenyl or 4-[1N-methyl-pyrazolyl]-phenyl, in which
R61 is 1-2C-alkoxy, amino, or -T2-N(R611)R612, in which
T2 is a bond or 1-2C-alkylene,
R611 is 1-2C-alkyl,
R612 is 1-2C-alkyl, or R611 and R612 together and with inclusion of the nitrogen atom, to which they are bonded, form a heterocyclic ring Het1, in which
Het1 is morpholino,
R7 is hydroxyl, or 2-aminophenyl, and the salts of these compounds.

Compounds according to embodiment C1 of aspect C of the present invention to be emphasized are, in one embodiment, those compounds of formula I
in which
R1 is hydrogen,
R2 is hydrogen,
R3 is hydrogen,
R4 is hydrogen,
R5 is hydrogen,
R6 is -T1-Q1, in which
T1 is a bond, either
Q1 is 3-(6-amino-pyridin-3-yl)-phenyl, 4-(6-amino-pyridin-3-yl)-phenyl, 3-(6-methoxy-pyridin-3-yl)-phenyl or 4-(6-methoxy-pyridin-3-yl)-phenyl, or
Q1 is 3-[2-(4-methyl-piperazin-1-yl)-pyridin-4-yl)]-phenyl or 4-[2-(4-methyl-piperazin-1-yl)-pyridin-4-yl)]-phenyl, or
Q1 is 3'-(R61)-1,1'-biphenyl-4-yl or 4'-(R61)-1,1'-biphenyl-4-yl, or
Q1 is 5-[2-(4-methyl-piperazin-1-yl)-pyridin-4-yl)]-thiophen-2-yl, or
Q1 is 5-[4-(R61)-phenyl]-thiophen-2-yl or 5-[3-(R61)-phenyl]-thiophen-2-yl, or
Q1 is 3-(1N-methyl-indol-5-yl)-phenyl, 4-(1N-methyl-indol-5-yl)-phenyl, 3-(1N-methyl-pyrazol-4-yl)-phenyl or 4-(1N-methyl-pyrazol-4-yl)-phenyl, or
Q1 is 5-(1N-methyl-pyrazol-4-yl)-thiophen-2-yl, or
Q1 is 3-(3,5-dimethyl-isoxazol-4-yl)-phenyl or 4-(3,5-dimethyl-isoxazol-4-yl)-phenyl, in which
R61 is -T2-N(R611)R612, in which
T2 is methylene, dimethylene or trimethylene, either
R611 and R612 are both methyl, or
R611 and R612 together and with inclusion of the nitrogen atom, to which they are bonded, form a heterocyclic ring Het1, in which
Het1 is morpholino or 4N-methyl-piperazino,
R7 is hydroxyl, and the salts of these compounds.

Compounds according to embodiment C1 of aspect C of the present invention to be emphasized are, in another embodiment, those compounds of formula I
in which
R1 is hydrogen,
R2 is hydrogen,
R3 is hydrogen,
R4 is hydrogen,
R5 is hydrogen,
R6 is -T1-Q1, in which
T1 is a bond, either
Q1 is 3-(6-amino-pyridin-3-yl)-phenyl, 4-(6-amino-pyridin-3-yl)-phenyl, 3-(6-methoxy-pyridin-3-yl)-phenyl or 4-(6-methoxy-pyridin-3-yl)-phenyl, or
Q1 is 3-[2-(4-methyl-piperazin-1-yl)-pyridin-4-yl)]-phenyl or 4-[2-(4-methyl-piperazin-1-yl)-pyridin-4-yl)]-phenyl, or
Q1 is 3'-(R61)-1,1'-biphenyl-4-yl or 4'-(R61)-1,1'-biphenyl-4-yl, or
Q1 is 5-[2-(4-methyl-piperazin-1-yl)-pyridin-4-yl)]-thiophen-2-yl, or
Q1 is 5-[4-(R61)-phenyl]-thiophen-2-yl or 5-[3-(R61)-phenyl]-thiophen-2-yl, or
Q1 is 3-(1N-methyl-indol-5-yl)-phenyl, 4-(1N-methyl-indol-5-yl)-phenyl, 3-(1N-methyl-pyrazol-4-yl)-phenyl or 4-(1N-methyl-pyrazol-4-yl)-phenyl, or
Q1 is 5-(1N-methyl-pyrazol-4-yl)-thiophen-2-yl, or
Q1 is 3-(3,5-dimethyl-isoxazol-4-yl)-phenyl or 4-(3,5-dimethyl-isoxazol-4-yl)-phenyl, in which
R61 is -T2-N(R611)R612, in which
T2 is methylene, dimethylene or trimethylene,
either
R611 and R612 are both methyl,
or
R611 and R612 together and with inclusion of the nitrogen atom, to which they are bonded, form a heterocyclic ring Het1, in which
Het1 is morpholino or 4N-methyl-piperazino,
R7 is 2-aminophenyl, and the salts of these compounds.

Compounds according to embodiment C2 of aspect C of the present invention to be emphasized are those compounds of formula I
in which
R1 is hydrogen,
R2 is hydrogen,
R3 is hydrogen,
R4 is hydrogen,
R5 is hydrogen,
R6 is -T1-Q1, in which
T1 is a bond,
either
Q1 is 3-(6-amino-pyridin-3-yl)-phenyl, 4-(6-amino-pyridin-3-yl)-phenyl, 3-(6-methoxy-pyridin-3-yl)-phenyl or 4-(6-methoxy-pyridin-3-yl)-phenyl, or
Q1 is 3'-(R61)-1,1'-biphenyl-4-yl or 4'-(R61)-1,1'-biphenyl-4-yl, or
Q1 is 3-(1N-methyl-indol-5-yl)-phenyl, 4-(1N-methyl-indol-5-yl)-phenyl, 3-(1N-methyl-pyrazol-4-yl)-phenyl or 4-(1N-methyl-pyrazol-4-yl)-phenyl, in which
R61 is -T2-N(R611)R612, in which
T2 is 1-2C-alkylene,
R611 and R612 together and with inclusion of the nitrogen atom, to which they are bonded, form a heterocyclic ring Het1, in which
Het1 is morpholino,
R7 is hydroxyl, or 2-aminophenyl, and the salts of these compounds.

Compounds according to embodiment C1 of aspect C of the present invention to be more emphasized are, in one embodiment, those compounds of formula I
in which
R1 is hydrogen,
R2 is hydrogen,
R3 is hydrogen,
R4 is hydrogen,
R5 is hydrogen,
R6 is -T1-Q1, in which
T1 is a bond,
Q1 is any one selected from 3-(6-amino-pyridin-3-yl)-phenyl, 4-(6-amino-pyridin-3-yl)-phenyl, 3-(6-methoxy-pyridin-3-yl)-phenyl, 4-(6-methoxy-pyridin-3-yl)-phenyl, 3-[2-(4-methyl-piperazin-1-yl)-pyridin-4-yl)]-phenyl, 4-[2-(4-methyl-piperazin-1-yl)-pyridin-4-yl)]-phenyl, 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 4'-(3-morpholin-4-yl-propyl)-biphenyl-3-yl, 4'-(4-methyl-piperazin-1-yl-methyl)-biphenyl-3-yl, 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 5-[2-(4-methyl-piperazin-1-yl)-pyridin-4-yl)]-thiophen-2-yl, 5-[4-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 4-(1N-methyl-indol-5-yl)-phenyl, 3-(1N-methyl-pyrazolyl)-phenyl, 4-(1N-methyl-pyrazol-4-yl)-phenyl, 5-(4-dimethylaminomethyl-phenyl)-thiophen-2-yl, 5-(1N-methyl-pyrazol-4-yl)-thiophen-2-yl, and 4-(3,5-dimethyl-isoxazol-4-yl)-phenyl,
R7 is hydroxyl, and the salts of these compounds.

Compounds according to embodiment C1 of aspect C of the present invention to be more emphasized are, in another embodiment, those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is any one selected from 3-(6-amino-pyridin-3-yl)-phenyl, 4-(6-amino-pyridin-3-yl)-phenyl, 3-(6-methoxy-pyridin-3-yl)-phenyl, 4-(6-methoxy-pyridin-3-yl)-phenyl, 3-[2-(4-methyl-piperazin-1-yl)-pyridin-4-yl)]-phenyl, 4-[2-(4-methyl-piperazin-1-yl)-pyridin-4-yl)]-phenyl, 3'-(2-morpholin-4-yl-ethyl)-biphenyl-4-yl, 3'-(2-morpholin-4-yl-ethyl)-biphenyl-3-yl, 4'-(2-morpholin-4-yl-ethyl)-biphenyl-4-yl, 4'-(2-morpholin-4-yl-ethyl)-biphenyl-3-yl, 3'-(morpholin-4-yl-methyl)-biphenyl-3-yl, 4'-(morpholin-4-yl-methyl)-biphenyl-3-yl, 4'-(3-morpholin-4-yl-propyl)-biphenyl-3-yl, 4'-(4-methyl-piperazin-1-yl-methyl)-biphenyl-3-yl, 2'-dimethylaminomethyl-biphenyl-4-yl, 4'-dimethylaminomethyl-biphenyl-4-yl, 2'-dimethylaminomethyl-biphenyl-3-yl, 4'-dimethylaminomethyl-biphenyl-3-yl, 5-[2-(4-methyl-piperazin-1-yl)-pyridin-4-yl)]-thiophen-2-yl, 5-[4-(2-morpholin-4-yl-ethyl)-phenyl]-thiophen-2-yl, 5-[4-(morpholin-4-yl-methyl)-phenyl]-thiophen-2-yl, 5-[3-(morpholin-4-yl-methyl)-phenyl]-thiophen-2-yl, 4-(1N-methyl-indol-5-yl)-phenyl, 3-(1N-methyl-pyrazol-4-yl)-phenyl, 4-(1N-methyl-pyrazol-4-yl)-phenyl, 5-(4-dimethylaminomethyl-phenyl)-thiophen-2-yl, 5-(1N-methyl-pyrazol-4-yl)-thiophen-2-yl, and 4-(3,5-dimethyl-isoxazol-4-yl)-phenyl,
R7 is 2-aminophenyl, and the salts of these compounds.

Compounds according to embodiment C1 of aspect C of the present invention to be in particular emphasized are, in one embodiment, those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is any one selected from 4-(6-amino-pyridin-3-yl)-phenyl, 4-[2-(4-methyl-piperazin-1-yl)-pyridin-4-yl)]-phenyl, 3-[2-(4-methyl-piperazin-1-yl)-pyridin-4-yl)]-phenyl, 4'-(2-morpholin-4-yl-ethyl)-biphenyl-3-yl, 4'-dimethylaminomethyl-biphenyl-4-yl, 5-[2-(4-methyl-piperazin-1-yl)-pyridin-4-yl)]-thiophen-2-yl, 4-(1N-methyl-pyrazol-4-yl)-phenyl, and 5-(4-dimethylaminomethyl-phenyl)-thiophen-2-yl,
R7 is hydroxyl, and the salts of these compounds.

Compounds according to embodiment C1 of aspect C of the present invention to be in particular emphasized are, in another embodiment, those compounds of formula I in which
R1 is hydrogen,
R2 is hydrogen,
R3 is hydrogen,
R4 is hydrogen,
R5 is hydrogen,
R6 is -T1-Q1, in which
T1 is a bond,
Q1 is any one selected from 4-(6-amino-pyridin-3-yl)-phenyl, 4-[2-(4-methyl-piperazin-1-yl)-pyridin-4-yl)]-phenyl, 3-[2-(4-methyl-piperazin-1-yl)-pyridin-4-yl)]-phenyl, 4'-(2-morpholin-4-yl-ethyl)-biphenyl-3-yl, 4'-dimethylaminomethyl-biphenyl-4-yl, 5-[2-(4-methyl-piperazin-1-yl)-pyridin-4-yl)]-thiophen-2-yl, 4-(1N-methyl-pyrazol-4-yl)-phenyl, and 5-(4-dimethylaminomethyl-phenyl)-thiophen-2-yl,
R7 is 2-aminophenyl, and the salts of these compounds.

A special interest in the compounds according to the present invention refers to those compounds of this invention which are included—within the scope of this invention—by one or, when possible, a combination of more of the following embodiments:

An embodiment of the compounds according to the present invention relates to those compounds of formula I, in which R1, R2, R3, R4 and R5 are all hydrogen.

A further embodiment of the compounds according to the present invention relates to those compounds of formula I, in which R7 is hydroxyl.

A further embodiment of the compounds according to the present invention relates to those compounds of formula I, in which R7 is 2-aminophenyl.

A further embodiment of the compounds according to the present invention relates to those compounds of formula I, in which R7 is aminopyridyl.

A further embodiment of the compounds according to the present invention relates to those compounds of formula I, in which R7 is Cyc1, whereby in a subembodiment thereof Cyc1 is 2-phenyl.

A further embodiment of the compounds according to the present invention relates to those compounds of formula I, in which T1 is a bond.

A further embodiment of the compounds according to the present invention relates to those compounds of formula I, in which R6 is substituted by R61, and is Aa1, Ha1 or Ha2.

A further embodiment of the compounds according to the present invention relates to those compounds of formula I, in which R6 is substituted by R61, and is Ah1 or Hh1.

A further embodiment of the compounds according to the present invention relates to those compounds of formula I, in which R6 is substituted by R61, and is Ha3.

A further embodiment of the compounds according to the present invention relates to those compounds of formula I, in which R6 is 3-(pyridinyl)-phenyl or 4-(pyridinyl)-phenyl, each of which is substituted by R61 on the pyridinyl moiety.

A further embodiment of the compounds according to the present invention relates to those compounds of formula I, in which R6 is 3-(pyridin-3-yl)-phenyl, 3-(pyridinyl)-phenyl, 4-(pyridin-3-yl)-phenyl, or 4-(pyridinyl)-phenyl, each of which is substituted by R61 on the pyridinyl moiety.

A further embodiment of the compounds according to the present invention relates to those compounds of formula I, in which R6 is 3-(pyridin-3-yl)-phenyl or 4-(pyridin-3-yl)-phenyl, each of which is substituted by R61 on the pyridinyl moiety.

A further embodiment of the compounds according to the present invention relates to those compounds of formula I, in which R6 is 3-[6-(R61)-pyridin-3-yl]-phenyl or 4-[6-(R61)-pyridin-3-yl]-phenyl.

A further embodiment of the compounds according to the present invention relates to those compounds of formula I, in which R6 is 3-(pyridin-4-yl)-phenyl or 4-(pyridin-4-yl)-phenyl, each of which is substituted by R61 on the pyridinyl moiety.

A further embodiment of the compounds according to the present invention relates to those compounds of formula I, in which R6 is 3-[2-(R61)-pyridin-4-yl]-phenyl or 4-[2-(R61)-pyridin-4-yl]-phenyl.

A further embodiment of the compounds according to the present invention relates to those compounds of formula I, in which R6 is 1,1'-biphenyl-4-yl or 1,1'-biphenyl-3-yl, each of which is substituted by R61 on the terminal phenyl moiety.

A further embodiment of the compounds according to the present invention relates to those compounds of formula I, in which R6 is 3'-(R61)-1,1'-biphenyl-4-yl, 4'-(R61)-1,1'-biphenyl-4-yl, 3'-(R61)-1,1'-biphenyl-3-yl or 4'-(R61)-1,1'-biphenyl-3-yl.

A further embodiment of the compounds according to the present invention relates to those compounds of formula I, in which R6 is 3'-(R61)-1,1'-biphenyl-4-yl or 4'-(R61)-1,1'-biphenyl-4-yl.

A further embodiment of the compounds according to the present invention relates to those compounds of formula I, in which R6 is 3'-(R61)-1,1'-biphenyl-3-yl or 4'-(R61)-1,1'-biphenyl-3-yl.

A further embodiment of the compounds according to the present invention relates to those compounds of formula I, in which R6 is 4'-(R61)-1,1'-biphenyl-3-yl or 4'-(R61)-1,1'-biphenyl-4-yl.

A further embodiment of the compounds according to the present invention relates to those compounds of formula I, in which R6 is pyridinyl-thiophenyl, which is substituted by R61 on the pyridinyl moiety.

A further embodiment of the compounds according to the present invention relates to those compounds of formula I, in which R6 is [2-(R61)-pyridin-4-yl]-thiophenyl, such as e.g. 5-[2-(R61)-pyridin-4-yl]-thiophen-2-yl.

A further embodiment of the compounds according to the present invention relates to those compounds of formula I, in which R6 is [6-(R61)-pyridin-3-yl]-thiophenyl, such as e.g. 5-[6-(R61)-pyridin-3-yl]-thiophen-2-yl.

A further embodiment of the compounds according to the present invention relates to those compounds of formula I, in which R6 is bipyridyl, which is substituted by R61 on the terminal pyridinyl moiety.

A further embodiment of the compounds according to the present invention relates to those compounds of formula I, in which R6 is [2-(R61)-pyridin-4-yl]-pyridinyl, such as e.g. 2-[2-(R61)-pyridin-4-yl]-pyridin-4-yl or 6-[2-(R61)-pyridin-4-yl]-pyridin-3-yl.

A further embodiment of the compounds according to the present invention relates to those compounds of formula I, in which R6 is [6-(R61)-pyridin-3-yl]-pyridinyl, such as e.g. 2-[6-(R61)-pyridin-3-yl]-pyridin-4-yl or 6-[6-(R61)-pyridin-3-yl]-pyridin-3-yl.

A further embodiment of the compounds according to the present invention relates to those compounds of formula I, in which R6 is phenyl-thiophenyl, which is substituted by R61 on the phenyl moiety.

A further embodiment of the compounds according to the present invention relates to those compounds of formula I, in which R6 is [3-(R61)-phenyl]-thiophenyl, such as e.g. 5-[3-(R61)-phenyl]-thiophen-2-yl.

A further embodiment of the compounds according to the present invention relates to those compounds of formula I, in which R6 is [4-(R61)-phenyl]-thiophenyl, such as e.g. 5-[4-(R61)-phenyl]-thiophen-2-yl.

A further embodiment of the compounds according to the present invention relates to those compounds of formula I, in which R6 is phenyl-pyridinyl, which is substituted by R61 on the phenyl moiety.

A further embodiment of the compounds according to the present invention relates to those compounds of formula I, in which R6 is [3-(R61)-phenyl]-pyridinyl, such as e.g. 2-[3-(R61)-phenyl]-pyridin-4-yl or 6-[3-(R61)-phenyl]-pyridin-3-yl.

A further embodiment of the compounds according to the present invention relates to those compounds of formula I, in which R6 is [4-(R61)-phenyl]-pyridinyl, such as e.g. 2-[4-(R61)-phenyl]-pyridin-4-yl or 6-[4-(R61)-phenyl]-pyridin-3-yl.

A further embodiment of the compounds according to the present invention relates to those compounds of formula I, in which R6 is [1N-(1-4C-alkyl)-indolyl]-phenyl or [1N-(1-4C-alkyl)-pyrazolyl]-phenyl.

A further embodiment of the compounds according to the present invention relates to those compounds of formula I, in which R6 is [1N-(1-2C-alkyl)-indol-5-yl]-phenyl or [1N-(1-2C-alkyl)-pyrazol-4-yl]-phenyl.

A further embodiment of the compounds according to the present invention relates to those compounds of formula I, in which R6 is 3-(1N-methyl-pyrazolyl)-phenyl or 4-(1N-methyl-pyrazol-4-yl)-phenyl.

A further embodiment of the compounds according to the present invention relates to those compounds of formula I, in which R6 is [1N-(1-2C-alkyl)-pyrazolyl]-pyridinyl, such as e.g. 2-(1N-methyl-pyrazol-4-yl)-pyridin-4-yl or 6-(1N-methyl-pyrazol-4-yl)-pyridin-3-yl.

A further embodiment of the compounds according to the present invention relates to those compounds of formula I, in which R6 is triazolyl-phenyl, which is substituted by R61 on the triazolyl moiety.

A further embodiment of the compounds according to the present invention relates to those compounds of formula I, in which R6 is {1N—(R61)-[1,2,3]triazolyl}-phenyl, such as e.g. 3-{1N—(R61)-[1,2,3]triazol-4-yl}-phenyl or 4-{1N—(R61)-[1,2,3]triazol-4-yl}-phenyl.

A further embodiment of the compounds according to the present invention relates to those compounds of formula I, in which R61 is -T2-N(R611)R612.

A further embodiment of the compounds according to the present invention relates to those compounds of formula I, in which T2 is a bond.

A further embodiment of the compounds according to the present invention relates to those compounds of formula I, in which T2 is 1-4C-alkylene, such as e.g. 1-2C-alkylene.

A further embodiment of the compounds according to the present invention relates to those compounds of formula I, in which T2 is methylene.

A further embodiment of the compounds according to the present invention relates to those compounds of formula I, in which T2 is dimethylene.

A further embodiment of the compounds according to the present invention relates to those compounds of formula I, in which T2 is trimethylene.

A further embodiment of the compounds according to the present invention relates to those compounds of formula I, in which R611 and R612 are both hydrogen.

A further embodiment of the compounds according to the present invention relates to those compounds of formula I, in which R611 and R612 are both methyl.

A further embodiment of the compounds according to the present invention relates to those compounds of formula I, in which R611 and R612 together and with inclusion of the nitrogen atom, to which they are attached, form a morpholino ring.

A further embodiment of the compounds according to the present invention relates to those compounds of formula I, in which R611 and R612 together and with inclusion of the nitrogen atom, to which they are attached, form a 4N-methyl-piperazino ring.

A further embodiment of the compounds according to the present invention relates to those compounds of formula I, in which R611 and R612 together and with inclusion of the nitrogen atom, to which they are attached, form a pyrrolidino ring.

A further embodiment of the compounds according to the present invention relates to those compounds of formula I, in which R611 and R612 together and with inclusion of the nitrogen atom, to which they are attached, form a piperidino ring.

A further embodiment of the compounds according to the present invention relates to those compounds of formula I, in which R61 is —O-T3-N(R613)R614.

A further embodiment of the compounds according to the present invention relates to those compounds of formula I, in which T3 is dimethylene.

A further embodiment of the compounds according to the present invention relates to those compounds of formula I, in which T3 is trimethylene.

A further embodiment of the compounds according to the present invention relates to those compounds of formula I, in which R613 and R614 are both methyl.

A further embodiment of the compounds according to the present invention relates to those compounds of formula I, in which R613 and R614 together and with inclusion of the nitrogen atom, to which they are attached, form a morpholino ring.

A further embodiment of the compounds according to the present invention relates to those compounds of formula I, in which R613 and R614 together and with inclusion of the nitrogen atom, to which they are attached, form a 4N-methyl-piperazino ring.

A further embodiment of the compounds according to the present invention relates to those compounds of formula I, in which R613 and R614 together and with inclusion of the nitrogen atom, to which they are attached, form a pyrrolidino ring.

A further embodiment of the compounds according to the present invention relates to those compounds of formula I, in which R613 and R614 together and with inclusion of the nitrogen atom, to which they are attached, form a piperidino ring.

A further embodiment of the compounds according to the present invention relates to those compounds of formula I, in which R61 is -T4-Het3, in which
T4 is a bond, methylene, dimethylene or trimethylene, and
Het3 is 1N-methyl-piperidin-4-yl.

A further embodiment of the compounds according to the present invention relates to those compounds of formula I, in which R61 is —O-T5-Het4, in which
T5 is a bond, methylene, dimethylene or trimethylene, and
Het4 is 1N-methyl-piperidin-4-yl.

A further embodiment of the compounds according to the present invention relates to those compounds of formula I, in which R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino) methyl, aminomethyl, acetylamino-methyl, methylsulphonylamino-methyl, cyclopentylaminomethyl, cyclopropylaminomethyl and hydroxymethyl; and R7 is hydroxyl.

A further embodiment of the compounds according to the present invention relates to those compounds of formula I, in which R61 is any one selected from 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsulphonylamino, dimethylsulphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino) methyl, aminomethyl, acetylamino-methyl, methylsulphonylamino-methyl, cyclopentylaminomethyl, cyclopropylaminomethyl and hydroxymethyl; and R7 is 2-aminophenyl.

A further embodiment of the compounds according to the present invention relates to those compounds of formula I, in which R6 is 4-(6-amino-pyridin-3-yl)-phenyl.

A further embodiment of the compounds according to the present invention relates to those compounds of formula I, in which R6 is 4-[2-(4-methyl-piperazin-1-yl)-pyridin-4-yl)]-phenyl.

A further embodiment of the compounds according to the present invention relates to those compounds of formula I, in which R6 is 3-[2-(4-methyl-piperazin-1-yl)-pyridin-4-yl)]-phenyl.

A further embodiment of the compounds according to the present invention relates to those compounds of formula I, in which R6 is 4'-(2-morpholin-4-yl-ethyl)-biphenyl-3-yl.

A further embodiment of the compounds according to the present invention relates to those compounds of formula I, in which R6 is 4'-dimethylaminomethyl-biphenyl-4-yl.

A further embodiment of the compounds according to the present invention relates to those compounds of formula I, in which R6 is 5-[2-(4-methyl-piperazin-1-yl)-pyridin-4-yl)]-thiophen-2-yl.

A further embodiment of the compounds according to the present invention relates to those compounds of formula I, in which R6 is 5-(4-dimethylaminomethyl-phenyl)-thiophen-2-yl.

A special embodiment of the compounds according to the present invention relates to those compounds of formula I, in which R1, R2, R3, R4 and R5 are all hydrogen, and R7 is hydroxyl.

Another special embodiment of the compounds according to the present invention relates to those compounds of formula I, in which R1, R2, R3, R4 and R5 are all hydrogen, and R7 is 2-aminophenyl.

It is to be understood, that the present invention also includes any or all possible combinations and subsets of the embodiments defined herein afore.

Exemplary compounds according to this invention may include any one selected from
1. (E)-N-Hydroxy-3-{1-[4-(1-methyl-1H-indol-5-yl)-benzenesulfonyl]-1H-pyrrol-3-yl}-acrylamide,
2. (E)-N-Hydroxy-3-{1-[4-(1-methyl-1H-pyrazol-4-yl)-benzenesulfonyl]-1H-pyrrol-3-yl}-acrylamide,
3. (E)-N-Hydroxy-3-{1-[4-(6-methoxy-pyridin-3-yl)-benzenesulfonyl]-1H-pyrrol-3-yl}-acrylamide,
4. (E)-3-{1-[4-(6-Amino-pyridin-3-yl)-benzenesulfonyl]-1H-pyrrol-3-yl}-N-hydroxy-acrylamide,
5. (E)-N-(2-Amino-phenyl)-3-{1-[4-(6-methoxy-pyridin-3-yl)-benzenesulfonyl]-1H-pyrrol-3-yl}-acrylamide,
6. (E)-N-(2-Amino-phenyl)-3-{1-[4-(6-amino-pyridin-3-yl)-benzenesulfonyl]-1H-pyrrol-3-yl}-acrylamide,
7. (E)-N-(2-Amino-phenyl)-3-{1-[4-(1-methyl-1H-pyrazol-4-yl)-benzenesulfonyl]-1H-pyrrol-3-yl}-acrylamide,
8. (E)-N-Hydroxy-3-{1-[4'-(2-morpholin-4-yl-ethyl)-biphenyl-4-sulfonyl]-1H-pyrrol-3-yl}-acrylamide,
9. (E)-N-Hydroxy-3-{1-[3'-(2-morpholin-4-yl-ethyl)-biphenyl-4-sulfonyl]-1H-pyrrol-3-yl}-acrylamide,
10. (E)-3-{1-[3-(6-Amino-pyridin-3-yl)-benzenesulfonyl]-1H-pyrrol-3-yl}-N-hydroxy-acrylamide,
11. (E)-N-Hydroxy-3-{1-[3-(6-methoxy-pyridin-3-yl)-benzenesulfonyl]-1H-pyrrol-3-yl}acrylamide,
12. (E)-N-Hydroxy-3-{1-[3-(1-methyl-1H-pyrazol-4-yl)-benzenesulfonyl]-1H-pyrrol-3-yl}-acrylamide, 13. (E)-N-Hydroxy-3-{1-[3-(1-methyl-1H-indol-5-yl)-benzenesulfonyl]-1H-pyrrol-3-yl}-acrylamide,
14. (E)-N-(2-Amino-phenyl)-3-{1-[3-(6-methoxy-pyridin-3-yl)-benzenesulfonyl]-1H-pyrrol-3-yl}-acrylamide,
15. (E)-N-(2-Amino-phenyl)-3-{1-[3-(1-methyl-1H-pyrazol-4-yl)-benzenesulfonyl]-1H-pyrrol-3-yl}-acrylamide,
16. (E)-N-Hydroxy-3-{1-[4'-(2-morpholin-4-yl-ethyl)-biphenyl-3-sulfonyl]-1H-pyrrol-3-yl}-acrylamide,
17. (E)-N-(2-Amino-phenyl)-3-{1-[3-(6-amino-pyridin-3-yl)-benzenesulfonyl]-1H-pyrrol-3-yl}-acrylamide,
18. (E)-N-(2-Amino-phenyl)-3-{1-[3'-(2-morpholin-4-yl-ethyl)-biphenyl-3-sulfonyl]-1H-pyrrol-3-yl}acrylamide,
19. (E)-N-(2-Amino-phenyl)-3-{1-[4'-(2-morpholin-4-yl-ethyl)-biphenyl-3-sulfonyl]-1H-pyrrol-3-yl}acrylamide,
20. (E)-N-Hydroxy-3-{1-[3'-(2-morpholin-4-yl-ethyl)-biphenyl-3-sulfonyl]-1H-pyrrol-3-yl}-acrylamide,
21. (E)-N-Hydroxy-3-[1-(2'-methanesulfonylamino-biphenyl-4-sulfonyl)-1H-pyrrol-3-yl]-acrylamide
22. (E)-N-hydroxy-3-[1-(3'-methanesulfonylamino-biphenyl-4-sulfonyl)-1H-pyrrol-3-yl]-acrylamide
23. (E)-N-Hydroxy-3-[1-(4'-methanesulfonylamino-biphenyl-sulfonyl)-1H-pyrrol-3-yl]-acrylamide
24. 4'-[3-((E)-2-Hydroxycarbamoyl-vinyl)-pyrrole-1-sulfonyl]-biphenyl-4-carboxylic acid (2-dimethylamino-ethyl)-amide,
25. 4'-[3-((E)-2-Hydroxycarbamoyl-vinyl)-pyrrole-1-sulfonyl]-biphenyl-3-carboxylic acid (2-dimethylamino-ethyl)-amide,
26. (E)-3-[1-(4'-Dimethylaminomethyl-biphenyl-4-sulfonyl)-1H-pyrrol-3-yl]-N-hydroxy-acrylamide,
27. (E)-3-[1-(2'-Dimethylaminomethyl-biphenyl-4-sulfonyl)-1H-pyrrol-3-yl]-N-hydroxy-acrylamide,
28. (E)-N-Hydroxy-3-(1-{4-[2-(4-methyl-piperazin-1-yl)-pyridin-4-yl]-benzenesulfonyl}-1H-pyrrol-3-yl)-acrylamide,
29. (E)-N-Hydroxy-3-{1-[4'-(toluene-4-sulfonylamino)-biphenyl-4-sulfonyl]-1H-pyrrol-3-yl}-acrylamide,
30. 3'-[3-((E)-2-Hydroxycarbamoyl-vinyl)-pyrrole-1-sulfonyl]-biphenyl-4-carboxylic acid (2-dimethylamino-ethyl)-amide,
31. (E)-N-Hydroxy-3-[1-(3'-morpholin-4-ylmethyl-biphenyl-3-sulfonyl)-1H-pyrrol-3-yl]-acrylamide,
32. (E)-N-Hydroxy-3-(1-{4'-[2-(4-methyl-piperazin-1-yl)-ethoxy]-biphenyl-3-sulfonyl}-1H-pyrrol-3-yl)-acrylamide,
33. (E)-N-Hydroxy-3-(1-{3-[2-(4-methyl-piperazin-1-yl)-pyridin-4-yl]-benzenesulfonyl}-1H-pyrrol-3-yl)-acrylamide,
34. (E)-N-Hydroxy-3-{1-[4'-(2-morpholin-4-yl-ethoxy)-biphenyl-3-sulfonyl]-1H-pyrrol-3-yl}-acrylamide,
35. (E)-N-(2-Amino-phenyl)-3-{1-[4-(1-benzyl-1H-pyrazol-4-yl)-benzenesulfonyl]-1H-pyrrol-3-yl}-acrylamide,
36. (E)-N-Hydroxy-3-[1-(4'-morpholin-4-ylmethyl-biphenyl-3-sulfonyl)-1H-pyrrol-3-yl]-acrylamide,
37. (E)-3-[1-(4'-Dimethylaminomethyl-biphenyl-3-sulfonyl)-1H-pyrrol-3-yl]-N-hydroxy-acrylamide,
38. (E)-N-Hydroxy-3-{1-[4'-(3-morpholin-4-yl-propoxy)-biphenyl-3-sulfonyl]-1H-pyrrol-3-yl}-acrylamide,
39. (E)-N-(2-Amino-phenyl)-3-[1-(4'-dimethylsulfamoyl-biphenyl-4-sulfonyl)-1H-pyrrol-3-yl]-acrylamide,
40. (E)-3-[1-(3'-Acetylamino-biphenyl-4-sulfonyl)-1H-pyrrol-3-yl]-N-(2-amino-phenyl)-acrylamide,
41. (E)-3-[1-(2'-Dimethylaminomethyl-biphenyl-3-sulfonyl)-1H-pyrrol-3-yl]-N-hydroxy-acrylamide,
42. (E)-N-Hydroxy-3-(1-{5-[2-(4-methyl-piperazin-1-yl)-pyridin-4-yl]-thiophene-2-sulfonyl}-1H-pyrrol-3-yl)-acrylamide,
43. (E)-N-Hydroxy-3-{1-[4'-(2-pyrrolidin-1-yl-ethoxy)-biphenyl-3-sulfonyl]-1H-pyrrol-3-yl}-acrylamide,
44. 4'-{3-[(E)-2-(2-Amino-phenylcarbamoyl)-vinyl]-pyrrole-1-sulfonyl}-biphenyl-3-carboxylic acid (2-dimethylamino-ethyl)-amide,
45. (E)-N-Hydroxy-3-{1-[4'-(3-morpholin-4-yl-propyl)-biphenyl-3-sulfonyl]-1H-pyrrol-3-yl}acrylamide,
46. (E)-3-{1-[5-(4-Dimethylaminomethyl-phenyl)-thiophene-2-sulfonyl]-1H-pyrrol-3-yl}-N-hydroxy-acrylamide,
47. (E)-N-(2-Amino-phenyl)-3-[1-(4'-dimethylaminomethyl-biphenyl-4-sulfonyl)-1H-pyrrol-3-yl]-acrylamide,
48. (E)-N-(2-Amino-phenyl)-3-(1-{4-[2-(4-methyl-piperazin-1-yl)-pyridinyl]-benzenesulfonyl}-1H-pyrrol-3-yl)-acrylamide,
49. (E)-3-[1-(4'-Acetylamino-biphenyl-4-sulfonyl)-1H-pyrrol-3-yl]-N-(2-amino-phenyl)-acrylamide,
50. (E)-N-Hydroxy-3-{1-[5-(3-morpholin-4-ylmethyl-phenyl)-thiophene-2-sulfonyl]-1H-pyrrol-3-yl}-acrylamide,
51. (E)-N-(2-Amino-phenyl)-3-[1-(3'-hydroxymethyl-biphenyl-4-sulfonyl)-1H-pyrrol-3-yl]-acrylamide,
52. (E)-N-(2-Amino-phenyl)-3-{1-[4-(3,5-dimethyl-isoxazol-4-yl)-benzenesulfonyl]-1H-pyrrol-3-yl}-acrylamide,
53. (E)-N-(2-Amino-phenyl)-3-[1-(4'-methanesulfonylamino-biphenyl-4-sulfonyl)-1H-pyrrol-3-yl]-acrylamide,
54. (E)-N-Hydroxy-3-{1-[5-(4-morpholin-4-ylmethyl-phenyl)-thiophene-2-sulfonyl]-1H-pyrrol-3-yl}-acrylamide,
55. (E)-N-Hydroxy-3-[1-(5-{4-[2-(4-methyl-piperazin-1-yl)-ethoxy]-phenyl}-thiophene-2-sulfonyl)-1H-pyrrol-3-yl]-acrylamide,
56. (E)-N-Hydroxy-3-(1-{5-[4-(2-morpholin-4-yl-ethoxy)-phenyl]-thiophene-2-sulfonyl}-1H-pyrrol-3-yl)-acrylamide,
57. (E)-N-Hydroxy-3-(1-{5-[4-(3-morpholin-4-yl-propoxy)-phenyl]-thiophene-2-sulfonyl}-1H-pyrrol-3-yl)-acrylamide,
58. (E)-N-Hydroxy-3-(1-{4'-[(2-methoxy-ethylamino)-methyl]-biphenyl-3-sulfonyl}-1H-pyrrol-3-yl)-acrylamide,
59. (E)-N-(2-Amino-phenyl)-3-[1-(3'-methanesulfonylamino-biphenyl-4-sulfonyl)-1H-pyrrol-3-yl]-acrylamide,
60. (E)-Hydroxy-3-{1-[5-(1-methyl-1H-pyrazol-4-yl)-thiophene-2-sulfonyl]-1H-pyrrol-3-yl}-acrylamide,
61. (E)-N-Hydroxy-3-(1-{5-[4-(2-morpholin-4-yl-ethyl)-phenyl]-thiophene-2-sulfonyl}-1H-pyrrol-3-yl)-acrylamide,
62. (E)-N-Hydroxy-3-{1-[4'-(4-methyl-piperazin-1-ylmethyl)-biphenyl-3-sulfonyl]-1H-pyrrol-3-yl}-acrylamide, and
63. (E)-3-[1-(4'-Cyclopropylaminomethyl-biphenyl-3-sulfonyl)-1H-pyrrol-3-yl]-N-hydroxy-acrylamide, and the salts thereof.

Further on, exemplary compounds according to this invention may also include any one selected from
64. (E)-N-Hydroxy-3-[1-(3'-morpholin-4-ylmethyl-biphenyl-4-sulfonyl)-1H-pyrrol-3-yl]-acrylamide,
65. (E)-3-[1-(4-Benzo[1,3]dioxol-5-yl-benzenesulfonyl)-1H-pyrrol-3-yl]-N-hydroxy-acrylamide,
66. (E)-3-[1-(3'-Amino-biphenyl-4-sulfonyl)-1H-pyrrol-3-yl]-N-hydroxy-acrylamide,
67. (E)-N-Hydroxy-3-[1-(4'-hydroxy-biphenyl-4-sulfonyl)-1H-pyrrol-3-yl]-acrylamide,
68. (E)-N-Hydroxy-3-(1-{4'-[2-(1-methyl-piperidin-4-yl)-ethoxy]-biphenyl-4-sulfonyl}-1H-pyrrol-3-yl)-acrylamide,
69. (E)-3-[1-(3'-Dimethylamino-biphenyl-4-sulfonyl)-1H-pyrrol-3-yl]-N-hydroxy-acrylamide, 70. (E)-3-{1-[4-(2,3-Dihydro-benzofuran-5-yl)-benzenesulfonyl]-1H-pyrrol-3-yl}-N-hydroxy-acrylamide,
71. (E)-N-Hydroxy-3-[1-(4'-morpholin-4-yl-biphenyl-4-sulfonyl)-1H-pyrrol-3-yl]-acrylamide,
72. (E)-N-Hydroxy-3-{1-[3'-(3-pyrrolidin-1-yl-propoxy)-biphenyl-4-sulfonyl]-1H-pyrrol-3-yl}-acrylamide,
73. (E)-N-Hydroxy-3-(1-{3'-[3-(4-methyl-piperazin-1-yl)-propoxy]-biphenyl-4-sulfonyl}-1H-pyrrol-3-yl)-acrylamide,
74. (E)-N-Hydroxy-3-{1-[3'-(3-morpholin-4-yl-propoxy)-biphenyl-4-sulfonyl]-1H-pyrrol-3-yl}-acrylamide,
75. (E)-N-Hydroxy-3-[1-(3'-morpholin-4-ylmethyl-biphenyl-4-sulfonyl)-1H-pyrrol-3-yl]-acrylamide,
76. (E)-N-Hydroxy-3-(1-{4'-[2-(4-methyl-piperazin-1-yl)-ethoxy]-biphenyl-4-sulfonyl}-1H-pyrrol-3-yl)-acrylamide,
77. (E)-N-Hydroxy-3-{1-[4'-(2-morpholin-4-yl-ethoxy)-biphenyl-4-sulfonyl]-1H-pyrrol-3-yl}-acrylamide,
78. (E)-N-Hydroxy-3-{1-[4'-(3-morpholin-4-yl-propoxy)-biphenyl-4-sulfonyl]-1H-pyrrol-3-yl}-acrylamide,
79. (E)-N-Hydroxy-3-(1-{4'-[3-(4-methyl-piperazin-1-yl)-propoxy]-biphenyl-4-sulfonyl)-1H-pyrrol-3-yl}-acrylamide,
80. (E)-N-Hydroxy-3-{1-[3'-(2-pyrrolidin-1-yl-ethoxy)-biphenyl-4-sulfonyl]-1H-pyrrol-3-yl}-acrylamide,
81. (E)-N-Hydroxy-3-{1-[4'-(3-pyrrolidin-1-yl-propoxy)-biphenyl-4-sulfonyl]-1H-pyrrol-3-yl}-acrylamide,
82. (E)-N-Hydroxy-3-[1-(4'-methoxy-biphenyl-4-sulfonyl)-1H-pyrrol-3-yl]-acrylamide,
83. (E)-N-Hydroxy-3-(1-{4-[1-(2-morpholin-4-yl-ethyl)-1H-[1,2,3]triazol-4-yl]-benzenesulfonyl}-1H-pyrrol-3-yl)-acrylamide,
84. (E)-3-[1-(4'-Cyclopentylaminomethyl-biphenyl-4-sulfonyl)-1H-pyrrol-3-yl]-N-hydroxy-acrylamide,
85. (E)-N-Hydroxy-3-[1-(3'-trifluoromethyl-biphenyl-4-sulfonyl)-1H-pyrrol-3-yl]-acrylamide,
86. (E-3-{1-[5-(3-Dimethylaminomethyl-phenyl)-thiophene-2-sulfonyl]-1H-pyrrol-3-yl}-N-hydroxy-acrylamide,
87. (E)-3-[1-(3-Dimethylaminomethyl-biphenyl-3-sulfonyl)-1H-pyrrol-3-yl]-N-hydroxy-acrylamide,
88. (E)-N-Hydroxy-3-{1-[4'-(2-morpholin-4-yl-ethyl)-biphenyl-3-sulfonyl]-1H-pyrrol-3-yl}-acrylamide,
89. (E)-N-(2-Amino-phenyl)-3-{1-[6-(4-dimethylaminomethyl-phenyl)-pyridine-3-sulfonyl]-1H-pyrrol-3-yl}-acrylamide,
90. (E)-N-Hydroxy-3-{1-[5-(2-methyl-thiazol-4-yl)-thiophene-2-sulfonyl]-1H-pyrrol-3-yl}-acrylamide,
91. (E)-3-[1-(4-Aminomethyl-biphenyl-3-sulfonyl)-1H-pyrrol-3-yl]-N-hydroxy-acrylamide,
92. (E)-N-Hydroxy-3-(1-{6-[4-(2-pyrrolidin-1-yl-ethoxy)-phenyl]-pyridine-3-sulfonyl}-1H-pyrrol-3-yl)-acrylamide,
93. (E)-3-[1-(4'-Aminomethyl-biphenyl-4-sulfonyl)-1H-pyrrol-3-yl]-N-(2-amino-phenyl)-acrylamide,
94. (E)-3-{1-[5-(3-Aminomethyl-phenyl)-thiophene-2-sulfonyl]-1H-pyrrol-3-yl}-N-hydroxy-acrylamide,
95. (E)-N-(2-Amino-phenyl)-3-{1-[5-(4-dimethylaminomethyl-phenyl)-thiophene-2-sulfonyl]-1H-pyrrol-3-yl}-acrylamide,
96. (E)-N-(2-Amino-phenyl)-3-[1-(3'-dimethylaminomethyl-biphenyl-sulfonyl)-1H-pyrrol-3-yl]-acrylamide,
97. (E)-3-{1-[4'-(Acetylamino-methyl)-biphenyl-4-sulfonyl]-1H-pyrrol-3-yl}-N-(2-amino-phenyl)-acrylamide,
98. (E)-N-(2-Amino-phenyl)-3-{1-[4'-(methanesulfonylamino-methyl)biphenyl-4-sulfonyl]-1H-pyrrol-3-yl}-acrylamide,
99. (E)-N-Hydroxy-3-(1-{5-[4-(2-pyrrolidin-1-yl-ethoxy)-phenyl]-thiophene-2-sulfonyl}-1H-pyrrol-3-yl)-acrylamide,
100. (E)-3-{1-[5-(4-Dimethylsulfamoyl-phenyl)-thiophene-2-sulfonyl]-1H-pyrrol-3-yl}-N-hydroxy-acrylamide,
101. (E)-N-(2-Amino-phenyl)-3-[1-(4'-methanesulfonylamino-biphenyl-3-sulfonyl)-1H-pyrrol-3-yl]-acrylamide,
102. (E)-N-(2-Amino-phenyl)-3-[1-(4'-dimethylaminomethyl-biphenyl-3-sulfonyl)-1H-pyrrol-3-yl]-acrylamide,
103. (E)-N-Hydroxy-3-{1-[2'-(4-methyl-piperazin-1-yl)-[2,4']bipyridinyl-5-sulfonyl]-1H-pyrrol-3-yl}-acrylamide,
104. (E)-N-(2-Amino-phenyl)-3-{1-[5-(1-methyl-1H-pyrazol-4-yl)-thiophene-2-sulfonyl]-1H-pyrrol-3-yl}-acrylamide,
105. (E)-3-{1-[6-(4-Dimethylaminomethyl-phenyl)-pyridine-3-sulfonyl]-1H-pyrrol-3-yl}-N-hydroxy-acrylamide,
106. (E)-N-(2-Amino-phenyl)-3-(1-{5-[2-(4-methyl-piperazin-1-yl)-pyridin-4-yl]-thiophene-2-sulfonyl}-1H-pyrrol-3-yl)-acrylamide,
107. (E)-N-(2-Amino-phenyl)-3-[1-(4'-morpholin-4-ylmethyl-biphenyl-4-sulfonyl)-1H-pyrrol-3-yl]-acrylamide,
108. (E)-N-(2-Amino-phenyl)-3-{1-[4'-(2-pyrrolidin-1-yl-ethoxy)-biphenyl-4-sulfonyl]-1H-pyrrol-3-yl}-acrylamide,
109. (E)-N-Hydroxy-3-(1-{4-[1-(2-piperidin-1-yl-ethyl)-1H-[1,2,3]triazol-4-yl]-benzenesulfonyl}-1H-pyrrol-3-yl)-acrylamide,
110. (E)-3-[1-(3'-Dimethylaminomethyl-biphenyl-3-sulfonyl)-1H-pyrrol-3-yl]-N-hydroxy-acrylamide,
111. (E)-N-(2-Amino-phenyl)-3-(1-{5-[4-(methynesulfonylamino-methyl)-phenyl]-thiophene-2-sulfonyl}-1H-pyrrol-3-yl)-acrylamide,
112. (E)-N-(2-Amino-phenyl)-3-{1-[3'-(methanesulfonylamino-methyl)-biphenyl-3-sulfonyl]-1H-pyrrol-3-yl}-acrylamide,
113. (E)-3-(1-{5-[4-(Acetylamino-methyl)-phenyl]-thiophene-2-sulfonyl}-1H-pyrrol-3-yl)N-(2-amino-phenyl)-acrylamide,
114. (E)-N-(2-Amino-phenyl)-3-{1-[5-(3-dimethylaminomethyl-phenyl)-thiophene-2-sulfonyl]-1H-pyrrol-3-yl}-acrylamide,
115. (E)-N-(2-Amino-phenyl)-3-[1-(3'-dimethylaminomethyl-biphenyl-3-sulfonyl)-1H-pyrrol-3-yl]-acrylamide,
116. (E)-3-[1-(3'-Dimethylaminomethyl-biphenyl-4-sulfonyl)-1H-pyrrol-3-yl]-N-hydroxy-acrylamide,
117. (E)-3-{1-[5-(3-Dimethylaminomethyl-phenyl)-thiophene-2-sulfonyl]-1H-pyrrol-3-yl}-N-hydroxy-acrylamide,
118. (E)-3-{1-[3-(Acetylamino-methyl)-biphenyl-3-sulfonyl]-1H-pyrrol-3-yl}-N-(2-amino-phenyl)-acrylamide,
119. (E)-N-(2-Amino-phenyl)-3-{1-[6-(1-methyl-1H-pyrazol-4-yl)-pyridine-3-sulfonyl]-1H-pyrrol-3-yl}-acrylamide,
120. (E)-N-Hydroxy-3-{1-[6-(1-methyl-1H-pyrazol-4-yl)-pyridine-3-sulfonyl]-1H-pyrrol-3-yl}-acrylamide, and
121. (E)-3-{1-[6-(3-Dimethylaminomethyl-phenyl)-pyridine-3-sulfonyl]-1H-pyrrol-3-yl}-N-hydroxy-acrylamide, and the salts thereof.

In an embodiment of the foregoing, exemplary compounds according to this invention may especially include any one selected from the group consisting of the compounds 2, 4, 7, 16, 26, 28, 32, 33, 38, 42 and 46 as mentioned afore, and the salts thereof.

The compounds according to the present invention can be prepared, for example, as shown in the reaction schemes below and according to the reaction steps specified as follows, or, particularly, in a manner as described by way of example in the following examples, or analogously or similarly thereto using preparation procedures and synthesis strategies known to the person skilled in the art.

In reaction scheme 1 the carbon chain of compounds of formula V, in which R1, R2, R4 and R5 have the meanings mentioned above, is lengthened, for example, by a condensation reaction (with a malonic acid derivative) or by a Wittig or Julia reaction or, particularly in the case when R2 is hydrogen, by a Horner-Wadsworth-Emmons reaction (with a P-(alkoxycarbonyl)-phosphonic acid dialkyl ester) to obtain compounds of formula IV, in which R1, R2, R3, R4 and R5 have the meanings mentioned above and PG1 stands for a suitable temporary protective group for the carboxyl group, for example tert-butyl or one of those art-known protective groups mentioned in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000).

Compounds of formula V, in which R1, R2, R4 and R5 have the meanings mentioned above, are known, or can be prepared according to art-known procedures, or can be obtained as described in the following examples for the case that R2 is hydrogen from compounds of formula VI.

Compounds of formula VI are known or are accessible in a known manner or as described in the following examples.

Reaction scheme 1

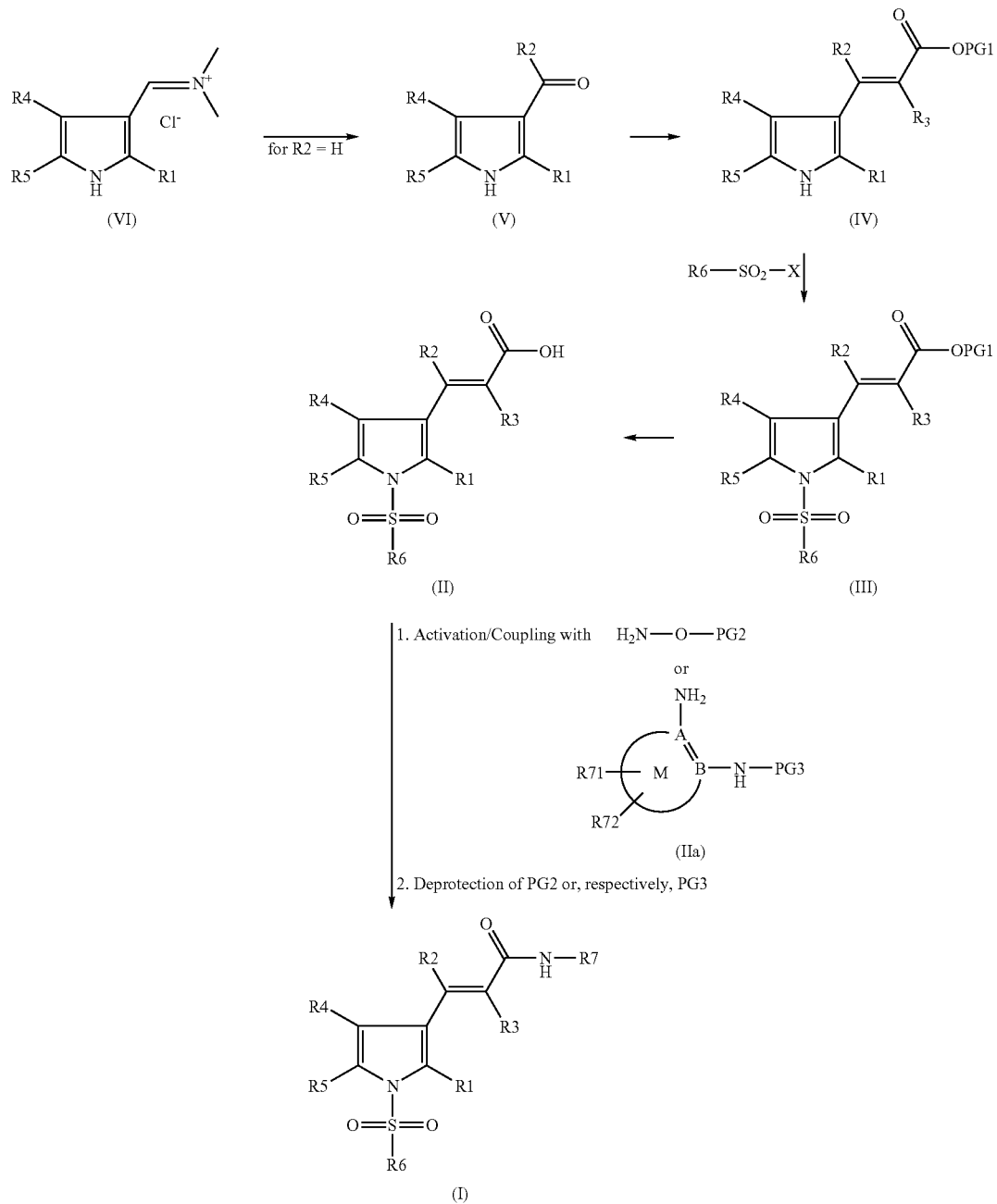

Compounds of formula IV, in which R1, R2, R3, R4 and R5 have the meanings mentioned above and PG1 stands for a said suitable protective group, can be reacted with compounds of formula R6—SO$_2$—X, in which R6 has the meanings mentioned above and X is a suitable leaving group, such as e.g. chlorine, to give the corresponding compounds of formula III.

In the next reaction step, the protective group PG1 of compounds of formula III can be removed in a manner as described in the following examples or according to an art-known manner to afford compounds of formula II.

Compounds of formula R6—SO$_2$—X are known or can be prepared in a known manner.

Compounds of formula II, in which R1, R2, R3, R4, R5 and R6 have the meanings given above, can be coupled with compounds of formulae H$_2$N—O-PG2, in which PG2 is a suitable oxygen protective group such as e.g. a suitable silyl or tetrahydropyran-2-yl protective group, or IIa, in which PG3 stands for a suitable nitrogen protective group such as e.g. the tert-butyloxycarbonyl protective group, by reaction with amide bond linking reagents optionally in the presence of coupling additives known to the person skilled in the art. Exemplary amide bond linking reagents known to the person skilled in the art which may be mentioned are, for example, carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetra-methyluronium tetrafluoroborate or O-(benzotriazol-1-yl)-N,N,N',N'-tetramthyl-uronium-hexafluorophosphate] and N,N'-carbonyldiimidazole.

Alternatively, compounds of formula II can be activated prior to the coupling reaction by forming an acid halide or acid anhydride optionally in an in-situ procedure without isolating the acid halide or acid anhydride.

Compounds of formulae H$_2$N—O-PG2 or IIa are known or can be prepared according to art-known processes.

Removal of the protective groups PG2 or PG3 can be obtained in a manner known for the person skilled in the art or as described in the following examples to give compounds of formula I, in which R1, R2, R3, R4, R5, R6 and R7 have the meanings mentioned above.

Compounds of formula I, in which R6 is Aa1, Ha1, Ha2, Ha3 or Ha4, or Hh1 or Ah1, can be prepared as outlined in the following reaction schemes, and specified below, or as described by way of example in the following examples, or analogously or similarly thereto.

Compounds of formula I, in which R6 is Aa1, Ha1, Ha2, Ha3 or Ha4 can be prepared as outlined in the following reaction scheme 1 or 2, and specified below, or as described by way of example in the following examples, or analogously or similarly thereto.

Reaction scheme 2:

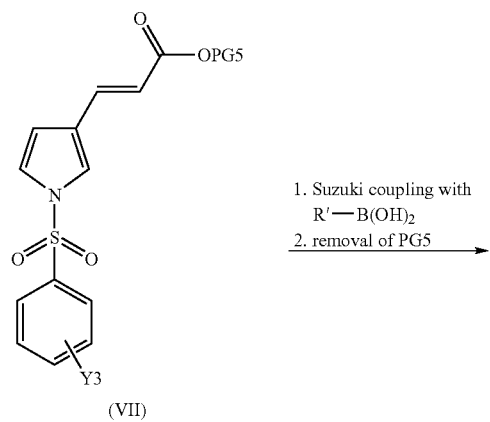

(VII)

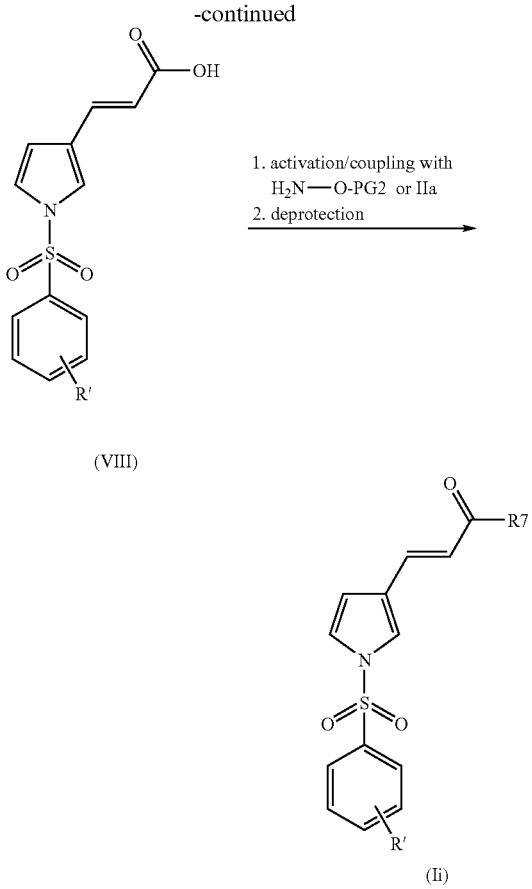

R': aryl or heteroaryl

As shown in reaction scheme 2 compounds of formula VII, in which Y3 is a suitable leaving group, such as e.g. iodine or bromine, and PG5 stands for a suitable temporary protective group for the carboxyl group, for example tert-butyl, can be reacted with boronic acids of formula R'—B(OH)$_2$, in which R' is the terminal aryl or heteroaryl moiety of the abovementioned Aa1, Ha1, Ha2, Ha3 or Ha4 radicals, or the boronic add esters (e.g. the pinacol esters) thereof, to give in an art-known Suzuki reaction the corresponding CC-coupled compounds, which are deprotected by removal of PG5 to give corresponding free adds of formula VIII, which can be coupled with compounds of formulae H$_2$N—O-PG2 or IIa as described above to give, after removal of PG2 or PG3, corresponding compounds of formula II.

Alternatively, as shown in reaction scheme 3 compounds of formula VII, in which Y3 is a suitable leaving group, such as e.g. trifluoromethylsulfonyloxy or, particularly, iodine or bromine, and PG5 stands for a suitable temporary protective group for the carboxyl group, for example tert-butyl, can be deprotected by removal of PG5, and the free carboxylic acid can be then coupled with compounds of formulae H$_2$N—O-PG2 or IIa as described above to give corresponding compounds of formula IX. Compounds of formula IX are reacted with boronic acids of formula R'—B(OH)$_2$, in which R' is the terminal aryl or heteroaryl moiety of the abovementioned Aa1, Ha1, Ha2, Ha3 or Ha4 radicals, or the boronic add esters (e.g. the pinacol esters) thereof, to give in an art-known Suzuki reaction the corresponding CC-coupled compounds, Reaction scheme 3:

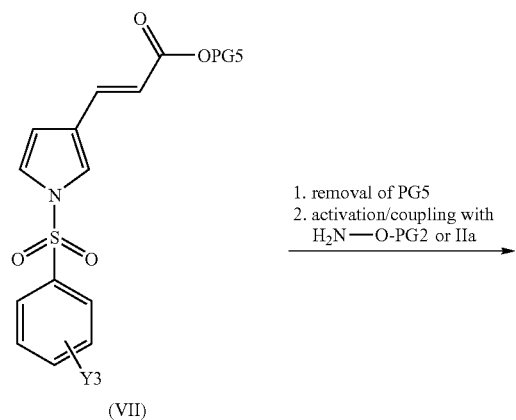

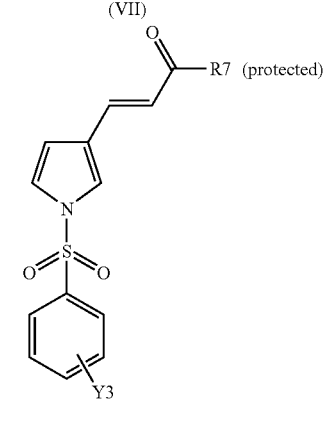

R': aryl or heteroaryl

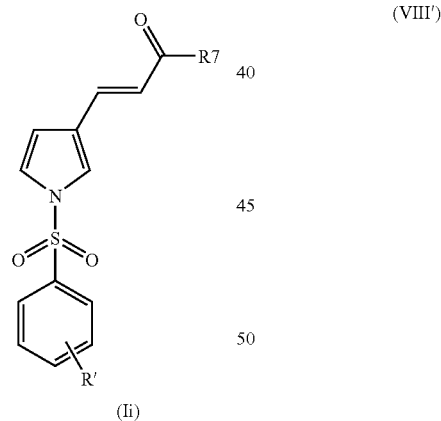

Reaction scheme 4:

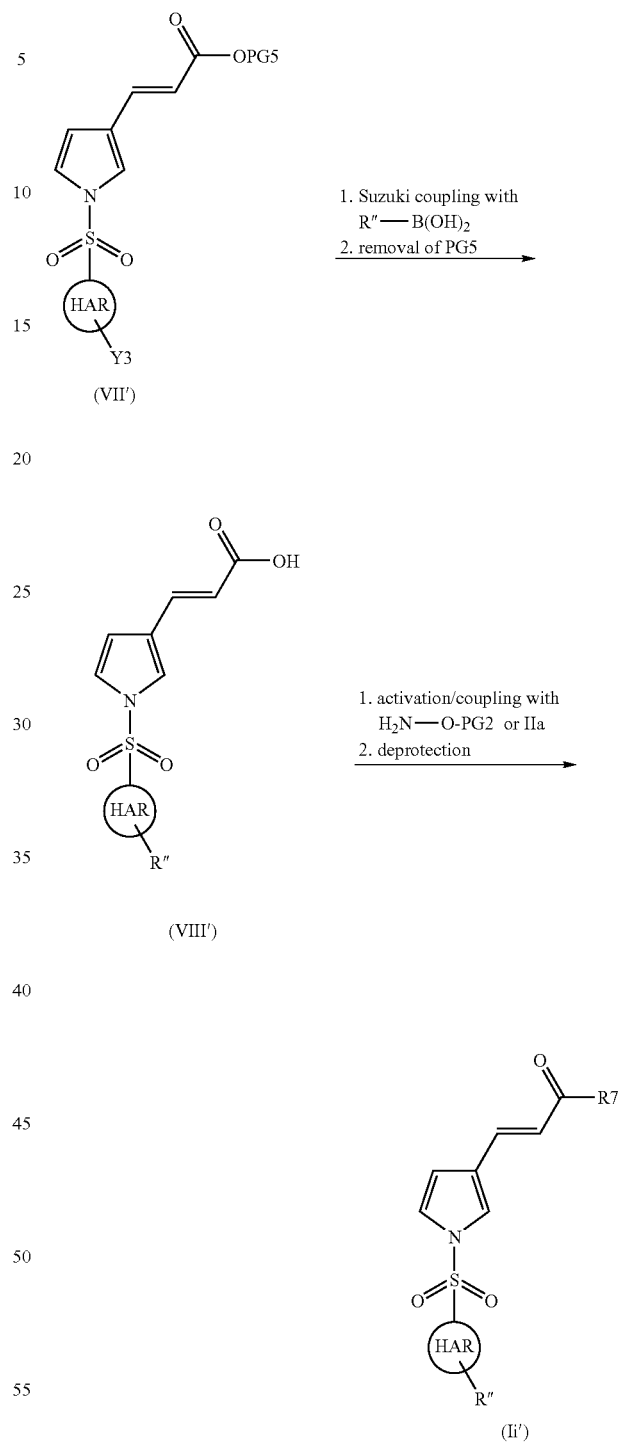

HAR: heteroaryl ring, e.g. pyridine or thiophene
R": aryl or heteroaryl

As shown in reaction scheme 4 or 5, compounds of formula I, in which R6 is Ah1 or Hh1, can be prepared analogously or similarly to the reactions outlined and specified above from the corresponding heteroarylsulphonylpyrrole derivatives of formula VII', in which HAR is the heteroaryl moiety of the abovementioned Ah1 or Hh1 radicals directly attached to the sulphonyl group, and the corresponding boronic acids of formula R"—B(OH)$_2$, in which R" is the terminal aryl or heteroaryl moiety of the abovementioned Ah1 or Hh1 radicals, or the boronic acid esters thereof, or as described by way of example in the following examples.

Reaction scheme 5:

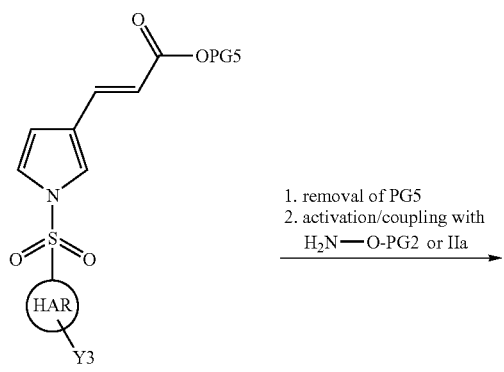

(VII')

1. removal of PG5
2. activation/coupling with H₂N—O-PG2 or IIa

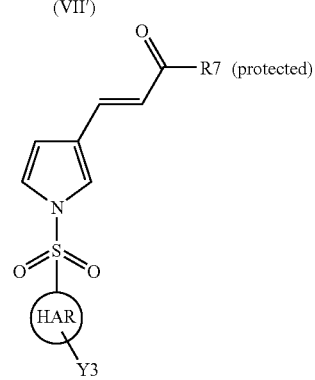

(IX')

1. Suzuki coupling with R''—B(OH)₂
2. deprotection of R7

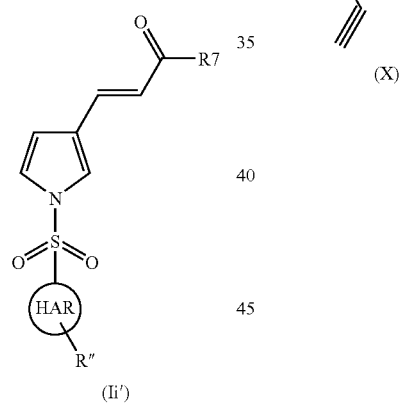

(Ii')

HAR: heteroaryl ring, e.g. pyridine or thiophene
R'': aryl or heteroaryl

Reaction scheme 6:

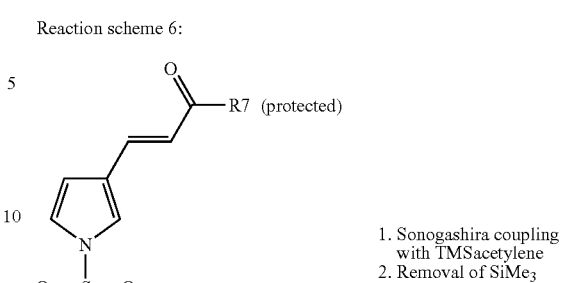

(IX)

1. Sonogashira coupling with TMSacetylene
2. Removal of SiMe₃

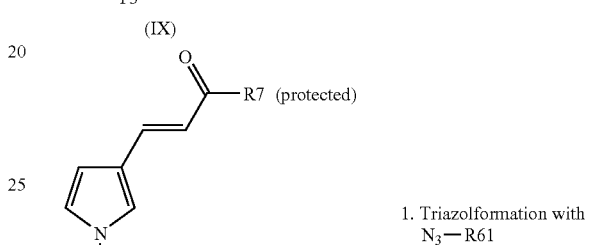

(X)

1. Triazolformation with N₃—R61
2. Deprotection of R7

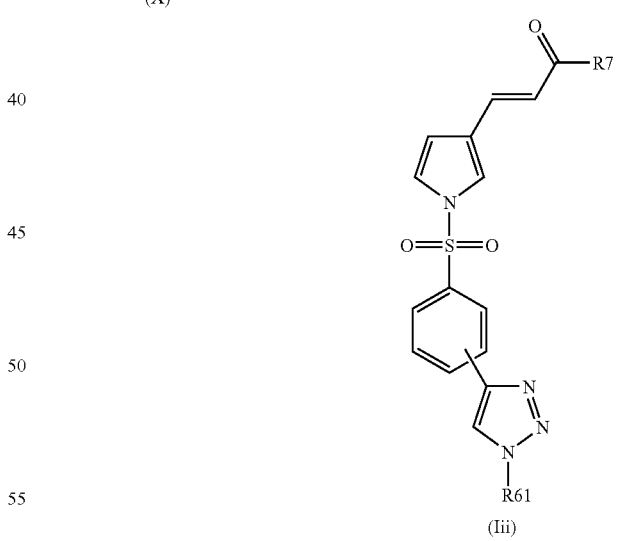

(Iii)

The Suzuki reactions can be carried out in a manner habitual per se to the skilled person or as described in the following examples, or analogously or similarly thereto.

Compounds of formula Ia, in which R' is [1,2,3]triazolyl can be obtained as shown in reaction scheme 6 from corresponding compounds of formula IX, in which Y3 is a suitable leaving group, such as e.g. iodine or bromine, which are reacted with TMS-acetylene under Sonogashira conditions to give, after removal of the TMS group, corresponding compounds of formula X. Compounds of formula X can be reacted with azides, e.g. azides of formula R61—H₃, to give in an art-known Huisgen reaction the corresponding triazoles, which are deprotected to give corresponding compounds of formula Iii.

Azides of formula R61—N₃ are known or can be obtained according to known procedures.

Starting from the appropriate starting compounds, compounds of formula VII or VII' or IX can be obtained according to the synthesis route shown in reaction scheme 1 and described above, according to art-known procedures, or analogously or similarly thereto.

The abovementioned compounds of formula R'—B(OH)$_2$ or R'''—B(OH)$_2$ are known or can be obtained according to art-known procedures.

When the protective groups PG2 or PG3 are deprotected or purification is carried out under the presence of an inorganic or organic acid (e.g. hydrochloric acid or formic acid), the compounds of formula I may be obtained -depending on their individual chemical nature and the individual nature of the acid used—as free base or containing said acid in an stoichiometric or non-stoichiometric quantity. The amount of the acid contained can be determined according to art-known procedures, e.g. by titration.

When the compounds of formula I are chiral compounds (e.g. by having one or more chiral centers), the invention refers to all conceivable stereoisomers, like e.g. diastereomers and enantomers, in substantially pure form as well as in any mixing ratio, including the racemates, as well as the salts thereof.

In general, enantiomerically pure compounds of this invention may be prepared according to art-known processes, such as e.g. via asymmetric syntheses using chiral synthons or chiral reagents; by chromatographic separation on chiral separating columns; by means of salt formation of the racemic compounds with optically active acids or bases, subsequent resolution of the salts and release of the desired compound from the salt; by derivatization with chiral auxiliary reagents, subsequent diastereomer separation and removal of the chiral auxiliary group; or by (fractional) crystallization from a suitable solvent.

The reactions mentioned above can be expediently carried out analogously to the methods known to the person skilled in the art or as described by way of example in the following examples.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The isolation and purification of the substances according to the invention is carried out in a manner known per se, e.g. by distilling off the solvent in vacuo and recrystallizing the resulting residue from a suitable solvent or subjecting it to one of the customary purification methods, such as, for example, column chromatography on suitable support material.

Optionally, compounds of formula I can be converted into their salts, or, optionally, salts of the compounds of formula I can be converted into the free compounds of formula I.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as methanol, ethanol or isopropanol) which contains the desired add or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically or pharmaceutically intolerable salts can be converted into pharmacologically tolerable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of the formula I. All these other possible synthesis routes are also part of this invention.

The present invention also relates to intermediates, including their salts, methods and processes useful in synthesizing compounds according to this invention.

Having described the invention in detail, the scope of the present invention is not limited only to those described characteristics or embodiments. As will be apparent to persons skilled in the art, modifications, analogies, variations, derivations, homologisatons and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples serve to illustrate the invention further without restricting it. Likewise, further compounds of the formula I including their salts, whose preparation is not explicitly described, can be prepared in an analogous manner or in a manner familiar per se to the person skilled in the art using customary process techniques.

Any or all of the compounds of formula I which are mentioned as final products in the following examples as well as their salts are a preferred subject of the present invention.

In the examples, MS stands for mass spectrum, M for molecular ion, TSP for Thermospray Ionization, ESI for Electrospray Ionization, El for Electron Ionization, h for hours, min for minutes. Other abbreviations used herein have the meanings customary per se to the person skilled in the art.

EXAMPLES

Final Products 1. (E)-N-Hydroxy-3-{1-[4-(1-methyl-1H-indol-5-yl)-benzenesulfonyl]-1H-pyrrol-3-yl}-acrylamide A mixture of 0.346 g (E)-3-{1-[4-(1-methyl-1H-indol-5-yl)-benzenesulfonyl]-1H-pyrrol-3-yl}-N-(tetrahydro-pyran-2-yloxy)-acrylamide with 20 ml methanol and 13.9 ml 0.5M aqueous HCl is stirred at ambient temperature for 24 h. The crude product is isolated and in case of incomplete deprotection the resulted mixture is treated again with 1N aqueous HCl until the reaction is at completion. The crude product is isolated by evaporation and the title compound is isolated by prep-HPLC chromatography using an ammonium formiate gradient. By this method 0.047 g of the title compound are obtained.

Melting point: 177.1-178.8° C., sinter beginning from 154° C.

2. (E)-N-Hydroxy-3-{1-[4-(1-methyl-1H-pyrazol-4-yl)-benzenesulfonyl]-1H-pyrrol-3-yl}-acrylamide The compound is prepared analogously to example 1. After evaporation of the methanol part of the reaction mixture the suspension of the product in the residual aqueous media is centrifuged and the resulting solid is dried in vacuo. Melting point: 201.8-204.2

Alternatively:

A mixture of 0.3 g (E)-3-{1-[4-(1-methyl-1H-pyrazol-4-yl)-benzenesulfonyl]-1H-pyrrol-3-yl}-N-(tetrahydro-pyran-2-yloxy)-acrylamide in 22.5 ml MeOH and 17.1 ml 0.5 M aqueous HCl is stirred overnight at ambient temperature. The resulting milky suspension is treated with 1.5 g NaHCO$_3$ (pH7), evaporated and coevaporated with EtOH. The resulting residue is purified by silica gel flash chromatography and the resulting product is further purified by repeated washing with MeOH/CHCl3. 151 mg of the title compound are obtained with a mp of 188-198° C. The compound contains 0.0 HCl/mol.

Alternatively a Compound with 0.88 HCl/mol is Obtained:

(E)-N-Hydroxy-3-{1-[4-(1-methyl-1H-pyrazol-yl)-benzenesulfonyl]-1H-pyrrol-3-yl}-acrylamide, compound with hydrochloric acid A mixture of 3.9 g (E)-3-{1-[4-(1-methyl-1H-pyrazol-4-yl)-benzenesulfonyl]-1H-pyrrol-3-yl}-N-(tetrahydro-pyran-2-yloxy)-acrylamide in 146.4 ml MeOH and 24.4 ml 0.5 M aqueous HCl is stirred overnight at ambient temperature. The resulting suspension is filtered. A product with 0.88 HCl/mol is obtained. The solid product sinters at 146° C.

3. (E)-N-Hydroxy-3-{1-[4-(6-methoxy-pyridin-3-yl)-benzenesulfonyl]-1H-pyrrol-3-yl}-acrylamide, Compound with Hydrochloric Acid The method which is used for the preparation is analogous to the method described for compound 1. After evaporation of the methanol part of the reaction mixture the suspension of the product in the residual aqueous media is centrifuged. The resulting solid is collected, washed with diisopropylether and dried in vacuo. Sinter: 154.7° C., Melting point: 157.9-163.2° C.

4. (E)-3-∴1-[4-(6-Amino-pyridin-3-yl)-benzenesulfonyl]-1H-pyrrol-3-yl)-N-hydroxy-acrylamide, compound with hydrochloric acid The method which is used for the preparation is analogous to the method described for compound 1. After evaporation of the methanol part of the reaction mixture the suspension of the product in the residual aqueous media is centrifuged. The resulting solid is collected, washed twice with diisopropylether and dried in vacuo. Melting point: 212.8-218.2° C. The compound contains 1.00 HCl/mol.

Alternatively:

[5-(4-{3-[(E)-2-(Tetrahydro-pyran-2-yloxycarbamoyl)-vinyl]-pyrrole-1-sulfonyl}phenyl)-pyridin-2-yl]-carbamic acid tert-butyl ester (0.933 g) is dissolved in 4N HCl in dioxane (41 mL) and MeOH (19 mL) and stirred for 1 hour at ambient temperature. The solution is evaporated and the residue is suspended in diethylether (15 mL). The solid is filtered and dried. 0.70 g of the title compound are obtained with a melting point of 212-224° C. The compound contains 0.98 HCl/mol.

5. (E)-N-(2-Amino-phenyl)-3-{1-[4-(6-methoxy-pyridin-3-yl)-benzenesulfonyl]-1H-pyrrol-3-yl}-acrylamide, Compound with Hydrochloric Acid A mixture of [2-((E)-3-{1-[4-(6-methoxy-pyridin-3-yl)-benzenesulfonyl]-1H-pyrrol-3-yl}-allanoylamino)-phenyl]-carbamic acid tert-butyl ester, 2.5 ml dioxane and 25 ml 4N HCl in dioxane is stirred at ambient temperature overnight. The solution is evaporated and the crude product is washed and dried in vacuo.

Melting point: sintering at 82.6° C.

6. (E)-N-(2-Amino-phenyl)-3-{1-[4-(6-amino-pyridin-3-yl)-benzenesulfonyl]-1H-pyrrol-3-yl}-acrylamide, Compound with Hydrochloric Acid The method which is used for the preparation is analogous to the method described for compound 5.

Melting point: 198.8-205.3° C.

Alternatively:

[2-((E)-3-{1-[4-(1-Methyl-1H-pyrazol-4-yl)-benzenesulfonyl]-1H-pyrrol-3-yl}-allanoylamino)-phenyl]-carbamic acid tert-butyl ester (4.00 g) is dissolved in 4N HCl in dioxane (120 mL) and the mixture is stirred for 4 days at ambient temperature. The resulting solid is filtered, washed with diethylether and dried. 3.44 g of the title compound are obtained with a melting point of 214-216° C. The compound contains 1.44 HCl/mol.

7. (E)-N-(2-Amino-phenyl)-3-{1-[4-(1-methyl-1H-pyrazol-4-yl)-benzenesulfonyl]-1H-pyrrol-3-yl}-acrylamide, Compound with Hydrochloric Acid The method used for the preparation is analogous to the method described for compound 5. During the deprotection procedure, starting material is detected. Thus, additional aqueous 1N HCl in water is added. The solvent is partly evaporated and the resulting suspension is centrifuged and the solid is collected. The resulting solid is washed with diisopropylether and dried in vacuo.

Sinter at 146.9° C., Melting point: 191.4-195.9° C.

8. (E)-N-Hydroxy-3-{1-[4'-(2-morpholin-4-yl-ethyl)-biphenyl-4-sulfonyl]-1H-pyrrol-3-yl}-acrylamide, Compound with Hydrochloric Acid The compound is prepared analogously to example 1. During the reaction, the product separates from the reaction mixture spontaneously. This solid is collected, washed with water and diisopropylether and dried in vacuo. mp: 169.4-174.8° C.

9. (E)-N-Hydroxy-3-{1-[3'-(2-morpholin-4-yl-ethyl)-biphenyl-4-sulfonyl]-1H-pyrrol-3-yl}-acrylamide, Compound with Hydrochloric Acid The compound is prepared analogously to example 1. During the reaction, the product separates from the reaction mixture spontaneously. This solid is collected, washed with water and diisopropylether and dried in vacuo. mp: 165.8-171.6° C.

Using similar procedures to those described herein, but with suitable choice of starting materials, further compounds may be prepared, such as e.g.:

10. (E)-3-{1-[3-(6-Amino-pyridin-3-yl)-benzenesulfonyl]-1H-pyrrol-3-yl}-N-hydroxy-acrylamide, compound with hydrochloric acid A mixture of 0.151 g (E)-3-{1-[3-(6-amino-pyridin-3-yl)-benzenesulfonyl]-1H-pyrrol-3-yl}-N-(tetrahydro-pyran-2-yloxy)-acrylamide with 5.0 ml methanol and 9.0 ml 1M aqueous HCl is stirred at ambient temperature for 3 days. The suspension is centrifuged and the resulting solid is washed with water and diisopropylether. The title compound is dried in vacuo. By this method 0.091 g of a colorless solid are obtained. Melting point: sinter is beginning from 193° C. on.

11. (E)-N-Hydroxy-3-{1-[3-(6-methoxy-pyridin-3-yl)-benzenesulfonyl]-1H-pyrrol-3-yl}-acrylamide, Compound with Formic Acid A mixture of 0.150 g (E)-3-{1-[3-(6-methoxy-pyridin-3-yl)-benzenesulfonyl]-1H-pyrrol-3-yl}-N-(tetrahydro-pyran-2-yloxy)-acrylamide with 5.0 ml methanol and 9.0 ml 1M aqueous HCl is stirred at ambient temperature. After 3 days the mixture is treated again with 1M aqueous HCl until the reaction is at completion. The solution is lyophilized. The crude product is isolated by prep HPLC chromatography using an ammonium formiate gradient. By this method 0.009 g of a colorless powder are obtained.

Melting point: 110-117° C. The compound contains formic acid.

12. (E)-N-Hydroxy-3-(1-[3-(1-methyl-1H-pyrazol-4-yl)-benzenesulfonyl]-1H-pyrrol-3-yl)-acrylamide A mixture of 0.086 g (E)-3-{1-[3-(1-methyl-1H-pyrazol-4-yl)-benzenesulfonyl]-1H-pyrrol-3-yl}-N-(tetrahydro-pyran-2-yloxy)-acrylamide with 3.0 ml methanol and 7.0 ml 1M aqueous HCl is stirred at ambient temperature for 24 h. The suspension is partly evaporated and the residual mixture is centrifuged. The product is washed with water and diisopropylether and dried in vacuo. By this method 0.045 g of a light pink powder are obtained. Melting point: 155-160° C., sinter is beginning from 85° C.

13. (E)-N-Hydroxy-3-{1-[3-(1-methyl-1H-indol-5-yl)-benzenesulfonyl]-1H-pyrrol-3-yl}-acrylamide

14. (E)-N-(2-Amino-phenyl)-3-{1-[3-(6-methoxy-pyridin-3-yl)-benzenesulfonyl]-1H-pyrrol-3-yl}-acrylamide, Compound with Hydrochloric Acid A mixture of 0.071 g [2-((E)-3-{1-[3-(6-methoxy-pyridin-3-yl)-benzenesulfonyl]-1H-pyrrol-3-yl}-allanoylamino)-phenyl]-carbamic acid tert-butyl ester with 2.0 ml dioxane and 15.0 ml 4M HCl in dioxane is stirred at ambient temperature for 4 days. The compound is isolated by PLC plate chromatography. By this method 0.043 g of a brown oil are obtained. The compound contains HCl. m/z (MH$^+$)=475.0

15. (E)-N-(2-Amino-phenyl)-3-{1-[3-(1-methyl-1H-pyrazol-4-yl)-benzenesulfonyl]-1H-pyrrol-3-yl}-acrylamide, Compound with Hydrochloric Acid A mixture of 0.138 g [2-((E)-3-{1-[3-(1-methyl-1H-pyrazol-4-yl)-benzenesulfonyl]-1H-pyrrol-3-yl}-allanoylamino)-phenyl]-carbamic acid tert-butyl ester with 4.0 ml dioxane and 30.0 ml 4M HCl in dioxane is stirred at ambient temperature for 24 h. The solution is lyophilized. The title compound is isolated by PLC plate chromatography. By this method 0.073 g of a light brown solid are obtained.

Melting point: 193-197° C., sinter is beginning from 164° C.

16. (E)-N-Hydroxy-3-{1-[4-(2-morpholin-4-yl-ethyl)-biphenyl-3-sulfonyl]-1H-pyrrol-3-yl}-acrylamide, Compound with Hydrochloric Acid A mixture of 0.148 g (E)-3-{1-[4'-(2-morpholin-4-yl-ethyl)-biphenyl-3-sulfonyl]-1H-pyrrol-3-yl}-N-(tetrahydro-pyran-2-yloxy)-acrylamide with 5.0 ml methanol and 8.0 ml 1M aqueous HCL is stirred at ambient temperature for 24 h. The suspension is partly evaporated and centrifuged. The resulting powder is washed with water and diisopropylether and dried in vacuo. By this method 0.073 g of a light brown solid are obtained. Melting point: 170-177° C., sinter is beginning from 154° C. The compound contains 0.99 HCl/mol.

Alternatively:
(E)-3-{1-[4'-(2-Morpholinyl-ethyl)-biphenyl-3-sulfonyl]-1H-pyrrol-3-yl}-N-(tetrahydro-pyran-2-yloxy)-acrylamide (5.50 g) is dissolved in MeOH (150 mL), treated with 1N HCl (200 mL) and stirred 2 h at ambient temperature. Subsequently the solvents are evaporated and the residue is washed with diethylether. 5.2 g of the title compound are obtained with an melting point of 178-182° C. The compound contains 1.2 HCl/mol.

17. (E)-N-(2-Amino-phenyl)-3-{1-[3-(6-amino-pyridin-3-yl)-benzenesulfonyl]-1H-pyrrol-3-yl}-acrylamide, Compound with Hydrochloric Acid A mixture of 0.204 g [2-((E)-3-{1-[3-(6-amino-pyridin-3-yl)-benzenesulfonyl]-1H-pyrrol-3-yl}-allanoylamino)-phenyl]-carbamic acid tert-butyl ester with 4.0 ml dioxane and 4M HCl in dioxane is stirred at ambient temperature for 24 h. The suspension is partly evaporated and centrifuged. The product is washed with diisopropylether and dried in vacuo. By this method 0.206 g of a yellow powder are obtained. Melting point: sinter is beginning at 111° C.

18. (E)-N-(2-Amino-phenyl)-3-{1-[3'-(2-morpholin-4-yl-ethyl)-biphenyl-3-sulfonyl]-1H-pyrrol-3-yl}-acrylamide, Compound with Hydrochloric Acid A mixture of 0.263 g [2-((E)-3-{1-[3'-(2-morpholin-4-yl-ethyl)-biphenyl-3-sulfonyl]-1H-pyrrol-3-yl}-allanoylamino)-phenyl]-carbamic acid tert-butyl ester with 7.0 ml dioxane and 55 ml 4M HCl in dioxane is stirred at ambient temperature for 48 h. The solution is lyophilized and isolated by PLC plate chromatography. By this method 0.082 g of a yellow oil are obtained.

m/z (MH$^+$)=557.2

19. (E)-N-(2-Amino-phenyl)-3-{1-[4'-(2-morpholin-4-yl-ethyl)-biphenyl-3-sulfonyl]-1H-pyrrol-3-yl}-acrylamide, Compound with Hydrochloric Acid A mixture of 0.329 g [2-((E)-3-{1-[4'-(2-morpholin-4-yl-ethyl)-biphenyl-3-sulfonyl]-1H-pyrrol-3-yl}-allanoylamino)-phenyl]-carbamic acid tert-butyl ester with 8.0 ml dioxane and 70.0 ml 4M HCL in dioxane is stirred at ambient temperature for 24 h. The solution is lyophilized and isolated by PLC plate chromatography. By this method 0.0319 of the title compound are obtained. Melting point: 82-90° C., sinter is beginning at 61° C.

20. (E)-N-Hydroxy-3-{1-[3'-(2-morpholin-4-yl-ethyl)-biphenyl-3-sulfonyl]-1H-pyrrol-3-yl}-acrylamide, Compound with Hydrochloric Acid A mixture of 0.110 g (E)-3-{1-[3'-(2-morpholin-4-yl-ethyl)-biphenyl-3-sulfonyl]-1H-pyrrol-3-yl}-N-(tetrahydro-pyran-2-yloxy)-acrylamide with 3.0 ml methanol and 6.0 ml 1M aqueous HCl is stirred at ambient temperature for 3 days. The suspension is centrifuged and washed with water. The crystals are dried in vacuo. By this method 0.076 g of the title compound are obtained. Melting point: 151-165° C., sinter is beginning from 80° C.

21. (E)-N-Hydroxy-3-[1-(2'-methanesulfonylamino-biphenyl-4-sulfonyl)-1H-pyrrol-3-yl]-acrylamide A mixture of 0.220 g (E)-3-[1-(2'-methanesulfonylamino-biphenyl-4-sulfonyl)-1H-pyrrol-3-yl]-N-(tetrahydro-pyran-2-yloxy)-acrylamide with 6.0 ml methanol and 13.0 ml 1M aqueous HCl is stirred at ambient temperature for 24 h. During evaporation the product starts to crystallize. The crystals are washed with water and diisopropylether. The crude product is purified by PLC plates chromatography. By this method 0.081 g of a red oil are obtained.

m/z (MH$^+$)=460.2

22. (E)-N-hydroxy-3-[1-(3'-methanesulfonylamino-biphenyl-4-sulfonyl)-1H-pyrrol-3-yl]-acrylamide A mixture of 0.334 g (E)-3-[1-(3'-methanesulfonylamino-biphenyl-4-sulfonyl)-1H-pyrrol-3-yl]-N-(tetrahydro-pyran-2-yloxy)-acrylamide with 11.0 ml methanol and 18.0 ml 1M aqueous HCL is stirred for 48 h. The suspension is evaporated and the solid is isolated and washed with water and diisopropylether. The crude product is purified by PLC plates chromatography. By this method 0.116 g of a red solid are obtained. Melting point: 137-148° C.

23. (E)-N-Hydroxy-3-[1-(4'-methanesulfonylamino-biphenyl-4-sulfonyl)-1H-pyrrol-3-yl]-acrylamide A mixture of 0.223 g (E)-3-[1-(4'-methanesulfonylamino-biphenyl-4-sulfonyl)-1H-pyrrol-3-yl]-N-(tetrahydro-pyran-2-yloxy)-acrylamide with 6.0 ml methanol and 12.0 ml 1M aqueous HCL is stirred at ambient temperature for 24 h. The suspension is evaporated and the solid is washed with water and diisopropylether. The title compound is dried in vacuo. By this method 0.155 g light pink solid are obtained. Melting point: 160-167° C.

24. 4'-[3-(E)-2-Hydroxycarbamoyl-vinyl)-pyrrole-1-sulfonyl]-biphenyl-4-carboxylic acid (2-dimethylamino-othyl)-amide, Compound with Hydrochloric Acid A mixture of 0.178 g 4'-{3-[(E)-2-(tetrahydro-pyran-2-yloxycarbamoyl)-vinyl]-pyrrole-1-sulfonyl}biphenyl-carboxylic acid (2-dimethylamino-ethyl)-amide with 5.0 ml methanol and 10.0 ml 1M aqueous HCL is stirred for 24 h at ambient temperature. The suspension is evaporated, centrifuged and the solid is washed with water and diisopropylether. The title compound is dried in vacuo. By this method 0.124 g of a light brown solid are obtained. Melting point: 119-126° C.

25. 4'-[3-(E)-2-Hydroxycarbamoyl-vinyl)-pyrrole-1-sulfonyl]-biphenyl-3-carboxylic acid (2-dimethylamino-ethyl)-amide, Compound with Hydrochloric Acid A mixture of 0.300 g 4'-{3-[(E)-2-(tetrahydro-pyran-2-yloxycarbamoyl)-vinyl]-pyrrole-1-sulfonyl}-biphenyl-3-carboxylic acid (2-dimethylamino-ethyl)-amide with 8.0 ml methanol and 17.0 ml 1M aqueous HCL is stirred at ambient temperature for 4 days. In case of incomplete deprotection, the suspension is treated again with 1M aqueous HCL until the reaction is at completion. The suspension is evaporated and the product is washed with water and diisopropylether. The title compound is dried in vacuo. By this method 0.161 g of a light brown solid are obtained. Melting point: 145-155° C., sinter is beginning from 68° C.

26. (E)-3-[1-(4'-Dimethylaminomethyl-biphenyl-4-sulfonyl)-1H-pyrrol-3-yl]-N-hydroxy-acrylamide, Compound with Hydrochloric Acid A mixture of 0.191 g (E)-3-[1-(4'-dimethylaminomethyl-biphenyl-4-sulfonyl)-1H-pyrrol-3-yl]-N-(tetrahydro-pyran-2-yloxy)-acrylamide with 5.0 ml methanol and 12.0 ml 1M aqueous HCL is stirred at ambient temperature for 24 h. The suspension is evaporated and the solid is washed with water and diisopropylether. The title compound is dried in vacuo. By this method 0.158 g white solid are obtained.

Melting point: 178-181° C. The compound contains 0.78 HCl/mol.

Alternatively: In an analog manner, 5.11 g of the title compound are obtained. The melting point is 202-203° C. with 1.01 HCl/mol.

(E)-3-[1-(4'-Dimethylaminomethyl-biphenyl-4-sulfonyl)-1H-pyrrol-3-yl]-N-hydroxy-acrylamide 250 mg (E)-3-[1-(4'-Dimethylaminomethyl-biphenyl-4-sulfonyl)-1H-pyrrol-3-yl]-N-hydroxy-acrylamide (compound with HCl) is extracted between ethylacetate and sodium hydroxide. The organic phase is dried over sodium sulfate, evaporated and dried in vacuo. By this method 111 mg of the free base is obtained.

(E)-3-[1-(4'-Dimethylaminomethyl-biphenyl-4-sulfonyl)-1H-pyrrol-3-yl]-N-hydroxy-acrylamide, compound with (E)-but-2-enedloic acid 500 mg (E)-3-[1-(4'-Dimethylaminomethyl-biphenyl-4-sulfonyl)-1H-pyrrol-3-yl]-N-hydroxy-acrylamide (compound with HCl) is extracted between ethylacetate and sodium hydroxide solution. The organic phase is dried over sodium sulfate, evaporated and dried in vacuo. 250 mg of the resulting solid is heated with 5 eq maleic acid in 40 ml isopropanol/0.3 ml water. During the mixture cools to ambient temperature a white solid precipitates. The solid is filtered and washed with isopropanol. By this method 200 mg of a colorless solid are obtained.

27. (E)-3-[1-(2'-Dimethylaminomethyl-biphenyl-4-sulfonyl)-1H-pyrrol-3-yl]-N-hydroxy-acrylamide, compound with hydrochloric acid A mixture of 0.176 g (E)-3-[1-(2'-dimethylaminomethyl-biphenyl-4-sulfonyl)-1H-pyrrol-3-yl]-N-(tetrahydro-pyran-2-yloxy)-acrylamide with 5.0 ml methanol and 10.0 ml 1M aqueous HCL is stirred at ambient temperature for 24 h. The suspension is evaporated and the solid is washed with water and diisopropylether. The title compound is dried in vacuo. By this method 0.096 g of a colorless solid are obtained. Melting point: 167-173° C., sinter is beginning from 134° C.

28. (E)-N-Hydroxy-3-(1-{4-[2-(4-methyl-piperazin-1-yl)-pyridin-4-yl]-benzenesulfonyl}-1H-pyrrol-3-yl)-acrylamide, Compound with Hydrochloric Acid A mixture of 0.235 g (E)-3-(1-{4-[2-(4-methyl-piperazin-1-yl)-pyridin-4-yl]-benzenesulfonyl}1H-pyrrol-3-yl)-N-

(tetrahydro-pyran-2-yloxy)-acrylamide with 5.0 ml methanol and 12.0 ml 1M aqueous HCL is stirred for 24 h. The suspension is evaporated and the solid is washed with water and diisopropylether.

The title compound is dried in vacuo. By this method 0.107 g light brown crystals are obtained. Melting point: 208-213° C.

Alternatively:

(E)-3-(1-{4-[2-(4-Methyl-piperazin-1-yl)-pyridinyl]-benzenesulfonyl}-1H-pyrrol-3-yl)-N-(tetrahydro-pyran-2-yloxy)-acrylamide (5.3 g) is dissolved in methanol (150 mL), treated with 1N HCl (50 mL) and are stirred 14 h at ambient temperature. The resulting solid is filtered, washed with diethylether and ethanol and dried. 3.99 g of the title compound with melting point of 216-217° C. are obtained. The compound contains 2.57 HCl/mol.

29. (E)-N-Hydroxy-3-{1-[4-(toluene-4-sulfonylamino)-biphenyl-4-sulfonyl]-1H-pyrrol-3-yl}-acrylamide A mixture of 0.278 g (E)-N-(tetrahydro-pyran-2-yloxy)-3-{1-[4'-(toluene-4-sulfonylamino)-biphenyl sulfonyl]-1H-pyrrol-3-yl}-acrylamide with 6.0 ml methanol and 13.0 ml 1M aqueous HCL is stirred at ambient temperature for 2 days. In case of incomplete deprotection the suspension is treated again with 1M aqueous HCl until the reaction is at completion. The mixture is evaporated and the resulting solid is washed with water and diisopropylether. The crude product is isolated by PLC plates chromatography. By this method 0.129 g of a red solid are obtained. Melting point: 119-126° C., sinter is beginning from 97° C.

30. 3'-3-((E)-2-Hydroxycarbamoyl-vinyl)-pyrrole-1sulfonyl]-biphenyl-4-carboxylic acid (2-dimethylamino-ethyl)-amide, Compound with Hydrochloric Acid A mixture of 0.216 g 3'-{3-[(E)-2-(tetrahydro-pyran-2-yloxycarbamoyl)-vinyl]-pyrrole-1-sulfonyl}-biphenyl-4-carboxylic acid (2-dimethylamino-ethyl)-amide with 5.0 ml methanol and 12.0 ml 1M aqueous HCL is stirred at ambient temperature for 24 h. The suspension is evaporated and the resulting solid is washed with water and diisopropylether. The title compound is dried in vacuo. By this method 0.142 g of a colorless solid are obtained. Melting point: 150-157° C., sinter is beginning from 141° C.

31. (E)-N-Hydroxy-3-[1-(3'-morpholin-4-ylmethylbiphenyl-3-sulfonyl)-1H-pyrrol-3-yl]-acrylamide, Compound with Hydrochloric Acid A mixture of 0.179 g (E)-3-[1-(3'-morpholin-4-ylmethylbiphenyl-3-sulfonyl)-1H-pyrrol-3-yl]-N -(tetrahydro-pyran-2-yloxy)-acrylamide with 4.0 ml methanol and 9.0 ml 1M aqueous HCL is stirred at ambient temperature for 24 h. The solvent is evaporated and the solid is crystallized from ethyl acetate and dried in vacuo. By this method 0.149 g light brown solid are obtained. Melting point: 118-122° C., sinter is beginning from 59° C.

32. (E)-N-Hydroxy-3-(1-{4'-[2-(4-methyl-piperazin-1-yl)-ethoxy]-biphenyl-3-sulfonyl}-1H-pyrrol-3-yl)-acrylamide, Compound with Hydrochloric Acid A mixture of 0.271 g (E)-3-(1-{4'-[2-(4-methyl-piperazin-1-yl)-ethoxy]-biphenyl-3-sulfonyl}-1H-pyrrol-3-yl)-N-(tetrahydro-pyran-2-yloxy)-acrylamide with 7.0 ml methanol and 15.0 ml 1M aqueous HCL is stirred for 24 h. The suspension is evaporated and the solid is washed with water and diisopropylether. The title compound is dried in vacuo. By this method 0.184 g of a light brown solid are obtained.

Melting point: 188-191° C., sinter is beginning from 102° C. The compound contains 1.6 HCl/mol.

Alternatively:

(E)-3-(1-{4'-[2-(4-methyl-piperazin-1-yl)-ethoxy]-biphenyl-3-sulfonyl}-1H-pyrrol-3-yl)-N-(tetrahydro-pyran-2-yloxy)-acrylamide (5.6 g) is dissolved in MeOH (150 mL), treated with 1N HCl (300 mL) and stirred for 14 h at ambient temperature. The resulting solid is filtered, washed with diethylether and dried in vacuum. 4.0 g are obtained with a melting point of 209-211° C. The compound contains 2.1 HCl/mol.

33. (E)-N-Hydroxy-3-(1-{3-[2-(4-methyl-piperazin-1-yl)-pyridin-4-yl]-benzenesulfonyl}-1H-pyrrol-3-yl)-acrylamide, compound with formic acid or hydrochloric acid A mixture of 0.195 g (E)-3-(1-{3-[2-(4-methyl-piperazin-1-yl)pyridin-4-yl]-benzenesulfonyl}-1H-pyrrol-3-yl)-N-(tetrahydro-pyran-2-yloxy)-acrylamide with 7.0 ml methanol and 10.0 ml 1M aqueous HCL is stirred at ambient temperature for 24 h. The solvent is lyophilized. The title compound is isolated by prep-HPLC chromatography using an ammonium formiate gradient. By this method 0.013 g white solid are obtained. The compound is isolated as formiate salt. Melting point: 116-122° C., sinter is beginning from 97° C.

Alternatively:

(E)-3-(1-{3-[2-(4-methyl-piperazin-1-yl)-pyridin-4-yl]-benzenesulfonyl}-1H-pyrrol-3-yl)-N-(tetrahydro-pyran-2-yloxy)-acrylamide (5.9 g) are dissolved in MeOH (150 mL), treated with 1N HCl (300 mL) and stirred for 14 h at ambient temperature. The resulting brownish solution is evaporated, the solid is suspended in diethylether, filtered and dried. 5.17 g of a compound with melting point of 214-216° C. are obtained. The compound contains 2.69 HCl/mol.

34. (E)-N-Hydroxy-3-{1-[4'-(2-morpholin-4-ylethoxy)-biphenyl-3-sulfonyl]-1H-pyrrol-3-yl}-acrylamide, Compound with Hydrochloric Acid A mixture of 0.196 g (E)-3-{1-[4'-(2-morpholin-4-ylethoxy)-biphenyl-3-sulfonyl]-1H-pyrrol-3-yl}-N-(tetrahydro-pyran-2-yloxy)-acrylamide with 4.0 ml methanol and 11.0 ml 1M aqueous HCL is stirred for 24 h. The suspension is evaporated and the resulting solid is washed with water and ethyl acetate. The title compound is dried in vacuo. By this method 0.141 g of a light yellow solid are obtained.

Melting point: 107-111° C., sinter is beginning from 82° C.

35. (E)-N-(2-Amino-phenyl)-3-{1-[4-(1-benzyl-1H-pyrazol-4-yl)-benzenesulfonyl]-1H-pyrrol-3-yl}-acrylamide, Compound with Hydrochloric Acid A mixture of 0.097 g [2-((E)-3-{1-[4-(1-benzyl-1H-pyrazol-4-yl)-benzenesulfonyl]-1H-pyrrol-3-yl}-allanoylamino)-phenyl]-carbamic acid tert-butyl ester with a little amount of dioxane and 23.0 ml 4M HCL in dioxane is stirred at ambient temperature for 24 h. The suspension is centrifuged and the solid is washed with diisopropylether. The title compound is dried in vacuo. By this method 0.062 g of a colorless solid are obtained. Melting point: 171° C., sinter is beginning from 156° C.

36. (E)-N-Hydroxy-3-[1-(4'-morpholin-4-ylmethyl-biphenyl-3-sulfonyl)-1H-pyrrol-3-yl]-acrylamide, compound with hydrochloric acid A mixture of 0.186 g (E)-3-[1-(4'-morpholin-4-ylmethyl-biphenyl-3-sulfonyl)-1H-pyrrol-3-yl]-N-(tetrahydro-pyran-2-yloxy)-acrylamide with 5.0 ml methanol and 11.0 ml 1M aqueous HCL is stirred at ambient temperature for 24 h. In case of incomplete deprotection the solvent is treated again with 1M aqueous HCL until the reaction is at completion. After 3 days the solvent is lyophilized and the title compound is crystallized in ethyl acetate. By this method 0.095 g of a red solid are obtained. Melting point: 72-76° C., sinter is beginning from 59° C.

37. (E)-3-[1-(4'-Dimethylaminomethyl-biphenyl-3-sulfonyl)-1H-pyrrol-3-yl]-N-hydroxy-acrylamide, compound with hydrochloric acid A mixture of 0.107 g (E)-3-[1-(4'-dimethylaminomethyl-biphenyl-3-sulfonyl)-)-1H-pyrrol-3-yl]-N-(tetrahydro-pyran-2-yloxy)-acrylamide with 5.0 ml methanol and 10.0 ml 1M aqueous HCL is stirred for 24 h. The solvent is lyophilized. By this method 0.062 g of a light brown amorph substance are obtained.
m/z (MH$^+$)=426.2

38. (E)-N-Hydroxy-3-{1-[4-(3-morpholin-4-yl-propoxy)-biphenyl-3-sulfonyl]-1H-pyrrol-3-yl}-acrylamide, Compound with Hydrochloric Acid A mixture of 0.253 g (E)-3-{1-[4'-(3-morpholin-4-yl-propoxy)-biphenyl-3-sulfonyl]-1H-pyrrol-3-yl}-N-(tetrahydro-pyran-2-yloxy)-acrylamide with 5.0 ml methanol and 14.0 ml 1M aqueous HCL is stirred for 24 h. The suspension is evaporated and the resulting solid is washed with water and ethyl acetate. The title compound is dried in vacuo. By this method 0.188 g of a colorless solid are obtained.

Melting point: 167-172° C., sinter is beginning from 157° C. The compound contains 0.98 HCl/mol.

Alternatively:
(E)-3-{1-[4'-(3-Morpholin-4-yl-propoxy)-biphenyl-3-sulfonyl]-1H-pyrrol-3-yl}-N-(tetrahydro-pyran-2-yloxy)-acrylamide (4.7 g) is dissolved in MeOH (50 mL), treated with 1N HCl (50 mL) and stirred for 14 h at ambient temperature. The resulting solid is filtered, washed with diethylether and dried. 2.66 g of the title compound are obtained with a melting point 175-178° C. The compound contains 1.26 HCl/mol.

39. (E)-N-(2-Amino-phenyl)-3-[1-(4'-dimethylsulfamoyl-biphenyl-4-sulfonyl)-1H-pyrrol-3-yl]-acrylamide, Compound with Hydrochloric Acid A mixture of 0.115 g (2-{(E)-3-[1-(4'-dimethylsulfamoyl-biphenyl-4-sulfonyl)-1H-pyrrol-3-yl]-allanoylamino}-phenyl)-carbamic acid tert-butyl ester with a little amount of dioxane and 15 ml 4M HCL in dioxane is stirred for 24 h. The suspension is centrifuged and the solid is washed with dioxane. The title compound is dried in vacuo. By this method 0.071 g of a colorless solid are obtained.
Melting point: 206-212° C.

40. (E)-3-[1-(3'-Acetylamino-biphenyl-4-sulfonyl)-1H-pyrrol-3-yl]-N-(2-amino-phenyl)-acrylamide, Compound with Hydrochloric Acid A mixture of 0.250 g (2-{(E)-3-[1-(3'-acetylamino-biphenyl-4-sulfonyl)-1H-pyrrol-3-yl]-allanoylamino}-phenyl)-carbamic acid tert-butyl ester with 15 ml 4M HCL in dioxane is stirred at ambient temperature for 24 h. The suspension is centrifuged and washed with dioxane and diisopropylether. The crude product is isolated by PLC plate chromatography. The title compound is dried in vacuo. By this method 0.095 g light yellow solid are obtained. Melting point: 135-140° C.

41. (E)-3-[1-(2'-Dimethylaminomethyl-biphenyl-3-sulfonyl)-1H-pyrrol-3-yl]-N-hydroxy-acrylamide, Compound with Hydrochloric Acid A mixture of 0.162 g (E)-3-[1-(2'-dimethylaminomethyl-biphenyl-3-sulfonyl)-1H-pyrrol-3-yl]-N-(tetrahydro-pyran-2-yloxy)-acrylamide with 5.0 ml methanol and 11.0 ml 1M aqueous HCL is stirred for 24 h. The suspension is filtered and washed with water and ethyl acetate. The title compound is dried in vacuo. By this method 0.078 g of a colorless solid are obtained. Melting point: 230-232° C., sinter is beginning from 218° C.

42. (E)-N-Hydroxy-3-(1-{5-[2-(4-methyl-piperazin-1-yl)-pyridin-4-yl]-thiophene-2-sulfonyl}-1H-pyrrol-3-yl)-acrylamide, Compound with Hydrochloric Acid A mixture of 0.072 g (E)-3-(1-{5-[2-(4-methyl-piperazin-1-yl)-pyridin-4-yl]-thiophene-2-sulfonyl}-1H-pyrrol-3-yl)-N-(tetrahydro-pyran-2-yloxy)-acrylamide with 2.0 ml methanol and 5.0 ml 1M aqueous HCL is stirred for 24 h. The solvent is lyophilized and the crude product is washed with ethyl acetate. The title compound is dried in vacuo. By this method 0.057 g of a light brown amorph substance are obtained.
m/z (MH$^+$)=474.2

Alternatively:
8.5 g (E)-3-(1-{5-[2-(4-Methyl-piperazin-1-yl)-pyridin-4-yl]-thiophene-2-sulfonyl}-1H-pyrrol-3-yl)-N-(tetrahydro-pyran-2-yloxy)-acrylamide is dissolved in 150 ml methanol. By adding 150 ml 1M aqueous HCl a solid precipitates. The suspension is stirred at ambient temperature for 24 h.

The solid is filtered, washed with diethylether and dried in vacuo.
By this method 4.8 g of the title compound are obtained.
Melting point: 226-230° C.; The compound contains HCl.

43. (E)-N-Hydroxy-3-{1-[4'-(2-pyrrolidin-1-yl-ethoxy)-biphenyl-3-sulfonyl]-1H-pyrrol-3-yl}-acrylamide, Compound with Hydrochloric Acid A mixture of 0.197 g (E)-3-{1-[4'-(2-pyrrolidin-1-yl-ethoxy)-biphenyl-3-sulfonyl]-1H-pyrrol-3-yl}-N-(tetrahydro-pyran-2-yloxy)-acrylamide with 5.0 ml methanol and 14.0 ml 1M aqueous HCL is stirred at ambient temperature for 24 h. The suspension is filtered and washed with water and diisopropylether.
The title compound is dried in vacuo. By this method 0.1349 of a light brown solid are obtained.
Melting point: 120-125° C., sinter is beginning from 90° C.

44. 4'-{3-[(E)-2-(2-Amino-phenylcarbamoyl)-vinyl]-pyrrole-1-sulfonyl}-biphenyl-3-carboxylic acid (2-dimethylamino-ethyl)-amide, compound with formic acid A mixture of 0.180 g [2-((E)-3'-{1-[3'-(2-dimethylamino-ethylcarbamoyl)-biphenyl-4-sulfonyl]-1H-pyrrol-3-yl}-allanoylamino)-phenyl]-carbamic acid tert-butyl ester with 4.0 ml dioxane and 40.0 ml 4 m HCL in dioxane is stirred at ambient temperature for 24 h. The solution is lyophilized. The crude product is isolated by prep-HPLC chromatography using an ammonium formate gradient. By this method 0.023 g yellow solid are obtained. Melting point 142-150° C., sinter is beginning from 128° C.

45. (E)-N-Hydroxy-3-{1-[4'-(3-morpholin-4-yl-propyl)-biphenyl-3-sulfonyl]-1H-pyrrol-3-yl}-acrylamide, Compound with Hydrochloric Acid A mixture of 0.154 g (E)-3-{1-[4'-(3-morpholin-4-yl-propyl)-biphenyl-3-sulfonyl]-1H-pyrrol-3-yl}-N-(tetrahydro-pyran-2-yloxy)-acrylamide with 4.0 ml methanol and 11.0 ml 1M aqueous HCL is stirred at ambient temperature for 24 h. The suspension is filtrated and the resulting solid is washed with water and ethyl acetate. The title compound is dried under vacuo. By this method 0.110 g of a colorless solid are obtained. Melting point: 215-217° C.

46. (E)-3-{1-[5-(4-Dimethylaminomethyl-phenyl)-thiophene-2-sulfonyl]-1H-pyrrol-3-yl}-N-hydroxy-acrylamide, Compound with Hydrochloric Acid A mixture of 0.068 g (E)-3-{1-[5-(4-dimethylaminomethyl-phenyl)-thiophene-2-sulfonyl]-1H-pyrrol-3-yl}-N-(tetrahydro-pyran-2-yloxy)-acrylamide with 2.0 ml methanol and 6.0 ml 1M aqueous HCL is stirred at ambient temperature for 24 h. The suspension is filtrated and the resulting solid is washed with water and ethyl acetate. The title compound is dried in vacuo. By this method 0.035 g of a light brown solid are obtained. The compound contains 0.72 HCl/mol. Melting point: 177-183° C.

Alternatively:

(E)-3-{1-[5-(4-Dimethylaminomethyl-phenyl)-thiophene-2-sulfonyl]-1H-pyrrol-3-yl}-N-(tetrahydro-pyran-2-yloxy)-acrylamide (5.4 g) are dissolved in methanol (100 mL) and treated with 1N HCl (100 mL). The mixture is stirred for 14 h at ambient temperature. The resulting solid is filtered and washed with diethylether and dried. 4.6 g of the title compound are obtained with a melting point of 198-203° C.

The compound contains 0.45 HCl/mol.

47. (E)-N-(2-Amino-phenyl)-3-[1-(4-dimethylaminomethyl-biphenyl-4-sulfonyl)-1H-pyrrol-3-yl]-acrylamide, compound with formic acid A mixture of 0.221 g (2-{(E)-3-[1-(4'-dimethylaminomethyl-biphenyl-4-sulfonyl)-1H-pyrrol-3-yl]-allanoylamino}-phenyl)-carbamic acid tert-butyl ester with 5.0 ml dioxane and 50.0 ml 4 m HCL in dioxane is stirred at ambient temperature for 48 h. The solution is lyophilized and the crude product is isolated by prep-HPLC chromatography using an ammonium formiate gradient. By this method 0.019 g yellow solid are obtained. Melting point: 211-216° C., sinter is beginning from 94° C.

48. (E)-N-(2-Amino-phenyl)-3-(1-{4-[2-(4-methyl-piperazin-1-yl)-pyridin-4-yl]-benzenesulfonyl}-1H-pyrrol-3-yl)-acrylamide, Compound with Hydrochloric Acid A mixture of 0.249 g {2-[(E)-3-(1-{4-[2-(4-methyl-piperazin-1-yl)-pyridin-4-yl]-benzenesulfonyl}-1H-pyrrol-3-yl)-allanoylamino]-phenyl}-carbamic acid tert-butyl ester with a little amount of dioxane and 15 ml 4M HCL in dioxane is stirred at ambient temperature for 24 h. The suspension is centrifuged and the resulting solid is washed with diisopropylether. The title compound is dried in vacuo. By this method 0.220 g of a colorless solid are obtained. Melting point: sinter is beginning from 199° C.

49. (E)-3-[1-(4'-Acetylamino-biphenyl-4-sulfonyl)-1H-pyrrol-3-yl]-N-(2-amino-phenyl)-acrylamide, compound with hydrochloric acid A mixture of 0.333 g (2-{(E)-3-[1-(4'-acetylamino-biphenyl-4-sulfonyl)-1H-pyrrol-3-yl]-allanoylamino}-phenyl)-carbamic acid tert-butyl ester with a little amount of dioxane and 15 ml 4M HCL in dioxane is stirred at ambient temperature for 24 h. The suspension is centrifuged and the resulting solid is washed with diisopropylether. The title compound is dried in vacuo. By this method 0.247 g of a colorless solid are obtained. Melting point: sinter is beginning from 181° C.

50. (E)-N-Hydroxy-3-{1-[5-(3-morpholin-4-ylmethyl-phenyl)-thiophene-2-sulfonyl]-1H-pyrrol-3-yl}-acrylamide, Compound with Hydrochloric Acid A mixture of 0.217 g (E)-3-{1-[5-(3-morpholin-4-ylmethyl-phenyl)-thiophene-2-sulfonyl]-1H-pyrrol-3-yl}-N-(tetrahydro-pyran-2-yloxy)-acrylamide with 5.0 ml methanol and 12.0 ml 1M aqueous HCL is stirred at ambient temperature for 24 h. The suspension is filtered and the resulting solid is washed with water and ethyl acetate. The title compound is dried in vacuo. By this method 0.162 g of a light brown solid are obtained. Melting point: 110-115° C.

51. (E)-N-(2-Amino-phenyl)-3-[1-(3'-hydroxymethyl-biphenyl-4-sulfonyl)-1H-pyrrol-3-yl]-acrylamide, Compound with Hydrochloric Acid A mixture of 0.257 g (2-{(E)-3-[1-(3'-hydroxymethyl-biphenyl-4-sulfonyl)-)-1H-pyrrol-3-yl]-allanoylamino}-phenyl)-carbamic acid tert-butyl ester with a little amount of dioxane and 15 ml 4M HCL in dioxane is stirred at ambient temperature for 24 h. The solution is evaporated and the title compound is isolated by flash chromatography. By this method 0.118 g of a yellow solid are obtained. Melting point: sinter is beginning from 103° C.

52. (E)-N-(2-Amino-phenyl)-3-{1-[4-(3,5-dimethyl-isoxazol-4-yl)-benzenesulfonyl]-1H-pyrrol-3-yl}-acrylamide A mixture of 0.020 g [2-((E)-3-{1-[4-(3,5-dimethyl-isoxazol-4-yl)-benzenesulfonyl]-1H-pyrrol-3-yl}-allanoylamino)-phenyl]-carbamic acid tert-butyl ester with a little amount of dioxane and 3 ml 4M HCL in dioxane is stirred at ambient temperature for 1 h. The suspension is centrifuged. The title compound is dried in vacuo. By this method 0.013 g of a red-brown amorph substance are obtained.

m/z (MH$^+$)=463.0

53. (E)-N-(2-Amino-phenyl)-3-[1-(4'-methanesulfonylamino-biphenyl-4-sulfonyl)-1H-pyrrol-3-yl]-acrylamide, Compound with Hydrochloric Acid A mixture of 0.030 g (2-{(E)-3-[1-(4'-methanesulfonylamino-biphenyl-4-sulfonyl)-1H-pyrrol-3-yl]-allanoylamino}-phenyl)-carbamic acid tert-butyl ester with a little amount of dioxane and 3.0 ml 4M HCL in dioxane is stirred at ambient temperature for 3 h. The solution is evaporated and the solid is filtrated. The title compound is dried in vacuo. By this method 0.026 g of a yellow solid are obtained.

m/z (MH$^+$)=537.0

54. (E)-N-Hydroxy-3-{1-[5-(4-morpholin-4-ylm-ethyl-phenyl)-thiophene-2-sulfonyl]-1H-pyrrol-3-yl}-acrylamide, Compound with Hydrochloric Acid A mixture of 0.231 g (E)-3-{1-[5-(4-morpholin-4-ylm-ethyl-phenyl)-thiophene-2-sulfonyl]-1H-pyrrol-3-yl}-N-(tetrahydro-pyran-2-yloxy)-acrylamide with 6.0 ml methanol and 17.0 ml 1M aqueous HCL is stirred at ambient temperature for 24 h. The suspension is filtered and the resulting solid is washed with water and ethyl acetate. The title compound is dried in vacuo. By this method 0.196 g of a light brown solid are obtained. Melting point: 172-178° C., sinter is beginning from 166° C.

55. (E)-N-Hydroxy-3-[1-(5-{4-[2-(4-methyl-piperazin-1-yl)-ethoxy]-phenyl}-thiophene-2-sulfonyl)-1H-pyrrol-3-yl]-acrylamide, Compound with Hydrochloric Acid A mixture of 0.180 g (E)-3-[1-(5-{4-[2-(4-methyl-piperazin-1-yl)-ethoxy]-phenyl}-thiophene-2-sulfonyl)-1H-pyrrol-3-yl]-N-(tetrahydro-pyran-2-yloxy)-acrylamide with 4.0 ml methanol and 12.0 ml 1M aqueous HCL is stirred at ambient temperature for 24 h. The suspension is filtered and washed with water and ethyl acetate. The title compound is dried in vacuo. By this method 0.103 g of a red amorph substance are obtained.

m/z(MH$^+$)=517.3

56. (E)-N-Hydroxy-3-(1-{5-[4-(2-morpholin-4-yl-ethoxy)-phenyl]-thiophene-2-sulfonyl}-1H-pyrrol-3-yl)-acrylamide, Compound with Hydrochloric Acid A mixture of 0.173 g (E)-3-(1-{5-[4-(2-morpholin-4-yl-ethoxy)-phenyl]-thiophene-2-sulfonyl}-1H-pyrrol-3-yl)-N-(tetrahydro-pyran-2-yloxy)-acrylamide with 4.0 ml methanol and 10.0 ml 1M aqueous HCL is stirred at ambient temperature for 24 h. The suspension is filtered and washed with water and ethyl acetate. The title compound is dried in vacuo. By this method 0.118 white solid are obtained. Melting point: 118-126° C.

57. (E)-N-Hydroxy-3-(1-{5-[4-(3-morpholin-4-yl-propoxy)-phenyl]-thiophene-2-sulfonyl}-1H-pyrrol-3-yl)-acrylamide, Compound with Hydrochloric Acid A mixture of 0.201 g (E)-3-(1-{5-[4-(3-morpholin-4-yl-propoxy)-phenyl]-thiophene-2-sulfonyl}-1H-pyrrol-3-yl)-N-(tetrahydro-pyran-2-yloxy)-acrylamide with 6.0 ml methanol and 10.0 ml 1M aqueous HCL is stirred for 24 h. The solution is lyophilized and the resulted oil is crystallized in ethyl acetate. The title compound is dried in vacuo. By this method 0.081 g of a light brown amorph substance are obtained.

m/z (MH$^+$)=518.3

58. (E)-N-Hydroxy-3-(1-{4'-[(2-methoxy-othy-lamino)-methyl]-biphenyl-3-sulfonyl}-1H-pyrrol-3-yl)-acrylamide, Compound with Hydrochloric Acid A mixture of 0.360 g (E)-3-(1-{4'-[(2-methoxy-ethylamino)-methyl]-biphenyl-3-sulfonyl}-1H-pyrrol-3-yl)-N-(tetrahydro-pyran-2-yloxy)-acrylamide with 5.0 ml methanol and 10.0 ml 1M aqueous HCL is stirred at ambient temperature for 16 h. The solvent is evaporated and the solid is washed with diethylether. Melting point 63-64° C.

59. (E)-N-(2-Amino-phenyl)-3-[1-(3'-methanesulfonylamino-biphenyl-4-sulfonyl)-1H-pyrrol-3-yl]-acrylamide, Compound with Formic Acid A mixture of 0.317 g (2-{(E)-3-[1-(3'-methanesulfonylamino-biphenyl-4-sulfonyl)-1H-pyrrol-3-yl]-allanoylamino}-phenyl)-carbamic acid tert-butyl ester with a little amount of dioxane and 15 ml 4M HCL in dioxane is stirred at ambient temperature for 24 h. The title compound is isolated by prep-HPLC chromatography using an ammonium formiate gradient. By this method 0.003 g yellow solid are obtained.

m/z (MH$^+$)=536.9

60. (E)-Hydroxy-3-{1-[5-(1-methyl-1H-pyrazol-4-yl)-thiophene-2-sulfonyl]-1H-pyrrol-3-yl}-acrylamide A mixture of 0.099 g (E)-3-{1-[5-(1-methyl-1H-pyrazol-4-yl)-thiophene-2-sulfonyl]-1H-pyrrol-3-yl}-N-(tetrahydro-pyran-2-yloxy)-acrylamide with 3.0 ml methanol and 6.0 ml 1M aqueous HCL is stirred at ambient temperature for 24 h. The suspension is filtered and washed with water and ethyl acetate. The title compound is dried in vacuo. By this method 0.037 g light pink solid are obtained. Melting point: 163-166° C.

61. (E)-N-Hydroxy-3-(1-{5-[4-(2-morpholin-4-yl-ethyl)-phenyl]-thiophene-2-sulfonyl}-1H-pyrrol-3-yl)-acrylamide, Compound with Hydrochloric Acid A mixture of 0.161 g (E)-3-(1-{5-[4-(2-morpholin-4-yl-ethyl)-phenyl]-thiophene-2-sulfonyl}-1H-pyrrol-3-yl)-N-(tetrahydro-pyran-2-yloxy)-acrylamide with 5.0 ml methanol with 8.0 ml 1M aqueous HCL is stirred at ambient temperature for 24 h. The suspension is filtered and the resulting solid is washed with water and diisopropylether. The title compound is dried in vacuo. By this method 0.126 g of a colorless solid are obtained. Melting point: sinter is beginning from 99° C.

62. (E)-N-Hydroxy-3-{1-[4'-(4-methyl-piperazin-1-ylmethyl)-biphenyl-3-sulfonyl]-1H-pyrrol-3-yl}-acrylamide, compound with hydrochloric acid A mixture of 0.250 g (E)-3-{1-[4'-(4-methyl-piperazin-1-ylmethyl)-biphenyl-3-sulfonyl]-1H-pyrrol-3-yl}-N-(tetrahydro-pyran-2-yloxy)-acrylamide with 5.0 ml methanol and 10.0 ml 1M aqueous HCL is stirred at ambient temperature for 16 h. The solvent is evaporated and the solid is washed with diethylether.

Melting point >225° C. decomp.

63. (E)-3-[1-(4-Cyclopropylaminomethyl-biphenyl-3-sulfonyl)-1H-pyrrol-3-yl]-N-hydroxy-acrylamide, compound with hydrochloric acid A mixture of 0.200 g (E)-3-[1-(4'-cyclopropylaminomethyl-biphenyl-3-sulfonyl)-1H-pyrrol-3-yl]-N-(tetrahydro-pyran-2-yloxy)-acrylamide with 5.0 ml methanol and 10.0 ml aqueous HCL is stirred at ambient temperature for 16 h. The solvent is evaporated and the resulting solid is washed with diethylether. The compound contains 1.41 HCl/mol. Melting point: 118-119° C.

64. (E)-N-Hydroxy-3-[1-(3'-morpholin-4-ylmethyl-biphenyl-4-sulfonyl)-1H-pyrrol-3-yl]-acrylamide, Compound with Hydrochloric Acid To a solution of (E)-N-Hydroxy-3-[1-(3'-morpholin-4-yl-methyl-biphenyl-4-sulfonyl)-1H-pyrrol-3-yl]-N-(tetrahydro-pyran-2-yloxy)-acrylamide (0.078 mmol) in DCM (2 ml) is added methanol (100 μl) and 4M HCl in Dioxan (200 μL). After stirring for 60 minutes the solvent is evaporated and the residue is taken up twice in acetonitril and evaporated under reduced pressure yielding the title product (0.062 mmol).
MS ([M-H$^+$]: 498.3; the compound contains HCl.
According to the procedure described in example 64 the following compounds 65 to 85 are prepared:

65. (E)-3-[1-(4-Benzo[1,3]dioxol-5-yl-benzenesulfonyl)-1H-pyrrol-3-yl]-N-hydroxy-acrylamide MS ([M-H$^+$]-ESI-neg: 411.0

66. (E)-3-[1-(3'-Amino-biphenyl-4-sulfonyl)-1H-pyrrol-3-yl]-N-hydroxy-acrylamide, compound with hydrochloric acid MS ([M-H$^+$]-ESI-neg: 382.0; the compound contains HCl.

67. (E)-N-Hydroxy-3-[1-(4'-hydroxy-biphenyl-4-sulfonyl)-1H-pyrrol-3-yl]acrylamide MS ([M-H$^+$]-ESI-neg: 383.3

68. (E)-N-Hydroxy-3-(1,4'-[2-(1-methyl-piperidin-4-yl)-ethoxy]biphenyl-4-sulfonyl)-1H-pyrrol-3-yl)-acrylamide, Compound with Hydrochloric Acid ESI-MS [MH$^+$]: 510.3; the compound contains HCl.

69. (E)-3-[1-(3'-Dimethylamino-biphenyl-4-sulfonyl)-1H-pyrrol-3-yl]-N-hydroxy-acrylamide, Compound with Hydrochloric Acid ESI-MS [MH$^+$]: 412.1; the compound contains HCl.

70. (E)-3-{1-[4-(2,3-Dihydro-benzofuran-5-yl)-benzenesulfonyl]-1H-pyrrol-3-yl}-N-hydroxy-acrylamide

ESI-MS [MH$^+$]: 411.1

71. (E)-N-Hydroxy-3-[1-(4'-morpholin-4-yl-biphenyl-4-sulfonyl)-1H-pyrrol-3-yl]-acrylamide, Compound with Hydrochloric Acid ESI-MS [MH$^+$]: 455.2; the compound contains HCl.

72. (E)-N-Hydroxy-3-{1-[3'-(3-pyrrolidin-1-yl-propoxy)-biphenyl-4-sulfonyl]-1H-pyrrol-3-yl}-acrylamide, Compound with Hydrochloric Acid ESI-MS [MH$^+$]: 496.3; the compound contains HCl.

73. (E)-N-Hydroxy-3-(1-{3'-[3-(4-methyl-piperazin-1-yl)-propoxy]-biphenyl-4-sulfonyl}-1H-pyrrol-3-yl)-acrylamide, Compound with Hydrochloric Acid ESI-MS [MH$^+$]: 525.3; the compound contains HCl.

74. (E)-N-Hydroxy-3-{1-[3'-(3-morpholin-4-yl-propoxy)-biphenyl-4-sulfonyl]-1H-pyrrol-3-yl}-acrylamide, Compound with Hydrochloric Acid ESI-MS [MH$^+$]: 512.3; the compound contains HCl.

75. (E)-N-Hydroxy-3-[1-(3'-morpholin-4-ylmethyl-biphenyl-4-sulfonyl)-1H-pyrrol-3-yl]-acrylamide, Compound with Hydrochloric Acid ESI-MS [MH$^+$]: 468.2; the compound contains HCl.

76. (E)-N-Hydroxy-3-(1-{4'-[2-(4-methyl-piperazin-1-yl)-ethoxy]-biphenyl-4-sulfonyl}-1H-pyrrol-3-yl)-acrylamide, Compound with Hydrochloric Acid ESI-MS [MH$^+$]: 511.5; the compound contains HCl.

77. (E)-N-Hydroxy-3-{1-([4-(2-morpholin-4-yl-ethoxy)-biphenyl-4-sulfonyl]-1H-pyrrol-3-yl}-acrylamide, Compound with Hydrochloric Acid ESI-MS [MH$^+$]: 498.2; the compound contains HCl.

78. (E)-N-Hydroxy-3-{1-[4'-(3-morpholin-4-yl-propoxy)-biphenyl-4-sulfonyl]-1H-pyrrol-3-yl}-acrylamide, Compound with Hydrochloric Acid ESI-MS [MH$^+$]: 512.3; the compound contains HCl.

79. (E)-N-Hydroxy-3-(1-{4'-[3-(4-methyl-piperazin-1-yl)-propoxy]-biphenyl-4-sulfonyl}-1H-pyrrol-3-yl)-acrylamide, Compound with Hydrochloric Acid ESI-MS [MH$^+$]: 525.2; the compound contains HCl.

80. (E)-N-Hydroxy-3-{1-[3'-(2-pyrrolidin-1-yl-ethoxy)-biphenyl-4-sulfonyl]-1H-pyrrol-3-yl}-acrylamide

ESI-MS [MH$^+$]: 482.2

81. (E)-N-Hydroxy-3-{1-[4'-(3-pyrrolidin-1-yl-propoxy)-biphenyl-4-sulfonyl]-1H-pyrrol-3-yl}-acrylamide

ESI-MS [MH$^+$]: 496.2

82. (E)-N-Hydroxy-3-[1-(4'-methoxy-biphenyl-4-sulfonyl)-1H-pyrrol-3-yl]-acrylamide ESI-MS (neg.) [M-H$^+$]: 397.0

83. (E)-N-Hydroxy-3-(1-{4-[1-(2-morpholin-4-yl-ethyl)-1H-[1,2,3]triazol-4-yl]-benzenesulfonyl}-1H-pyrrol-3-yl)-acrylamide, Compound with Hydrochloric Acid ESI-MS [MH$^+$]: 473.3; the compound contains HCl.

84. (E)-3-[1-(4'-Cyclopentylaminomethyl-biphenyl-4-sulfonyl)-1H-pyrrol-3-yl]-N-hydroxy-acrylamide, compound with hydrochloric acid ESI-MS [MH$^+$]: 466.2; the compound contains HCl.

85. (E)-N-Hydroxy-3-[1-(3'-trifluoromethyl-biphenyl-4-sulfonyl)-1H-pyrrol-3-yl]acrylamide

ESI-MS [MH$^+$]: 437.0

86. (E-3-{1-[5-(3-Dimethylaminomethyl-phenyl)-thiophene-2-sulfonyl]-1H-pyrrol-3-yl}-N-hydroxy-acrylamide, compound with hydrochloric acid A mixture of 0.133 g (E)-3-{1-[5-(3-Dimethylaminomethyl-phenyl)-thiophene-2-sulfonyl]-1H-pyrrol-3-yl}-N-(tetrahydropyran-2-yloxy)-acrylamide with 4 ml methanol and 20 ml 0.1M aqueous HCl is stirred at ambient temperature for 24 h. Overnight a solid precipitates, methanol and HCl is evaporated. The residue is washed with ethylacetate and dried in vacuo. 0.056 mg of the title compound is obtained by this method. The compound contains HCl.

87. (E)-3-[1-(3-Dimethylaminomethyl-biphenyl-3-sulfonyl)-1H-pyrrol-3-yl]-N-hydroxy-acrylamide, compound with hydrochloric acid A mixture of 0.188 g (E)-3-[1-(3'-Dimethylaminomethyl-biphenyl-3-sulfonyl)-1H-pyrrol-3-yl]-N-(tetrahydro-pyran-2-yloxy)-acrylamide with 5 ml methanol and 30 ml 0.1M aqueous HCl is stirred at ambient temperature for 24 h. The suspension is evaporated, water is added and the solution is lyophilized. The obtained residue is washed with etylacetate and dried in vacuo. By this method 0.128 mg yellow solid of the title compound is obtained. The compound contains HCl.

Sinter: 88° C.

88. (E)-N-Hydroxy-3-{1-[4-(2-morpholin-4-yl-ethyl)-biphenyl-3-sulfonyl]-1H-pyrrol-3-yl}-acrylamide, compound with (E)-but-2-enedloic acid 200 mg of (E)-N-Hydroxy-3-{1-[4'-(2-morpholin-4-yl-ethyl)-biphenyl-3-sulfonyl]-1H-pyrrol-3-yl}acrylamide (compound with HCl) is extracted between ethylacetate/water end the organic phase is dried and evaporated. 180 mg yellow solid are obtained. The solid is heated with 217 mg maleic acid in 15 ml isopropanole/0.1 ml water. During the cooling of the solution, a white solid precipitates. The solid is filtered and washed with isopropanol. By this method 150 mg of a colorless solid are obtained.

The compound contains (E)-but-2-enedioic acid.

89. (E)-N-(2-Amino-phenyl)-3-{1-[6-(4-dimethylaminomethyl-phenyl)-pyridine-3-sulfonyl]-1H-pyrrol-3-yl}-acrylamide, Compound with Hydrochloric Acid A mixture of 190 mg [2-((E)-3-{1-[6-(4-Dimethylaminomethyl-phenyl)-pyridine-3-sulfonyl]-1H-pyrrol-3-yl}allanoylamino)-phenyl]-carbamic acid tert-butyl ester and 15 ml 4 M HCl in dioxane is stirred at ambient temperature for 24 h. HCl in dioxane is evaporated and the crude product is purified by silica gel flash chromatography. By this method 120 mg of the title compound are obtained.

Melting point: 224-229° C.; The compound contains HCl.

90. (E)-N-Hydroxy-3-{1-[5-(2-methyl-thiazol-4-yl)-thiophene-2-sulfonyl]-1H-pyrrol-3-yl}-acrylamide, Compound with Hydrochloric Acid 88 mg of (E)-3-{1-[5-(2-Methyl-thiazol-4-yl)-thiophene-2-sulfonyl]-1H-pyrrol-3-yl}-N-(tetrahydro-pyran-2-yloxy)acrylamide is dissolved in 2 ml methanol. By adding 7 ml 1M aqueous HCl a solid precipitates. The suspension is stirred at ambient temperature for 24 h. The solid is filtered, washed with etylacetate and dried in vacuo. By this method 61 mg of a beige solid are obtained.

Melting point: slow decomposition: 85-130° C.; The compound contains HCl.

91. (E)-3-[1-(4-Aminomethyl-biphenyl-3-sulfonyl)-1H-pyrrol-3-yl]-N-hydroxy-acrylamide, compound with trifluoroacetic acid 206 mg of (3'-{3-[(E)-2-(Tetrahydro-pyran-2-yloxycarbamoyl)-vinyl]-pyrrole-1-sulfonyl}-biphenyl-4-ylmethyl)-carbamic acid tert-butyl ester are dissolved in 0.1 ml TFA/5 ml dichloromethane. The solution is stirred at ambient temperature for 6 h. TFA/dichloromethane is evaporated, the solid is taken up in water, filtered and dried in vacuo. By this method 24 mg of the title compound is obtained.

Melting point: slow decomposition: 81° C.; The compound contains 2,2,2-trifluoro-acetic acid.

92. (E)-N-Hydroxy-3-(1-{6-[4-(2-pyrrolidin-1-yl-ethoxy)-phenyl]-pyridine-3-sulfonyl}-1H-pyrrol-3-yl)-acrylamide, Compound with Hydrochloric Acid 117 mg of (E)-3-(1-{6-[4-(2-Pyrrolidin-1-yl-ethoxy)-phenyl]-pyridine-3-sulfonyl}-1H-pyrrol-3-yl)-N-(tetrahydro-pyran-2-yloxy)-acrylamide are dissolved in 3 ml methanol. By adding 8 ml 1M aqueous HCl a solid precipitates. The suspension is stirred at ambient temperature for 24 h.

The solid is filtered, dissolved in water and lyophilized. By this method 23 mg of a red solid are obtained.

Melting point: 192-195° C.; The compound contains HCl.

93. (E)-3-[1-(4-Aminomethyl-biphenyl-4-sulfonyl)-1H-pyrrol-3-yl]-N-(2-amino-phenyl)-acrylamide, compound with hydrochloric acid 380 mg of [2-((E)-3-{1-[4'-(tert-Butoxycarbonylaminomethyl)-biphenyl-4-sulfonyl]-1H-pyrrol-3-yl}-allanoylamino)-phenyl]-carbamic acid tert-butyl ester are suspended in 15 ml 4 M HCl in dioxane. The suspension is stirred for 24 h at ambient temperature. The precipitated solid is filtered, washed with diisopropylether and dried in vacuo. By this method 240 mg of the title compound are obtained.

Melting point: 278-280° C.; The compound contains HCl.

94. (E)-3-{1-[5-(3-Aminomethyl-phenyl)-thiophene-2-sulfonyl]-1H-pyrrol-3-yl}-N-hydroxy-acrylamide, compound with hydrochloric acid 105 mg of (E)-3-{1-[5-(3-Aminomethyl-phenyl)-thiophene-2-sulfonyl]-1H-pyrrol-3-yl}-N-(tetrahydro-pyran-2-yloxy)-acrylamide is solved in 6 ml methanol. By adding 20 ml 0.1M aqueous HCl a solid precipitates. The suspension is stirred at ambient temperature for 24 h. Solvents are evaporated, the solid is filtered and dried in vacuo. By this method 28 mg of a pink solid are obtained.

Melting point: 209-213° C.; The compound contains HCl.

95. (E)-N-(2-Amino-phenyl)-3-{1-[5-(4-dimethylaminomethyl-phenyl)-thiophene-2-sulfonyl]-1H-pyrrol-3-yl}-acrylamide, Compound with Hydrochloric Acid 120 mg of [2-((E)-3-{1-[5-(4-Dimethylaminomethyl-phenyl)-thiophene-2-sulfonyl]-1H-pyrrol-3-yl}-allanoylamino)-phenyl]-carbamic acid tert-butyl ester are suspended in 15 ml 4 M HCl in dioxane. The suspension is stirred for 24 h at ambient temperature. HCl in dioxane is evaporated and the crude product is purified by silica gel flash chromatography. By this method 90 mg of the title compound are obtained.
Melting point: 164-169° C. The compound contains HCl.

96. (E)-N-(2-Amino-phenyl)-3-[1-(3'-dimethylaminomethyl-biphenyl-4-sulfonyl)-1H-pyrrol-3-yl]-acrylamide, Compound with Hydrochloric Acid 290 mg of (2-{(E)-3-[1-(3'-Dimethylaminomethyl-biphenyl-4-sulfonyl)-1H-pyrrol-3-yl]allanoylamino}-phenyl)-carbamic acid tert-butyl ester are suspended in 15 ml 4 M HCl in dioxane. The suspension is stirred for 24 h at ambient temperature. HCl in dioxane is evaporated and the crude product is washed with diisopropylether and dried in vacuo. By this method 230 mg of the title compound are obtained.
Melting point: 163-166° C.; The compound contains HCl.

97. (E)-3-{1-[4'-(Acetylamino-methyl)-biphenyl-4-sulfonyl]-1H-pyrrol-3-yl}-N-(2-amino-phenyl)-acrylamide, compound with hydrochloric acid 200 mg of [2-((E)-3-{1-[4'-(Acetylamino-methyl)-biphenyl-4-sulfonyl]-1H-pyrrol-3-yl}-allanoylamino)-phenyl]-carbamic acid tert-butyl ester are suspended in 15 ml 4 M HCl in dioxane for 24 h at ambient temperature. HCl in dioxane is evaporated and the crude product is washed with diisopropylether and dried in vacuo. By this method 167 mg white solid are obtained.
Melting point: 169-175° C.; The compound contains HCl.

98. (E)-N-(2-Amino-phenyl)-3-{1-[4'-(methanesulfonylamino-methyl)biphenyl-4-sulfonyl]-1H-pyrrol-3-yl}-acrylamide, Compound with Hydrochloric Acid 150 mg of [2-((E)-3-{1-[4'-(Methanesulfonylamino-methyl)-biphenyl-4-sulfonyl]-1H-pyrrol-3-yl}-allanoylamino)-phenyl]-carbamic acid tert-butyl ester are suspended in 15 ml 4 M HCl in dioxane for 24 h at ambient temperature. HCl in dioxane is evaporated and the crude product is washed with diisopropylether and dried in vacuo. By this method 100 mg of the title compound are obtained.
Melting point: 184-193° C.; The compound contains HCl.

99. (E)-N-Hydroxy-3-(1-{5-([4-(2-pyrrolidin-1-yl-ethoxy)-phenyl]-thiophene-2-sulfonyl}-1H-pyrrol-3-yl)-acrylamide, Compound with Hydrochloric Acid 209 mg of (E)-3-(1-{5-[4-(2-Pyrrolidin-1-yl-ethoxy)-phenyl]-thiophene-2-sulfonyl}-1H-pyrrol-3-yl)-N-(tetrahydro-pyran-2-yloxy)-acrylamide is solved in 5 ml methanol. By adding 15 ml 1M aqueous HCl a solid precipitates. The suspension is stirred at ambient temperature for 24 h. Solvents are evaporated, the solid is collected, washed with water and ethylacetate and dried in vacuo. By this method 117 mg of a beige solid are obtained.
Melting point: 109-113° C.; The compound contains HCl.

100. (E)-3-{1-[5-(4-Dimethylsulfamoyl-phenyl)-thiophene-2-sulfonyl]-1H-pyrrol-3-yl}-N-hydroxy-acrylamide, compound with hydrochloric acid 148 mg of (E)-3-{1-[5-(4-Dimethylsulfamoyl-phenyl)-thiophene-2-sulfonyl]-1H-pyrrol-3-yl}-N-(tetrahydro-pyran-2-yloxy)-acrylamide is solved in 4 ml methanol. By adding 11 ml 1M aqueous HCl a solid precipitates. The suspension is stirred at ambient temperature for 24 h. Solvents are evaporated, the solid is filtered, washed with water and ethylacetate and dried in vacuo. By this method 101 mg of a yellow solid are obtained.
Melting point: 167-172° C.; Sinter 66° C.; The compound contains HCl.

101. (E)-N-(2-Amino-phenyl)-3-[1-(4'-methanesulfonylamino-biphenyl-3-sulfonyl)-1H-pyrrol-3-yl]-acrylamide, Compound with Hydrochloric Acid 182 mg of (2-{(E)-3-[1-(4'-Methanesulfonylamino-biphenyl-3-sulfonyl)-1H-pyrrol-3-yl]-allanoylamino}-phenyl)-carbamic acid tert-butyl ester are suspended in 3 ml dioxane and 15 ml 4 M HCl in dioxane. The suspension is stirred for 24 h at ambient temperature. The solution is lyophilized. By this method 175 mg of the title compound are obtained.
Sinter: 62° C.; The compound contains HCl.

102. (E)-N-(2-Amino-phenyl)-3-[1-(4'-dimethylaminomethyl-biphenyl-3-sulfonyl)-1H-pyrrol-3-yl]-acrylamide, Compound with Hydrochloric Acid 237 mg of (2-{(E)-3-[1-(4'-Dimethylaminomethyl-biphenyl-3-sulfonyl)-1H-pyrrol-3-yl]-allanoylamino}-phenyl)-carbamic acid tert-butyl ester are suspended in 3 ml dioxane and 20 ml 4 M HCl in dioxane. The suspension is stirred for 24 h at ambient temperature. The solution is lyophilized and purified by PLC plate chromatography. By this method 35 mg of a yellow solid are obtained.
Melting point: 204-207° C.; Sinter 81° C.; The compound contains HCl.

103. (E)-N-Hydroxy-3-{1-[2'-(4-methyl-piperazin-1-yl)-[2,4']bipyridinyl-5-sulfonyl]-1H-pyrrol-3-yl}-acrylamide, Compound with Hydrochloric Acid 122 mg of (E)-3-{1-[2'-(4-Methyl-piperazin-1-yl)-[2,4'] bipyridinyl-5-sulfonyl]-1H-pyrrol-3-yl}-N-(tetrahydro-pyran-2-yloxy)-acrylamide are dissolved in 3 ml methanol. By adding 10 ml 1M aqueous HCl a solid precipitates. The suspension is stirred at ambient temperature for 24 h. The solid is filtered, washed with water and ethylacetate and dried in vacuo. By this method 46 mg of a brown solid are obtained.
Melting point: 212-216° C.; The compound contains HCl.

104. (E)-N-(2-Amino-phenyl)-3-{1-[5-(1-methyl-1H-pyrazol-4-yl)-thiophene-2-sulfonyl]-1H-pyrrol-3-yl}-acrylamide, Compound with Hydrochloric Acid 99 mg [2-((E)-3-{1-[5-(1-Methyl-1H-pyrazol-4-yl)-thiophene-2-sulfonyl]-1H-pyrrol-3-yl}-allanoylamino)-phenyl]-carbamic acid tert-butyl ester are suspended in 2 ml dioxane and 25 ml 4 M HCl in dioxane. The suspension is stirred for 24 h at ambient temperature. Methanol is added and the solution is lyophilized and purified by PLC plate chromatography. By this method 23 mg of a yellow solid are obtained. The compound contains HCl.

105. (E)-3-{1-[6-(4-Dimethylaminomethyl-phenyl)-pyridine-3-sulfonyl]-1H-pyrrol-4-yl}-N-hydroxy-acrylamide, compound with hydrochloric acid 36 mg of (E)-3-{1-[6-(4-Dimethylaminomethyl-phenyl)-pyridine-3-sulfonyl]-1H-pyrrol-3-yl}-N-(tetrahydropyran-2-yloxy)-acrylamide is dissolved in 2 ml methanol. By adding 7 ml 0.1M aqueous HCl a solid precipitates. The suspension is stirred at ambient temperature for 24 h. Methanole is evaporated. The solid is filtered, solved in methanol/dichloromethane, evaporated and dried in vacuo. By this method 17 mg of a grey solid are obtained.

Melting point: 197-200° C.; The compound contains HCl.

106. (E)-N-(2-Amino-phenyl)-3-(1-{5-[2-(4-methyl-piperazin-1-yl)-pyridin-4-yl]-thiophene-2-sulfonyl}-1H-pyrrol-3-yl)-acrylamide, Compound with Hydrochloric Acid 189 mg {2-[(E)-3-(1-{5-[2-(4-Methyl-piperazin-1-yl)-pyridinyl]-thiophene-2-sulfonyl}-1H-pyrrol-3-yl)-allanoylamino]-phenyl}-carbamic acid tert-butyl ester are suspended in 4 ml dioxane and 40 ml 4 M HCl in dioxane. The suspension is stirred for 24 h at ambient temperature. The solvents are evaporated, the solid is collected, washed with ethylacetate and dried in vacuo. By this method 149 mg of a beige solid are obtained.

Sinter: 129° C.; The compound contains HCl.

107. (E)-N-(2-Amino-phenyl)-3-[1-(4-morpholin-4-ylmethyl-biphenyl-4-sulfonyl)-1H-pyrrol-3-yl]-acrylamide, Compound with Hydrochloric Acid 89 mg (2-{(E)-3-[1-(4'-Morpholin-4-ylmethyl-biphenyl-4-sulfonyl)-1H-pyrrol-3-yl]-allanoylamino}-phenyl)-carbamic acid tert-butyl ester are suspended in 10 ml 4 M HCl in dioxane. The suspension is stirred for 24 h at ambient temperature. Solvents are evaporated, and crude product is purified by silica gel flash chromatography. By this method 52 mg of a colorless solid are obtained.

Melting point: 196-201° C.; The compound contains HCl.

108. (E)-N-(2-Amino-phenyl)-3-{1-[4'-(2-pyrrolidin-1-yl-ethoxy)-biphenyl 4-sulfonyl]-1H-pyrrol-3-yl}-acrylamide, Compound with Hydrochloric Acid 100 mg [2-((E)-3-{1-[4'-(2-Pyrrolidin-1-yl-ethoxy)-biphenyl-4-sulfonyl]-1-H-pyrrol-3-yl}-allanoylamino)-phenyl]-carbamic acid tert-butyl ester are suspended in 10 ml 4 M HCl in dioxane. The suspension is stirred for 24 h at ambient temperature. The solvents are evaporated, the solid is washed twice with diisopropylether and dried in vacuo. By this method 61 mg of a colorless solid are obtained.

Melting point: 172-180° C.; The compound contains HCl.

109. (E)-N-Hydroxy-3-(1-{4-[1-(2-piperidin-1-yl-ethyl)-1H-[1,2,3]triazol-4-yl]-benzenesulfonyl}-1H-pyrrol-3-yl)-acrylamide, Compound with Hydrochloric Acid Starting from the appropriate starting compound, which is prepared analogously or similarly as described for (E)-N-(tetrahydro-pyran-2-yloxy)-3-(1-{4-[1-(2-morpholin-4-yl-ethyl)-1H-[1,2,3]triazol-4-yl]-benzenesulfonyl}-1H-pyrrol-3-yl)-acrylamide the title compound is prepared according to the procedure described in example 64.

ESI-MS ([M-H$^+$]): 471.2; The compound contains HCl.

110. (E)-3-[1-(3'-Dimethylaminomethyl-biphenyl-3-sulfonyl)-1H-pyrrol-3-yl]-N-hydroxy-acrylamide, compound with hydrochloric acid 188 mg (E)-3-[1-(3'-Dimethylaminomethyl-biphenyl-3-sulfonyl)-1H-pyrrol-3-yl]-N-(tetrahydro-pyran-2-yloxy-acrylamide are dissolved in 5 ml methanol. By adding 30 ml 0.1M aqueous HCl a yellow solid precipitates. The suspension is stirred at ambient temperature for 24 h. Solvents are evaporated and the product is lyophilized. The product is washed with ethylacetate and dried in vacuo. By this method 128 mg of a yellow solid are obtained. The compound contains HCl.

Sinter: 88° C., MH$^+$: 426.1

111. (E)-N-(2-Amino-phenyl)-3-(1-{5-[4-(methyne-sulfonylamino-methyl)-phenyl]-thiophene-2-sulfonyl}-1H-pyrrol-3-yl)-acrylamide, Compound with Hydrochloric Acid 231 mg {2-[(E)-3-(1-{5-[4-(Methanesulfonylamino-methyl)-phenyl]-thiophene-2-sulfonyl}-1H-pyrrol-3-yl)-allanoylamino]-phenyl}-carbamic acid tert-butyl ester are suspended in 16 ml 4 M HCl in dioxane. The suspension is stirred at ambient temperature overnight Solvents are evaporated. The residue is dissolved in methanol, by adding ethylacetate a solid precipitates. The solid is washed with ethylacetate and dried in vacuo. By this method 72 mg of a bright brown solid are obtained. The compound contains HCl.

Sinter: 169° C., MH$^+$: 556.9

112. (E)-N-(2-Amino-phenyl)-3-{1-[3-(methane-sulfonylamino-methyl)-biphenyl-3-sulfonyl]-1H-pyrrol-3-yl}-acrylamide, Compound with Hydrochloric Acid 209 mg [2-((E)-3-{1-[3'-(Methanesulfonylamino-methyl)-biphenyl-3-sulfonyl]-1H-pyrrol-3-yl}-allanoylamino)-phenyl]-carbamic acid tert butyl ester are suspended in 17 ml 4 M HCl in dioxane. The suspension is stirred for 24 h at ambient temperature. Solvents are evaporated and the residue is crystallised with ethylacetate. The solid is filtered and dried in vacuo. By this method 157 mg of a yellow solid are obtained. The compound contains HCl.

MH$^+$: 550.9

113. (E)-3-(1-{5-[4-(Acetylamino-methyl)-phenyl]-thiophene-2-sulfonyl}-1H-pyrrol-3-yl)-N-(2-amino-phenyl)-acrylamide, Compound with Hydrochloric Acid 200 mg {2-[(E)-3-(1-(5-[4-(Acetylamino-methyl)-phenyl]-thiophene-2-sulfonyl}-1H-pyrrol-3-yl)-allanoylamino]-phenyl)-carbamic acid tert butyl ester are suspended in 15 ml 4M HCL in dioxane. The suspension is stirred for 24 h at ambient temperature. Solvents are evaporated. The residue is washed with ethylacetate and dried in vacuo. By this method 161 mg of a yellow solid are obtained. The compound contains HCl.

Sinter: 156° C., MH$^+$: 520.9

114. (E)-N-(2-Amino-phenyl)-3-{1-[5-(3-dimethylaminomethyl-phenyl)-thiophene-2-sulfonyl]-1H-pyrrol-3-yl}-acrylamide, Compound with Hydrochloric Acid 213 mg [2-((E)-3-{1-[5-(3-Dimethylaminomethyl-phenyl)-thiophene-2-sulfonyl]-1H-pyrrol-3-yl}-allanoylamino)-phenyl]-carbamic acid tert butyl ester are suspended in 16 ml 4 M HCl in dioxane. The suspension is stirred for 24 h at ambient temperature. Solvents are evaporated. The residue is washed with ethylacetate and dried in vacuo. By this method 181 mg of the title compound are obtained. The compound contains HCl.

Sinter: 89° C., MH$^+$: 507.1

115. (E)-N-(2-Amino-phenyl)-3-[1-(3'-dimethylaminomethyl-biphenyl-3-sulfonyl)-1H-pyrrol-3-yl]-acrylamide, Compound with Hydrochloric Acid 90 mg (2-{(E)-3-[1-(3'-Dimethylaminomethyl-biphenyl-3-sulfonyl)-1H-pyrrol-3-yl]-allanoylamino}-phenyl)-carbamic acid tert butyl ester are suspended in 8 ml 4 M HCl in dioxane. The suspension is stirred for 24 h at ambient temperature. Solvents are evaporated and residue is solved in DMSO/MeOH 1:1 and lyophilized. By this method 72 mg of the title compound are obtained. The compound contains HCl.

MH$^+$: 501.0

116. (E)-3-[1-(3'-Dimethylaminomethyl-biphenyl-4-sulfonyl)-1H-pyrrol-3-yl]-N-hydroxy-acrylamide, compound with hydrochloric acid 209 mg (E)-3-[1-(3'-Dimethylaminomethyl-biphenyl-4-sulfonyl)-1H-pyrrol-3-yl]-N-(tetrahydro-pyran-2-yloxy)-acrylamide are dissolved in 5 ml methanol. By adding 32 ml 0.1M HCl a white solid precipitates. The suspension is stirred overnight at ambient temperature. The solid is filtered, washed with ethylacetate and dried in vacuo. By this method 144 mg of a white solid are obtained. The compound contains HCl.

MH$^+$: 426.2

117. (E)-3-{1-[5-(3-Dimethylaminomethyl-phenyl)-thiophene-2-sulfonyl]-1H-pyrrol-3-yl}-N-hydroxy-acrylamide, Compound with Hydrochloric Acid 133 mg (E)-3-{1-[5-(3-Dimethylaminomethyl-phenyl)-thiophene-2-sulfonyl]-1H-pyrrol-3-yl}-N-(tetrahydro-pyran-2-yloxy-acrylamide are dissolved in 4 ml methanol. By adding 20 ml 0.1M aqueous HCl a solid precipitates. The suspension is stirred overnight at ambient temperature. Solvents are evaporated, solid is washed with ethylacetate and dried in vacuo. By this method 65 mg of the title compound are obtained. The compound contains HCl.

MH$^+$: 432.0

118. (E)-3-{1-[3-Acetylamino-methyl)-biphenyl-3-sulfonyl]-1H-pyrrol-3-yl}-N-(2-amino-phenyl)-acrylamide, compound with hydrochloric acid 260 mg [2-((E)-3-{1-[3'-(Acetylamino-methyl)-biphenyl-3-sulfonyl]-1H-pyrrol-3-yl}-allanoylamino)-phenyl]-carbamic acid tert butyl ester are suspended in 20 ml 4 M HCl in dioxane. The suspension is stirred overnight at ambient temperature. Solvents are evaporated. The residue is solved in acetonitrile/water and lyophilized. By this method 193 mg of a yellow solid are obtained. The compound contains HCl.

MH$^+$: 515.0

119. (E)-N-(2-Amino-phenyl)-3-{1-[6-(1-methyl-1H-pyrazol-4-yl)-pyridine-3-sulfonyl]-1H-pyrrol-3-yl}-acrylamide, Compound with Hydrochloric Acid 50 mg [2-((E)-3-{1-[6-(1-Methyl-1H-pyrazol-4-yl)-pyridine-3-sulfonyl]-1H-pyrrol-3-yl}-allanoylamino)-phenyl]-carbamic acid tert butyl ester are suspended in 4 ml 4 M HCl in dioxane. The suspension is stirred overnight at ambient temperature. Solvents are evaporated. The residue is washed with ethylacetate and dried in vacuo. The compound contains HCl.

MH$^+$: 449.3

120. (E)-N-Hydroxy-3-(1-[6-(1-methyl-1H-pyrazol-4-yl)-pyridine-3-sulfonyl]-1H-pyrrol-3-yl)-acrylamide, compound with hydrochloric acid 93 mg (E)-3-{1-[6-(1-Methyl-1H-pyrazol-4-yl)-pyridine-3-sulfonyl]-1H-pyrrol-3-yl}-N-(tetrahydro-pyran-2-yloxy-acrylamide are solved in 6 ml methanol. By adding 10 ml 0.1M aqueous HCl a solid precipitates. The suspension is stirred overnight at ambient temperature. Solvents are evaporated, solid is washed with ethylacetate and dried in vacuo. By this method 60 mg of a yellow solid are obtained. The compound contains HCl.

MH$^+$: 374.0

121. (E)-3-{1-[6-(3-Dimethylaminomethyl-phenyl)-pyridine-3-sulfonyl]-1H-pyrrol-3-yl}-N-hydroxy-acrylamide, compound with hydrochloric acid 87 mg (E)-3-{1-[6-(3-Dimethylaminomethyl-phenyl)-pyridine-3-sulfonyl]-1H-pyrrol-3-yl}-N-(tetrahydro-pyran-2-yloxy)-acrylamide are solved in 2 ml methanol. By adding 13 ml 0.1 N HCl a solid precipitates. The suspension is stirred overnight at ambient temperature. Solvents are evaporated. The residue is solved in acetonitrile/water and lyophilized afterwards.

MH$^+$: 427.2

Starting Materials

A1. (E)-3-{1-[4-(1-Methyl-1H-Indol-5-yl)-benzenesulfonyl]-1H-pyrrol-3-yl}-N-(tetrahydro-pyran-2-yloxy)-acrylamide A mixture of 0.4 g (E)-3-[1-(4-Bromo-benzenesulfonyl)-1H-pyrrol-3-yl]-N-(tetrahydro-pyran-2-yloxy)-acrylamide, 0.231 g N-Methylindol-5-boronic acid and 14 ml dimethoxyethane is slightly heated and to this mixture are added bis(triphenylphosphine)palladium(II)chloride and 1.5 ml of a 2M aqueous sodium sulfate solution. This mixture is heated to reflux temperature under an inert gas atmosphere overnight. After cooling the mixture is filtered, evaporated and the residue is partitioned between ethyl acetate and a 5% aqueous solution of sodium bicarbonate. The organic phase is dried and evaporated and the residue is purified by silica gel flash chromatography.

A2. [2-((E)-3-{1-[4-(6-Methoxy-pyridin-3-yl)benzenesulfonyl]-1H-pyrrol-3-yl}-allanoylamino)-phenyl]-carbamic acid tert-butyl ester To mixture of 0.3 g (2-{(E)-3-[1-(4-Iodo-benzenesulfonyl)-1H-pyrrol-3-yl]-allanoylamino}-phenyl)-carbamic acid tert-butyl ester, 0.116 g 2-methoxy-5-pyridineboronic acid and 11 ml dimethoxyethane are added under an inert gas atmosphere 0.9 ml of an aqueous solution of 2N sodium sulfate and 70 mg of bis-(triphenylphosphine)palladium-(II) chloride. The mixture is refluxed for 24 h and after filtration and evaporation the residue is extracted between ethyl acetate and a 5% aqueous solution of sodium bicarbonate. The organic phase is dried and evaporated and th4e crude product is purified by silica gel flash chromatography. 87% of a colorless solid are obtained.

A3. [5-(4-{3-[(E)-2-(Tetrahydro-pyran-2-yloxycarbamoyl)-vinyl]-pyrrole-1-sulfonyl}-phenyl)-pyridin-2-yl]-carbamic acid tert-butyl ester (E)-3-[1-(4-Bromo-benzenesulfonyl)-1H-pyrrol-3-yl]-N-(tetrahydro-pyran-2-yloxy)-acrylamide (0.95 g) and [5-(4,4,5,5-tetramethyl-[1,3,2]dioxaborolan-2-yl)-pyridin-2-yl]- carbamic acid tert-butyl ester (1.00 g) are dissolved under an inert gas atmosphere in dimethylethylenglycole (35 mL), and Pd(PPh3)₃Cl2 (0.22 g) and a sodium carbonate solution (2.21 g dissolved in 21 water) is added and it is heated for 0.5 h at 90° C. After cooling the mixture is diluted with water, extracted with chloroform, and the combined organic phases are dried and evaporated. The residue is purified by silica gel flash chromatography CHCl₃/THF (4:1). 0.97 g of the title compound are obtained with a melting point of 140-146° C.

A4. (E)-3-{1-[4-(1-Methyl-1H-pyrazol-4-yl)-benzenesulfonyl]-1H-pyrrol-3-yl}-N-(tetrahydro-pyran-2-yloxy)-acrylamide (E)-3-[1-(4-Bromo-benzenesulfonyl)-1H-pyrrol-3-yl]-N-(tetrahydro-pyran-2-yloxy)-acrylamide (966 mg) and 1-methyl-4-(4,4,5,5-tetramethyl-[1,3,2]dioxaborolan-2-yl)-1H-pyrazole (662 mg) are dissolved in DME (35 mL) and (Ph3P)3PdCl2 (298 mg) and 2M Na₂CO₃-solution (3.2 mL) are added. The mixture is heated 16 h to reflux temperature. The mixture is filtered and evaporated and the crude product is purified by silica gel flash chromatography.

A5. [2-((E)-3-{1-[4-(1-Methyl-1H-pyrazol-4-yl)-benzenesulfonyl]-1H-pyrrol-3-yl}-allanoylamino)-phenyl]-carbamic acid tert-butyl ester (2{(E)-3-[1-(4-Bromo-benzenesulfonyl)-1H-pyrrol-3-yl]-allanoylamino}-phenyl)-carbamic acid tert-butyl ester (3.0 g) and 1-methyl-4-(4,4,5,5-tetramethyl-[1,3,2]dioxaborolan-2-yl)-1H-pyrazole (1.71 g) are dissolved in DME (93 mL), (Ph3P)3PdCl2 (580 mg) and 2M Na₂CO₃-solution (55 mL) are added and the resulting mixture is heated under reflux temperature under an inert gas atmosphere. The solution is filtered and evaporated. The residue is treated with water and dichloromethane. The organic phase is separated, dried and evaporated. The crude product is purified by silica gel flash chromatography. The title compound is obtained in 902 mg yield.

A6. (E)-3-{1-[4'-(2-Morpholin-4-yl-ethyl)-biphenyl-3-sulfonyl]-1H-pyrrol-3-yl}-N-(tetrahydro-pyran-2-yloxy)-acrylamide (E)-3-[1-(3-Bromo-benzenesulfonyl)-1H-pyrrol-3-yl]-N-(tetrahydro-pyran-2-yloxy)-acrylamide (7.60 g) and 4-{2-[4-(4,4,5,5-tetramethyl-[1,3,2]dioxaborolan-2-yl)-phenyl]-ethyl}-morpholin (8.00 g) are dissolved in DME (300 mL). (Ph3P)3PdCl2 (2.40 g) and a 2M Na₂CO₃-solution (25 mL) are added and the mixture is heated 5 h to reflux temperature under an inert gas atmosphere. The reaction mixture is filtered and evaporated. After addition of a NaHCO₃-solution and ethyl acetate, the organic phase is dried and evaporated. The crude product is purified by silica gel flash chromatography. 8.1 g of the title compound are obtained.

A7. (E)-3-(1-{4-[2-(4-Methyl-piperazin-1-yl)-pyridin-4-yl]-benzenesulfonyl}-1H-pyrrol-3-yl)-N-(tetrahydro-pyran-2-yloxy)-acrylamide (E)-3-[1-(4-Bromo-benzenesulfonyl)-1H-pyrrol-3-yl]-N-(tetrahydro-pyran-2-yloxy)-acrylamide (6.8 g) and 1-methyl-4-[4-(4,4,5,5-tetramethyl-[1,3,2]dioxaborolan-2-yl)-pyridin-2-yl]-piperazine (5.0 g) are dissolved in DME (300 mL). Under an inert gas atmosphere are added (Ph3P)₃PdCl2 (2.1 g) and 2M Na₂CO₃-solution (44 mL). The mixture is heated to 100° C. for 2.5 h. After filtration and extraction, the crude product from the organic phase is purified by silica gel flash chromatography. By means of chloroform/EtOH (30:1-19:1). 5.3 g of the title compound are obtained as brownish oil.

In a similar way is obtained (E)-3-(1-{3-[2-(4-methyl-piperazin-1-yl)-pyridinyl]-benzenesulfonyl}-1H-pyrrol-3-yl)-N-(tetrahydro-pyran-2-yloxy)-acrylamide (9.2 g) from the corresponding bromo-compound (10.9 g).

A8. (E)-3-{1-([4-(3-Morpholin-4-yl-propoxy)-biphenyl-3-sulfonyl]-1H-pyrrol-3-yl}-N-(tetrahydro-pyran-2-yloxy)-acrylamide (E)-3-[1-(3-Bromo-benzenesulfonyl)-1H-pyrrol-3-yl]-N-(tetrahydro-pyran-2-yloxy)-acrylamide (4.6 g) and 4-{3-[4-(4,4,5,5-tetramethyl-[1,3,2]dioxaborolan-2-yl)-phenoxy]-propyl}-morpholine (3.9 g) are dissolved in DME (200 mL). Under an inert gas atmosphere are added are added (Ph3P)3PdCl2 (1.4 g) and 2M Na₂CO₃-solution (31 mL). The mixture is heated to 100° C. for 2 h. After filtration and extraction, the crude product from the organic phase is purified by silica gel flash chromatography. 4.7 g of the title compound are obtained as brownish oil.

A9. (E)-3-(1-{4'-[2-(4-Methyl-piperazin-1-yl)-ethoxy]-biphenyl-3-sulfonyl}-1H-pyrrol-3-yl)-N-(tetrahydro-pyran-2-yloxy)-acrylamide (E)-3-[1-(3-Bromo-benzenesulfonyl)-1H-pyrrol-3-yl]-N-(tetrahydro-pyran-2-yloxy)-acrylamide (7.9 g) and 1-methyl-4-{2-[4-(4,4,5,5-tetramethyl-[1,3,2]dioxaborolan-2-yl)-phenoxy]-ethyl}-piperazine (9.0 g) are dissolved in DME (300 mL). Under an inert gas atmosphere there are added (Ph3P)₃PdCl2 (2.4 g) and 2M Na₂CO₃-solution (50 mL) and the mixture is heated to 100° C. for 2 h. The mixture is filtered, evaporated and the residue is treated with ethyl acetate and 5% solution of NaHCO₃. The organic phase is dried and evaporated and the crude product is purified by silica gel flash chromatography. 5.7 g of the Ube compound are obtained.

A10. (E)-3-{1-[5-(4-Dimethylaminomethyl-phenyl)-thiophene-2-sulfonyl]-1H-pyrrol-3-yl}-N-(tetrahydro-pyran-2-yloxy)-acrylamide E)-3-[1-(5-Bromo-thiophene-2-sulfonyl)-1H-pyrrol-3-yl]-N-(tetrahydro-pyran-2-yloxy)-acrylamide (6.4 g) and dimethyl-[4-(4,4,5,5-tetramethyl-[1,3,2]dioxaborolan-2-yl)-benzyl]-amine (4.0 g) are dissolved in DME (300 mL). Under an inert gas atmosphere there are added (Ph3P)3PdCl2 (1.9 g) and 2M Na₂CO₃-solution (42 mL) and the mixture is heated to 100° C. for 2 h. The mixture is filtered, evaporated and the residue is treated with ethyl acetate and 5% solution of NaHCO₃. The organic phase is dried and evaporated and the crude product is purified by silica gel flash chromatography. 5.4 g of the title compound are obtained.

The requisit boronic acids or boronic acid esters can be prepared according to WO 2005/070900 or US 2002026052 or as described by way of example below, or analogously or similarly thereto. Further information for the preparation of boronic acids and their esters can be found in J Organic Chem 2000, 65, 6458, J Organic Chem 1997, 62, 164 or Synthesis, 2003, 469-483.

[5-(4,4,5,5-Tetramethyl-[1,3,2]dioxaborolan-2-yl)-pyridin-2-yl]-carbamic acid tert-butyl ester 5-Bromo-2-[(tert-butoxycarbonyl)amino]pyridine (1.00 g), potassium acetate (1.08 g), the corresponding diborane ester (1.02 g) and PdCl$_2$(dppf) (90 mg) are dissolved in DMF (22 mL) and heated 1 h to 80° C. After addition of additional catalyst (90 mg) and one further hour at 80° C., the mixture is evaporated and the residue is purified by silica gel flash chromatography.

With the choice of the appropriate starting materials further relevant starting compounds, which afford final compounds of this invention, can be prepared analogously or similarly as described herein.

General Procedure Suzuki Coupling

Under nitrogen a microwave vial is charged with (E)-3-[1-(4-Iodo-benzenesulfonyl)-1H-pyrrol-3-yl]-N-(tetrahydro-pyran-2-yloxy)-acrylamide (0.30 mmol), Boronic acid (0.36 mmol), bis(triphenylphosphine)palladium(II)chloride (0.015 mmol), Cs$_2$CO$_3$ (0.42 mmol), ethanol (0.3 ml), water (0.5 ml) and dimethoxyethane (1.2 ml). The reaction mixture is heated in a Personal Chemistry Microwave oven at 140° C. for 900 seconds. After filtration over alumina (500 mg; neutral, activity II -III) using DCM/MeOH 4:1 as eluent and evaporation of the solvent the crude product is purified by prep. HPLC.

Sonogashira Coupling (E)-N-(Tetrahydro-pyran-2-yloxy)-3-[1-(4-trimethyl-silanylethynyl-benzenesulfonyl)-1H-pyrrol-3-yl]-acrylamide Under nitrogen a microwave vial is charged with (E)-3-[1-(4-Iodo-benzenesulfonyl)-1H-pyrrol-3-yl]-N-(tetrahydro-pyran-2-yloxy)-acrylamide (5.00 mmol), Trimethylsilylacetylene (6.00 mmol), CuI (0.50 mmol), bis(triphenylphosphine)palladium(II)chloride (0.25 mmol), triethylamine (10.0 mmol) and THF (8 ml). The reaction mixture is heated in a Personal Chemistry Microwave oven at 100° C. for 3600 seconds. Methanol is added to the reaction mixture and the solution is filtered over alumina (10 g, neutral, activity II-III) using MeOH as eluent. After evaporation of the solvent the crude product is purified by prep. HPLC yielding the title compound as yellow powder (2.29 mmol).

Deprotection (E)-3-[1-(4-Ethynyl-benzenesulfonyl)-1H-pyrrol-3-yl]-N-(tetrahydro-pyran-2-yloxy)-acrylamide To a stirred solution of (E-N-(Tetrahydro-pyran-2-yloxy)-3-[1-(4-trimethylsilanylethynyl-benzenesulfonyl)-1H-pyrrol-3-yl]-acrylamide (0.139 mmol) in methanol (1.2 ml) is added KF (0.26 mmol). After 15 min the solvent is evaporated and the residue is taken up in DCM and filtered over alumina (1 g, neutral, activity II-III) using DCM as eluent. After evaporation of the solvent 0.0801 mmol of the title compound are obtained.

Triazol Formation (E)-N-(Tetrahydro-pyran-2-yloxy)-3-(1-{4-[1-(2-morpholin-4-yl-ethyl)-1H-[1,2,3]triazol-4-yl]-benzenesulfonyl}-1H-pyrrol-3-yl)-acrylamide To a stirred mixture of 2-morpholino-ethylazide (0.30 mmol) in water (2 ml) are added CuSO$_4$ pentahydrate (0.02 mmol), sodiumascorbate (0.04 mmol) and (E)-3-[1-(4-Ethynyl-benzenesulfonyl)-1H-pyrrol-3-yl]-N-(tetrahydro-pyran-2-yloxy)-acrylamide (0.30 mmol) in t-BuOH (1 ml) at room temperature. The reaction mixture is stirred over night. After addition of DCM the organic phase is separated, evaporated under reduced pressure and purified by prep. HPLC yielding 0.081 mmol of the title compound.

B1. (E)-[1-(4-Bromo-benzenesulfonyl)-1H-pyrrol-3-yl]-(tetrahydro-pyran-2-yloxy)-acrylamide To a mixture of 3.16 g (E)-3-[1-(4-Bromo-benzenesulfonyl)-1H-pyrrol-3-yl]-acrylic acid and 170 ml DMF are added 1.06 g HOBtxH$_2$O and 7.02 g Et$_3$N. This mixture is stirred for 70 min at ambient temperature. 3.99 g EDCxHCl are added and the reaction mixture is stirred for additional 45 min. 0.812 g O-(tetrahydro-2H-pyran-2-yl)-hydroxylamin are added and the reaction mixture is stirred overnight. The solvent is evaporated and the residue is partitioned between ethyl acetate and water. The organic phase is dried, evaporated and the crude product is purified by silica gel flash chromatography.

B2. (2-{(E)-3-[1-(4-Iodo-benzenesulfonyl)-1H-pyrrol-3-yl]allanoylamino}-phenyl)-carbamic acid tert-butyl ester A mixture of 2.5 g (E)-3-[1-(4-Iodo-benzenesulfonyl)-1H-pyrrol-3-yl]-acrylic acid is dissolved in 140 ml DMF. To this mixture are added 0.949 g HOBtxH$_2$O, and 6.27 g Et$_3$N. After 30 min 3.57 g EDCxHCl are added and the resulting mixture is stirred for 30 min. Now 1.29 g of N-boc-o-phenylenediamine are added and the reaction mixture is stirred overnight. The solvent is evaporated and the residue is partitioned between ethyl acetate and water. The organic phase is dried and evaporated and the crude product is purified by silica gel flash chromatography.

B3. (E)-3-[1-(5-Bromo-thiophene-2-sulfonyl)-1H-pyrrol-3-yl]-N-(tetrahydro-pyran-2-yloxy)-acrylamide A mixture of 3.8 g (E)-3-[1-(5-bromo-thiophene-2-sulfonyl)-1H-pyrrol-3-yl]-acrylic acid with 200 ml DMF and 1.6 g HOBtxH$_2$O and 15.0 ml triethylamine is stirred at ambient temperature for 0.5 h. Then 6.04 g EDCxHCL are added and the suspension is stirred again for 0.5 h. Finally 1.23 g O-(tetrahydro-2H-pyran-2-yl)hydroxylamine are added and the suspension is stirred at ambient temperature for 24 h. The DMF is evaporated and the residue is extracted with ethyl acetate and water. The organic layer is dried over sodium sulfate and evaporated. The title product is isolated by flash chromatography. By this method 4.6 g of a yellow foam are obtained.

B4. (2-(E)-3-[1-(5-Bromo-thiophene-2-sulfonyl)-1H-pyrrol-3-yl]-allanoylamino)-phenyl)-carbamic acid tert-butyl ester A mixture of 4.1 g (E)-3-[1-(5-bromo-thiophene-2-sulfonyl)-1H-pyrrol-3-yl]-acrylic acid with 200 ml DMF and 1.8 g HOBt$^x$H$_2$O and 16.0 ml triethylamine is stirred for 0.5 h. Then it is added 6.6 g EDC$^x$HCL and stirred for 0.5 h. After that 2.4 g (2-amino-phenyl)-carbamic acid tert-butyl ester are added and the suspension is stirred at ambient temperature for 24 h. The DMF is evaporated and the residue is extracted with ethyl acetate and water. The organic layer is dried over sodium sulfate and evaporated. The title product is isolated by flash chromatography. By this method 3.7 g of a colorless solid is obtained.

B5. (2{(E)-3-[1-(3-Bromo-benzenesulfonyl)-1H-pyrrol-3-yl]-allanoylamino}-phenyl)-carbamic acid tert-butyl ester A mixture of 5.4 g (E)-3-[1-(3-bromo-benzenesulfonyl)-1H-pyrrol-3-yl]-acrylic acid with 300 ml DMF and 2.34 g HOBt.H$_2$O and 21.0 ml Triethylamine is stirred at ambient temperature for 0.5 h. Then it is added 8.8 g EDC.HCL and it is stirred again at ambient temperature for 0.5 h. Finally 3.2 g (2-amino-phenyl)-carbamic acid tert-butyl ester are added and the suspension is stirred at ambient temperature for 24 h. The DMF is evaporated and the residue is extracted with ethyl acetate and water. The organic layer is dried over sodium sulfate. The title product is isolated by flash chromatography. By this method 6.3 g of a yellow foam is obtained.

B6. (E)-3-[1-(3-Bromo-benzenesulfonyl)-1H-pyrrol-3-yl]-N-(tetrahydro-pyran-2-yloxy)-acrylamide A mixture of 6.1 g (E)-3-[1-(3-bromo-benzenesulfonyl)-1H-pyrrol-3-yl]-acrylic acid with 300 ml DMF and 2.6 g HOBt.H$_2$O and 24.0 ml triethylamine is stirred at ambient temperature for 0.5 h. Then 9.8 g EDC.HCL is added and the suspension is stirred again at ambient temperature for 0.5 h. After that 2.0 g O-(tetrahydro-2H-pyran-2-yl)hydroxylamine are added and the suspension is stirred at ambient temperature for 24 h. The DMF is evaporated and the residue is extracted with ethyl acetate and water. The organic layer is dried over sodium sulfate. The title compound is isolated by flash chromatography. By this method 6.3 g of a yellow foam are obtained.

B7. (2-{(E)-3-[1-(4-Bromo-benzenesulfonyl)-1H-pyrrol-3-yl]-allanoylamino}-phenyl)-carbamic acid tert-butyl ester A mixture of 3.1 g (E)-3-[1-(4-bromo-benzenesulfonyl)-1H-pyrrol-3-yl]-acrylic acid with 170 ml DMF and 1.3 g HOBt.H$_2$O and 12.0 ml triethylamine is stirred for 0.5 h. Then 4.9 g EDC.HCL is added and the suspension is stirred again at ambient temperature for 0.5 h. After that 1.8 g (2-amino-phenyl)-carbamic acid tert-butyl ester are added and the mixture is stirred at ambient temperature for 24 h. The DMF is evaporated and the residue is extracted with ethyl acetate and water. The organic layer is dried over sodium sulfate. The title compound is isolated by flash chromatography.

B8. (E)-3-[1-(4-Iodo-benzenesulfonyl)-1H-pyrrol-3-yl]-N-(tetrahydro-pyran-2-yloxy)-acrylamide The title compound is prepared in a similar or analog fashion as described for compound B1.

C1. (E)-3-[1-(4-Bromo-benzenesulfonyl)-1H-pyrrol-3-yl]-acrylic acid

The title compound is prepared similarly to the corresponding iodo-analogue C2.

C2. (E)-3-[1-(4-Iodo-benzenesulfonyl)-1H-pyrrol-3-yl]-acrylic acid

A mixture of 6.69 g (E)-3-[1-(4-Iodo-benzenesulfonyl)-1H-pyrrol-3-yl]-acrylic acid tert-butyl ester in 180 ml dichloromethane and 18.1 ml TFA is stirred at ambient temperature over the weekend. The reaction mixture is evaporated and the crude product is washed with toluene and dried in vacuo.

C3. (E)-3-[1-(4-Bromo-benzenesulfonyl)-1H-pyrrol-3-yl]-acrylic acid

A mixture of 7.0 g (E)-3-[1-(4-bromo-benzenesulfonyl)-1H-pyrrol-3-yl]-acrylic acid tert-butyl ester with 200 ml dichloromethane and 21.0 ml TFA is stirred at ambient temperature for 24 h. The dichloromethane and TFA is evaporated and the residue is coevaporated with toluene for 3 times. By this method 6.0 g of the title compound is obtained.

C4. (E)-3-[1-(3-Bromo-benzenesulfonyl)-1H-pyrrol-3-yl]-acrylic acid

A mixture of 2.0 g (E)-3-[1-(3-bromo-benzenesulfonyl)-1H-pyrrol-3-yl]-acrylic acid tert-butyl ester with 60 ml dichloromethane and 6.0 ml TFA is stirred at ambient temperature for 24 h. The dichloromethane and TFA is evaporated and the residue is coevaporated with toluene for a few times. By this method 0.77 g brown solid is obtained.

C5. (E)-3-[1-(5-Bromo-thiophene-2-sulfonyl)-1H-pyrrol-3-yl]-acrylic acid

A mixture of 4.5 g (E)-3-[1-(5-bromo-thiophene-2-sulfonyl)-1H-pyrrol-3-yl]-acrylic acid tert-butyl ester with 85.0 ml dichloromethane and 13.0 ml TFA is stirred at ambient temperature for 24 h. The dichloromethane and TFA is evaporated and the residue is coevaporated with toluene for 3 times. By this method 3.8 g light pink solid is obtained.

D1. (E)-3-[1-(4-Iodo-benzenesulfonyl)-1H-pyrrol-3-yl]-acrylic acid tert-butyl ester A mixture of 0.85 g NaH (60% in oil) in 70 ml THF is cooled to −30° C. and 5 g (E)-3-(1H-Pyrrol-3-yl)-acrylic acid tert-butyl ester are added at this temperature. The mixture is stirred for 30 min and 9.4 g 4-iodobenzenesolfonylchloride are added at −30° C. The reaction mixture is stirred for 5 h at ambient temperature and quenched with 25 ml of water. The organic phase is separated and the aqueous phase is washed three times with 40 ml ethyl acetate. The combined organic extracts are dried over sodium sulfate and evaporated. The crude product is purified by silica gel flash chromatography.

D2. (E)-3-[1-(5-Bromo-thiophene-2-sulfonyl)-1H-pyrrol-3-yl]-acrylic acid tert-butyl ester A mixture of 0.53 g NaH (60%) with 40.0 ml THF is cooled down to −30° C. and 3.1 g (E)-3-(1H-pyrrol-3-yl)-acrylic acid tert-butyl ester are added. During the addition it is liberated a gas. The solution is stirred at ambient temperature for 0.5 h. Then 5.0 g of 5-bromothiophene-2-sulfonylchloride is added by -30° C. The mixture is stirred at ambient temperature for 24 h. The NaH is hydrolyzed with water and the solution is extracted with ethyl acetate. The title compound is isolated by flash chromatography. By this method 4.5 g of colorless crystals are obtained.

D3. (E)-3-[1-(3-Bromo-benzenesulfonyl)-1H-pyrrol-3-yl]-acrylic acid tert-butyl ester A mixture of 0.77 g NaH (60%) with 65.0 ml THF is cooled to −30° C. Then 3.2 g 3.1 g (E)-3-(1H-pyrrol-3-yl)-acrylic acid tert-butyl ester are added. During the addition there is liberated a gas. The solution is stirred at ambient temperature for 0.5 h. Finally 5.0 g 3-bromobenzenesulfonylchloride are added at −30° C. The suspension is stirred at ambient temperature for 24 h. The suspension is treated with water and the solution is extracted with ethyl acetate. The organic layer is dried over sodium sulfate and evaporated. The residue (oil) is crystallized from methanol. The crystals are dried in vacuo. By this method 5.7 g of colorless crystals are obtained.

D4. (E)-3-[1-(4-Bromo-benzenesulfonyl)-1H-pyrrol-3-yl]-acrylic acid tertbutyl ester A mixture of 0.85 g NaH with 70.0 ml THF is cooled to −30° C. and 5.0 g (E)-3-(1H-pyrrol-3-yl)-acrylic acid tert-butyl ester are added. During the addition there is liberated a gas. The solution is stirred at ambient temperature for 0.5 h. Then 7.9 g 4-bromobenzenesulfonylchloride is added by -30° C. The suspension is stirred at ambient temperature for 3 h. The mixture is treated with water and then it is extracted with ethyl acetate. The title compound is isolated by flash chromatography. By this method 7.0 g of a colorless solid are obtained.

E1. (E)-3-(1H-Pyrrol-3-yl)-acrylic acid tert-butyl ester 5.29 g of sodium hydride 60% is suspended in 100 ml of tetrahydrofurane under nitrogen at −30° C. 27.81 g of tert-butyl diphosphono acetate are added to the suspension and warmed slowly to room temperature and stirred for 30 minutes. Afterwards the mixture is recooled at −30° C. and it is added 5.24 g of 1H-pyrrol-3-carbaldehyde (compound F1) and stirred at −30° C. for 30 minutes. The suspension is warmed slowly to room temperature and 200 ml of aqueous ammonia solution are added. Then it is extracted with ethyl acetate. The combined organic phase is dried over $Na_2SO_4$, filtered and evaporated under vacuo. The crude product is purified by silica gel flash chromatography using a gradient of n-hexane-ethyl acetate from 2:1 to 1:1 to give 9.68 g of the title compound as a pale yellow solid.

MS (EI): 193.1 ($M^+$); 137.1 ($M^+$-$C_4H_8$, 100%) $^1$H-NMR (DMSO-d6): 1.45 (s, 9H); 5.96 (d, J=15.7 Hz, 1H); 6.40 (m, 1H); 6.78 (m, 1H); 7.19 (m, 1H); 7.47 (d, J=15.7 Hz, 1H); 11.11 (bs, exchangeable, 1H)

F1. 1H-Pyrrol-3-carbaldehyde 4.70 g of dimethyl-(1H-pyrrol-3-ylmethylene)-ammonium chloride (compound G1) are dissolved in 500 ml of 5.0% aqueous sodium hydroxide solution and stirred for 4 hours at ambient temperature. Afterwards the reaction mixture is extracted exhaustively with $CH_2Cl_2$. The combined organic phase is dried over $Na_2SO_4$. Then it is filtered and evaporated under vacuo. The crude product is purified by a silica gel flash chromatography using petroleum ether/diethylether 1:1 eluent to yield 3.01 g of the title compound as a pale yellow solid.

MS (EI):95.1 ($M^+$, 100%) $^1$H-NMR (DMSO-d6): 6.42 (dd, $J_1$=1.5 Hz, $J_2$=6.5 Hz, 1H); 6.90 (m, 1H), 7.69 (dd, $J_1$=1.5 Hz, $J_2$=6.4 Hz, 1H); 9.68 (s, 1H); 11.59 (bs, exchangeable, 1H)

G1. Dimethyl-(1H-pyrrol-4-ylmethylene)-ammonium chloride 10.60 g of (chloromethylene)dimethylammonium chloride and 6.25 g of N-(triisopropylsilyl)-pyrrole are suspended in 200 ml of $CH_2Cl_2$ under nitrogen at 0-5° C. The suspension is warmed to 60° C. and stirred for 30 minutes. Afterwards the mixture is cooled to ambient temperature. The suspension is filtered and washed with diethylether to give 5.67 g of the title compound as grey solid.

MS (ESI): 123.3 ($MH^+$, 100%) $^1$H-NMR (DMSO-d6): 3.55 (s, 3H); 3.63 (s, 3H); 6.82 (m, $J_1$=1.4 Hz, $J_2$=1.5 Hz, $J_3$=$J_4$=4.8 Hz, 1H); 7.22 (dd, $J_1$=4.7 Hz, $J_2$=4.9, 1H), 8.00 (dd, $J_1$=1.6 Hz, $J_2$=1.7 Hz, 1H); 8.78 (s, 1H); 12.94 (bs, exchangeable, 1H)

Using similar procedures to those described to attain to the abovementioned examples, but with suitable choice of the starting materials, which are described explicitly herein or which can be prepared in a manner known to the person skilled in the art or analogously or similarly to the materials described herein, further relevant compounds can be prepared.

Commercial Utility

The compounds according to this invention have valuable pharmacological properties and effects, which make them commercially applicable, such as e.g. they are commercially utilizable by properties related with inhibiting histone deacetylase activity and function.

"Histone deacetylase" (HDAC) means an enzyme with an activity towards the F-acetyl group of lysine residues within a substrate protein. HDAC substrates are histone H2A, H2B, H3 or H4 proteins and isoforms but substrate proteins different to histones like, but not limited to, heat shock protein 90 (Hsp90), tubulin or the tumor suppressor protein p53 exist. In particular histone deacetylases catalyse the hydrolysis the ε-acetyl group of lysine residues within these substrate proteins, forming the free amino group of lysine.

Inhibition of histone deacetylase by compounds according to this invention means inhibiting the activity and function of one or more HDAC isoenzymes, in particular isoenzymes selected from the so far known histone deacetylases, namely HDAC 1, 2, 3 and 8 (class I) and HDAC 4, 5, 6, 7, 10 (class II), HDAC 11 as well as the NAD+ dependent class III (Sir2 homologues). In some preferred embodiment this inhibition is at least about 50%, more preferable at least 75% and still more preferable above 90%. Preferably, this inhibition is specific to a specific histone deacetylase class (eg HDAC class I enzymes), a selection of isoenzymes of highest pathophysiological relevance (eg HDAC 1, 2, 3 enzymes) or a single isoenzyme (eg the HDAC 1 enzyme). A histone deacetylase inhibitor in the meaning of this invention is therefore a compound capable of interacting with a histone deacetylase and inhibiting its activity, in particular its enzymatic activity. In this context "head group" defines the residues within a histone deacetylase inhibitor responsible for interacting with the active site of the enzyme, eg the $Zn^{2+}$ ion.

The inhibition of histone deacetylases is determined in biochemical assays of various formats and sources of enzymatic activity. HDAC activity is used either derived from nuclear or cellular extracts or by heterologous expression of defined HDAC isoenzymes in *E. coli*, insect cells or mammalian cells. Since HDAC isoenzymes are active in multiprotein complexes and form homo- and heterodimeres, nuclear extracts derived from human cancer cells, for example the human cervical carcinoma cell line HeLa, are preferred. These nuclear extracts contain class I and class II enzymes, but are enriched in class I enzymes. For expression of recombinant HDAC isoenzymes, mammalian expression systems like HEK293 cells are preferred. The HDAC isoenzyme is expressed as a fusion protein with an affinity tag, like the FLAG epitope. By affinity chromatography, the tagged protein is purified alone or in complex with endogenous proteins (eg other HDAC isoenzmyes and coactivators/platform proteins). The biochemical assays are well described and well known to persons skilled in the art. As substrates, histone proteins, peptides derived from histone proteins or other HDAC substrates as well as acetylated lysine mimetics are used. One preferred promiscuous HDAC substrate is the tripeptide Ac-NH-GGK(Ac), coupled with the fluorophore 7-aminomethylcoumarin (AMC).

The invention further relates to the use of the compounds according to this invention for inhibiting histone deacetylase activity in cells and tissues, causing hyperacetylation of substrate proteins and as functional consequence, for example, the induction or repression of gene expression, induction of protein degradation, cell cycle arrest, induction of differentiation and/or induction of apoptosis.

The cellular activity of a histone deacetylase inhibitor includes any cellular effect related to histone deacetylase inhibition, in particular protein hyperacetylation, transcriptional repression and activation, induction of apoptosis, differentiation and/or cytotoxicity.

The term "induction of apoptosis" and analogous terms are used to identify a compound which executes programmed cell death in cells contacted with that compound. "Apoptosis" is defined by complex biochemical events within the contacted cell, such as the activation of cysteine specific proteinases ("caspases") and the fragmentation of chromatin. Induction of apoptosis in cells contacted with the compound might not necessarily coupled with inhibition of cell proliferation or cell differentiation. Preferably, the inhibition of proliferation, induction of differentiation and/or induction of apoptosis is specific to cells with aberrant cell growth.

"Induction of differentiation" is defined as a process of cellular reprogramming leading to a reversible or irreversible cell cycle arrest in G0 and re-expression of a subset of genes typical for a certain specialized normal cell type or tissue (eg re-expression of milk fat proteins and fat in mammary carcinoma cells).

"Cytotoxicity" in general means arresting proliferation and/or inducing apoptotic cell death in vitro in mammalian cells, in particular human cancer cells.

Assays for quantification of cell proliferation, apoptosis or differentiation are well known to experts and state of the art. For example, metabolic activity which is linked to cellular proliferation is quantified using the Alamar Blue/Resazurin assay (O'Brian et al. Eur j Biochem 267, 5421-5426, 2000) and induction of apoptosis is quantified by measurement of chromatin fragmentation with the cell death detection ELISA commercialized by Roche. Examples for cellular assays for the determination of hyperacetylation of HDAC substrates are given by measuring core histone acetylation using specific antibodies by Western blotting, reporter gene assays using respective responsive promoters or promoter elements (eg the p21 promotor or the sp1 site as responsive element) or finally by image analysis again using acetylation specific antibodies for core histone proteins.

Compounds according to this invention can be commercially applicable due to their HDAC inhibitory, anti-proliferative and/or apoptosis inducing activity, which may be beneficial in the therapy or prophylaxis of diseases responsive thereto, such as e.g. any of those diseases mentioned herein.

The invention further relates to a method for treating, ameliorating or preventing cellular neoplasia by administration of an effective amount of a compound according to this invention to a mammal, in particular a human in need of such treatment. A "neoplasia" is defined by cells displaying aberrant cell proliferation and/or survival and/or a block in differentiation. The term "neoplasia" includes benign neoplasia, which is described by hyperproliferation of cells, incapable of forming an aggressive, metastasizing tumor in-vivo, and, in contrast, malignant neoplasia, which is described by cells with multiple cellular and biochemical abnormalities, capable of forming a systemic disease, for example forming tumor metastasis in distant organs.

Compounds according to this invention can be particularly used for the treatment of malignant neoplasia, also described as cancer, characterized by tumor cells finally metastasizing into distinct organs or tissues. Examples of malignant neoplasia treated with compounds according to the present invention include solid and hematological tumors. Solid tumors are exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasia include inherited cancers exemplified by Retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Neoplastic cell proliferation might also effect normal cell behaviour and organ function. For example the formation of new blood vessels, a process described as neovascularization, is induced by tumors or tumor metastases. Compounds according to this invention can be commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics.

This drug resistance is caused by various cellular and molecular mechanisms like overexpression of drug efflux pumps, mutation within the cellular target protein or fusion proteins formed by chromosomal translocations. The commercial applicability of compounds according to the present invention is not limited to $1^{st}$ line treatment of patients. Patients with resistance to cancer chemotherapeutics or target specific anti-cancer drugs can be also amenable for treatment with these compounds for e.g. $2^{nd}$ or $3^{rd}$ line treatment cycles. A prominent example is given by acute promyelocytic leukemia patients with the PML-RARα fusion protein, resistant to standard therapy with retinoids. These patents can be resensitized towards retinoids by treatment with HDAC inhibitory drugs like the compounds according to the present invention.

The invention further provides to a method for treating a mammal, in particular a human, bearing a disease different to cellular neoplasia, sensitive to histone deacetylase inhibitor therapy comprising administering to said mammal a pharmacologically active and therapeutically effective and tolerable amount of a compound according to this invention. These non malignant diseases include (i) arthropathies and osteopathological diseases such as rheumatoid arthritis, osteoarthrtis, gout, polyarthritis and psoriatic arthritis (ii) autoimmune diseases like systemic lupus erythematosus and transplant rejection (iii) hyperproliferative diseases such as psoriasis or smooth muscle cell proliferation including vascular proliferative disorders, atherosclerosis and restenosis (iv) acute and chronic inflammatory diseases and dermal diseases such as ulcerative colitis, Crohns disease, allergic rhinitis, allergic dermatitis, cystic fibrosis, chronic obstructive bronchitis and asthma (v) endometriosis, uterine fibroids, endometrial hyperplasia and benign prostate hyperplasia (vi) cardiac dysfunction (vii) inhibiting immunosuppressive conditions like HIV infections (viii) neuropathological disorders like Parkinson disease, Alzheimer disease or polyglutamine related disorders (ix) pathological conditions amenable to treatment by potentiating of endogenous gene expression as well as enhancing transgene expression in gene therapy.

Compounds according to the present invention may commercially applicable for treatment, prevention or amelioration of the diseases of benign and malignant behavior as described herein, such as, for example, (hyper)proliferative diseases and/or disorders responsive to induction of apoptosis and/or disorders responsive to cell differentiation, e.g. benign or malignant neoplasia, particularly cancer, such as e.g. any of those cancer diseases described above.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability (e.g. solubility behaviour).

The present invention further includes a method for the treatment of mammals, including humans, which are suffering from one of the abovementioned conditions, illnesses, disorders or diseases. The method comprises that a pharmacologically active and therapeutically effective and tolerable amount of one or more of the compounds according to this invention, which function by inhibiting histone deacetylases and—in general—by modulating protein acetylation, induce various cellular effects, in particular induction or repression of gene expression, arresting cell proliferation, inducing cell differentiation and/or inducing apoptosis, is administered to the subject in need of such treatment.

The invention further includes a method for treating diseases and/or disorders responsive or sensitive to the inhibition of histone deacetylases, particularly those diseases mentioned above, such as e.g. cellular neoplasia or diseases different to cellular neoplasia as indicated above, in mammals, including humans, suffering therefrom comprising administering to said mammals in need thereof a pharmacologically active and therapeutically effective and tolerable amount of one or more of the compounds according to the present invention.

The present invention further includes a therapeutic method useful to modulate protein acetylation, gene expression, cell proliferation, cell differentiation and/or apoptosis in vivo in diseases mentioned above, in particular cancer, comprising administering to a subject in need of such therapy a pharmacologically active and therapeutically effective and tolerable amount of one or more of the compounds according to this invention, which function by inhibiting histone deacetylases.

The present invention further provides a method for regulating endogenous or heterologous promotor activity by contacting a cell with a compound according to this invention.

The invention further relates to the use of the compounds according to the present invention for the production of pharmaceutical compositions which are employed for the treatment and/or prophylaxis and/or amelioration of the diseases, disorders, illnesses and/or conditions as mentioned herein.

The invention further relates to the use of the compounds according to the present invention for the production of pharmaceutical compositions which are employed for the treatment and/or prophylaxis of diseases and/or disorders responsive or sensitive to the inhibition of histone deacetylases, particularly those diseases mentioned above, such as e.g. cellular neoplasia or diseases different to cellular neoplasia as indicated above.

The invention further relates to the use of the compounds according to the present invention for the production of pharmaceutical compositions having histone deacetylase inhibitory activity.

The invention further relates to the use of the compounds according to the present invention for the production of pharmaceutical compositions for inhibiting or treating cellular neoplasia, such as benign or malignant neoplasia, e.g. cancer.

The invention further relates to the use of the compounds according to the present invention for the production of pharmaceutical compositions which can be used for treating, preventing or ameliorating of diseases responsive to arresting aberrant cell growth, such as e.g. (hyper)proliferative diseases of benign or malignant behaviour, such as e.g. any of those diseases mentioned herein, particularly cancer, such as e.g. any of those cancer diseases described herein above.

The invention further relates to the use of the compounds according to the present invention for the production of pharmaceutical compositions which can be used for treating, preventing or ameliorating of disorders responsive to induction of apoptosis, such as e.g. any of those diseases mentioned herein, particularly cancer, such as e.g. any of those cancer diseases described herein above.

The invention further relates to the use of the compounds according to the present invention for the production of pharmaceutical compositions which can be used for treating, preventing or ameliorating of disorders responsive to induction of differentiation, such as e.g. any of those diseases mentioned herein, particularly cancer, such as e.g. any of those cancer diseases described herein above.

The invention further relates to the use of the compounds according to the present invention for the production of pharmaceutical compositions which can be used for treating, preventing or ameliorating of benign or malignant neoplasia, particularly cancer, such as e.g. any of those cancer diseases described herein above.

The invention further relates to the use of the compounds according to the present invention for the production of pharmaceutical compositions for the treatment of a disease different to a cellular neoplasia and sensitive to histone deacetylase inhibitor therapy, such as the non-malignant diseases mentioned before.

The invention further relates to the use of the compounds according to the present invention for the production of pharmaceutical compositions for inhibiting histone deacetylase activity in the treatment of diseases responsive to said inhibition or to the functional consequences thereof.

The invention further relates to a method for treating, preventing or ameliorating the diseases, disorders, illnesses and/or conditions mentioned herein in a mammal, in particular a human patient, comprising administering a pharmacologically active and therapeutically effective and tolerable amount of one or more compounds according to the present invention to said mammal in need thereof.

The invention further relates to the compounds according to this invention for use in the treatment and/or prophylaxis of diseases, especially the diseases mentioned.

The invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The invention further relates to a combination comprising one or more of the compounds according to this invention and a pharmaceutically acceptable diluent, excipient and/or carrier, e.g. for treating, preventing or ameliorating (hyper)proliferative diseases of benign or malignant behaviour and/or disorders responsive to induction of apoptosis, such as, for example, benign or malignant neoplasia, e.g. cancer, such as e.g. any of those cancer diseases described herein above.

The invention further relates to pharmaceutical compositions according to this invention having histone deacetylases inhibitory activity.

The invention further relates to pharmaceutical compositions according to this invention having apoptosis inducing activity.

The invention further relates to pharmaceutical compositions according to this invention having anti-proliferative activity.

The invention further relates to pharmaceutical compositions according to this invention having cell differentiation inducing activity.

The invention further relates to the use of a pharmaceutical composition comprising one or more of the compounds according to this invention and a pharmaceutically acceptable carrier or diluent in the manufacture of a pharmaceutical product, such as e.g. a commercial package, for use in the treatment and/or prophylaxis of the diseases as mentioned.

Additionally, the invention relates to an article of manufacture, which comprises packaging material and a pharmaceutical agent contained within said packaging material, wherein the pharmaceutical agent is therapeutically effective for inhibiting the effects of histone deacetylases, ameliorating the symptoms of an histone deacetylase mediated disorder, and wherein the packaging material comprises a label or package insert which indicates that the pharmaceutical agent is useful for preventing or treating histone deacetylase mediated disorders, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, compounds according to this invention are in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the compounds of the invention (=active compounds) is carried out in the order of magnitude customary for histone deacetylases inhibitors. Topical application forms (such as ointments) for the treatment of dermatoses thus contain the active compounds in a concentration of, for example, 0.1-99%. The customary dose in the case of systemic therapy (p.o.) may be between 0.03 and 60 mg/kg per day, (i.v.) may be between 0.03 and 60 mg/kg/h. In another embodiment, the customary dose in the case of systemic therapy (p.o.) is between 0.3 and 30 mg/kg per day, (i.v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Depending upon the particular disease, to be treated or prevented, additional therapeutic active agents, which are normally administered to treat or prevent that disease, may optionally be coadministered with the compounds according to the present invention. As used herein, additional therapeutic agents that are normally administered to treat or prevent a particular disease are known as appropriate for the disease being treated.

For example, compounds according to this invention may be combined with one or more standard therapeutic agents or radiation used for treatment of the diseases as mentioned before.

Thus, in one particular embodiment compounds according to this invention may be combined with one or more art-known anti-cancer agents, such as e.g. with one or more art-known chemotherapeutic and/or target specific anti-cancer agents as described below, and/or radiation.

Examples of known chemotherapeutic anti-cancer agents frequently used in combination therapy include, but not are limited to (i) alkylating/carbamylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof, epothilones such as Epothilone B (Patupilone®), Aza-epothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxins (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) or premetrexed (Alimta®).

Examples of target specific anti-cancer drug classes used in experimental or standard cancer therapy include but are not limited to (i) kinase inhibitors such as e.g. Imatinib (Glivec®), ZD-1839/Gefitinib (Iressa®), Bay43-9006 (Sorafenib), SU11248/Sunitinib (Sutent®) or OSI-774/Erlotinib (Tarceva®);

(ii) proteasome inhibitors such as PS-341/Bortezumib (Velcade®); (iii) heat shock protein 90 inhibitors like 17-allylaminogeldanamycin (17-AAG); (iv) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib); (v) monoclonal antibodies such as Trastuzumab (Herceptin®) or Rituximab (MabThera/Rituxan®) or Alemtuzumab (Campath®) or Tositumab (Bexxar®) or C225/Cetuximab (Erbitux®) or Avastin (see above) as well as mutants and conjugates of monoclonal antibodies, e.g. Gemtuzumab ozogamicin (Mylotarg®) or Ibritumomab tiuxetan (Zevalin®), and antibody fragments; as well as mutants and conjugates of monoclonal antibodies and antibody fragments; (vi) oligonucleotide based therapeutics like G-3139/Oblimersen (Genasense®); (vii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (viii) protease inhibitors (ix) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors.

Other known target specific anti-cancer agents which can be used for combination therapy include bleomycin, retinoids such as all-trans retinoic acid (ATRA), DNA methyltransferase inhibitors such as the 2-deoxycytidine derivative Decitabine (Docagen®) and 5-Azacytidine, alanosine, cytokines such as interleukin-2, interferons such as interferon α2 or interferon-γ, death receptor agonists, such as TRAIL, DR4/5 agonistic antibodies, FasL and TNF-R agonists, and finally histone deacetylase inhibitors different to the compounds according to this invention such as SAHA, PXD101, MS275, MGCD0103, Depsipeptide/FK228, NVP-LBH589, NVP-LAQ824, Valproic acid (VPA) and butyrates.

As exemplary anti-cancer agents for use in combination with the compounds according to this invention in the cotherapies mentioned herein any of the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PATUPILONE, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VERTEPORFIN, VINBLASTINE, VINCRISTINE, VINDESINE, VINORELBINE, VOROZOLE and ZEVALIN.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware on the base of his/her expert knowledge of the kind, total daily dosage(s) and administration form(s) of the additional therapeutic agent(s) coadministered. Said total daily dosage(s) can vary within a wide range.

In practicing the present invention and depending on the details, characteristics or purposes of their uses mentioned above, the compounds according to the present invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular, art-known ant-cancer agents (chemotherapeutic and/or target specific anti-cancer agents), such as e.g. any of those mentioned above.

In this context, the present invention further relates to a combination comprising a first active ingredient, which is at least one compound according to this invention, and a second active ingredient, which is at least one art-known standard therapeutic, for example an art-known anti-cancer agent, such as e.g. one or more of those mentioned herein above, for separate, sequential, simultaneous, concurrent or chronologically staggered use in therapy, such as e.g. in therapy of any of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy, such as e.g. in therapy of diseases responsive or sensitive to the inhibition of histone deacetylases, particularly (hyper)proliferative diseases and/or disorders responsive to induction of apoptosis, such as e.g. any of those diseases mentioned herein, like benign or malignant neoplasia, especially cancer, particularly any of those cancer diseases described above.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known ant-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat diseases responsive or sensitive to the inhibition of histone deacetylases, such as e.g. cellular neoplasia or diseases different to cellular neoplasia as indicated above, particularly cancer, such as e.g. any of those cancer diseases described above.

The present invention further relates to a combined preparation comprising at least one compound according to this invention and at least one art-known ant-cancer agent for simultaneous, concurrent, sequential or separate administration.

In this connection, the present invention further relates to combinations, compositions, formulations, preparations or kits according to the present invention having histone deacetylases inhibitory activity.

Also in this connection, the present invention further relates to combinations, compositions, formulations, preparation or kits according to the present invention having anti-(hyper)proliferative and/or apoptosis inducing activity.

In addition, the present invention further relates to a method for treating in combination therapy diseases responsive or sensitive to the inhibition of histone deacetylases, such as e.g. those mentioned above, e.g. (hyper)proliferative diseases and/or disorders responsive to induction of apoptosis, like cancer, in a patient comprising administering a combination, composition, formulation, preparation or kit as described herein to said patient in need thereof.

In addition, the present invention further relates to a method for treating diseases responsive or sensitive to the inhibition of histone deacetylases, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patent comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patent comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing, or ameliorating diseases responsive or sensitive to the inhibition of histone deacetylases, particularly those diseases mentioned herein, such as e.g. benign or malignant neoplasia, particularly cancer.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known ant-cancer agents mentioned.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a disease responsive or sensitive the inhibition of histone deacetylases, such as, for example, one of those diseases mentioned herein, e.g. benign or malignant neoplasia, particularly cancer, like any one of those cancer diseases mentioned herein.

In addition, compounds according to the present invention can be used in the pre- or post-surgical treatment of cancer.

In further addition, compounds according to the present invention can be used in combination with radiation therapy, in particular in sensitization of cancer patients towards standard radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

Biological Investigations

Isolation of HDAC Activity from HeLa Cell Nuclei:

HDAC activity is isolated from nuclear HeLa extracts according to a method original described by Dignam et al. (Nucl. Acids Res. 11, pp 1475, 1983). Briefly, nuclei isolated from HeLa cells (CIL SA, Seneffe, Belgium) are resuspended in buffer C (20 mM Hepes pH 7.9, 25% v:v glycerol, 0.42M NaCl, 1.5 mM $MgCl_2$, 0.2 mM EDTA, 0.5 mM PefaBloc and 0.5 mM DTT) and stirred for 30 min on ice. After centrifugation, the supernatant is dialysed against buffer D (40 mM Tris HCl pH 7.4, 100 mM KCl, 0.2 mM EDTA, 0.5 mM DTT and 25% v:v glycerol) for 5 h at 4° C. After dialysis and centrifugation, the supernatant is stored in aliquots at −80° C. and used for Western blot analysis as well as the enzymatic assay as described in the following.

Isolation of rHDAC1

Human HDAC1 fused with the flag epitope is stably expressed in Hek293 cells. After mass cultivation in DMEM with supplements and 2% fetal calf serum, cells are lysed and flag-HDAC1 purified by M2-agarose affinity chromatography as described (Sigma Art. No. A-2220). Fractions from the purification are analysed by Western blot as well as for enzymatic activity as described below.

Fluorimetric HDAC Activity Assay:

The HDAC enzyme activity assay is done as described by Wegener et al. (Chem. & Biol. 10, 61-68, 2003). Briefly 40 μl of a 1:100 dilution (=0.4 μl) nuclear HeLa extract (mixture of class I and II HDACs), 29 μl enzyme buffer (15 mM Tris HCl pH 8.1, 0.25 mM EDTA, 250 mM NaCl, 10% v:v glycerol) and 1 μl test compound are added to a well of a 96 well microtiter plate and reaction started by addition of 30 µl substrate (Ac-NH-GGK(Ac)-AMC; final concentration 25 µM and final volume 100 µl). After incubation for 90 min at 30° C., reaction is terminated by the addition of 25 µl stop solution (50 mM Tris HCl pH 8, 100 mM NaCl, 0.5 mg/ml trypsine and 2 µM TSA). After incubation at room temperature for further 40 min, fluorescence is measured using a Wallac Victor 1420 multilabel counter (Ex 355 nm, Em 460 nm) for quantification of AMC (7-amino-4-methylcoumarin) generated by trypsine cleavage of the deacetylated peptide. For the calculation of $IC_{50}$ values the fluorescence in wells without test compound (1% DMSO, negative control is set as 100% enzymatic activity and the fluorescence in wells with 2 µM TSA (positive control) are set at 0% enzymatic activity. The corresponding $IC_{50}$ values of the compounds for HDAC inhibitory activity are determined from the concentration-effect curves by means of non-linear regression.

The HDAC1 enzymatic assay is done with slight modifications with recombinant flag-HDAC1 protein isolated from HEK293 cell lysates. About 14 ng/well flag-HDAC1 are incubated with 6 µM Ac-NH-GGK(Ac)-AMC substrate for 3 h at 30° C. Termination of the reaction and all further steps are done as described for HeLa cell nuclear extracts as a source for HDAC enzymatic activity.

Representative inhibitory values (expressed by $IC_{50}$ values) of HDAC activity derived from HeLa cell nuclear extracts for compounds according to the present invention follow from the following table 1, in which the numbers of the compounds correspond to the numbers of the examples.

TABLE 1

| Compound | HDAC inhibitory activity $IC_{50}$ |
|---|---|
| 1 to 7 | The $IC_{50}$ values of these listed compounds are in the range from 0.75 nM to 7.5 µM |
| 8, 9, 10, 11, 12, 14, 16 to 34, 35, 36 to 38, 40 to 48, 50 to 52, 53, 54 to 59, 60, 61, 62 and 63 | The $IC_{50}$ values of these listed compounds are in the range from 0.32 nM to 10 µM |
| 64 to 68, 70 to 85, 89 to 108 | The $IC_{50}$ values of these listed compounds are in the range from 1.7 nM to 32 µM |

Representative inhibitory values (expressed by $IC_{50}$ values) of rHDAC1 activity for compounds according to the present invention follow from the following table 1a, in which the numbers of the compounds correspond to the numbers of the examples.

TABLE 1a

| Compound | $IC_{50}$ |
|---|---|
| 1 to 12, 14, 16 to 68, 70 to 85, 89 to 108 | The $IC_{50}$ values of these listed compounds are in the range from 1 nM to 0.94 µM |

Cellular Histone H3 Acetylation Assay:

To assess the cellular efficacy of an histone deactylase inhibitor in vitro, an assay is set up in black clear-bottom 96-well plates and optimized for use on the Cellomics "ArrayScan II" platform for a quantitative calculation of histone acetylation. The protocol uses a polyclonal rabbit antibody, specifically binding to acetylated lysine 9+14 of human histone H3 on fixed cells with an Alexa Fluor 488 labeled goat ant rabbit-IgG used for counterstaining (modified from Braunger et al. MCR annual conference 2003, Abstract 4556).

$5 \times 10^3$ HeLa cervical carcinoma cells/well (ATCC CCL-2) in 200 µl Dulbecco's modified Eagle's medium (DMEM) containing 10% fetal calf serum are seeded at day 1 in Packard view plates and incubated for 24 h under standard cell culture conditions. On day 2, 2 µl test compound (100× final concentration) is added and incubation continued for further 24 h. On day 3, the culture medium is discarded and attached cells fixed for 15 min at room temperature by addition of 100 µl fixation buffer (3.7% v:v formaldehyde in phosphate buffered saline/PBS). After discarding the fixation buffer and one wash with PBS, cells are permeabilized at room temperature by addition of 100 µl/well permeabilization buffer (30.8 mM NaCl, 0.54 mM $Na_2HPO_4$, 0.31 mM $KH_2PO_4$, 5% v:v Triton X-100) for 15 min at room temperature. After discarding the permeabilization buffer and washing twice with 100 µl/well blocking solution (PBS with 0.05% v:v Tween 20 and 5% w:v milk powder) at room temperature, the $1^{st}$ antibody (anti-K9+ 14 histone H3 antibody, Calbiochem No. 382158) in blocking solution (50 µl/well) is added. After incubation for 1 h at 37° C., the wells are washed twice at room temperature with 100 µl/well blocking solution before addition of the $2^{nd}$ antibody (goat-anti-rabbit Alexa Fluor 488; MoBiTec No. A-11008) in blocking solution (50 µl/well). After further incubation for 1 h at 37° C., wells are washed twice with 100 µl/well blocking solution room temperature. Finally, 100 d/well PBS are added and image analysis performed on the Cellomics "ArrayScan II" platform. For calculation of $EC_{50}$ values, the nuclear fluorescence in cells treated with and without a reference HDAC inhibitor (eg NVP-LBH-589) are taken as a positive and negative control. For $EC_{50}$ determination, the percentage of positive cells is determined and $EC_{50}$ calculation done from concentration-effect curves by means of non-linear regression.

Representative histone H3 acetylating cellular potency values (expressed by $EC_{50}$ values) for compounds according to the present invention follows from the following table 2, in which the numbers of the compounds correspond to the numbers of the examples.

TABLE 2

| Compound | $EC_{50}$ (µM) |
|---|---|
| 1 to 7 | The $EC_{50}$ values of these listed compounds are in the range from 0.28 to 5.3 |
| 8, 9, 10, 12, 16, 17, 18, 20 to 31, 33, 34, 36 to 38, 42, 43, 45 to 47, 54, 56 to 59, 62 and 63 | The $EC_{50}$ values of these listed compounds are in the range from 0.027 to 4.4 |
| 64 to 68, 70 to 72, 74 to 78, 81, 90, 96 to 99, 102, 104, 106 to 108, | The $EC_{50}$ values of these listed compounds are in the range from 0.0052 to 5.8 |

Cellular Cytotoxicity Assay:

The anti-proliferative activity of the histone deacetylase inhibitory compounds as described herein, is evaluated with the HeLa cervical carcinoma cell line (ATCC CCL2) using the Alamar Blue (Resazurin) cell viability assay (O'Brien et al. Eur J Biochem 267, 5421-5426, 2000). Resazurin is reduced to the fluorescent resorufin by cellular dehydrogenase activity, correlating with viable, proliferating cells. Test compounds are dissolved as 10 mM solutions in dimethylsulfoxide (DMSO) and subsequently diluted in semi-logarithmic steps. HeLa cells are seeded into 96 well flat bottom plates at a density of 3000 cells per well in a volume of 200 μl per well. 24 hours after seeding 1 μl each of the compound dilutions are added into each well of the 96 Well plate. Each compound dilution is tested as quadruplicates. Wells containing untreated control cells are filled with 200 μl DMEM medium containing 0.5% v:v DMSO. The cells are then incubated with the substances for 48 hours at 37° C. in a humidified atmosphere containing 5% carbon dioxide. To determine the viability of the cells, 20 μl of an Resazurin solution (Sigma; 90 mg/l) are added. After 4 hours incubation at 37° C. the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilites are expressed as % values. The corresponding $IC_{50}$ values of the compounds for cytotoxic activity are determined from the concentration-effect curves by means of non-linear regression.

Representative ant-proliferative/cytotoxic potency values (expressed by $IC_{50}$ values) for compounds according to the present invention follows from the following table 3, in which the numbers of the compounds correspond to the numbers of the examples.

TABLE 3

| Compound | $IC_{50}$ (μM) |
| --- | --- |
| 1 to 7 | The $IC_{50}$ values of these listed compounds are in the range from 0.078 to 2.3 |
| 8, 9, 10, 11, 12, 14, 16 to 34, 36 to 52, 54 to 59, 60, 61, 62 and 63 | The $IC_{50}$ values of these listed compounds are in the range from 0.006 to 20 |
| 64 to 68, 70 to 85, 89 to 108 | The $IC_{50}$ values of these listed compounds are in the range from 0.014 to 6.7 |

Apoptosis Induction

The induction of apoptosis is measured by using the cell death detection ELISA (Art. No. 1774425, Roche Biochemicals, Mannheim, Germany). A549 NSCLC cells are seeded into 96 well flat bottom plates at a density of 3×10 E3 cells/well in a total volume of 100 μl/well. 24 hours after seeding, 1 μl each of the compound dilutions in DMEM are added in a total volume of 100 μl into each well Final volume 200 μl/well). Each compound dilution is tested at least as triplicates. Wells containing untreated control cells are filled with 200 μl, DMEM containing 0.5 vol % DMSO. The cells are incubated with test compound for 48 hours at 37° C. in a humidified atmosphere containing 5% carbon dioxide. As a positive control for the induction of apoptosis, cells are treated with 50 μM Cisplatin (Gry Pharmaceuticals, Kirchzarten, Germany). Medium is then removed and the cells lysed in 200 μl lysis buffer. After centrifugation as described by the manufacturer, 10 μl of cell lysate is processed as described in the protocol. The degree of apoptosis is calculated as follows: The absorbance at 405 nm obtained with lysates from cells treated with 50 μM cisplatin is set as 100 cpu (cisplatin units), while an absorbance at 405 nm of 0.0 is set as 0.0 cpu. The degree of apoptosis is expressed as cpu in relation to the value of 100 cpu reached with the lysates obtained from cells treated with 50 μM cisplatin.

Representative apoptosis inducing potency values (expressed by cpu values) for compounds according to the present invention follows from the following table 4, in which the numbers of the compounds correspond to the numbers of the examples.

TABLE 4

| Compound | cpu @ 10 μM |
| --- | --- |
| 1 to 10, 12, 16, 26 and 46 | The cpu values of these listed compounds are in the range from 15.3 to 349.3 |

The invention claimed is:
1. A compound of formula I

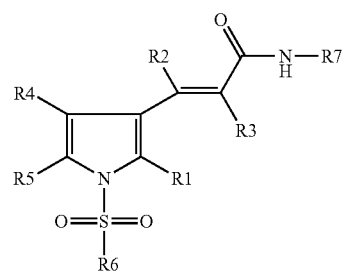

in which
R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond or 1-4C-alkylene,
either
Q1 is substituted by R61 and/or R62, and is Aa1, Hh1, Ha1, Ha2, Ha3, Ha4 or Ah1,
or
Q1 is unsubstituted, and is Ha2, Ha3 or Ha4,
in which
R61 is 1-4C-alkyl, phenyl-1-4C-alkyl, 1-4C-alkoxy, hydroxyl, trifluoromethyl, cyano, halogen, completely or predominantly fluorine-substituted 1-4C-alkoxy, hydroxy-1-4C-alkyl, 1-4C-alkoxy-1-4C-alkyl, 1-4C-alkylsulphonylanino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)R612, -U-T3-N(R613)R614, -T4-Het3, or -V-T5-Het4, in which
T2 is a bond or 1-4C-alkylene,
R611 is hydrogen, 1-4C-alkyl, 3-7C-cycloalkyl, 3-7C-cycloalkylmethyl, hydroxy-2-4C-alkyl, 1-4C-alkoxy-2-4C-alkyl, 1-4C-alkylcarbonyl, or 1-4C-alkylsulphonyl,
R612 is hydrogen or 1-4C-alkyl,
or
R611 and R612 together and with inclusion of the nitrogen atom, to which they are bonded, form a heterocyclic ring Het1, in which
Het1 is morpholino, thiomorpholino, S-oxo-thiomorpholino, S,S-dioxo-thiomorpholino, piperidino, pyrrolidino, piperazino, or 4N-(1-4C-alkyl)-piperazino,
U is —O—(oxygen) or —C(O)NH—,
T3 is 2-4C-alkylene,
R613 is hydrogen, 1-4C-alkyl, 3-7C-cycloalkyl, 3-7C-cycloalkylmethyl, hydroxy-2-4C-alkyl, 1-4C-alkoxy-2-4C-alkyl, 1-4C-alkylcarbonyl, or 1-4C-alkylsulphonyl
R614 is hydrogen or 1-4C-alkyl, or
R613 and R614 together and with inclusion of the nitrogen atom, to which they are bonded, form a heterocyclic ring Het2, in which Het2 is morpholino, thiomorpholino, S-oxo-thiomorpholino, S,S-dioxo-thiomorpholino, piperidino, pyrrolidino, piperazino, or 4N-(1-4C-alkyl)-piperazino, T4 is a bond or 1-4C-alkylene, Het3 is 1N-(1-4C-alkyl)-piperidinyl or 1N-(1-4C-alkyl)-pyrrolidinyl, V is —O—(oxygen) or —C(O)NH—, T5 is a bond or 1-4C-alkylene, Het4 is 1N-(1-4C-alkyl)-piperidinyl or 1N-(1-4C-alkyl)-pyrrolidinyl, R62 is 1-4C-alkyl, 1-4C-alkoxy or halogen, Aa1 is a bisaryl radical made up of two aryl groups, which are independently selected from the group consisting of phenyl and naphthyl, and which are linked together via a single bond, Hh1 is a bisheteroaryl radical made up of two heteroaryl groups, which are independently selected from the group consisting of monocyclic 5- and 6-membered heteroaryl radicals comprising one or two heteroatoms, each of which is selected from the group consisting of nitrogen, oxygen and sulfur, and which are linked together via a single bond, Ah1 is an arylheteroaryl radical made up of an aryl group selected from the group consisting of phenyl and naphthyl, and a heteroaryl group selected from the group consisting of monocyclic 5- and 6-membered heteroaryl radicals comprising one or two heteroatoms, each of which is selected from the group consisting of nitrogen, oxygen and sulfur, wherein said aryl and heteroaryl groups are linked together via a single bond, and wherein Ah1 is bonded via said heteroaryl moiety to the parent molecular group, Ha1 is a heteroarylaryl radical made up of a heteroaryl group selected from the group consisting of monocyclic 5- and 6-membered heteroaryl radicals comprising one or two heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha1 is bonded via said aryl moiety to the parent molecular group, Ha2 is a heteroarylaryl radical made up of a heteroaryl group selected from the group consisting of fused bicyclic 9- and 10-membered heteroaryl radicals comprising one, two or three heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha2 is bonded via said aryl moiety to the parent molecular group, Ha3 is a heteroarylaryl radical made up of a heteroaryl group selected from the group consisting of monocyclic 5-membered heteroaryl radicals comprising three or four heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha3 is bonded via said aryl moiety to the parent molecular group, Ha4 is a heteroarylaryl radical made up of a heteroaryl group selected from the group consisting of partially saturated fused bicyclic 9- and 10-membered heteroaryl radicals comprising a heteroatom-free beuzene ring and one or two heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha4 is bonded via said aryl moiety to the parent molecular group, R7 is hydroxyl, or Cyc1, in which Cyc1 is a ring system of formula Ia

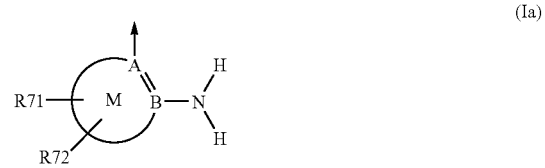

in which

A is C (carbon),

B is C (carbon),

R71 is hydrogen, halogen, 1-4C-alkyl, or 1-4C-alkoxy,

R72 is hydrogen, halogen, 1-4C-alkyl, or 1-4C-alkoxy,

M with inclusion of A and B is either a ring Ar2 or a ring Har2, in which

Ar2 is a benzene ring,

Har2 is a monocyclic 5- or 6-membered unsaturated heteroaromatic ring comprising one to three heteroatoms, each of which is selected from the group consisting of nitrogen, oxygen and sulfur, or a salt thereof.

2. A compound of formula I according to claim 1, in which

R1 is hydrogen,
R2 is hydrogen,
R3 is hydrogen,
R4 is hydrogen,
R5 is hydrogen,
R6 is -T1-Q1, in which
T1 is a bond, either Q1 is substituted by R61 and/or R62 on the terminal ring, and is Aa1, Hh1, Ha1, Ha2, Ha3, Ha4 or Ah1, or Q1 is unsubstituted, and is Ha2, Ha3 or Ha4, in which R61 is methyl, methoxy, hydroxyl, tritluoromethyl, hydroxymethyl, methylsuiphonylamino, methylcarbonylamino, dimethylaminosuiphonyl, -T2-N(R611)R612, -U-T3-N(R613)R614, -T4-Het3, or -V-T5-Het4, in which T2 is a bond, methylene, dimethylene or trimethylene, R611 is hydrogen, methyl, cyclopropyl, cyclopentyl, 2-methoxyethyl, acetyl or methylsulphonyl, R612 is hydrogen or methyl, or R611 and R612 together and with inclusion of the nitrogen atom, to which they are bonded, form a heterocyclic ring Het1, in which Het1 is morpholino, piperidino, pyrrolidino, piperazino or 4-methyl-piperazino, U is —O—(oxygen) or —C(O)NH—, T3 is dimethylene or trimethylene, R613 is hydrogen, methyl, cyclopropyl, cyclopentyl, 2-methoxyethyl, acetyl or methylsuiphonyl, R614 is hydrogen or methyl, or R613 and R614 together and with inclusion of the nitrogen atom, to which they are bonded, form a heterocyclic ring Het2, in which Het2 is morpholino, piperidino, pyrrolidino, piperazino or 4-methyl-piperazino, T4 is a bond, methylene, dimethylene or trimethylene, Het3 is 1-methyl-piperidinyl or 1-methyl-pyrrolidinyl, V is —O—(oxygen) or —C(O)NH—, T5 is a bond, methylene, dimethylene or trimethylene, Het4 is 1-methyl-piperidinyl or 1-methyl-pyrrolidinyl, R62 is methyl, Aa1 is 1,1'-biphenyl-3-yl, or 1,1'-biphenyl-4-yl, Hh1 is a bisheteroaryl radical made up of two heteroaryl groups, which are independently selected from the group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, and which are linked together via a single bond, Ah1 is a phenyl-heteroaryt radical made up of an phenyl group and a heteroaryl group selected from the group consisting of pyrrolyl, furanyl, thiophenyl, oxazolyl, isoxazolyl, thiazolyl, isothiazolyl, imidazolyl, pyramlyl, pyridinyl, pyrimidinyl, pyrazinyl and pyridazinyl, wherein said phenyl and heteroaryl groups are linked together via a single bond, and wherein Ah1 is bonded via said heteroaryl moiety to the parent molecular group, Ha1 is a 3-(heteroaryl)-phenyl or 4-(heteroaryl)-phenyl radical each made up of a heteroaryl group selected from the group consisting of pyrrolyl, furanyl, thiophenyl, oxazolyl, isoxazolyl, thiazolyl, isothiazolyl, imidazolyl, pyrazolyl, pyridinyl, pyrimidinyl, pyrazinyl and pyridazinyl, and a phenyl group, wherein said heteroaryl and phenyl groups are linked together via a single bond, and wherein Ha1 is bonded via said phenyl moiety to the to the parent molecular group, Ha2 is a 3-(heteroaryl)-phenyl or 4-(heteroaryl)-phenyl radical each made up of a heteroaryl group selected from the group consisting of indolyl, benzothiophenyl, benzofuranyl, benzoxazolyl, beuzothiazolyl, indazolyl, benzimidazolyl, benzisoxazolyl, benzisothiazolyl, benzofurazanyl, benzotriazolyl, benzothiadiazolyl, quinolinyl, isoquinolinyl, quinazolinyl, quinoxalinyl, cinnolinyl, indolizinyl and naphthyridinyl, and a phenyl group, wherein said heteroaryl and phenyl groups are linked together via a single bond, and wherein Ha2 is bonded via said phenyl moiety to the to the parent molecular group, Ha3 is a 3-(heteroaryl)-phenyl or 4-(heteroaryl)-phenyl radical each made up of a heteroaryl group selected from the group consisting of thiadiazolyl, oxadiazolyl, triazolyl and tetrazolyl, and a phenyl group, wherein said heteroaryl and phenyl groups are linked together via a single bond, and wherein Ha3 is bonded via said phenyl moiety to the to the parent molecular group, Ha4 is a 3-(heteroaryl)-phenyl or 4-(heteroaryl)-phenyl radical each made up of a heteroaryl group selected from the group consisting of indolinyl, isoindolinyl, 1,2,3,4-tetrahydroquinolinyl, 1,2,3,4-tetrahydroisoquinolinyl, 2,3-dihydrobenzofuranyl, 2,3-dihydrobenzothiophenyl, benzo[1,3]dioxolyl, 2,3-dihydrobenzo [1,4]dioxinyl, chromanyl, chromenyl and 2,3-dihydrobenzo[1,4]oxazinyl, and a phenyl group, wherein said heteroaryl and phenyl groups are linked together via a single bond, and wherein Ha3 is bonded via said phenyl moiety to the parent molecular group, R7 is hydroxyl, or 2-aminophenyl, or a salt thereof.

3. A compound of formula I according to claim 1, in which

R1 is hydrogen,

R2 is hydrogen,

R3 is hydrogen,

R4 is hydrogen,

R5 is hydrogen,

R6 is -T1-Q1, in which

T1 is a bond;

either

Q1 is substituted by R61 on the terminal ring, and is Aa1 or Ah1, in which

Aa1 is 1,1'-biphenyl-3-yl, or 1,1'-biphenyl-4-yl,

Ah1 is phenyl-thiophenyl, or phenyl-pyridinyl,

R61 is selected from the group consisting of 3-morpholin-4-yl-propyl, 2-morpholin-4-yl-ethyl, morpholin-4-yl-methyl, 3-(4-methyl-piperazin-1-yl)-propyl, 2-(4-methyl-piperazin-1-yl)-ethyl, (4-methyl-piperazin-1-yl)-methyl, 3-pyrrolidin-1-yl-propyl, 2-pyrrolidin-1-yl-ethyl, pyrrolidin-1-yl-methyl, 3-piperidin-1-yl-propyl, 2-piperidin-1-yl-ethyl, piperidin-1-yl-methyl, 3-morpholin-4-yl-propoxy, 2-morpholin-4-yl-ethoxy, 3-pyrrolidin-1-yl-propoxy, 2-pyrrolidin-1-yl-ethoxy, 3-(4-methyl-piperazin-1-yl)-propoxy, 2-(4-methyl-piperazin-1-yl)-ethoxy, 3-(1-methyl-piperidin-4-yl)-propoxy, 2-(1-methyl-piperidin-4-yl)-ethoxy, 3-piperidin-1-yl-propoxy, 2-piperidin-1-yl-ethoxy, dimethylaminomethyl, 2-dimethylamino-ethyl, 3-dimethylamino-propyl, methylsuiphonytamino, dimethylsuiphamoyl, acetamido, amino, dimethylamino, morpholino, piperidino, pyrrolidino, 4-methyl-piperazino, hydroxy, trifluoromethyl, methoxy, (2-dimethylamino-ethylamino)-carbonyl, (2-methoxy-ethylamino)methyl, aminomethyl, acetylamino-methyl, methylsuiphonylamino-methyl, cyclopentylaminomethyl, cyclopropylaminomethyl and hydroxymethyl;

or

Q1 is substituted by R61 on the terminal ring, and is Hh1 or Ha1, in which

Hh1 is pyridinyl-thiophenyl, or bipyridyl,

Ha1 is 3-(pyridinyl)-phenyl, or 4-(pyridinyl)-phenyl,

R61 is selected from the group consisting of methylsulphonylamino, acetamido, amino, dimethylamino, morpholino, piperidino, pyrrolidino, 4-methyl-piperazino, hydroxy, trifluoromethyl and methoxy;

or

Q1 is 3-(1-methyl-pyrazol-4-yl)-phenyl, 4-(1-methyl-pyrazol-4-yl)-phenyl, 3-(2-methyl-thiazol-4-yl)-phenyl, 4-(2-methyl-thiazol-4-yl)-phenyl, 3-(3,5-dimethyl-isoxazol-4-yl)-phenyl, 4-(3,5-dimethyl-isoxazol-4-yl)-phenyl, (1-methyl-pyrazol-4-yl)thiophenyl (1-methyl-pyrazol-4-yl)-pyridinyl, (2-methyl-thiazol-4-yl)-thiophenyl, (2-methyl-thiazol-4-yl)-pyridinyl, 3-(benzo[1,3]dioxol-5-yl)-phenyl, 4-(benzo[1,3]dioxol-5-yl)-phenyl, 3-(2,3-dihydrobenzofuran-5-yl)-phenyl, 4-(2,3-dihydrobenzofuran-5-yl)-phenyl, 3-(1-methyl-indol-5-yl)-phenyl, or 4-(1-methyl-indol-5-yl)-phenyl;

or

Q1 is 3-[1N-(R61)-pyrazol-4-yl]-phenyl, 4-[1N-(R61)-pyrazol-4-yl]-phenyl, [1N-(R61)-pyrazol-4-yl)-thiophenyl, [1N-(R61)-pyrazol-4-yl)-pyridinyl, 3-[1N-(R61)-triazol-4-yl]-phenyl, or 4-[1N-(R61)-triazol-4-yl]-phenyl, in which
R61 is selected from the group consisting of 3-morpholin-4-yl-propyl, 2-morpholin-4-yl-ethyl, 3-(4-methyl-piperazin-1-yl)-propyl, 2-(4-methyl-piperazin-1-yl)-ethyl, 3-pyrrolidin-1-yl-propyl, 2-pyrrolidin-1-yl-ethyl, 3-piperidin-1-yl-propyl, 2-piperidin-1-yl-ethyl, 2-dimethylamino-ethyl and 3-dimethylamino-propyl;

R7 is hydroxyl, or 2-aminophenyl;
or a salt thereof.

4. A compound of formula I according to claim 1, in which
R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond or 1-4C-alkylene,
either
Q1 is substituted by R61 and/or R62, and is Aa1, Hh1, Ha1, Ha2, Ha3 or Ah1,
or
Q1 is unsubstituted, and is Ha2 or Ha3,
in which
R61 is 1-4C-alkyl, phenyl-1-4C-alkyl, 1-4C-alkoxy, hydroxyl, trifluoromethyl, cyano, halogen, completely or predominantly fluorine-substituted 1-4C-alkoxy, hydroxy-1-4C-alkyl, 1-4C-alkoxy-1-4C-alkyl, 1-4C-alkylsulphonylamino, tolylsulphonylamino, phenylsulphonylamino, 1-4C-alkylcarbonylamino, carbamoyl, sulphamoyl, mono- or di-1-4C-alkylaminocarbonyl, mono- or di-1-4C-alkylaminosulphonyl, -T2-N(R611)612, or -U-T3-N(R613)R614, in which
T2 is a bond or 1-4C-alkylene,
611 is hydrogen, 1-4C-alkyl, 3-7C-cycloalkyl, 3-7C-cycloalkylmethyl, hydroxy-2-4C-alkyl or 1-4C-alkoxy-2-4C-alkyl,
612 is hydrogen or 1-4C-alkyl,
or R611 and R612 together and with inclusion of the nitrogen atom, to which they are bonded, form a heterocyclic ring Het 1, in which
Het1 is morpholino, thiomorpholino, S-oxo-thiomorpholino, S,S-dioxo-thiomorpholino, piperidino, pyrrolidino, piperazino, or 4N-(1-4C-alkyl)-piperazino,
U is —O—(oxygen) or —C(O)NH—,
T3 is 2-4C-alkylene,
R613 is hydrogen, 1-4C-alkyl, 3-7C-cycloalkyl, 3-7C-cycloalkylmethyl, hydroxy-2-4C-alkyl or 1-4C-alkoxy-2-4C-alkyl,
R614 is hydrogen or 1-4C-alkyl,
or
R613 and R614 together and with inclusion of the nitrogen atom, to which they are bonded, form a heterocyclic ring Het2, in which
Het2 is morpholino, thiomorpholino, S-oxo-thiomorpholino, S,S-dioxo-thiomorpholino, piperidino, pyrrolidino, piperazino, or 4N-(1-4C-alkyl)-piperazino,
R62 is 1-4C-alkyl, 1-4C-alkoxy or halogen,
Aa1 is a bisaryl radical made up of two aryl groups, which are independently selected from the group consisting of phenyl and naphthyl, and which are linked together via a single bond,
Hh1 is a bisheteroaryl radical made up of two heteroaryl groups, which are selected independently from the group consisting of monocyclic 5- and 6-membered heteroaryl radicals comprising one or two heteroatoms, each of which is selected from the group consisting of nitrogen, oxygen and sulfur, and which are linked together via a single bond,
Ah1 is an arylheteroaryl radical made up of an aryl group selected from the group consisting of phenyl and naphthyl, and a heteroaryl group selected from the group consisting of monocyclic 5- and 6-membered heteroaryl radicals comprising one or two heteroatoms, each of which is selected from the group consisting of nitrogen, oxygen and sulfur, wherein said aryl and heteroaryl groups are linked together via a single bond, and wherein Ah1 is bonded via said heteroaryl moiety to the parent molecular group,
Ha1 is a heteroarylaryl radical made up of a heteroaryl group selected from the group consisting of monocyclic 5- and 6-membered heteroaryl radicals comprising one or two heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha1 is bonded via said aryl moiety to the to the parent molecular group,
Ha2 is a heteroarylaryl radical made up of a heteroaryl group selected from the group consisting of fused bicyclic 9- and 10-membered heteroaryl radicals comprising one, two or three heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha2 is bonded via said aryl moiety to the parent molecular group,
Ha3 is a heteroarylaryl radical made up of a heteroaryl group selected from the group consisting of monocyclic 5-membered heteroaryl radicals comprising three or four heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha3 is bonded via said aryl moiety to the parent molecular group,
R7 is hydroxyl, or Cyc1, in which
Cyc 1 is a ring system of formula Ia

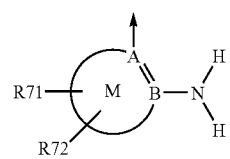

(Ia)

in which
A is C (carbon),
B is C (carbon),
R71 is hydrogen, halogen, 1-4C-alkyl, or 1-4C-alkoxy,
R72 is hydrogen, halogen, 1-4C-alkyl, or 1-4C-alkoxy,
M with inclusion of A and B is either a ring Ar2 or a ring Har2, in which
Ar2 is a benzene ring,
Har2 is a monocyclic 5- or 6-membered unsaturated heteroaromatic ring comprising one to three heteroatoms, each of which is selected from the group consisting of nitrogen, oxygen and sulfur, or a salt thereof.

5. A compounds of formula I according to claim 1, in which
R1 is hydrogen,
R2 is hydrogen,
R3 is hydrogen,
R4 is hydrogen,
R5 is hydrogen,
R6 is -T1-Q1, in which
T1 is a bond,
Q1 is substituted by R61 and/or R62 on the terminal ring, and is Aa1, Hh1, Ha1, Ha2 or Ah 1,
in which
R61 is 1-2C-alkyl, 1-2C-alkoxy, halogen, hydroxy-1-2C-alkyl, 1-2C-alkylsulphonylamino, 1-2C-alkylcarbonylamino, di-1-2C-alkylaminosulphonyl, -T2-N(R611)R612, or -U-T3-N(R613)R614, in which
T2 is a bond or straight chain 1-4C-alkylene,
R611 is hydrogen, 1-2C-alkyl, 3-5C-cycloalkyl or 1-2C-alkoxy-2-3C-alkyl,
R612 is hydrogen or 1-2C-alkyl,
or
R611 and R612 together and with inclusion of the nitrogen atom, to which they are bonded, form a heterocyclic ring Het1, in which
Het 1 is morpholino, piperidino, pyrrolidino, piperazino or 4N-(1-2C-alkyl)-piperazino,
U is —O—(oxygen) or —C(O)NH—,
T3 is straight chain 2-4C-alkylene,
R613 is hydrogen, 1-2C-alkyl, 3-5C-cycloalkyl or 1-2C-alkoxy-2-3C-alkyl,
R614 is hydrogen or 1-2C-alkyl,
or
R613 and R614 together and with inclusion of the nitrogen atom, to which they are bonded, form a heterocyclic ring Het2, in which
Het2 is morpholino, piperidino, pyrrolidino, piperazino or 4N-(1-4C-alkyl)-piperazino,
R62 is 1-2C-alkyl,
Aa1 is 1,1'-biphen-3-yl or 1,1'-biphen-4-yl,
Hh 1 is a bisheteroaryl radical made up of a heteroaryl group selected from the group consisting of monocyclic 5- and 6-membered heteroaryl radicals comprising one or two heteroatoms, each of which is selected from the group consisting of nitrogen, oxygen and sulfur, and a thiophenyl group, wherein said heteroaryl and thiophenyl groups are linked together via a single bond, and wherein Hh1 is bonded via said thiophenyl moiety to the parent molecular group,
Ah 1 is phenyl-thiophenyl,
Ha1 is a 3-(heteroaryl)-phenyl or 4-(heteroaryl)-phenyl radical each made up of a heteroaryl group selected from the group consisting of monocyclic 5- and 6-membered heteroaryl radicals comprising one or two heteroatoms, each of which is selected from the group consisting of nitrogen, oxygen and sulfur, and a phenyl group, wherein said heteroaryl and phenyl groups are linked together via a single bond, and wherein Ha1 is bonded via said phenyl moiety to the parent molecular group,
Ha2 is a 3-(heteroaryl)-phenyl or 4-(heteroaryl)-phenyl radical each made up of a heteroaryl group selected from the group consisting of fused bicyclic 9- and 10-membered heteroaryl radicals comprising one or two heteroatoms, each of which is selected from the group consisting of nitrogen, oxygen and sulfur, and a phenyl group, wherein said heteroaryl and phenyl groups are linked together via a single bond, and wherein Ha2 is bonded via said phenyl moiety to the parent molecular group, R7 is hydroxyl, or 2-aminophenyl,
or a salt thereof.

6. A compound of formula I according to claim 1, in which
R1 is hydrogen,
R2 is hydrogen,
R3 is hydrogen,
R4 is hydrogen,
R5 is hydrogen,
R6 is -T1-Q1, in which
T1 is a bond,
Q1 is substituted by R61 on the terminal ring, and is Aa1 or Ah1, in which
Aa1 is 1,1'-biphen-3-yl or 1,1'-biphen-4-yl,
Ah1 is phenyl-thiophenyl,
R61 is hydroxymethyl, methylsulphonylamino, methylcarbonylamino, dimethylaminosuiphonyl, -T2-N(R611)R612, or -U-T3-N(R613)R614, in which
T2 is methylene, dimethylene or trimethylene,
R611 is methyl, cyclopropyl or 2-methoxyethyl,
R612 is hydrogen or methyl,
or
R611 and R612 together and with inclusion of the nitrogen atom, to which they are bonded, form a heterocyclic ring Het1, in which
Het1 is morpholino, piperidino, pyrrolidino or 4N-methyl-piperazino,
U is —O—(oxygen) or —C(O)NH—,
T3 is dimethylene or trimethylene,
R613 is methyl,
R614 is methyl,
or
R613 and R614 together and with inclusion of the nitrogen atom, to which they are bonded, form a heterocyclic ring Het2, in which
Het2 is morpholino, piperidino, pyrrolidino or 4N-methyl-piperazino,
or
Q1 is substituted by R61 on the terminal ring, and is Hh1 or Ha1, in which
Hh1 is pyridinyl-thiophenyl,
Ha1 is 3-(pyridinyl)-phenyl or 4-(pyridinyl)-phenyl,
R61 is methoxy, or -T2-N(R611)R612, in which
T2 is a bond,
R611 is hydrogen or methyl,
R612 is hydrogen or methyl,
or
R611 and R612 together and with inclusion of the nitrogen atom, to which they are bonded, form a heterocyclic ring Het1, in which
Het1 is morpholino, piperidino, pyrrolidino or 4N-methyl-piperazino,
or
Q1 is 3-(1N-methyl-pyrazolyl)-phenyl, 4-(1N-methyl-pyrazolyl)-phenyl, 3-(1N-methyl-indolyl)-phenyl or 4-(1N-methyl-indolyl)-phenyl,
R7 is hydroxyl, or 2-aminophenyl,
or a salt thereof.

7. A compound of formula I according to claim 1, in which
R1 is hydrogen,
R2 is hydrogen,
R3 is hydrogen,
R4 is hydrogen,
R5 is hydrogen,
R6 is -T1-Q1, in which
T1 is a bond,
Q1 is selected from the group consisting of 3'-(2-morpholin-4-yl-ethyl)-biphen-4-yl, 3'-(2-morpholin-4-ylethyl)-biphen-3-yl, 4'-(2-morpholin-4-yl-ethyl)-biphen-4-yl, 4'-(2-morpholin-4-yl-ethyl)-biphen-3-yl, 3'-(morpholin-4-yl-methyl)-biphen-3-yl, 4'-(morpholin-4-yl-methyl)-biphen-3-yl, 4'-(3-morpholin-4-yl-propyl)-biphen-3-yl, 4'-(4-methyl-piperazin-1-ylmethyl)-biphen-3-yl, 4'-(2-morpholin-4-yl-ethoxy)-biphen-3-yl, 4'-(3-morpholin-4-yl-propoxy)-biphen-3-yl, 4'[2-(4-methyl-piperazin-1-yl)-ethoxy]-biphen-3-yl, 4'-(2-pyrrolidin-1-yl-ethoxy]-biphen-3-yl, 2'-dimethylaminomethyl-biphen-4-yl, 4'-dimethylaminomethyl-biphen-4-yl, 2'-dimethylaminomethyl-biphen-3-yl, 4'-dimethylaminomethyl-biphen-3-yl, 3'-[(2-dimethylamino-ethylamino)-carbonyl]-biphen-4-yl, 4'-[(2-dimethylamino-ethylamino)-carbonyl]-biphen-4-yl, 4'-[(2-dimethylamino-ethylamino)-carbonyl]-biphen-3-yl, 2'-methylsulphonylamino-biphen-4-yl, 3'-methylsulphonylamino-biphen-4-yl, 4'-methylsulphonylamino-biphen-4-yl, 4'-dimethylsulphamoyl-biphen-4-yl, 3'-acetamido-biphen-4-yl, 4'-acetamido-biphen-4-yl, 4'-(2-methoxy-ethylamino)methyl-biphen-3-yl, 4'-cyclopropylaminomethyl-biphen-3-yl, 3'-hydroxymethyl-biphen-4-yl, 5-[2-(4-methyl-piperazin-1-yl)-pyridin-4-yl]-thiophen-2-yl, 5-(1N-methyl-pyrazol-4-yl)-thiophen-2-yl, 5-[4-(2-morpholin-4-yl-ethyl)-phenyl]-thiophen-2-yl, 5-[4-(morpholin-4-yl-methyl)-phenyl]-thiophen-2-yl, 5-[3-morpholin-4-yl-methyl)-phenyl]-thiophen-2-yl, 5-[4-(2-morpholin-4-yl-ethoxy)-phenyl]-thiophen-2-yl, 5-[4-(3-morpholin-4-yl-propoxy)-phenyl]-thiophen-2-yl, 5-{4-[2-(4-methyl-piperazin-1-yl)-ethoxy]-phenyl}-thiophen-2-yl, 5-(4-dimethylaminomethyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, 3-[6-amino-pyridin-3-yl]-phenyl, 4-[6-methoxy-pyridin-3-yl]-phenyl, 3-[6-methoxy-pyridin-3-yl]-phenyl, 3-(1N-methyl-pyrazol-4-yl)-phenyl, 4-(1N-methyl-pyrazol-4-yl)-phenyl, 4-(3,5-dimethyl-isoxazol-4-yl)-phenyl, and 4-(1N-methyl-indol-5-yl)-phenyl, R7 is hydroxyl, or 2-aminophenyl, or a salt thereof.

8. A compound of formula I according to claim 1, in which
R1 is hydrogen,
R2 is hydrogen,
R3 is hydrogen,
R4 is hydrogen,
R5 is hydrogen,
R6 is -T1-Q1, in which
T1 is a bond,
Q1 is selected from the group consisting of 4'-(2-morpholin-4-yl-ethyl)-biphen-3-yl, 4'-(3-morpholin-4-yl-propoxy)-biphen-3-yl, 4'-[2-(4-methyl-piperazin-1-yl)-ethoxy]-biphen-3-yl, 4'-dimethylaminomethyl-biphen-4-yl, 5-[2-(4-methyl-piperazin-1-yl)-pyridin-4-yl]-thiophen-2-yl, 5-(4-dimethylaminomethyl-phenyl)-thiophen-2-yl, 4-[2-(4-methyl-piperazin-1-yl)-pyridin-4-yl]-phenyl, 3-[2-(4-methyl-piperazin-1-yl)-pyridin-4-yl]-phenyl, 4-[6-amino-pyridin-3-yl]-phenyl, and 4-(1N-methyl-pyrazol-4-yl)-phenyl,
R7 is hydroxyl or 2-aminophenyl,
or a salt thereof.

9. A compound of formula I according to claim 1 in which
R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond, or 1-4C-alkylene,
either
Q1 is substituted by R61 and/or R62, and is Aa1, Hh1, Ha1, Ha2, Ha3 or Ah1,
or
Q1 is unsubstituted, and is Ha2 or Ha3,
in which
R61 is 1-4C-alkyl, 1-4C-alkoxy, hydroxyl, trifluoromethyl, cyano, halogen, completely or predominantly fluorine-substituted 1-4C-alkoxy, or -T2-N(R611)R612, in which
T2 is a bond or 1-4C-alkylene,
R611 is hydrogen or 1-4C-alkyl,
R612 is hydrogen or 1-4C-alkyl,
or
R611 and R612 together and with inclusion of the nitrogen atom, to which they are bonded, form a heterocyclic ring Het1, in which
Het1 is morpholino, thiomorpholino, S-oxo-thiomorpholino, S,S-dioxo-thiomorpholino, piperidino, pyrrolidino, piperazino, or 4N-(1-4C-alkyl)-piperazino,
R62 is 1-4C-alkyl, 1-4C-alkoxy or halogen,
Aa1 is a bisaryl radical made up of two aryl groups, which are independently selected from the group consisting of phenyl and naphthyl, and which are linked together via a single bond,
Hh1 is a bisheteroaryl radical made up of two heteroaryl groups, which are independently selected from the group consisting of monocyclic 5- and 6-membered heteroaryl radicals comprising one or two heteroatoms, each of which is selected from the group consisting of nitrogen, oxygen and sulfur, and which are linked together via a single bond,
Ah1 is an aryl-heteroaryl radical made up of an aryl group selected from the group consisting of phenyl and naphthyl, and a heteroaryl group selected from the group consisting of monocyclic 5- and 6-membered heteroaryl radicals comprising one or two heteroatoms, each of which is selected from the group consisting of nitrogen, oxygen and sulfur, wherein said aryl and heteroaryl groups are linked together via a single bond, and wherein Ah1 is bonded via said heteroaryl moiety to the parent molecular group,
Ha1 is a heteroarylaryl radical made up of a heteroaryl group selected from the group consisting of monocyclic 5- and 6-membered heteroaryl radicals comprising one or two heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha1 is bonded via said aryl moiety to the parent molecular group,
Ha2 is a heteroarylaryl radical nude up of a heteroaryl group selected from the group consisting of fused bicyclic 9- and 10-membered heteroaryl radicals comprising one, two or three heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha2 is bonded via said aryl moiety to the to the parent molecular group,
Ha3 is a heteroarylaryl radical nude up of a heteroaryl group selected from the group consisting of monocyclic 5-membered heteroaryl radicals comprising three or four heteroatoms, each of which is selected from the group consisting of nitrogen, oxygen and sulfur, and an aryl group selected from the group consisting of phenyl and naphthyl, wherein said heteroaryl and aryl groups are linked together via a single bond, and wherein Ha3 is bonded via said aryl moiety to the parent molecular group, R7 is hydroxyl, or Cyc1, in which Cyc 1 is a ring system of formula Ia

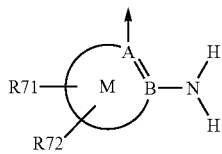

in which

A is C (carbon),

B is C (carbon),

R71 is hydrogen, halogen, 1-4C-alkyl, or 1-4C-alkoxy,

R72 is hydrogen, halogen, 1-4C-alkyl, or 1 -4C-alkoxy,

M with inclusion of A and B is either a ring Ar2 or a ring Har2, in which

Ar2 is a benzene ring,

Har2 is a monocyclic 5- or 6-membered unsaturated heteroaromatic ring comprising one to three heteroatoms, each of which is selected from the group consisting of nitrogen, oxygen and sulfur, or a salt thereof.

10. A compound of formula I according to claim 1 in which

R1 is hydrogen,

R2 is hydrogen,

R3 is hydrogen,

R4 is hydrogen,

R5 is hydrogen,

R6 is -T1-Q1, in which

T1 is a bond, either

Q1 is 3-[2-amino-pyridin-3-yl]-phenyl, 4-[2-amino-pyridin-3-yl)]-phenyl, 3-[2-methoxy -pyridin-3-yl)]-phenyl, or 4-[2methoxy-pyridin-3-yl)]-phenyl, or Q1 is 3'-(R61)-1,1 '-biphen-4-yl or 4'-(R6 1)-1,1'-biphen-4-yl, or Q1 is 3-[1N-methyl-indol-5-yf]-phenyl, 4-[1N-methyl-indol-5-yl]-phenyl, 3-[1N-methyl -pyrazol-4-yl]-phenyl or 4-[1N-methyl-pyrazol-4-yl]-phenyl, in which R61 is -T2-N(R611)R612, in which T2 is 1-2C-alkylene, R611 and R612 together and with inclusion of the nitrogen atom, to which they are bonded, form a heterocyclic ring Het1, in which Het1 is morpholino, R7 is hydroxyl, or 2-aminophenyl, or a salt thereof.

11. A compound of formula I according to claim 1 which is selected from the group consisting of (E)-N-Hydroxy-3- {1-[4-(1-methyl-1H-indol-5-yl)-benzenesulfonyl]-1H-pyrrol-3-yl}-acrylamide, (E)-N-Hydroxy-3- {1-[4-(1-methyl-1H-pyrazol-4-yl)-benzenesulfonyl]- 1H-pyrrol-3-yl}acrylamide, (E)-N-Hydroxy-3-{1-[4-(6-methoxy-pyridin-3-yl)-benzesulfonyl]-1H-pyrrol-3-yl}-acrylamide, (E)-3-{1-[4-(6-Amino-pyridin-3-yl)-benzenesulfonyl]-1H-pyrrol-3-yl}-N-hydroxy-acrylamide, (E)-N-(2-Amino-phenyl)-3-{1-[4-(6-methoxy-pyridin-3-yl)-benzenesulfonyl]-1H-pyrrol-3-yl}-acrylamide, (E)-N-(2-Amino-phenyl)-3 -{1-[4-(6-amino-pyridin-3-yl)-benzenesulfonyl]-1H-pyrrol-3-yl}-acrylamide, (E)-N-(2-Amino-phenyl)-3- {1-[4-(1-methyl-1H-pyrazol-4-yl)-benzenesulfonyl]-1H-pyrrol-3-yl}-acrylamide, (E)-N-Hydroxy-3-{1-[4'-(2-morpholin-4-yl-ethyl)-bipheny-4-sulfonyl]-1H-pyrrol-3-yl}-acrylamide, (E)-N-Hydroxy-3-{1-[3 '-(2-morpholin-4-yl-ethyl)-biphenyl-4-sulfnyl]-1H-pyrrol-3-yl}-acrylamide, (E)-3-{1-[3-(6Amino-pyridin-3-yl )-benzenesulfonyl]-1H-pyrrol-3-yl}-N-hydroxy-acrylamide, (E)-N-Hydroxy-3-{1-[3-(6-methoxy-pyridin-3-yl)-benzenesulfonyl]- 1H-pyrrol-3 -yl}-acrylamide, (E)-N-Hydroxy-3-{1-[3-(1-methyl-1H-pyrazol-4-yl)-benzenesulfonyl]- 1H-pyrrol-3-yl}-acrylamide, (E)-N-Hydroxy-3-{1-[3-(1-methyl-1H-indol-5-yl)-benzenesulfonyl]-1H-pyrrol-3-yl}-acrylamide, (E)-N-(2-Amino-phenyl)-3-{1-[3-(6-methoxy-pyridin-3-yl)-benzenesulfonyl]- 1H-pyrrol-3-yl}-acrylamide, (E)-N-(2-Amino-phenyl)-3-{1-[3-(1-methyl-1H-pyrazol-4-yl)-benzenesulfonyl]- 1H-pyrrol-3-yl}-acrylamide, (E)-N-Hydroxy-3-{1-[4'-(2-morpholin-4-yl-ethyl)-biphenyl-3-Sulfonyl]-1H-pyrrol-3-yl}-acrylamide, (E)-N-(2-Amino-phenyl)-3-{1-[3-(6-amino-pyridin-3-yl)-benzenesulfonyl]- 1H-pyrrol-3-yl }-acrylamide, (E)-N-(2-Amino-phenyl)-3 -{1-[3'-(2-morpholin-4-yl-ethyl)-3-sulfonyl]-1H-pyrrol-3-yl}-acrylamide, (E)-N-(2-Amino-phenyl)-3-{1[4'-(2-morpholin-4-yl-ethyl)-biphenyl-3-sulfonyl]-1H-pyrrol-3-yl}-acrylamide, (E)-N-I-Hydroxy-3-{1-[3'-(2-morpholin-4-yl-ethyl)-biphenyl-3-sulfonyl]-1H-pyrrol-3-yl}-acrylamide, (E)-N-Hydroxy-3-[1-(2'-methanesulfonylamino-biphenyl-4-sulfonyl)- 1H-pyrrol-3]-yl-acrylamide, (E)-N-hydroxy-3-[1-(3'-methanesulfonylamino-biphenyl-4-sulfonyl)- 1H-pyrrol-3-yl]-acrylamide, (E)-N-Hydroxy-3-[1-(4'-methanesulfonylamino-biphenyl-4-sulfonyl)-1H-pyrrol-3-yl]-acrylamide, 4'-[3-((E)-2-Hydroxycarbamoyl-vinyl)-pyrrole- 1-sulfonyl]-biphenyl-4-carboxylic acid (2-dimethylaminoethyl)-amide, 4'-[3-((E)-2-Hydroxycarbamoyl-vinyl)-pyrrole-1-sulfonyl]-biphenyl-3-carboxylic acid (2-dimethylaminoethyl)-amide, (E)-3-[1-(4'-Dimethylaminomethyl-biphenyl-4-sulfonyl)-1H-pyrrol-3-yl]-N-hydroxy-acrylamide, (E)-3-[1-(2'-Dimethylaminomethyl-biphenyl-4-sulfonyl)-1H-pyrrol-3-yl]-N-hydroxy-acrylamide, (E)-N-Hydroxy-3-(1-{4-[2-(4-methyl-piperazin- 1-yl)-pyridin-4-yl]-benzenesulfonyl}-1H-pyrrol-3-yl)-acrylamide, (E)-N-Hydroxy-3-{1-[4'(toluene-4-sulfonylamino)-biphenyl-4-sulfonyl]- 1H-pyrrol-3-yl }-acrylamide, 3'-[3-((E)-2-Hydroxycarbamoyl-vinyl)-pyrrole-1-sulfonyl]-biphenyl-4-carboxylic acid (2-dimethylaminoethyl)-amide, (E)-N-Hydroxy-3-[1-(3-morpholin-4-ylmethyl-biphenyl-3-sulfonyl)- 1H-pyrrol-3-yl]-acrylamide, (E)-N-Hydroxy-3-(1-{4'-[2-(4-methyl-piperazin- 1-yl)-ethoxy]-biphenyl-3-sulfonyl}- 1H-pyrrol-3-yl) -acrylamide, (E)-N-Hydroxy-3-(1- {3-[2-(4-methyl-piperazin- 1-yl)-pyridin-4-yl]-benzenesulfonyl}-1H-pyrrol-3-yl)-acrylamide,
(E)-N-Hydroxy-3-{1-[4'-(2-morpholin-4-yl-ethoxy)-biphenyl-3-sulphonyl]-1H-pyrrol-3-yl }-acrylamide,
(E)-N-(2-Amino-phenyl)-3-{1-[4-(1-benzyl-1H-pyrazol-4-yl)-benzenesulfonyl]-1H-pyrrol-3-yl }-acrylamide,
(E)-N-Hydroxy-3-[1-(4'-morpholin-4-ylmethyl-biphenyl-3-sulfonyl)-1H-pyrrol-3-yl]-acrylamide,
(E)-3-[1-(4'-Dimethylaminomethyl-biphenyl-3-sulfonyl)-1H-pyrrol-3-yl]-N-hydroxy-acrylamide,
(E)-N-Hydroxy-3-{1-[4'-(3-morpholin-4-yl-propoxy)-biphenyl-3-sulfonyl]- 1H-pyrrol-3-yl}-acrylamide,
(E)-N-(2-Amino-phenyl)-3-[1-(4'-dimethylsulfamoyl-biphenyl-4-sulfonyl)-1H-pyrrol-3-yl]-acrylamide,
(E)-3-[1-(3Acetylamino-bipheny-4-sulfonyl)-1H-pyrrol-3-yl]-N-(2-amino-phenyl)-acrylamide,
(E)-3-[1-(2'-Dimethylaminomethyl-biphenyl-3-sulfonyl)-1H-pyrrol-3-yl]-N-hydroxy-acrylamide,
(E)-N-Hydroxy-3-(1-{5-[2-(4-methyl-piperazin-1-yl)-pyridin-4-yl]-thiophene-2-sulfonyl}-1H-pyrrol -3-yl)-acrylamide,
(E)-N-Hydroxy-3-{1-[4'-(2-pyrrolidin-1-yl-ethoxy)-biphenyl-3-sulfonyl]-1H-pyrrol-3-yl }-acrylamide,
4'-{3-[(E)-2-(2-Amino-phenylcarbamoyl)-vinyl]-pyrrole-1-sulfonyl}-biphenyl-3-carboxylic acid (2-dimethylamino-ethyl)-amide,
(E)-N-Hydroxy-3-{1-[4'-(3-morpholin-4-yl-propyl)-biphenyl-3-sulfonyl]-1H-pyrrol-3-yl}-acrylamide,
(E)-3-{1-[5-(4-Dimethylaminomethyl-phenyl)-thiophene-2-sulfonyl]-1H-pyrrol-3-yl}-N-hydroxy -acrylamide,
(E)-N-(2-Amino-phenyl)-3-[1-(4'-dimethylaminomethy-biphenyl-4-sulfonyl)-1H-pyrrol-3-yl]-acrylamide,
(E)-N-(2-Amino-phenyl)-3-(1-{4-[2-(4-methyl-piperazin- 1-yl)-pyridin-4-yl]-benzenesulfonyl}-1H -pyrrol-3-yl)-acrylamide,
(E)-3-[1-(4'-Acetylamino-biphenyl-4-sulfonyl)-1H-pyrrol-3-yl]-N-(2-amino-phenyl)-acrylamide,
(E)-N-Hydroxy-3-{1-[5-(3-morpholin-4-ylmethyl-phenyl)-thiophene-2-sulfonyl]-1H-pyrrol-3-yl}-acrylamide,
(E)-N-(2-Amino-phenyl)-3-[1-(3'-hydroxymethyl-biphenyl-4-sulfonyl)-1H-pyrrol-3-yl]-acrylamide,
(E)-N-(2-Amino-phenyl)-3-{1-[4-(3,5-dimethyl-isoxazol-4-yl)-benzenesulfonyl]-1H-pyrrol-3-yl]-acrylamide,
(E)-N-(2-Amino-phenyl)-3-[1-(4'-methanesulfonyamino-bipheny4-sulfonyl)-1H-pyrrol-3-yl]-acrylamide,
(E)-N-Hydroxy-3-{1-[5-(4-morpholin-4-ylmethyl-phenyl)-thiophene-2-sulfonyl]-1H-pyrrol-3-yl}-acrylamide,
(E)-N-Hydroxy-3-[1-(5-{4-[2-(4-methyl-piperazin- 1-yl)-ethoxy]-phenyl}-thiophene-2-sulfonyl)-1H -pyrrol-3-yl]-acrylamide,
(E)-N-Hydroxy-3-(1-{5-[4-(2-morpholin-4-yl-ethoxy)-phenyl]-thiophene-2-sulfonyl}-1H-pyrrol-3-yl)-acrylamide,
(E)-N-Hydroxy-3-(1-{5-[4-(3-morpholin-4-yl-propoxy)-phenyl]-thiophene-2-sulfonyl}-1H-pyrrol-3-yl)-acrylamide,
(E)-N-Hydroxy-3-(1-{4'-[(2-methoxy-ethylamino)-methyl]-biphenyl-3-sulfonyl}- 1H-pyrrol-3-yl) -acrylamide,
(E)-N-(2-Amino-phenyl)-3-[1-(3'-methanesulfonylamino-biphenyl-4-sulfonyl)- 1H-pyrrol-3-yl]-acrylamide,
(E)-Hydroxy-3-{1-[5-(1-methyl-1H-pyrazol-4-yl)-thiophene-2-sulfonyl]-11H-pyrrol-3-yl}-acrylamide,
(E)-N-Hydroxy-3-(1-{5-[4-(2-morpholin-4-yl-ethyl)-phenyl]-thiophene-2-sulfonyl}-1H-pyrrol-3-yl) -acrylamide,
(E)-N-Hydroxy-3-{1-[4'-(4-methyl-piperazin- 1-ylmethyl)-biphenyl-3-sulfonyl]-1H-pyrrol-3-yl}-acrylamide,
(E)-3-[1-(4'-Cyclopropylaminomethyl-biphenyl-3-sulfonyl)-1H-pyrrol-3-yl]-N-hydroxy-acrylamide,
(E)-N-Hydroxy-3-[1-(3'-morpholin-4-ylmethyl-biphenyl-4-sulfonyl)-1H-pyrrol-3-yl]-acrylamide,
(E)-3-[1 -(4-Benzo[1,3]dioxol-5-yl-benzenesulfonyl)-1 H-pyrrol-3-yl]-N-hydroxy-acrylamide,
(E)-3-[1-(3'-Amino-biphenyl-4-sulfonyl)-1H-pyrrol-3-yl]-N-hydroxy-acrylamide,
(E)-N-Hydroxy-3-[1-(4'-hydroxy-biphenyl-4-sulfonyl)-1H-pyrrol-3-yl]-acrylamide,
(E)-N-Hydroxy-3-(1-{4'-[2-(1-methyl-piperidin-4-yl)-ethoxy]-biphenyl-4-sulfonyl}-1H-pyrrol-3-yl) -acrylamide,
(E)-3-[1-(3'-Dimethylamino-biphenyl-4-sulfonyl)-1H-pyrrol-3-yl]-N-hydroxy-acrylamide,
(E)-3-{1-[4-(2,3-Dihydro-benzofuran-5 -yl)-benzenesulfonyl]-1H-pyrrol-3-yl}-N-hydroxy -acrylamide,
(E)-N-Hydroxy-3-[1-(4'-morpholin-4-yl-biphenyl-4-sulfonyl)-1H-pyrrol-3-yl]-acrylamide,
(E)-N-Hydroxy-3-{1-[3'-(3-pyrrolidin- 1-yl-propoxy)-biphenyl-4-sulfonyl]- 1H-pyrrol-3-yl}-acrylamide,
(E)-N-Hydroxy-3-(1-{3'-[3-(4-methyl-piperazin- 1-yl)-propoxyl]-biphenyl-sulfonyl}-1H-pyrrol-3-yl)-acrylamide,
(E)-N-Hydroxy-3-{1-[3'-(3-morpholin-4-yl-propoxy)-biphenyl-4-sulfonyl]-1H-pyrrol-3-yl}-acrylamide,
(E)-N-Hydroxy-3-[1-(3'-morpholin-4-ylmethyl-biphenyl-4-sulfonyl)-1H-pyrrol-3-yl]-acrylamide,
(E)-N-Hydroxy-3-(1-{4'-[2-(4-methyl-piperazin- 1-yl)-ethoxy]-biphenyl-4-sulfonyl}-1H-pyrrol-3-yl) -acrylamide,
(E)-N-Hydroxy-3-{1-[4'-(2-morpholin-4-yl-ethoxy)-biphenyl-4-sulfonyl]-1H-pyrrol-3-yl}-acrylamide,
(E)-N-Hydroxy-3-{1-[4'-(3-morpholin-4-yl-propoxy)-biphenyl-4-sulfonyl]-1H-pyrrol-3-yl}-acrylamide,
(E)-N-Hydroxy-3-(1-{4'-[3-(4-methyl-piperazin-1-yl)-propoxy]-biphenyl-4-sulfonyl}-1H-pyrrol-3-yl)-acrylamide,
(E)-N-Hydroxy-3-{1-[3'-(2-pyrrolidin-1-yl-ethoxy)-biphenyl-4-sulfonyl]-1H-pyrrol-3-yl}-acrylamide,
(E)-N-Hydroxy-3-{1-[4'-(3-pyrrolidin-1-yl-propoxy)-biphenyl-4-sulfonyl]-1H-pyrrol-3-yl}-acrylamide,
(E)-N-Hydroxy-3-[1-(4'-methoxy-biphenyl-4-sulfonyl)-1H-pyrrol-3-yl]-acrylamide,
(E)-N-Hydroxy-3-(1-{4-[1-(2-morpholin-4-yl-ethyl)- 1H-[1,2,3]triazol-4-yl]-benzenesulfonyl}-1H -pyrrol-3-yl)-acrylamide,
(E)-3-[1-(4'-Cyclopentylaminomethyl-biphenyl-4-sulfonyl)-1H-pyrrol-3-yl]-N-hydroxy-acrylamide,
(E)-N-Hydroxy-3-[1-(3'-trifluoromethyl-biphenyl-4-sulfonyl)-1 H-pyrrol-3-yl]-acrylamicle,
(E-3-{1-[5-(3-Dimethylaminomethyl-phenyl)-thiophene-2-sulfonyl]-1H-pyrrol-3-yl}-N-hydroxy -acrylamide,
(E)-3-[1-(3'-Dimethylaminomethyl-biphenyl-3-sulfonyl)-1H-pyrrol-3-yl]-N-hydroxy-acrylamide,
(E)-N-Hydroxy-3-{1-[4'-(2-morpholin-4-yl-ethyl)-biphenyl-3-sulfonyl]- 1H-pyrrol-3-yl}-acrylamide, (E)-N-(2-Amino-phenyl)-3-{1-[6-(4-dimethylaminomethyl-phenyl)-pyridine-3-sulfonyl]-1H-pyrrol -3-yl}-acrylamide,
(E)-N-Hydroxy-3-{1-[5-(2-methyl-thiazol-4-yl)-thiophene-2-sulfonyl]- 1H-pyrrol-3-yl]-acrylamide,
(E)-3-[1-(4'-Aminomethyl-biphenyl-3-sulfonyl)-1H-pyrrol-3-yl]-N-hydroxy-acrylamide,
(E)-N-Hydroxy-3-(1-{6-[4-(2-pyrrolidin- 1-yl-ethoxy)-phenyl]-pyridine-3-sulfonyl}-1H-pyrrol-3-yl) -acrylamide,
(E)-3-[1-(4'-Aminomethyl-biphenyl-4-sulfonyl)-1H-pyrrol-3-yl]-N-(2-amino-phenyl)-acrylamide,
(E)-3-{1-[5-(3-Aminomethyl-phenyl)-thiophene-2-sulfonyl]-1H-pyrrol-3-yl}-N-hydroxy-acrylamide,
(E)-N-(2-Amino-phenyl)-3-{1-[5-(4-dimethylaminomethyl-phenyl)-thiophene-2-sulfonyl]-1H-pyrrol -3-yl}-acrylamide,
(E)-N-(2-Amino-phenyl)-3-[1-(3'-dimethylaminomethyl-biphenyl-4-sulfonyl)-1H-pyrrol-3-yl]-acrylamide,
(E)-3-{1-[4'-(Acetylamino-methyl)-biphenyl-4-sulfonyl]-1H-pyrrol-3-yl}-N-(2-amino-phenyl) -acrylamide,
(E)-N-(2-Amino-phenyl)-3-{1-[4'-(methanesulfonylamino-methyl)-bipheny-4-sulfonyl]-1H-pyrrol -3-yl}-acrylamide,
(E)-N-Hydroxy-3-(1-{5-[4-(2-pyrrolidin-1-yl-ethoxy)-phenyl]-thiophene-2-sulfonyl}-1H-pyrrol-3-yl)-acrylamide,
(E)-3-{1-[5-(4-Dimethylsulfamoyl-phenyl)-thiophene-2-sulfonyl]-1H-pyrrol-3-yl}-N-hydroxy -acrylamide,
(E)-N-(2-Amino-phenyl)-3 -[1-(4'-methanesulfonylamino-biphenyl-3-sulfonyl)-1H-pyrrol-3-yl]-acrylamide,
(E)-N-(2-Amino-phenyl)-3-[1-(4'-dimethylaminomethyl-biphenyl-3-sulfonyl)-1H-pyrrol-3-yl]-acrylamide,
(E)-N-Hydroxy-3-{1-[2'-(4-methyl-piperazin-1-yl)-[2,4'] bipyridinyl-5-sulfonyl]- 1H-pyrrol-3-yl}-acrylamide,
(E)-N-(2-Amino-phenyl)-3-{1-[5-(1-methyl-1H-pyrazol-4-yl)-thiophene-2-sulfonyl]-1H-pyrrol-3-yl}-acrylamide,
(E)-3-{1-[6-(4-Dimethylaminomethyl-phenyl)-pyridine-3-sulfonyl]- 1H-pyrrol-3-yl}-N-hydroxy -acrylamide,
(E)-N-(2-Amino-phenyl)-3-(1-{5-[2-(4-methyl-piperazin- 1-yl)-pyridin-4-yl]-thiophene-2-sulfonyl}-1H-pyrrol-3-yl)-acrylamide,
(E)-N-(2-Amino-phenyl)-3-[1-(4'-morpholin-4-ylmethyl-biphenyl-4-sulfonyl)-1H-pyrrol-3-yl]-acrylamide,
(E)-N-(2-Amino-phenyl)-3-{1-[4'-(2-pyrrolidin-1-yl-ethoxy)-biphenyl-4-sulfonyl]-1H-pyrrol-3-yl}-acrylamide,
(E)-N-Hydroxy-3-(1-{4-[1-(2-piperidin- 1-yl-ethyl)- 1H-[1,2,3]triazol-4-yl]-benzenesulfonyl}-1 H -pyrrol-3-yl)-acrylamide,
(E)-3-[1-(3'-Dimethylaminomethyl-biphenyl-3-sulfonyl)-1H-pyrrol-3-yl]-N-hydroxy-acrylamide,
(E)-N-(2-Amino-phenyl)-3-(1-{5-[4-(methynesulfonylamino-methyl)-phenyl]-thiophene-2-sulfonyl}-1H-pyrrol-3-yl)-acrylamide,
(E)-N-(2-Amino-phenyl)-3-{1-[3'-(methanesulfonylamino-methyl)-biphenyl-3-sulfonyl]-1H-pyrrol -3-yl}-acrylamide,
(E)-3-(1-{5-[4-(Acetylamino-methyl)-phenyl]-thiophene-2-sulfonyl}-1H-pyrrol-3-yl)-N-(2-amino -phenyl)-acrylamide,
(E)-N-(2-Amino-phenyl)-3-{1-[5-(3-dimethylaminomethyl-phenyl)-thiophene-2-sulfonyl]-1H-pyrrol -3-yl}-acrylamide,
(E)-N-(2-Amino-phenyl)-3-[1-(3'-dimethylaminomethyl-biphenyl-3-sulfonyl)- 1H-pyrrol-3-yl]-acrylamide,
(E)-3-[1-(3'Dimethylaminomethyl-biphenyl-4-sulfonyl)-1H-pyrrol-3-yl]-N-hydroxy-acrylamide,
(E)-3-{1-[5-(3-Dimethylaminomethyl-phenyl)-thiophene-2-sulfonyl]-1H-pyrrol-3-yl}-N-hydroxy -acrylamide,
(E)-3-{1-[3'-(Acetylamino-methyl)-biphenyl-3 -sulfonyl]-1H-pyrrol-3-yl}-N-(2-amino-phenyl) -acrylamide,
(E)-N-(2-Amino-phenyl)-3-{1-[6-(1-methyl-1H-pyrazol-4-yl)-pyridine-3-sulfonyl]- 1H-pyrrol-3-yl}-acrylamide,
(E)-N-Hydroxy-3-{1-[6-(1-methyl-1H-pyrazol-4-yl)-pyridine-3-sulfonyl]-1H-pyrrol-3-yl}-acrylamide, and
(E)-3-{1-[6-(3-Dimethylaminomethyl-phenyl)-pyridine-3-sulfonyl]-1H-pyrrol-3-yl}-N-hydroxy -acrylamide,
and salts thereof.

12. A compound of formula I according to claim 1, in which R7 is hydroxyl, or a salt thereof.

13. A compound of formula I according to claim 1, in which R7 is 2-aminophenyl, or a salt thereof.

14. A pharmaceutical composition comprising one or more compounds as claimed in claim 1, together with a pharmaceutically acceptable excipient, diluent and/or carrier.

15. A method for treating cervical carcinoma in a patient, comprising administering to said patient a therapeutically effective and tolerable amount of a compound as claim in claim 1.

16. A combination comprising
a first active ingredient, which is at least one compound according to claim 1, and a second active ingredient, which is at least one anti-cancer agent selected from the group consisting of chemotherapeutic anti-cancer agents and target-specific anti-cancer agents, for separate, sequential, simultaneous, concurrent or chronologically staggered use in therapy.

17. The combination according to claim 16, in which said chemotherapeutic anti-cancer agents are selected from (i) alkylating/carbamylating agents; (ii) platinum derivatives; (iii) antimitotic agents/tubulin inhibitors and epothulones; (iv) topoisomerase inhibitors, epipodophyllotoxines, and camptothecin and camptothecin analogs; (v) pyrimidine antagonists; (vi) purin antagonists; and (vii) folic acid antagonists.

18. The combination according to claim 16, in which said target-specific anti-cancer agents are selected from (i) kinase inhibitors; (ii) proteasome inhibitors; (iii) histone deacetylase inhibitors; (iv) heat shock protein 90 inhibitors; (v) vascular targeting agents (VAT) and anti-angiogenic drugs and KDR tyrosine kinase inhibitors; (vi) monoclonal antibodies, mutants and conjugates of monoclonal antibodies, and antibody fragments; (vii) oligonucleotide based therapeutics; (viii) Toll-like receptor/TLR 9 agonists, TLR 7 agonists and analogues thereof, or TLR 7/8 agonists; (ix) protease inhibitors (x) hormonal therapeutics; (xi) bleomycin; (xii) retinoids; (xiii) DNA methyltransferase inhibitors; (xiv) alanosine; (xv) cytokines; (xvi) interferons; and (xvii) death receptor agonists.

* * * * *